US012653781B2

(12) United States Patent
Xu et al.

(10) Patent No.: US 12,653,781 B2
(45) Date of Patent: *Jun. 16, 2026

(54) FORMULATIONS OF ANTI-INTERLEUKIN 1 RECEPTOR 1 ANTIBODIES

(71) Applicant: Kiniksa Pharmaceuticals, GmbH, Zug (CH)

(72) Inventors: Jianwen Xu, Lexington, MA (US); Ajit D'Souza, Lexington, MA (US)

(73) Assignee: Kiniksa Pharmaceuticals GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 19/394,710

(22) Filed: Nov. 19, 2025

(65) Prior Publication Data

US 2026/0076903 A1 Mar. 19, 2026

Related U.S. Application Data

(63) Continuation of application No. 19/275,155, filed on Jul. 21, 2025, now Pat. No. 12,502,352, which is a continuation of application No. 19/249,751, filed on Jun. 25, 2025.

(60) Provisional application No. 63/762,497, filed on Feb. 24, 2025, provisional application No. 63/670,418, filed on Jul. 12, 2024, provisional application No. 63/664,017, filed on Jun. 25, 2024, provisional application No. 63/663,761, filed on Jun. 25, 2024.

(51) Int. Cl.

| | |
|---|---|
| *A61K 9/08* | (2006.01) |
| *A61K 39/00* | (2006.01) |
| *A61K 47/12* | (2006.01) |
| *A61K 47/22* | (2006.01) |
| *A61K 47/26* | (2006.01) |
| *C07K 16/28* | (2006.01) |

(52) U.S. Cl.
CPC ............... *A61K 9/08* (2013.01); *A61K 47/12* (2013.01); *A61K 47/22* (2013.01); *A61K 47/26* (2013.01); *C07K 16/2866* (2013.01); *A61K 2039/545* (2013.01); *C07K 2317/52* (2013.01); *C07K 2317/565* (2013.01); *C07K 2317/92* (2013.01)

(58) Field of Classification Search
CPC . A61K 9/00; A61K 9/08; A61K 47/00; A61K 47/12; A61K 47/22; A61K 47/26; A61K 2039/00; A61K 2039/545; A61K 39/00; C07K 16/2866; C07K 2317/52; C07K 2317/565; C07K 2317/92; C07K 16/28
See application file for complete search history.

(56) References Cited

U.S. PATENT DOCUMENTS

| | | | |
|---|---|---|---|
| 5,334,380 A | 8/1994 | Kilbourn et al. | |
| 9,683,038 B2 | 6/2017 | Thuren et al. | |
| 9,925,263 B2 | 3/2018 | Larson et al. | |
| 10,000,565 B2 | 6/2018 | Basson et al. | |
| 10,041,044 B2 | 8/2018 | Walsh et al. | |
| 10,517,933 B2 | 12/2019 | Fatatis et al. | |
| 10,646,569 B2 | 5/2020 | Shenoy | |
| 10,961,585 B2 | 3/2021 | Hatchwell et al. | |
| 10,975,145 B2 | 4/2021 | Thuren et al. | |
| 11,385,238 B2 | 7/2022 | Ren et al. | |
| 11,504,431 B2 | 11/2022 | Prausnitz et al. | |
| 12,502,352 B1 * | 12/2025 | D'Souza ................. | A61K 9/08 |
| 2003/0049255 A1 | 3/2003 | Sims et al. | |
| 2006/0171948 A1 | 8/2006 | Weinstein et al. | |
| 2007/0248597 A1 | 10/2007 | Henley et al. | |
| 2011/0014189 A1 | 1/2011 | Soula et al. | |
| 2013/0149312 A1 | 6/2013 | Finch et al. | |
| 2014/0199320 A1 | 7/2014 | Jankovic et al. | |
| 2014/0314746 A1 | 10/2014 | Artlett et al. | |
| 2016/0228371 A1 | 8/2016 | Schultz et al. | |
| 2018/0105589 A1 | 4/2018 | Dillon et al. | |
| 2019/0218614 A1 | 7/2019 | Walsh et al. | |
| 2020/0352857 A1 | 11/2020 | Gu et al. | |
| 2020/0355582 A1 | 11/2020 | Wu | |
| 2021/0041453 A1 | 2/2021 | Benchaar et al. | |
| 2021/0155701 A1 | 5/2021 | Hoshino et al. | |
| 2021/0371512 A1 | 12/2021 | Thuren et al. | |
| 2022/0089724 A1 | 3/2022 | Peddareddigari | |
| 2022/0137010 A1 | 5/2022 | Wen | |
| 2022/0137061 A1 | 5/2022 | Wu et al. | |
| 2022/0146413 A1 | 5/2022 | Duff et al. | |
| 2022/0187398 A1 | 6/2022 | Hwang et al. | |
| 2022/0211813 A1 | 7/2022 | Soriano et al. | |

(Continued)

FOREIGN PATENT DOCUMENTS

| | | |
|---|---|---|
| EP | 0661992 B1 | 1/2004 |
| EP | 1712239 A2 | 10/2006 |

(Continued)

OTHER PUBLICATIONS

International Search Report for PCT/IB2025/056476 dated Sep. 29, 2025 (6 pages).
Dillon, Thomas M., et al., "Structural and Functional Characterization of Disulfide Isoforms of the Human IgG2 Subclass", The Journal of Biological Chemistry, vol. 283, No. 23, Jun. 6, 2008, pp. 16206-16215, DOI 10.1074/jbc.M709988200, (10 pages).
Liu, Y. Diana , et al., "Human IgG2 Antibody Disulfide Rearrangement in Vivo", The Journal of Biological Chemistry, vol. 283, No. 43, Oct. 24, 2008, pp. 29266-29272 (7 pages).

(Continued)

*Primary Examiner* — D. L. Jones

(74) *Attorney, Agent, or Firm* — Proskauer Rose LLP

(57) ABSTRACT

The present invention provides, among other things, stable formulations comprising an anti-Interleukin 1 Receptor 1 (IL1R1) antibody at a concentration of between than 50-200 mg/ml, wherein the formulation comprises less than 130 mM arginine and a pH of 4.4-6.5, wherein the amount of HMW species in the formulation increases less than 2% upon storage at 25° C. for at least 4 weeks.

24 Claims, 10 Drawing Sheets

Specification includes a Sequence Listing.

(56) References Cited

U.S. PATENT DOCUMENTS

| | | | |
|---|---|---|---|
| 2022/0233710 A1 | 7/2022 | Wang et al. |
| 2022/0260584 A1 | 8/2022 | Bondarenko et al. |
| 2022/0356240 A1 | 11/2022 | Saffitz |
| 2023/0035363 A1 | 2/2023 | Xiang et al. |

FOREIGN PATENT DOCUMENTS

| | | | |
|---|---|---|---|
| WO | 9406457 | A1 | 3/1994 |
| WO | 2004022718 | A2 | 3/2004 |
| WO | 2008030931 | A2 | 3/2008 |
| WO | 2009036209 | A2 | 3/2009 |
| WO | 2009037190 | A2 | 3/2009 |
| WO | 2010052505 | A1 | 5/2010 |
| WO | 2013045404 | A2 | 4/2013 |
| WO | 2013049278 | A1 | 4/2013 |
| WO | 2014129914 | A1 | 8/2014 |
| WO | 2015038811 | A2 | 3/2015 |
| WO | 2015063770 | A1 | 5/2015 |
| WO | 2015083120 | A1 | 6/2015 |
| WO | 2015095772 | A2 | 6/2015 |
| WO | 2015195842 | A1 | 12/2015 |
| WO | 2018064307 | A2 | 4/2018 |
| WO | 2018064307 | A4 | 9/2018 |
| WO | 2018206565 | A1 | 11/2018 |
| WO | 2019067639 | A1 | 4/2019 |
| WO | 2019173719 | A1 | 9/2019 |
| WO | 2022061092 | A1 | 3/2022 |
| WO | 2022098595 | A1 | 5/2022 |
| WO | 2022167916 | A1 | 8/2022 |
| WO | 2022226177 | A1 | 10/2022 |

OTHER PUBLICATIONS

Strickley, Robert G., et al., "A review of formulations of commercially available antibodies", Journal of Pharmaceutical Sciences, vol. 110, No. 7, Mar. 1, 2021 (75 pages).

Wang, Wei , et al., "Antibody structure, instability, and formulation", Journal of Pharmaceutical Sciences, Elsevier Inc, vol. 96, No. 1, Jan. 1, 2007 (Jan. 1, 2007), (26 pages).

Warne, Nicholas W., "Development of high concentration protein biopharmaceuticals: The use of platform approaches in formulation development", European Journal of Pharmaceutics and Biopharmaceutics, Elsevier Science Publishers B.V., Amsterdam, NL, vol. 78, No. 2, Mar. 3, 2011 (5 pages).

* cited by examiner

FIG. 2

FORMULATIONS OF ANTI-INTERLEUKIN 1 RECEPTOR 1 ANTIBODIES

CROSS-REFERENCE TO RELATED APPLICATIONS

This application is a continuation application of U.S. application Ser. No. 19/275,155, filed on Jul. 21, 2025, which is a continuation application of U.S. application Ser. No. 19/249,751, filed Jun. 25, 2025, which claims priority to, and the benefit of, U.S. Provisional Application No. 63/762,497, filed Feb. 24, 2025, U.S. Provisional Application No. 63/670,418, filed Jul. 12, 2024, U.S. Provisional Application No. 63/664,017, filed Jun. 25, 2024, and U.S. Provisional Application No. 63/663,761, filed Jun. 25, 2024, the disclosure of each of which is hereby incorporated by reference in its entirety.

INCORPORATION-BY-REFERENCE OF SEQUENCE LISTING

The present specification includes a Sequence Listing submitted electronically as an XML file named "KPL-060US3_SL.XML". The XML file was generated Nov. 19, 2025, and is 12,735 bytes in size. The entire contents of the Sequence Listing are incorporated by reference herein.

BACKGROUND

Developments in biotechnology have made it possible to produce a large variety of monoclonal antibodies for pharmaceutical applications. Because antibodies are larger and more complex than traditional organic and inorganic drugs, the formulation of such proteins poses special problems. One of the problems is the elevated viscosity values of antibody formulations, especially at high protein concentrations. Another problem is maintaining stability in antibody formulations, which is a critical concern for regulatory agencies. The delivery of high protein concentration is often required for subcutaneous administration due to volume limitations and dose requirements. Subcutaneous administration is an attractive route of delivery because it is less invasive for patients and reduces inconvenience and discomfort for them. Proteins tend to form viscous solutions at high concentration because of their macromolecular nature and potential for intermolecular interactions.

Furthermore, each antibody has a unique amino acid sequence and three-dimensional structure, leading to differences in physicochemical properties like isoelectric point, hydrophobicity, and surface charge distributions. The optimal pH, ionic strength, buffer type and excipients required for stabilization vary for each antibody based on its specific structural characteristics. A "one-size-fits-all" formulation is not feasible.

SUMMARY OF THE INVENTION

The present invention provides, among other things, stable formulations comprising an anti-Interleukin 1 Receptor 1 (IL1R1) antibody at a concentration of greater than 80 mg/ml with a pH ranging from 4.4-6.5, wherein the amount of high molecular weight (HMW) species in the formulation increases less than 2% upon storage at 25° C. for at least 4 weeks. As described herein, the present invention is, in part, based on a finding that the use of arginine at a concentration of less than about 130 mM stabilizes the formulation such that the amount of HMW species in the formulation increases less than 40% upon storage at a high temperature (e.g., 40° C.). It was determined that at certain concentrations arginine can cause destabilization of an IL1R1 antibody. This was surprising as arginine is a frequently used excipient for enhancing protein refolding and reducing aggregation. Arginine is also used to reduce viscosity of high concentration antibody formulations. As such, it is typically desirable to use arginine at a high concentration to prevent aggregation while reducing viscosity of antibody formulations. In fact, several antibody formulations use arginine at a high concentration, such as 31.6 mg/ml Arg-HCl (150 mM) and at 26.1 mg/ml Arg (150 mM) in ADUHELM® and ENSPRYNG® formulations, respectively. The present invention is, in part, based on the identification of anti-IL1-R1 antibody formulations comprising a relatively low concentration of arginine (e.g., <130 mM) with high stability and low viscosity. In some embodiments, the amount of HMW species in the formulation increases less than 15% upon storage at 40° C. for 4 weeks. In some embodiments, the formulation comprises less than 130 mM of arginine.

In one aspect, the present invention provides, among other things, a stable formulation comprising an anti-interleukin-1 receptor 1 (IL1R1) antibody, wherein the formulation comprises less than 130 mM arginine and a pH of 4.4-6.5, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In some embodiments, the anti-IL1R1 antibody has a pI of 7.4 to 7.8. In some embodiments, the anti-IL1R1 antibody has a pI of 7.6.

In some embodiments, a formulation comprises a buffer.

In some embodiments, the buffer is present at a concentration of 10 mM to 150 mM. In some embodiments, the buffer is present at a concentration of 15 mM to 100 mM. In some embodiments, the buffer is present at a concentration of 15 mM to 75 mM. In some embodiments, the buffer is present at a concentration of 25 mM to 50 mM. In some embodiments, the buffer is present at a concentration of 10 mM. In some embodiments, the buffer is present at a concentration of 15 mM. In some embodiments, the buffer is present at a concentration of 20 mM. In some embodiments, the buffer is present at a concentration of 25 mM. In some embodiments, the buffer is present at a concentration of 10 mM. In some embodiments, the buffer is present at a concentration of 30 mM. In some embodiments, the buffer is present at a concentration of 40 mM. In some embodiments, the buffer is present at a concentration of 50 mM. In some embodiments, the buffer is present at a concentration of 60 mM. In some embodiments, the buffer is present at a concentration of 70 mM. In some embodiments, the buffer is present at a concentration of 75 mM.

In some embodiments, the buffer comprises acetate, succinate, histidine, or phosphate. In some embodiments, the buffer is acetate. In some embodiments, the buffer is succinate. In some embodiments, the buffer is histidine. In some embodiments, the buffer is phosphate.

In some embodiments, the concentration of acetate, succinate, histidine, or phosphate is present at a concentration of 10 mM to 150 mM. In some embodiments, the concentration of acetate, succinate, histidine, or phosphate is present at a concentration of 15 mM and 100 mM. In some embodiments, the concentration of acetate, succinate, histidine, or phosphate is present at a concentration of 15 to 75 mM. In some embodiments, the concentration of acetate, succinate, histidine, or phosphate is present at a concentration of 25 mM to 50 mM.

In some embodiments, the pH of the stable formulation is 4.0 to 6.5. In some embodiments, the pH of the stable formulation is 4.4 to 6.5. In some embodiments, the pH of the stable formulation is 4.5 to 6.5. In some embodiments, the pH of the stable formulation is 4.5 to 6.0. In some embodiments, the pH of the stable formulation is 4.4 to 5.7. In some embodiments, the pH of the stable formulation is 4.4 to 5.4. In some embodiments, the pH of the stable formulation is 4.7 to 5.1. In some embodiments, the pH of the stable formulation is 4.7 to 5.7. In some embodiments, the pH of the stable formulation is 5.0 to 5.4. In some embodiments, the pH of the stable formulation is 5.0 to 5.5. In some embodiments, the pH of the stable formulation is 4.5 to 5.5. In some embodiments, the pH of the stable formulation is 5.0 to 6.1. In some embodiments, the pH of the stable formulation is 4.0. In some embodiments, the pH of the stable formulation is 4.1. In some embodiments, the pH of the stable formulation is 4.2. In some embodiments, the pH of the stable formulation is 4.3. In some embodiments, the pH of the stable formulation is 4.4. In some embodiments, the pH of the stable formulation is 4.5. In some embodiments, the pH of the stable formulation is 4.6. In some embodiments, the pH of the stable formulation is 4.7. In some embodiments, the pH of the stable formulation is 4.8. In some embodiments, the pH of the stable formulation is 4.9. In some embodiments, the pH of the stable formulation is 5.0. In some embodiments, the pH of the stable formulation is 5.1. In some embodiments, the pH of the stable formulation is 5.2. In some embodiments, the pH of the stable formulation is 5.3. In some embodiments, the pH of the stable formulation is 5.4. In some embodiments, the pH of the stable formulation is 5.5. In some embodiments, the pH of the stable formulation is 5.6. In some embodiments, the pH of the stable formulation is 5.7. In some embodiments, the pH of the stable formulation is 5.8. In some embodiments, the pH of the stable formulation is 5.9. In some embodiments, the pH of the stable formulation is 6.0. In some embodiments, the pH of the stable formulation is 6.1. In some embodiments, the pH of the stable formulation is 6.2. In some embodiments, the pH of the stable formulation is 6.3. In some embodiments, the pH of the stable formulation is 6.4. In some embodiments, the pH of the stable formulation is 6.5. In some embodiments, the pH of the stable formulation is 6.6. In some embodiments, the pH of the stable formulation is 6.7. In some embodiments, the pH of the stable formulation is 6.8. In some embodiments, the pH of the stable formulation is 6.9. In some embodiments, the pH of the stable formulation is 7.0.

In some embodiments, the stable formulation comprises arginine, which is present at a concentration of 10 mM to 100 mM. In some embodiments, arginine is present at a concentration of 15 mM to 80 mM. In some embodiments, arginine is present at a concentration of 15 mM to 75 mM. In some embodiments, arginine is present at a concentration of 10 mM to 50 mM. In some embodiments, the formulation comprises less than 130 mM arginine. In some embodiments, the formulation comprises less than 125 mM arginine. In some embodiments, the formulation comprises less than 120 mM arginine. In some embodiments, the formulation comprises less than 115 mM arginine. In some embodiments, the formulation comprises less than 110 mM arginine. In some embodiments, the formulation comprises less than 100 mM arginine. In some embodiments, the formulation comprises less than 90 mM arginine. In some embodiments, the formulation comprises less than 80 mM arginine. In some embodiments, the formulation comprises less than 75 mM arginine. In some embodiments, the formulation comprises less than 70 mM arginine. In some embodiments, the formulation comprises less than 60 mM arginine. In some embodiments, the formulation comprises less than 55 mM arginine. In some embodiments, the formulation comprises less than 50 mM arginine. In some embodiments, the formulation comprises less than 45 mM arginine. In some embodiments, the formulation comprises less than 40 mM arginine. In some embodiments, the formulation comprises less than 35 mM arginine. In some embodiments, the formulation comprises less than 30 mM arginine. In some embodiments, the formulation comprises less than 25 mM arginine. In some embodiments, the formulation comprises less than 20 mM arginine. In some embodiments, the formulation comprises less than 15 mM arginine. In some embodiments, the formulation comprises less than 10 mM arginine. In some embodiments, the formulation is substantially free or arginine. In some embodiments, arginine is not added to a formulation. In some embodiments, arginine is not detectable in a formulation.

In some embodiments, the formulation comprises 50 mM arginine. In some embodiments, the formulation comprises 55 mM arginine. In some embodiments, the formulation comprises 60 mM arginine. In some embodiments, the formulation comprises 65 mM arginine. In some embodiments, the formulation comprises 66 mM arginine. In some embodiments, the formulation comprises 67 mM arginine. In some embodiments, the formulation comprises 68 mM arginine. In some embodiments, the formulation comprises 69 mM arginine. In some embodiments, the formulation comprises 70 mM arginine. In some embodiments, the formulation comprises 75 mM arginine. In some embodiments, the formulation comprises 80 mM arginine. In some embodiments, the formulation comprises 85 mM arginine. In some embodiments, the formulation comprises 90 mM arginine. In some embodiments, the formulation comprises 95 mM arginine. In some embodiments, the formulation comprises 100 mM arginine.

In some embodiments, the stable formulation comprises a sugar.

In some embodiments, the sugar is trehalose. In some embodiments, the sugar is sucrose. In some embodiments, the sugar is lactose. In some embodiments, the sugar is mannitol. In some embodiments, the sugar is mellibiose. In some embodiments, the sugar is melezitose. In some embodiments, the sugar is raffinose. In some embodiments, the sugar is mannotriose. In some embodiments, the sugar is stachyose.

In some embodiments, the stable formulation comprises a sugar at concentrations of 0-20% (w/v). In some embodiments, the sugar is present at concentrations of 1-15% (w/v). In some embodiments, the sugar is present at concentrations of 2-10% (w/v). In some embodiments, the sugar is present at concentrations of 3-8% (w/v). In some embodiments, the sugar is present at concentrations of 2% (w/v). In some embodiments, the sugar is present at concentrations of 3% (w/v). In some embodiments, the sugar is present at concentrations of 4% (w/v). In some embodiments, the sugar is present at concentrations of 5% (w/v). In some embodiments, the sugar is present at concentrations of 6% (w/v). In some embodiments, the sugar is present at concentrations of 7% (w/v). In some embodiments, the sugar is present at concentrations of 8% (w/v). In some embodiments, the sugar is present at concentrations of 9% (w/v). In some embodiments, the sugar is present at concentrations of 10% (w/v).

In some embodiments, the stable formulation comprises a surfactant.

In some embodiments, the surfactant is polysorbate-20. In some embodiments, the surfactant is polysorbate-80.

In some embodiments, the stable formulation comprises a surfactant, which is present at concentrations of 0% to 0.1% (w/v). In some embodiments, the surfactant is present at concentrations of 0.001% to 0.05% (w/v).

In some embodiments, the stable formulation comprises a salt.

In some embodiments, the salt is sodium chloride. In some embodiments, the salt is potassium chloride. In some embodiments, the salt is magnesium chloride. In some embodiments, the salt is calcium chloride.

In some embodiments, the stable formulation comprises a salt, wherein the salt is present at concentrations of 5 mM to 300 mM. In some embodiments, the stable formulation comprises a salt, wherein the salt is present at concentrations of 10 mM to 250 mM. In some embodiments, the stable formulation comprises a salt, wherein the salt is present at concentrations of 25 mM to 200 mM. In some embodiments, the stable formulation comprises a salt, wherein the salt is present at concentrations of 50 mM to 150 mM. In some embodiments, the stable formulation comprises a salt, wherein the salt is present at concentrations of 40 mM to 80 mM. In some embodiments, the salt is present at concentrations of 50 mM to 75 mM. In some embodiments, the salt is present at a concentration of 200 mM. In some embodiments, the salt is present at a concentration of 175 mM. In some embodiments, the salt is present at a concentration of 150 mM. In some embodiments, the salt is present at a concentration of 125 mM. In some embodiments, the salt is present at a concentration of 100 mM. In some embodiments, the salt is present at a concentration of 80 mM. In some embodiments, the salt is present at a concentration of 75 mM. In some embodiments, the salt is present at a concentration of 70 mM. In some embodiments, the salt is present at a concentration of 65 mM. In some embodiments, the salt is present at a concentration of 60 mM. In some embodiments, the salt is present at a concentration of 55 mM. In some embodiments, the salt is present at a concentration of 50 mM. In some embodiments, the salt is present at a concentration of 45 mM. In some embodiments, the salt is present at a concentration of 40 mM. In some embodiments, the salt is present at a concentration of 35 mM. In some embodiments, the salt is present at a concentration of 30 mM. In some embodiments, the salt is present at a concentration of 25 mM. In some embodiments, the salt is present at a concentration of 20 mM. In some embodiments, the salt is present at a concentration of 15 mM. In some embodiments, the salt is present at a concentration of 10 mM.

In some embodiments, the stable formulation comprises an amino acid.

In some embodiments, the amino acid is a basic amino acid. In some embodiments, the amino acid is an acidic amino acid. In some embodiments, the amino acid is lysine. In some embodiments, the amino acid is arginine. In some embodiments, the amino acid is glutamate. In some embodiments, the amino acid is aspartate. In some embodiments, the amino acid is alanine. In some embodiments, the amino acid is proline. In some embodiments, the amino acid is methionine. In some embodiments, the amino acid is glycine.

In some embodiments, the amino acid is present at a concentration of 15 mM to 150 mM. In some embodiments, the amino acid is present at a concentration of 25 mM to 100 mM. In some embodiments, the amino acid is present at a concentration of 75 mM.

In one aspect, the present invention provides, among other things, a stable formulation comprising an ant-interleukin-1 receptor 1 (IL1R1) antibody, a stable formulation comprising an anti-interleukin-1 receptor 1 (IL1R1) antibody, wherein the formulation comprises 20 mM to 60 mM acetate, a basic amino acid, and pH of 4.2 to 5.5, wherein the anti-IL1R1 antibody comprises a HCDR1 of SEQ ID NO: 5 (FHWIA), a HCDR2 or SEQ ID NO: 6 (IIHPG-ASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In some embodiments, the stable formulation has a pH of 5.0 to 5.5. In some embodiments, the stable formulation has a pH of 5.1 to 5.3. In some embodiments, the stable formulation has a pH of 5.2.

In one aspect, the present invention provides, among other things, a stable formulation comprising an anti-interleukin-1 receptor 1 (IL1R1) antibody, wherein the formulation comprises 20 mM to 60 mM acetate, a sugar, and a pH of 4.2 to 5.7, and wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In one aspect, the present invention provides, among other things, a stable formulation comprising an ant-interleukin-1 receptor 1 (IL1R1) antibody, wherein the formulation comprises 10 mM to 50 mM histidine, an amino acid, and a pH of 5.5 to 6.5, and wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In some embodiments, the amino acid is a basic amino acid, an acidic amino acid, proline or a combination thereof.

In one aspect, the present invention provides, among other things, a stable formulation comprising an anti-interleukin-1 receptor 1 (IL1R1) antibody, wherein the formulation comprises 10 mM to 50 mM histidine, a sugar, and a pH of 5.5 to 6.5, and wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In some embodiments, the stable formulation has a pH of 4.7 to 5.7. In some embodiments, the stable formulation has a pH of 5.0 to 5.4. In some embodiments, the stable formulation has a pH of 5.5 to 6.5. In some embodiments, the stable formulation has a pH of 6.0 to 6.3. In some embodiments, the stable formulation has a pH of 6.1.

In one aspect, the present invention provides, among other things, a stable formulation comprising an anti-interleukin-1 receptor 1 (IL1R1) antibody, wherein the formulation comprises 25 mM to 75 mM succinate, a basic amino acid, and a pH of 5.0 to 6.0, and wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In one aspect, the present invention provides, among other things, a stable formulation comprising an anti-interleukin-1 receptor 1 (IL1R1) antibody, wherein the formulation comprises 25 mM to 75 mM succinate, a salt, and a pH of 5.0 to 6.0, and wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In one aspect, the present invention provides, among other things, a stable formulation comprising an anti-interleukin-1 receptor 1 (IL1R1) antibody, wherein the formulation comprises 20 mM to 60 mM succinate, a sugar, and a pH of 5.0 to 6.0, and wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of greater than 80 mg/ml.

In some embodiments, the stable formulation has a pH of 5.0 to 6.0. In some embodiments, the pH is 5.2 to 5.8. In some embodiments, the pH is 5.4 to 5.7. In some embodiments, the pH is 5.6.

In some embodiments, the stable formulation comprises the anti-IL1R1 antibody at a concentration of greater than 50 mg/ml. In some embodiments, the stable formulation comprises the anti-IL1R1 antibody at a concentration of greater than 60 mg/ml. In some embodiments, the stable formulation comprises the anti-IL1R1 antibody at a concentration of greater than 70 mg/ml. In some embodiments, the stable formulation comprises the anti-IL1R1 antibody at a concentration of greater than 80 mg/ml. In some embodiments, the stable formulation comprises the anti-IL1R1 antibody at a concentration of greater than 90 mg/ml. In some embodiments, the stable formulation comprises the anti-IL1R1 antibody at a concentration of greater than 100 mg/ml. In some embodiments, the stable formulation comprises the anti-IL1R1 antibody at a concentration of greater than 110 mg/ml. In some embodiments, the stable formulation comprises the anti-IL1R1 antibody at a concentration of greater than 120 mg/ml. In some embodiments, the stable formulation comprises the anti-IL1R1 antibody at a concentration of greater than 125 mg/ml. In some embodiments, the stable formulation comprises the anti-IL1R1 antibody at a concentration of greater than 130 mg/ml. In some embodiments, the stable formulation comprises the anti-IL1R1 antibody at a concentration of greater than 140 mg/ml. In some embodiments, the stable formulation comprises the anti-IL1R1 antibody at a concentration of greater than 150 mg/ml. In some embodiments, the stable formulation comprises the anti-IL1R1 antibody at a concentration of greater than 160 mg/ml. In some embodiments, the stable formulation comprises the anti-IL1R1 antibody at a concentration of greater than 170 mg/ml. In some embodiments, the stable formulation comprises the anti-IL1R1 antibody at a concentration of greater than 180 mg/ml.

In some embodiments, the stable formulation comprises the anti-IL1R1 antibody at a concentration of 50 mg/mL to 250 mg/mL. In some embodiments, the stable formulation comprises the anti-IL1R1 antibody at a concentration of 80 mg/mL to 200 mg/mL. In some embodiments, the anti-IL1R1 antibody is present at a concentration of 100 mg/mL to 150 mg/mL. In some embodiments, the stable formulation comprises the anti-IL1R1 antibody at a concentration of 50 mg/mL to 150 mg/mL. In some embodiments, the stable formulation comprises the anti-IL1R1 antibody at a concentration of 135 mg/mL to 165 mg/mL. In some embodiments, the stable formulation comprises the anti-IL1R1 antibody at a concentration of 145 mg/mL to 160 mg/mL. In some embodiments, the anti-IL1R1 antibody is present at a concentration of 50 mg/mL. In some embodiments, the anti-IL1R1 antibody is present at a concentration of 80 mg/mL. In some embodiments, the anti-IL1R1 antibody is present at a concentration of 100 mg/mL. In some embodiments, the anti-IL1R1 antibody is present at a concentration of 110 mg/mL. In some embodiments, the anti-IL1R1 antibody is present at a concentration of 120 mg/mL. In some embodiments, the anti-IL1R1 antibody is present at a concentration of 125 mg/mL. In some embodiments, the anti-IL1R1 antibody is present at a concentration of 130 mg/mL. In some embodiments, the anti-IL1R1 antibody is present at a concentration of 135 mg/mL. In some embodiments, the anti-IL1R1 antibody is present at a concentration of 140 mg/mL. In some embodiments, the anti-IL1R1 antibody is present at a concentration of 145 mg/mL. In some embodiments, the anti-IL1R1 antibody is present at a concentration of 150 mg/mL. In some embodiments, the anti-IL1R1 antibody is present at a concentration of 155 mg/mL. In some embodiments, the anti-IL1R1 antibody is present at a concentration of 160 mg/mL. In some embodiments, the anti-IL1R1 antibody is present at a concentration of 165 mg/mL. In some embodiments, the anti-IL1R1 antibody is present at a concentration of 170 mg/mL. In some embodiments, the anti-IL1R1 antibody is present at a concentration of 175 mg/mL. In some embodiments, the anti-IL1R1 antibody is present at a concentration of 180 mg/mL. In some embodiments, the anti-IL1R1 antibody is present at a concentration of 185 mg/mL. In some embodiments, the anti-IL1R1 antibody is present at a concentration of 190 mg/mL. In some embodiments, the anti-IL1R1 antibody is present at a concentration of 200 mg/mL. In some embodiments, the anti-IL1R1 antibody is present at a concentration of 225 mg/mL. In some embodiments, the anti-IL1R1 antibody is present at a concentration of 250 mg/mL. In some embodiments, the anti-IL1R1 antibody is present at a concentration of 275 mg/mL. In some embodiments, the anti-IL1R1 antibody is present at a concentration of 300 mg/mL.

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH 5.2, 7% w/v sucrose, and 0.02% w/v polysorbate 20, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8

(RASQSIGSSLH), a LCDR2 of SEQ ID NO: 9 (YASQSFS), and a LCDR3 of SEQ ID NO: 10 (HQSSSLPLT).

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH of 4.5-5.7, 7% w/v sucrose, and 0.02% w/v polysorbate 20, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation has a pH of 4.5 to 5.0. In some embodiments, the stable formulation has a pH of 4.7 to 5.7. In some embodiments, the stable formulation has a pH of 5.0 to 5.4.

In one aspect, the present invention provides, among other things, a stable formulation comprising an anti-interleukin-1 receptor 1 (IL1R1) antibody, wherein the formulation comprises: the anti-IL1R1 antibody at a concentration of 135 mg/mL to 165 mg/mL, 25 mM sodium acetate, a pH of 4.7 to 5.7, 7% w/v sucrose, and 0.02% w/v polysorbate 20, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation comprises the anti-IL1R1 antibody at a concentration of 145-160 mg/ml. In some embodiments, the stable formulation comprises the anti-IL1R1 antibody at a concentration of 150 mg/ml. In some embodiments, the stable formulation has a pH of 5.0 to 5.4. In some embodiments, the stable formulation has a pH of 5.2.

In one aspect, the present invention provides, among other things, a stable formulation comprising an anti-interleukin-1 receptor 1 (IL1R1) antibody, wherein the formulation comprises: the anti-IL1R1 antibody at a concentration of 145 mg/mL to 160 mg/mL, 25 mM sodium acetate, a pH of 5.0 to 5.4, 7% w/v sucrose, and 0.02% w/v polysorbate 20, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation comprises the anti-IL1R1 antibody at a concentration of 150 mg/ml. In some embodiments, the stable formulation has a pH of 5.2.

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH of 5.2, 7% w/v sucrose, and 0.02% w/v polysorbate 20, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT).

In some embodiments, the pH is 4.5. In some embodiments, the pH is 4.6. In some embodiments, the pH is 4.7.

In some embodiments, the pH is 4.8. In some embodiments, the pH is 4.9. In some embodiments, the pH is 5.0. In some embodiments, the pH is 5.1. In some embodiments, the pH is 5.2. In some embodiments, the pH is 5.3. In some embodiments, the pH is 5.4. In some embodiments, the pH is 5.5. In some embodiments, the pH is 5.6. In some embodiments, the pH is 5.7.

In one aspect, the present invention provides, among other things, a stable formulation comprising an anti-interleukin-1 receptor 1 (IL1R1) antibody, wherein the formulation comprises: the anti-IL1R1 antibody at a concentration of 135 mg/mL to 165 mg/mL, 25 mM sodium acetate, a pH of 4.4 to 5.4, 25.9 mg/ml proline, and 0.02% w/v polysorbate 20, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation comprises the anti-IL1R1 antibody at a concentration of 145-160 mg/ml. In some embodiments, the stable formulation comprises the anti-IL1R1 antibody at a concentration of 150 mg/ml. In some embodiments, the stable formulation has a pH of 4.6 to 5.2. In some embodiments, the stable formulation has a pH of 4.7 to 5.1. In some embodiments, the stable formulation has a pH of 4.9 to 5.2. In some embodiments, the stable formulation has a pH of 4.7 to 5.1. In some embodiments, the stable formulation has a pH of 4.9.

In one aspect, the present invention provides, among other things, a stable formulation comprising an anti-interleukin-1 receptor 1 (IL1R1) antibody, wherein the formulation comprises: the anti-IL1R1 antibody at a concentration of 135 mg/mL to 165 mg/mL, 25 mM sodium acetate, a pH of 4.6 to 5.2, 25.9 mg/ml proline, and 0.02% w/v polysorbate 20, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation comprises the anti-IL1R1 antibody at a concentration of 145-160 mg/ml. In some embodiments, the stable formulation comprises the anti-IL1R1 antibody at a concentration of 150 mg/ml. In some embodiments, the stable formulation has a pH of 4.7 to 5.1. In some embodiments, the stable formulation has a pH of 4.9.

In one aspect, the present invention provides, among other things, a stable formulation comprising an anti-interleukin-1 receptor 1 (IL1R1) antibody, wherein the formulation comprises: the anti-IL1R1 antibody at a concentration of 145 mg/mL to 160 mg/mL, 25 mM sodium acetate, a pH of 4.7 to 5.1, 25.9 mg/ml proline, and 0.02% w/v polysorbate 20, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation comprises the anti-IL1R1 antibody at a concentration of 150 mg/ml. In some embodiments, the stable formulation has a pH of 4.9.

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH of 4.4 to 5.4, 25.9 mg/ml proline, and 0.02% w/v polysorbate 20, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT). In some embodiments, the stable formulation has a pH of 4.6 to 5.2. In some embodiments, the stable formulation has a pH of 4.7 to 5.1.

In some embodiments, the pH is 4.4. In some embodiments, the pH is 4.5. In some embodiments, the pH is 4.6. In some embodiments, the pH is 4.7. In some embodiments, the pH is 4.8. In some embodiments, the pH is 4.9. In some embodiments, the pH is 5.0. In some embodiments, the pH is 5.1. In some embodiments, the pH is 5.2. In some embodiments, the pH is 5.3. In some embodiments, the pH is 5.4.

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH 5.0, 25.9 mg/ml proline, and 0.02% w/v polysorbate 20, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT).

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH 4.9, 25.9 mg/ml proline, and 0.02% w/v polysorbate 20, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT).

In one aspect, the present invention provides, among other things, a stable formulation comprising an anti-interleukin-1 receptor 1 (IL1R1) antibody, wherein the formulation comprises: 150 mg/mL anti-IL1R1 antibody, 25 mM sodium acetate, a pH 5.0, 66.5 mM arginine, 3.5% w/v sucrose, and 0.02% w/v polysorbate 20, wherein the anti-IL1R1 antibody comprises a HCDR1 of SEQ ID NO: 5 (FHWIA), a HCDR2 or SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT).

In some embodiments, the stable formulation comprises the anti-IL1R1 antibody comprises a variable heavy chain (VH) of SEQ ID NO: 3 and a variable light chain (VL) of SEQ ID NO: 4.

In some embodiments, the stable formulation comprises the anti-IL1R1 antibody, wherein the anti-IL1R1 antibody comprises a IgG2 Fc region.

In some embodiments, the stable formulation comprises the anti-IL1R1 antibody, wherein the anti-IL1R1 antibody comprises a heavy chain of SEQ ID NO: 1 and a light chain of SEQ ID NO: 2.

In some embodiments, the stable formulation comprises the anti-IL1R1 antibody, wherein at least 95% of the anti-IL1R1 antibody exists as a monomer after 3 rounds of freeze and thaw cycles.

In some embodiments, the stable formulation comprises the anti-IL1R1 antibody, wherein at least 98% of the anti-IL1R1 antibody exists as a monomer after 3 rounds of freeze and thaw cycles.

In some embodiments, the amount of HMW species in the formulation increases less than 0.2% after 3 rounds of freeze and thaw cycles.

In some embodiments, the amount of HMW species in the formulation increases less than 0.3% after 6 rounds of freeze and thaw cycles.

In some embodiments, the stable formulation comprises the anti-IL1R1 antibody, wherein the amount of HMW species in the formulation increases less than 10% upon storage at 5° C. for 4 weeks. In some embodiments, the stable formulation comprises the anti-IL1R1 antibody, wherein the amount of HMW species in the formulation increases less than 9% upon storage at 5° C. for 4 weeks. In some embodiments, the stable formulation comprises the anti-IL1R1 antibody, wherein the amount of HMW species in the formulation increases less than 8% upon storage at 5° C. for 4 weeks. In some embodiments, the stable formulation comprises the anti-IL1R1 antibody, wherein the amount of HMW species in the formulation increases less than 7% upon storage at 5° C. for 4 weeks. In some embodiments, the stable formulation comprises the anti-IL1R1 antibody, wherein the amount of HMW species in the formulation increases less than 6% upon storage at 5° C. for 4 weeks. In some embodiments, the stable formulation comprises the anti-IL1R1 antibody, wherein the amount of HMW species in the formulation increases less than 5% upon storage at 5° C. for 4 weeks. In some embodiments, the stable formulation comprises the anti-IL1R1 antibody, wherein the amount of HMW species in the formulation increases less than 4% upon storage at 5° C. for 4 weeks. In some embodiments, the stable formulation comprises the anti-IL1R1 antibody, wherein the amount of HMW species in the formulation increases less than 3% upon storage at 5° C. for 4 weeks. In some embodiments, the stable formulation comprises the anti-IL1R1 antibody, wherein the amount of HMW species in the formulation increases less than 2% upon storage at 5° C. for 4 weeks. In some embodiments, the stable formulation comprises the anti-IL1R1 antibody, wherein the amount of HMW species in the formulation increases less than 1% upon storage at 5° C. for 4 weeks. In some embodiments, the stable formulation comprises the anti-IL1R1 antibody, wherein the amount of HMW species in the formulation increases less than 0.8% upon storage at 5° C. for 4 weeks. In some embodiments, the stable formulation comprises the anti-IL1R1 antibody, wherein the amount of HMW species in the formulation increases less than 0.6% upon storage at 5° C. for 4 weeks. In some embodiments, the stable formulation comprises the anti-IL1R1 antibody, wherein the amount of HMW species in the formulation increases less than 0.5% upon storage at 5° C. for 4 weeks. In some embodiments, the stable formulation comprises the anti-IL1R1 antibody, wherein the amount of HMW species in the formulation increases less than 0.4% upon storage at 5° C. for 4 weeks. In some embodiments, upon storage at 5° C. for 4 weeks, the amount of HMW species in the formulation does not substantially increase.

In some embodiments, upon storage at 25° C. for 4 weeks, the amount of HMW species in the formulation increases less than 35%. In some embodiments, upon storage at 25° C.

for 4 weeks, the amount of HMW species in the formulation increases 30% or less. In some embodiments, upon storage at 25° C. for 4 weeks, the amount of HMW species in the formulation increases 25% or less. In some embodiments, upon storage at 25° C. for 4 weeks, the amount of HMW species in the formulation increases less than 20%. In some embodiments, upon storage at 25° C. for 4 weeks, the amount of HMW species in the formulation increases less than 15%. In some embodiments, upon storage at 25° C. for 4 weeks, the amount of HMW species in the formulation increases less than 10%. In some embodiments, the stable formulation comprises the anti-IL1R1 antibody, wherein the amount of HMW species in the formulation increases less than 5% upon storage at 25° C. for 4 weeks. In some embodiments, the stable formulation comprises the anti-IL1R1 antibody, wherein the amount of HMW species in the formulation increases less than 4% upon storage at 25° C. for 4 weeks. In some embodiments, the stable formulation comprises the anti-IL1R1 antibody, wherein the amount of HMW species in the formulation increases less than 3% upon storage at 25° C. for 4 weeks. In some embodiments, the stable formulation comprises the anti-IL1R1 antibody, wherein the amount of HMW species in the formulation increases less than 2% upon storage at 25° C. for 4 weeks. In some embodiments, the stable formulation comprises the anti-IL1R1 antibody, wherein the amount of HMW species in the formulation increases less than 1.5% upon storage at 25° C. for 4 weeks. In some embodiments, the stable formulation comprises the anti-IL1R1 antibody, wherein the amount of HMW species in the formulation increases less than 1.4% upon storage at 25° C. for 4 weeks. In some embodiments, the stable formulation comprises the anti-IL1R1 antibody, wherein the amount of HMW species in the formulation increases less than 1.2% upon storage at 25° C. for 4 weeks. In some embodiments, the stable formulation comprises the anti-IL1R1 antibody, wherein the amount of HMW species in the formulation increases less than 1% upon storage at 25° C. for 4 weeks. In some embodiments, the stable formulation comprises the anti-IL1R1 antibody, wherein the amount of HMW species in the formulation increases less than 0.8% upon storage at 25° C. for 4 weeks. In some embodiments, upon storage at 25° C. for 4 weeks, the amount of HMW species in the formulation does not substantially increase.

In some embodiments, upon storage at 40° C. for 4 weeks, the amount of HMW species in the formulation increases less than 255%. In some embodiments, upon storage at 40° C. for 4 weeks, the amount of HMW species in the formulation increases less than 200%. In some embodiments, upon storage at 40° C. for 4 weeks, the amount of HMW species in the formulation increases less than 100%. In some embodiments, the stable formulation comprises the anti-IL1R1 antibody, wherein the amount of HMW species in the formulation increases less than 50% upon storage at 40° C. for 4 weeks. In some embodiments, the stable formulation comprises the anti-IL1R1 antibody, wherein the amount of HMW species in the formulation increases less than 38% upon storage at 40° C. for 4 weeks. In some embodiments, the stable formulation comprises the anti-IL1R1 antibody, wherein the amount of HMW species in the formulation increases less than 50% upon storage at 35° C. for 4 weeks. In some embodiments, the stable formulation comprises the anti-IL1R1 antibody, wherein the amount of HMW species in the formulation increases less than 40% upon storage at 40° C. for 4 weeks. In some embodiments, the stable formulation comprises the anti-IL1R1 antibody, wherein the amount of HMW species in the formulation increases less than 30% upon storage at 40° C. for 4 weeks. In some embodiments, the stable formulation comprises the anti-IL1R1 antibody, wherein the amount of HMW species in the formulation increases less than 25% upon storage at 40° C. for 4 weeks. In some embodiments, the stable formulation comprises the anti-IL1R1 antibody, wherein the amount of HMW species in the formulation increases less than 20% upon storage at 40° C. for 4 weeks. In some embodiments, the stable formulation comprises the anti-IL1R1 antibody, wherein the amount of HMW species in the formulation increases less than 25% upon storage at 40° C. for 4 weeks. In some embodiments, the stable formulation comprises the anti-IL1R1 antibody, wherein the amount of HMW species in the formulation increases less than 20% upon storage at 40° C. for 4 weeks. In some embodiments, the stable formulation comprises the anti-IL1R1 antibody, wherein the amount of HMW species in the formulation increases less than 15% upon storage at 40° C. for 4 weeks. In some embodiments, the stable formulation comprises the anti-IL1R1 antibody, wherein the amount of HMW species in the formulation increases less than 10% upon storage at 40° C. for 4 weeks. In some embodiments, the stable formulation comprises the anti-IL1R1 antibody, wherein the amount of HMW species in the formulation increases less than 5% upon storage at 40° C. for 4 weeks. In some embodiments, the stable formulation comprises the anti-IL1R1 antibody, wherein the amount of HMW species in the formulation increases less than 4% upon storage at 40° C. for 4 weeks.

In some embodiments, upon storage at 5° C. for 4 weeks, the amount of fragments in the formulation increases less than 15%. In some embodiments, upon storage at 5° C. for 4 weeks, the amount of fragments in the formulation increases less than 14%. In some embodiments, upon storage at 5° C. for 4 weeks, the amount of fragments in the formulation increases less than 13%. In some embodiments, upon storage at 5° C. for 4 weeks, the amount of fragments in the formulation increases less than 12%. In some embodiments, upon storage at 5° C. for 4 weeks, the amount of fragments in the formulation increases less than 11%. In some embodiments, upon storage at 5° C. for 4 weeks, the amount of fragments in the formulation increases less than 10%. In some embodiments, the stable formulation comprises the anti-IL1R1 antibody, wherein fragments in the formulation increases less than 1% upon storage at 5° C. for 4 weeks. In some embodiments, the stable formulation comprises the anti-IL1R1 antibody, wherein fragments in the formulation increases less than 0.5% upon storage at 5° C. for 4 weeks. In some embodiments, the stable formulation comprises the anti-IL1R1 antibody, wherein fragments in the formulation increases less than 0.4% upon storage at 5° C. for 4 weeks. In some embodiments, the stable formulation comprises the anti-IL1R1 antibody, wherein fragments in the formulation increases less than 0.3% upon storage at 5° C. for 4 weeks. In some embodiments, the stable formulation comprises the anti-IL1R1 antibody, wherein fragments in the formulation increases less than 0.2% upon storage at 5° C. for 4 weeks. In some embodiments, the stable formulation comprises the anti-IL1R1 antibody, wherein fragments in the formulation increases less than 0.1% upon storage at 5° C. for 4 weeks. In some embodiments, upon storage at 5° C. for 4 weeks, the amount of fragments in the formulation does not substantially increase.

In some embodiments, the stable formulation comprises the anti-IL1R1 antibody, wherein fragments in the formulation increase less than 25% upon storage at 25° C. for 4 weeks. In some embodiments, the stable formulation comprises the anti-IL1R1 antibody, wherein fragments in the formulation increase less than 22% upon storage at 25° C. for 4 weeks. In some embodiments, the stable formulation comprises the anti-IL1R1 antibody, wherein fragments in the formulation increase less than 20% upon storage at 25° C. for 4 weeks. In some embodiments, the stable formulation comprises the anti-IL1R1 antibody, wherein fragments in the formulation increase less than 1% upon storage at 25° C. for 4 weeks. In some embodiments, the stable formulation comprises the anti-IL1R1 antibody, wherein fragments in the formulation increase less than 0.5% upon storage at 25° C. for 4 weeks. In some embodiments, the stable formulation comprises the anti-IL1R1 antibody, wherein fragments in the formulation increase less than 0.4% upon storage at 25° C. for 4 weeks. In some embodiments, the stable formulation comprises the anti-IL1R1 antibody, wherein fragments in the formulation increase less than 0.3% upon storage at 25° C. for 4 weeks. In some embodiments, the stable formulation comprises the anti-IL1R1 antibody, wherein fragments in the formulation increase less than 0.2% upon storage at 25° C. for 4 weeks. In some embodiments, the stable formulation comprises the anti-IL1R1 antibody, wherein fragments in the formulation increase less than 0.1% upon storage at 25° C. for 4 weeks. In some embodiments, upon storage at 25° C. for 4 weeks, the amount of fragments in the formulation does not substantially increase.

In some embodiments, the stable formulation comprises the anti-IL1R1 antibody, wherein the amount of fragments in the formulation increases less than 90% upon storage at 40° C. for 4 weeks. In some embodiments, the stable formulation comprises the anti-IL1R1 antibody, wherein the amount of fragments in the formulation increases less than 86% upon storage at 40° C. for 4 weeks. In some embodiments, the stable formulation comprises the anti-IL1R1 antibody, wherein the amount of fragments in the formulation increases less than 5% upon storage at 40° C. for 4 weeks. In some embodiments, the stable formulation comprises the anti-IL1R1 antibody, wherein the amount of fragments in the formulation increases less than 4% upon storage at 40° C. for 4 weeks. In some embodiments, the stable formulation comprises the anti-IL1R1 antibody, wherein the amount of fragments in the formulation increases less than 3% upon storage at 40° C. for 4 weeks. In some embodiments, the stable formulation comprises the anti-IL1R1 antibody, wherein the amount of fragments in the formulation increases less than 2% upon storage at 40° C. for 4 weeks. In some embodiments, the stable formulation comprises the anti-IL1R1 antibody, wherein the amount of fragments in the formulation increases less than 1% upon storage at 40° C. for 4 weeks. In some embodiments, upon storage at 40° C., for 4 weeks the amount of fragments in the formulation does not substantially increase.

In some embodiments, the stable formulation comprises the anti-IL1R1 antibody, wherein the amount of acidic species in the formulation increases less than 2% upon storage at 5° C. for 4 weeks. In some embodiments, the stable formulation comprises the anti-IL1R1 antibody, wherein the amount of acidic species in the formulation increases less than 1.5% upon storage at 5° C. for 4 weeks. In some embodiments, the stable formulation comprises the anti-IL1R1 antibody, wherein the amount of acidic species in the formulation increases less than 1.2% upon storage at 5° C. for 4 weeks. In some embodiments, the stable formulation comprises the anti-IL1R1 antibody, wherein the amount of acidic species in the formulation increases less than 1% upon storage at 5° C. for 4 weeks. In some embodiments, the stable formulation comprises the anti-IL1R1 antibody, wherein the amount of acidic species in the formulation increases less than 0.5% upon storage at 5° C. for 4 weeks. In some embodiments, the stable formulation comprises the anti-IL1R1 antibody, wherein the amount of acidic species in the formulation increases less than 0.4% upon storage at 5° C. for 4 weeks. In some embodiments, the stable formulation comprises the anti-IL1R1 antibody, wherein the amount of acidic species in the formulation increases less than 0.3% upon storage at 5° C. for 4 weeks. In some embodiments, the stable formulation comprises the anti-IL1R1 antibody, wherein the amount of acidic species in the formulation increases less than 0.2% upon storage at 5° C. for 4 weeks. In some embodiments, the stable formulation comprises the anti-IL1R1 antibody, wherein the amount of acidic species in the formulation increases less than 0.1% upon storage at 5° C. for 4 weeks. In some embodiments, the stable formulation comprises the anti-IL1R1 antibody, wherein the amount of acidic species in the formulation does not substantially increase upon storage 5° C. for 4 weeks.

In some embodiments, upon storage at 25° C. for 4 weeks, the amount of acidic species in the formulation increases less than 2%. In some embodiments, upon storage at 25° C. for 4 weeks, the amount of acidic species in the formulation increases less than 1.5%. In some embodiments, upon storage at 25° C. for 4 weeks, the amount of acidic species in the formulation increases less than 1.2%. In some embodiments, the stable formulation comprises the anti-IL1R1 antibody, wherein the amount of acidic species in the formulation increases less than 1% upon storage at 25° C. for 4 weeks. In some embodiments, the stable formulation comprises the anti-IL1R1 antibody, wherein the amount of acidic species in the formulation increases less than 0.5% upon storage at 25° C. for 4 weeks. In some embodiments, the stable formulation comprises the anti-IL1R1 antibody, wherein the amount of acidic species in the formulation increases less than 0.4% upon storage at 25° C. for 4 weeks. In some embodiments, the stable formulation comprises the anti-IL1R1 antibody, wherein the amount of acidic species in the formulation increases less than 0.3% upon storage at 25° C. for 4 weeks. In some embodiments, the stable formulation comprises the anti-IL1R1 antibody, wherein the amount of acidic species in the formulation increases less than 0.2% upon storage at 25° C. for 4 weeks. In some embodiments, the stable formulation comprises the anti-IL1R1 antibody, wherein the amount of acidic species in the formulation increases less than 0.1% upon storage at 25° C. for 4 weeks. In some embodiments, the stable formulation comprises the anti-IL1R1 antibody, wherein the amount of acidic species in the formulation does not substantially increase upon storage at 25° C. for 4 weeks.

In some embodiments, the stable formulation comprises the anti-IL1R1 antibody, wherein the amount of acidic species in the formulation increases less than 30% upon storage at 40° C. for 4 weeks. In some embodiments, the stable formulation comprises the anti-IL1R1 antibody, wherein the amount of acidic species in the formulation increases less than 26% upon storage at 40° C. for 4 weeks. In some embodiments, upon storage at 40° C. for 4 weeks, the amount of acidic species in the formulation increases less than 25%. In some embodiments, upon storage at 40° C. for 4 weeks, the amount of acidic species in the formulation increases less than 20%. In some embodiments, the stable formulation comprises the anti-IL1R1 antibody, wherein the amount of acidic species in the formulation increases less than 10% upon storage at 40° C. for 4 weeks. In some embodiments, the stable formulation comprises the anti-IL1R1 antibody, wherein the amount of acidic species in the formulation increases less than 8% upon storage at 40° C. for 4 weeks. In some embodiments, the stable formulation comprises the anti-IL1R1 antibody, wherein the amount of acidic species in the formulation increases less than 7% upon storage at 40° C. for 4 weeks.

In some embodiments, the stable formulation has a viscosity of less than 25 cp at 20° C. In some embodiments, the stable formulation has a viscosity of 15 cp or less at 20° C.

BRIEF DESCRIPTION OF THE DRAWINGS

The drawings herein are for illustrative purposes only and should not be limiting.

FIG. 2 depicts an exemplary bar graph of the experimentally determined diffusion interaction coefficients ($K_D$) for each formulation at an antibody concentration ranging from 1 mg/mL to 20 mg/mL.

DEFINITIONS

Figure 1:
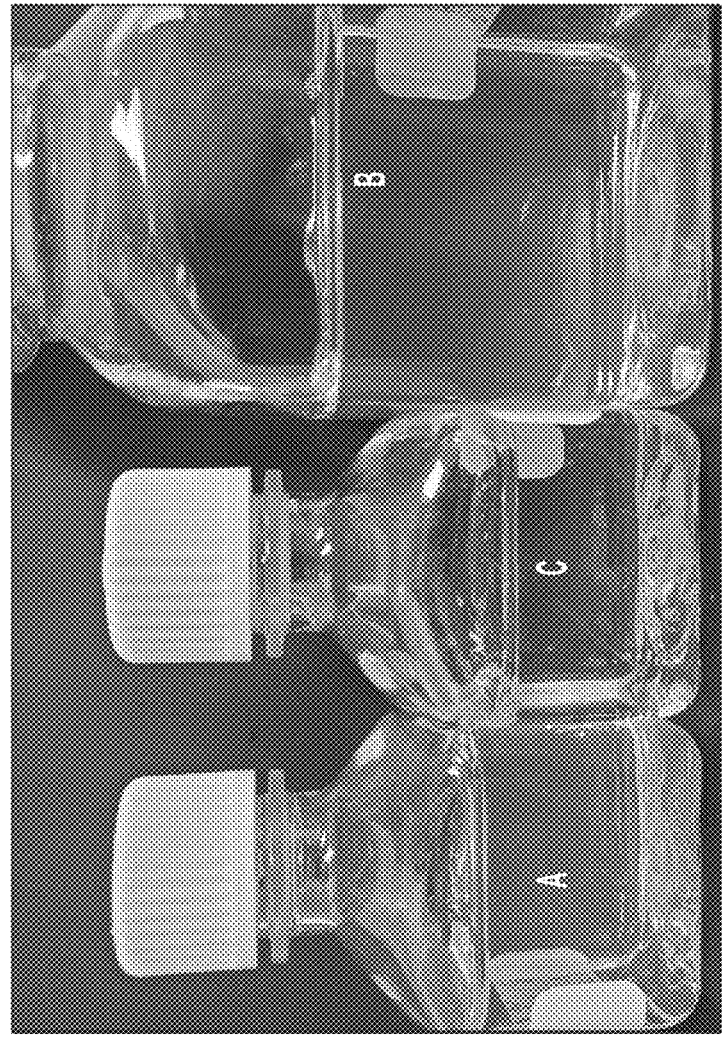
FIG. 1 is an exemplary photograph of anti-IL1-R1 antibody formulations, showing their visual appearance after short-term storage at 25° C. and 40° C.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Any numerical values used in this application are meant to cover any variations within the standard deviation or normal fluctuations appreciated by one of ordinary skill in the relevant art.

Acidic Species: As used herein, the term "acidic species" refers to the variants of a protein, e.g., an antibody or antigen binding fragment thereof, which are characterized by an overall acidic charge relative to the main species. Acidic species can be detected by charge based separation techniques such as, for example and without limitation, isoelectric focusing (IEF) gel electrophoresis, capillary isoelectric focusing (cIEF) gel electrophoresis, cation exchange chromatography (CEX), and anion exchange chromatography (AEX). In some embodiments, the level of acidic species is determined by imaging capillary isoelectric focusing (iCIEF).

Acidic species are variants with lower apparent pI relative to the main species when antibodies are analyzed using IEF based methods. When analyzed by chromatography-based methods, acidic species are defined based on their retention times relative to the main peak. Acidic species are the variants that elute earlier than the main peak from AEX.

Acidic species of an antibody may include charge variants, structure variants, and/or fragmentation variants. Exemplary charge variants include, but are not limited to, deamidation variants, afucosylation variants, methylglyoxal variants, glycation variants, and citric acid variants. Exemplary structure variants include, but are not limited to, glycosylation variants and acetonation variants. Exemplary fragmentation variants include, but are not limited to, any truncated protein species from the protein of interest due to dissociation of peptide chain, enzymatic and/or chemical modifications, including, but not limited to, Fc and Fab fragments, fragments missing a Fab, fragments missing a heavy chain variable domain, C-terminal truncation variants, variants with the excision of N-terminal Asp in the light chain, and variants having N-terminal truncation of the light chain. Other acidic species variants also include, but are not limited to, unpaired disulfides, host cell proteins, and host nucleic acids, chromatographic materials, and media components. The acidic species may be the result of product preparation, storage, and/or purification.

Amino acid: As used herein, the term "amino acid," in its broadest sense, refers to any compound and/or substance that can be incorporated into a polypeptide chain. In some embodiments, an amino acid has the general structure $H_2N$—$C(H)(R)$—COHO. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. In some embodiments, an amino acid is a standard amino acid, which refers to any of the twenty standard 1-amino acids commonly found in naturally occurring peptides. In some embodiments, an amino acid is a nonstandard amino acid, which refers to any amino acid, other than the standard amino acids, regardless of whether it is prepared synthetically or obtained from a natural source. In some embodiments, an amino acid is a synthetic amino acid, which encompasses chemically modified amino acids, including but not limited to salts, amino acid derivatives (such as amides), and/or substitutions. Amino acids, including carboxyl- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Delivery: As used herein, the term "delivery" encompasses both local, subcutaneous and systemic delivery.

Half-life: As used herein, the term "half-life" is the time required for a quantity such as nucleic acid or protein concentration or activity to fall to half of its value as measured at the beginning of a time period.

IL1R1: As used herein, the terms "Interleukin 1, Receptor Type 1", IL-1R1" or "IL1R1" refer to a cytokine receptor that belongs to the interleukin-1 receptor family. IL-1R1 is also known as CD121 Antigen-Like Family Member A, CD121A, CD121a Antigen, IL-1RA, D2S1473, P80, EC 3.2.2.6, or CRMO3. IL-1R1 is a receptor for interleukin-1 alpha (IL1α), interleukin-1 beta (IL1β), and interleukin-1 receptor antagonist (IL1Ra). It is an important mediator involved in many cytokine-induced immune and inflammatory responses (see PCT Publication No. WO2004022718, the entire contents of which, including the sequences described therein, are incorporated herein by reference). Upon binding of a cytokine, e.g., IL1α and IL-10, to IL-1R1, a shared co-receptor, IL-1RAcP, is recruited by binding to the composite surface of the cytokine and primary receptor complex, resulting in the creation of a trimeric signaling complex. In the resting state, IL-1R1 and the co-acceptor, IL-1RAcP, are present on the cell membrane. Once IL-1 (either IL-1α or IL-10) binds to IL-1R1, a structural change occurs that allows IL-1RAcP to bind to IL-1R1. The trimeric complex allows for the approximation of the TIR domains of each receptor chain. MyD88 then binds to the TIR domains. The binding of MyD88 triggers a cascade of kinases that produce a strong pro-inflammatory signal leading to activation of NFκB.

Stability: As used herein, the term "stable" refers to the ability of the therapeutic agent (e.g., an antibody) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., antibodies). In the context of a formulation a stable formulation is one in which the therapeutic agent therein essentially retains its physical and/or chemical integrity and biological activity upon storage and during processes (such as freeze/ thaw, mechanical mixing and lyophilization). For protein stability, it can be measured by formation of high molecular weight (HMW) aggregates, loss of enzyme activity, generation of peptide fragments and shift of charge profiles. For the purpose of the present application, the term high molecular weight species (HMW) of the product and "aggregates" are used interchangeably.

Suitable for subcutaneous delivery: As used herein, the phrase "suitable for subcutaneous delivery" or "formulation for subcutaneous delivery" as it relates to the pharmaceutical compositions of the present invention generally refers to the stability, viscosity, and solubility properties of such compositions, as well as the ability of such compositions to deliver an effective amount of antibody contained therein to the targeted site of delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, stable formulations comprising an anti-Interleukin 1 Receptor 1 (IL1R1) antibody at a concentration of greater than 80 mg/ml with a pH ranging from 4.4 to 6.5, wherein the amount of HMW species in the formulation increases less than 2% upon storage at 25° C. for at least 4 weeks. In some embodiments, the amount of HMW species in the formulation increases less than 40% upon storage at 40° C. for 4 weeks. In some embodiments, the stable formulations comprise an anti-interleukin 1 receptor 1 (IL1R1) antibody at a concentration of greater than 80 mg/ml with a pH ranging from 4.0 to 7.4 and less than 130 mM of arginine. In some embodiments, the formulation is suitable for subcutaneous delivery. In some embodiments, stable formulations of the present invention are suitable for treating diseases and disorders associated with IL1R1.

Various aspects of the invention are described in detail in the following sections. The use of sections is not meant to limit the invention. Each section can apply to any aspect of the invention. In this application, the use of "or" means "and/or" unless stated otherwise, and in the context of a range of values, the use of the term "between" means a range between X and Y that includes the endpoints X and Y.

Anti-Interleukin 1 Receptor 1 (IL1R1) Antibodies

In some embodiments, inventive compositions and methods provided by the present invention are used to deliver an anti-IL1R1 antibody to a subject in need.

```
Anti-IL1R1 Heavy Chain Amino Acid Sequence
                                       (SEQ ID NO: 1)
EVQLMQSGAEVKKPGESLKISCKGSGYSFSFHWIAWVRQMPGKGLEWM

GIIHPGASDTRYSPSFQGQVTISADNSNSATYLQWSSLKASDTAMYFC

ARQRELDYFDYWGQGTLVTVSSASTKGPSVFPLAPCSRSTSESTAALG

CLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLF

PPKPKDTLMISRTPEVTCVVVDVSHEDPEVQFNWYVDGVEVHNAKTKP

REEQFNSTFRVVSVLTVVHQDWLNGKEYKCKVSNKGLPAPIEKTISKT

KGQPREPQVYTLPPSREEMTKNQVSLTCLVKGFYPSDIAVEWESNGQP

ENNYKTTPPMLDSDGSFFLYSKLTVDKSRWQQGNVFSCSVMHEALHNH

YTQKSLSLSPGK
```

In some embodiments, an anti-IL1R1 antibody comprises a heavy chain that is at least 85% identical to SEQ ID NO: 1. In some embodiments, an anti-IL1R1 antibody comprises a heavy chain that is at least 90% identical to SEQ ID NO:1. In some embodiments, an anti-IL1R1 antibody comprises a heavy chain that is at least 92% identical to SEQ ID NO:1. In some embodiments, an anti-IL1R1 antibody comprises a heavy chain that is at least 93% identical to SEQ ID NO:1. In some embodiments, an anti-IL1R1 antibody comprises a heavy chain that is at least 94% identical to SEQ ID NO:1. In some embodiments, an anti-IL1R1 antibody comprises a heavy chain that is at least 95% identical to SEQ ID NO:1. In some embodiments, an anti-IL1R1 antibody comprises a heavy chain that is at least 96% identical to SEQ ID NO:1. In some embodiments, an anti-IL1R1 antibody comprises a heavy chain that is at least 97% identical to SEQ ID NO:1. In some embodiments, an anti-IL1R1 antibody comprises a heavy chain that is at least 98% identical to SEQ ID NO:1. In some embodiments, an anti-IL1R1 antibody comprises a heavy chain that is at least 99% identical to SEQ ID NO:1. In some embodiments, an anti-IL1R1 antibody comprises a heavy chain of SEQ ID NO:1.

```
Anti-IL1R1 Light Chain Amino Acid Sequence
                                       (SEQ ID NO: 2)
EIVLTQSPDFQSVTPKEKVTITCRASQSIGSSLHWYQQKPDQSPKLLI

KYASQSFSGVPSRFSGSGSGTDFTLTINSLEAEDAAAYYCHQSSSLPL

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

In some embodiments, an anti-IL1R1 antibody comprises a light chain that is at least 85% identical to SEQ ID NO: 2. In some embodiments, an anti-IL1R1 antibody comprises a light chain that is at least 90% identical to SEQ ID NO:2. In some embodiments, an anti-IL1R1 antibody comprises a light chain that is at least 92% identical to SEQ ID NO:2. In some embodiments, an anti-IL1R1 antibody comprises a light chain that is at least 93% identical to SEQ ID NO:2. In some embodiments, an anti-IL1R1 antibody comprises a light chain that is at least 94% identical to SEQ ID NO:2. In some embodiments, an anti-IL1R1 antibody comprises a light chain that is at least 95% identical to SEQ ID NO:2. In some embodiments, an anti-IL1R1 antibody comprises a light chain that is at least 96% identical to SEQ ID NO:2. In some embodiments, an anti-IL1R1 antibody comprises a light chain that is at least 97% identical to SEQ ID NO:2. In some embodiments, an anti-IL1R1 antibody comprises a light chain that is at least 98% identical to SEQ ID NO:2. In some embodiments, an anti-IL1R1 antibody comprises a light chain that is at least 99% identical to SEQ ID NO:2. In some embodiments, an anti-IL1R1 antibody comprises a light chain of SEQ ID NO:2.

```
Anti-IL1R1 Heavy Chain Variable Domain (VH)
Amino Acid Seequence
                                       (SEQ ID NO: 3)
EVQLMQSGAEVKKPGESLKISCKGSGYSFSFHWIAWVRQMPGKGLEWM

GIIHPGASDTRYSPSFQGQVTISADNSNSATYLQWSSLKASDTAMYFC

ARQRELDYFDYWGQGTLVTVSS
```

In some embodiments, an anti-IL1R1 antibody comprises a VH that is at least 85% identical to SEQ ID NO:3. In some embodiments, an anti-IL1R1 antibody comprises a VH that is at least 90% identical to SEQ ID NO:3. In some embodiments, an anti-IL1R1 antibody comprises a VH that is at least 92% identical to SEQ ID NO:3. In some embodiments, an anti-IL1R1 antibody comprises a VH that is at least 93% identical to SEQ ID NO:3. In some embodiments, an anti-IL1R1 antibody comprises a VH that is at least 94% identical to SEQ ID NO:3. In some embodiments, an anti-IL1R1 antibody comprises a VH that is at least 95% identical to SEQ ID NO:3. In some embodiments, an anti-IL1R1 antibody comprises a VH that is at least 96% identical to SEQ ID NO:3. In some embodiments, an anti-IL1R1 antibody comprises a VH that is at least 97% identical to SEQ ID NO:3. In some embodiments, an anti-IL1R1 antibody comprises a VH that is at least 98% identical to SEQ ID NO:3. In some embodiments, an anti-IL1R1 antibody comprises a VH that is at least 99% identical to SEQ ID NO:3. In some embodiments, an anti-IL1R1 antibody comprises a VH of SEQ ID NO:3.

```
Anti-IL1R1 Light Chain Variable Domain (VL)
Amino Acid Seequence
                              (SEQ ID NO: 4)
EIVLTQSPDFQSVTPKEKVTITCRASQSIGSSLHWYQQKPDQSPKLLI

KYASQSFSGVPSRFSGSGSGTDFTLTINSLEAEDAAAYYCHQSSSLPL

TFGGGTKVEIK
```

In some embodiments, an anti-IL1R1 antibody comprises a VL that is at least 85% identical to SEQ ID NO:4. In some embodiments, an anti-IL1R1 antibody comprises a VL that is at least 90% identical to SEQ ID NO:4. In some embodiments, an anti-IL1R1 antibody comprises a VL that is at least 92% identical to SEQ ID NO:4. In some embodiments, an anti-IL1R1 antibody comprises a VL that is at least 93% identical to SEQ ID NO:4. In some embodiments, an anti-IL1R1 antibody comprises a VL that is at least 94% identical to SEQ ID NO:4. In some embodiments, an anti-IL1R1 antibody comprises a VL that is at least 95% identical to SEQ ID NO:4. In some embodiments, an anti-IL1R1 antibody comprises a VL that is at least 96% identical to SEQ ID NO:4. In some embodiments, an anti-IL1R1 antibody comprises a VL that is at least 97% identical to SEQ ID NO:4. In some embodiments, an anti-IL1R1 antibody comprises a VL that is at least 98% identical to SEQ ID NO:4. In some embodiments, an anti-IL1R1 antibody comprises a VL that is at least 99% identical to SEQ ID NO:4. In some embodiments, an anti-IL1R1 antibody comprises a VL of SEQ ID NO:4.

TABLE A

| CDR amino acids sequences | | |
|---|---|---|
| CDR | Amino acid sequence | SEQ ID NO |
| HCDR1 | FHWIA | SEQ ID NO: 5 |
| HCDR2 | IIHPGASDTRYSPSFQG | SEQ ID NO: 6 |
| HCDR3 | QRELDYFDY | SEQ ID NO: 7 |
| LCDR1 | RASQSIGSSLH | SEQ ID NO: 8 |
| LCDR2 | YASQSFS | SEQ ID NO: 9 |
| LCDR3 | HQSSSLPLT | SEQ ID NO: 10 |

Anti-IL1R1 Light Chain Amino Acid Sequence—Constant Domain

```
                              (SEQ ID NO: 11)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK
```

Anti-IL1R1 Light Chain Amino Acid Sequence—Constant Domain

```
                              (SEQ ID NO: 12)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC
```

In some embodiments of the invention, an anti-IL1-R1 antibody comprises a heavy chain complementarity-determining region 1 (HCDR1) defined by SEQ ID NO: 5, a heavy chain complementarity-determining region 2 (HCDR2) defined by SEQ ID NO: 6, and a heavy chain complementarity-determining region 3 (HCDR3) defined by SEQ ID NO: 7; and a light chain complementarity-determining region 1 (LCDR1) defined by SEQ ID NO: 8, a light chain complementarity-determining region 2 (LCDR2) defined by SEQ ID NO: 9, and a light chain complementarity-determining region 3 (LCDR3) defined by SEQ ID NO: 10.

Formulation

Antibody aggregation (i.e., HMW species of antibody) is a common problem in antibody formulation, and often results from increased concentration of the antibody. The presence of aggregates in antibody drug products can induce adverse immune responses in patients that may affect safety and efficacy, and so it is of concern to both manufacturers and regulatory agencies. The instant present disclosure provides a means for achieving a high concentration and low antibody aggregation formulation. Formulations of the present disclosure can be advantageous for therapeutic purposes, as they are high in protein concentration suitable for delivery in small volume injections.

The majority of biologic products (including antibodies) are subject to numerous degradative processes which frequently arise from non-enzymatic reactions in solution (e.g., oxidation and deamidation). These reactions may have a long-term impact on product stability, safety and efficacy. These degradation reactions can be slowed, if not eliminated, by storage of product at subzero temperatures, thus gaining a tremendous advantage for the manufacturer in terms of flexibility and availability of supplies over the product life-cycle. Although freezing is often the safest and most reliable method of biologics product storage, it has inherent risks. Freezing and thawing can induce stress in proteins through cold denaturation, by introducing ice-liquid interfaces, and by freeze-concentration (cryoconcentration) of solutes when the water crystallizes.

Stability of a protein in a formulation may also be defined in terms of the percentage of monomer, aggregate (HMW), or fragment, charged species, or combinations thereof, of the protein in the formulation observed over time. In one aspect of the present disclosure, a stable formulation is a formulation having less than 10% to less than 5% of the protein being present as aggregate in the formulation upon storage at 5° C. or 25° C.

In some embodiments, the present disclosure also provides a method for adjusting a certain characteristic, such as the osmolality and/or viscosity, as desired in high antibody concentration solutions, by adding non-ionic excipients, without changing other desired features, such as non-opalescence. Examples of non-ionizable excipients which may be added to the aqueous formulation of the present disclosure for altering desired characteristics of the formulation include, but are not limited to, mannitol, sorbitol, a non-ionic surfactant (e.g., polysorbate 20, polysorbate 40, polysorbate 60 or polysorbate 80), sucrose, trehalose, raffinose, and maltose.

Amino Acids

Amino acids can act as tonicity agents, protein stabilizers, antioxidants, and viscosity reducing agents in antibody formulations.

In some embodiments of the invention, a formulation comprises one or more amino acids. In some embodiments, a formulation comprises a basic amino acid. In some embodiments, a formulation comprises an acidic amino acid. In some embodiment, a formulation comprises a non-polar amino acid.

In some embodiments, an amino acid is present in the formulation at a concentration of 10-500 mM. In some embodiments, an amino acid is present in the formulation at a concentration of 10-300 mM. In some embodiments, an amino acid is present in the formulation at a concentration of 25-250 mM. In some embodiments, an amino acid is present in the formulation at a concentration of 50-150 mM. In some embodiments, an amino acid is present in the formulation at a concentration of 25-75 mM. In some embodiments, an amino acid is present in the formulation at a concentration of 10 mM. In some embodiments, an amino acid is present in the formulation at a concentration of 15 mM. In some embodiments, an amino acid is present in the formulation at a concentration of 20 mM. In some embodiments, an amino acid is present in the formulation at a concentration of 25 mM. In some embodiments, an amino acid is present in the formulation at a concentration of 30 mM. In some embodiments, an amino acid is present in the formulation at a concentration of 35 mM. In some embodiments, an amino acid is present in the formulation at a concentration of 40 mM. In some embodiments, an amino acid is present in the formulation at a concentration of 45 mM. In some embodiments, an amino acid is present in the formulation at a concentration of 50 mM. In some embodiments, an amino acid is present in the formulation at a concentration of 55 mM. In some embodiments, an amino acid is present in the formulation at a concentration of 60 mM. In some embodiments, an amino acid is present in the formulation at a concentration of 65 mM. In some embodiments, an amino acid is present in the formulation at a concentration of 70 mM. In some embodiments, an amino acid is present in the formulation at a concentration of 75 mM. In some embodiments, an amino acid is present in the formulation at a concentration of 80 mM. In some embodiments, an amino acid is present in the formulation at a concentration of 85 mM. In some embodiments, an amino acid is present in the formulation at a concentration of 90 mM. In some embodiments, an amino acid is present in the formulation at a concentration of 95 mM. In some embodiments, an amino acid is present in the formulation at a concentration of 100 mM. In some embodiments, an amino acid is present in the formulation at a concentration of 110 mM. In some embodiments, an amino acid is present in the formulation at a concentration of 120 mM. In some embodiments, an amino acid is present in the formulation at a concentration of 125 mM. In some embodiments, an amino acid is present in the formulation at a concentration of 130 mM. In some embodiments, an amino acid is present in the formulation at a concentration of 140 mM. In some embodiments, an amino acid is present in the formulation at a concentration of 150 mM. In some embodiments, an amino acid is present in the formulation at a concentration of 160 mM. In some embodiments, an amino acid is present in the formulation at a concentration of 170 mM. In some embodiments, an amino acid is present in the formulation at a concentration of 175 mM. In some embodiments, an amino acid is present in the formulation at a concentration of 180 mM. In some embodiments, an amino acid is present in the formulation at a concentration of 190 mM. In some embodiments, an amino acid is present in the formulation at a concentration of 200 mM. In some embodiments, an amino acid is present in the formulation at a concentration of 225 mM. In some embodiments, an amino acid is present in the formulation at a concentration of 250 mM.

In some embodiments, an amino acid is present in the formulation at a concentration of less than 150 mM. In some embodiments, an amino acid is present in the formulation at a concentration of less than 125 mM. In some embodiments, an amino acid is present in the formulation at a concentration of less than 120 mM. In some embodiments, an amino acid is present in the formulation at a concentration of less than 110 mM. In some embodiments, an amino acid is present in the formulation at a concentration of less than 100 mM. In some embodiments, an amino acid is present in the formulation at a concentration of less than 90 mM. In some embodiments, an amino acid is present in the formulation at a concentration of less than 80 mM. In some embodiments, an amino acid is present in the formulation at a concentration of less than 75 mM. In some embodiments, an amino acid is present in the formulation at a concentration of less than 70 mM. In some embodiments, an amino acid is present in the formulation at a concentration of less than 65 mM. In some embodiments, an amino acid is present in the formulation at a concentration of less than 60 mM. In some embodiments, an amino acid is present in the formulation at a concentration of less than 55 mM. In some embodiments, an amino acid is present in the formulation at a concentration of less than 50 mM. In some embodiments, an amino acid is present in the formulation at a concentration of less than 40 mM. In some embodiments, an amino acid is present in the formulation at a concentration of less than 30 mM. In some embodiments, an amino acid is present in the formulation at a concentration of less than 25 mM.

In some embodiments of the invention, a formulation comprises one or more amino acids. It is contemplated that the one or more amino acids in the formulation, individually or combined, are typically present in a concentration of 10 mM to 300 mM. In some embodiments, the one or more amino acids in the formulation, individually or combined, are present at a concentration of 10 mM to 250 mM. In some embodiments, the one or more amino acids in the formulation, individually or combined, are present at a concentration of 10 mM to 225 mM. In some embodiments, the one or more amino acids in the formulation, individually or combined, are present at a concentration of 10 mM to 200 mM. In some embodiments, the one or more amino acids in the formulation, individually or combined, are present at a concentration of 10 mM to 175 mM. In some embodiments, the one or more amino acids in the formulation, individually or combined, are present at a concentration of 10 mM to 150 mM. In some embodiments, the one or more amino acids in the formulation, individually or combined, are present at a concentration of 10 mM to 125 mM. In some embodiments, the one or more amino acids in the formulation, individually or combined, are present at a concentration of 10 mM to 100 mM. In some embodiments, the one or more amino acids in the formulation, individually or combined, are present at a concentration of 10 mM to 75 mM. In some embodiments, the one or more amino acids in the formulation, individually or combined, are present at a concentration of 10 mM to 50 mM. In some embodiments, the one or more amino acids in the formulation, individually or combined, are present at a concentration of 10 mM to 25 mM. In some embodiments, the one or more amino acids in the formulation, individually or combined, are present at a concentration of 20 mM to 250 mM. In some embodiments, the one or more amino acids in the formulation, individually or combined, are present at a concentration of 25 mM to 250 mM. In some embodiments, the one or more amino acids in the formulation, individually or combined, are present at a concentration of 50 mM to 250 mM. In some embodiments, the one or more amino acids in the formulation, individually or combined, are present at a concentration of 75 mM to 250 mM. In some embodiments, the one or more amino acids in the formulation, individually or combined, are present at a concentration of 100 mM to 250 mM. In some embodiments, the one or more amino acids in the formulation, individually or combined, are present at a concentration of 125 mM to 250 mM. In some embodiments, the one or more amino acids in the formulation, individually or combined, are present at a concentration of 150 mM to 250 mM. In some embodiments, the one or more amino acids in the formulation, individually or combined, are present at a concentration of 175 mM to 250 mM. In some embodiments, the one or more amino acids in the formulation, individually or combined, are present at a concentration of 200 mM to 250 mM. In some embodiments, the one or more amino acids in the formulation, individually or combined, are present at a concentration of 5 mM to 35 mM, of 10 mM to 35 mM, or of 15 mM to 30 mM.

Basic Amino Acid

In some embodiments, a formulation comprises a basic amino acid. In some embodiments, a basic amino acid is lysine. In some embodiments, a basic amino acid is arginine. In some embodiments, a basic amino acid is histidine.

In some embodiments, arginine is L-arginine. In some embodiments, arginine is D-arginine. In some embodiments, arginine is arginine-HCl.

Arginine is a frequently used amino acid in antibody formulations to enhance protein refolding and to reduce protein-protein interaction and aggregation. Arginine is also used to reduce viscosity of high concentration antibody formulations. As such, it is desirable to use arginine at high concentration to prevent aggregation while reducing viscosity of antibody formulations. In fact, several antibody formulations use arginine at a high concentration, such as at 31.6 mg/ml Arg-HCl (150 mM) and at 26.1 mg/ml L-Arg (150 mM) in ADUHELM® and ENSPRYNG® formulations, respectively. The present invention is, in part, based on the surprising determination that the anti-IL1R1 antibody is susceptible to aggregation in formulations comprising higher concentrations of arginine. Accordingly, one aspect of the invention is a stable formulation for an anti-IL1R1 antibody that comprises arginine at a concentration of less than about 130 mM (e.g., ≤130 mM) with high stability and low viscosity.

In some embodiments, a basic amino acid is present in the formulation at a concentration of 10-500 mM. In some embodiments, a basic amino acid is present in the formulation at a concentration of 10-300 mM. In some embodiments, a basic amino acid is present in the formulation at a concentration of 25-250 mM. In some embodiments, a basic amino acid is present in the formulation at a concentration of 50-150 mM. In some embodiments, a basic amino acid is present in the formulation at a concentration of 50-100 mM. In some embodiments, a basic amino acid is present in the formulation at a concentration of 25-75 mM. In some embodiments, a basic amino acid is present in the formulation at a concentration of 50-75 mM.

In some embodiments, a basic amino acid is present in the formulation at a concentration of 10 mM. In some embodiments, a basic amino acid is present in the formulation at a concentration of 15 mM. In some embodiments, a basic amino acid is present in the formulation at a concentration of 20 mM. In some embodiments, a basic amino acid is present in the formulation at a concentration of 25 mM. In some embodiments, a basic amino acid is present in the formulation at a concentration of 30 mM. In some embodiments, a basic amino acid is present in the formulation at a concentration of 35 mM. In some embodiments, a basic amino acid is present in the formulation at a concentration of 40 mM. In some embodiments, a basic amino acid is present in the formulation at a concentration of 45 mM. In some embodiments, a basic amino acid is present in the formulation at a concentration of 50 mM. In some embodiments, a basic amino acid is present in the formulation at a concentration of 55 mM. In some embodiments, a basic amino acid is present in the formulation at a concentration of 60 mM. In some embodiments, a basic amino acid is present in the formulation at a concentration of 65 mM. In some embodiments, a basic amino acid is present in the formulation at a concentration of 70 mM. In some embodiments, a basic amino acid is present in the formulation at a concentration of 75 mM. In some embodiments, a basic amino acid is present in the formulation at a concentration of 80 mM. In some embodiments, a basic amino acid is present in the formulation at a concentration of 85 mM. In some embodiments, a basic amino acid is present in the formulation at a concentration of 90 mM. In some embodiments, a basic amino acid is present in the formulation at a concentration of 95 mM. In some embodiments, a basic amino acid is present in the formulation at a concentration of 100 mM. In some embodiments, a basic amino acid is present in the formulation at a concentration of 110 mM. In some embodiments, a basic amino acid is present in the formulation at a concentration of 120 mM. In some embodiments, a basic amino acid is present in the formulation at a concentration of 125 mM. In some embodiments, a basic amino acid is present in the formulation at a concentration of 130 mM. In some embodiments, a basic amino acid is present in the formulation at a concentration of 140 mM. In some embodiments, a basic amino acid is present in the formulation at a concentration of 150 mM. In some embodiments, a basic amino acid is present in the formulation at a concentration of 160 mM. In some embodiments, a basic amino acid is present in the formulation at a concentration of 170 mM. In some embodiments, a basic amino acid is present in the formulation at a concentration of 175 mM. In some embodiments, a basic amino acid is present in the formulation at a concentration of 180 mM. In some embodiments, a basic amino acid is present in the formulation at a concentration of 190 mM. In some embodiments, a basic amino acid is present in the formulation at a concentration of 200 mM. In some embodiments, a basic amino acid is present in the formulation at a concentration of 225 mM. In some embodiments, a basic amino acid is present in the formulation at a concentration of 250 mM. In some embodiments, a formulation is substantially free of a basic amino acid.

In some embodiments, a basic amino acid is present in the formulation at a concentration of less than 150 mM. In some embodiments, a basic amino acid is present in the formulation at a concentration of less than 125 mM. In some embodiments, a basic amino acid is present in the formulation at a concentration of less than 120 mM. In some embodiments, a basic amino acid is present in the formulation at a concentration of less than 110 mM. In some embodiments, a basic amino acid is present in the formulation at a concentration of less than 100 mM. In some embodiments, a basic amino acid is present in the formulation at a concentration of less than 90 mM. In some embodiments, a basic amino acid is present in the formulation at a concentration of less than 80 mM. In some embodiments, a basic amino acid is present in the formulation at a concentration of less than 75 mM. In some embodiments, a basic amino acid is present in the formulation at a concentration of less than 70 mM. In some embodiments, a basic amino acid is present in the formulation at a concentration of less than 65 mM. In some embodiments, a basic amino acid is present in the formulation at a concentration of less than 60 mM. In some embodiments, a basic amino acid is present in the formulation at a concentration of less than 55 mM. In some embodiments, a basic amino acid is present in the formulation at a concentration of less than 50 mM. In some embodiments, a basic amino acid is present in the formulation at a concentration of less than 40 mM. In some embodiments, a basic amino acid is present in the formulation at a concentration of less than 30 mM. In some embodiments, a basic amino acid is present in the formulation at a concentration of less than 25 mM. In some embodiments, a basic amino acid is present in the formulation at a concentration of less than 20 mM. In some embodiments, a basic amino acid is present in the formulation at a concentration of less than 15 mM. In some embodiments, a basic amino acid is present in the formulation at a concentration of less than 10 mM.

In some embodiments, arginine is present in the formulation at a concentration of less than 150 mM. In some embodiments, arginine is present in the formulation at a concentration of less than 140 mM. In some embodiments, arginine is present in the formulation at a concentration of less than 130 mM. In some embodiments, arginine is present in the formulation at a concentration of less than 125 mM. In some embodiments, arginine is present in the formulation at a concentration of less than 120 mM. In some embodiments, arginine is present in the formulation at a concentration of less than 110 mM. In some embodiments, arginine is present in the formulation at a concentration of less than 100 mM. In some embodiments, arginine acid is present in the formulation at a concentration of less than 90 mM. In some embodiments, an arginine is present in the formulation at a concentration of less than 80 mM. In some embodiments, arginine is present in the formulation at a concentration of less than 75 mM. In some embodiments, arginine is present in the formulation at a concentration of less than 70 mM. In some embodiments, arginine is present in the formulation at a concentration of less than 65 mM. In some embodiments, arginine is present in the formulation at a concentration of less than 60 mM. In some embodiments, arginine is present in the formulation at a concentration of less than 55 mM. In some embodiments, arginine is present in the formulation at a concentration of less than 50 mM. In some embodiments, arginine is present in the formulation at a concentration of less than 40 mM. In some embodiments, arginine is present in the formulation at a concentration of less than 30 mM. In some embodiments, arginine is present in the formulation at a concentration of less than 25 mM. In some embodiments, arginine is present in the formulation at a concentration of less than 20 mM. In some embodiments, arginine is present in the formulation at a concentration of less than 15 mM. In some embodiments, arginine is present in the formulation at a concentration of less than 10 mM. In some embodiments, a formulation is substantially free of arginine.

In some embodiments, arginine is present in the formulation at a concentration of 20-150 mM. In some embodiments, arginine is present in the formulation at a concentration of 25-125 mM. In some embodiments, arginine is present in the formulation at a concentration of 30-100 mM. In some embodiments, arginine is present in the formulation at a concentration of 50-75 mM. In some embodiments, arginine is present in the formulation at a concentration of 50-100 mM. In some embodiments, arginine is present in the formulation at a concentration of 50-70 mM. In some embodiments, arginine is present in the formulation at a concentration of 25-80 mM.

In some embodiments, arginine is present in the formulation at a concentration of 150 mM. In some embodiments, arginine is present in the formulation at a concentration of 125 mM. In some embodiments, arginine is present in the formulation at a concentration of 120 mM. In some embodiments, arginine is present in the formulation at a concentration of 110 mM. In some embodiments, arginine is present in the formulation at a concentration of 100 mM. In some embodiments, arginine acid is present in the formulation at a concentration of 90 mM. In some embodiments, an arginine is present in the formulation at a concentration of 80 mM. In some embodiments, arginine is present in the formulation at a concentration of 75 mM. In some embodiments, arginine is present in the formulation at a concentration of 70 mM. In some embodiments, arginine is present in the formulation at a concentration of 69 mM. In some embodiments, arginine is present in the formulation at a concentration of 68 mM. In some embodiments, arginine is present in the formulation at a concentration of 67 mM. In some embodiments, arginine is present in the formulation at a concentration of 66 mM. In some embodiments, arginine is present in the formulation at a concentration of 65 mM. In some embodiments, arginine is present in the formulation at a concentration of 64 mM. In some embodiments, arginine is present in the formulation at a concentration of 63 mM. In some embodiments, arginine is present in the formulation at a concentration of 62 mM. In some embodiments, arginine is present in the formulation at a concentration of 61 mM. In some embodiments, arginine is present in the formulation at a concentration of 60 mM. In some embodiments, arginine is present in the formulation at a concentration of 55 mM. In some embodiments, arginine is present in the formulation at a concentration of 50 mM. In some embodiments, arginine is present in the formulation at a concentration of 40 mM. In some embodiments, arginine is present in the formulation at a concentration of 30 mM. In some embodiments, arginine is present in the formulation at a concentration of 25 mM. In some embodiments, arginine is present in the formulation at a concentration of 20 mM. In some embodiments, arginine is present in the formulation at a concentration of 15 mM. In some embodiments, arginine is present in the formulation at a concentration of 10 mM.

In some embodiments, lysine is present in the formulation at a concentration of 5-300 mM. In some embodiments, lysine is present in the formulation at a concentration of 10-250 mM. In some embodiments, lysine is present in the formulation at a concentration of 20-150 mM. In some embodiments, lysine is present in the formulation at a concentration of 25-125 mM. In some embodiments, lysine is present in the formulation at a concentration of 30-100 mM. In some embodiments, lysine is present in the formulation at a concentration of 50-75 mM. In some embodiments, lysine is present in the formulation at a concentration of 25-80 mM.

In some embodiments, lysine is present in the formulation at a concentration of 150 mM. In some embodiments, lysine is present in the formulation at a concentration of 125 mM. In some embodiments, lysine is present in the formulation at a concentration of 120 mM. In some embodiments, lysine is present in the formulation at a concentration of 110 mM. In some embodiments, lysine is present in the formulation at a concentration of 100 mM. In some embodiments, lysine acid is present in the formulation at a concentration of 90 mM. In some embodiments, lysine is present in the formulation at a concentration of 80 mM. In some embodiments, lysine is present in the formulation at a concentration of 75 mM. In some embodiments, lysine is present in the formulation at a concentration of 70 mM. In some embodiments, lysine is present in the formulation at a concentration of 65 mM. In some embodiments, lysine is present in the formulation at a concentration of 60 mM. In some embodiments, lysine is present in the formulation at a concentration of 55 mM. In some embodiments, lysine is present in the formulation at a concentration of 50 mM. In some embodiments, lysine is present in the formulation at a concentration of 40 mM. In some embodiments, lysine is present in the formulation at a concentration of 30 mM. In some embodiments, lysine is present in the formulation at a concentration of 25 mM. In some embodiments, lysine is present in the formulation at a concentration of 20 mM. In some embodiments, lysine is present in the formulation at a concentration of 15 mM. In some embodiments, lysine is present in the formulation at a concentration of 10 mM.

In some embodiments, lysine is present in the formulation at a concentration of less than 150 mM. In some embodiments, lysine is present in the formulation at a concentration of less than 125 mM. In some embodiments, lysine is present in the formulation at a concentration of less than 120 mM. In some embodiments, lysine is present in the formulation at a concentration of less than 110 mM. In some embodiments, lysine is present in the formulation at a concentration of less than 100 mM. In some embodiments, lysine acid is present in the formulation at a concentration of less than 90 mM. In some embodiments, lysine is present in the formulation at a concentration of less than 80 mM. In some embodiments, lysine is present in the formulation at a concentration of less than 75 mM. In some embodiments, lysine is present in the formulation at a concentration of less than 70 mM. In some embodiments, lysine is present in the formulation at a concentration of less than 65 mM. In some embodiments, lysine is present in the formulation at a concentration of less than 60 mM. In some embodiments, lysine is present in the formulation at a concentration of less than 55 mM. In some embodiments, lysine is present in the formulation at a concentration of less than 50 mM. In some embodiments, lysine is present in the formulation at a concentration of less than 40 mM. In some embodiments, lysine is present in the formulation at a concentration of less than 30 mM. In some embodiments, lysine is present in the formulation at a concentration of less than 25 mM. In some embodiments, a formulation is substantially free of lysine.

In some embodiments, histidine is present in the formulation at a concentration of 5-300 mM. In some embodiments, histidine is present in the formulation at a concentration of 10-250 mM. In some embodiments, histidine is present in the formulation at a concentration of 20-150 mM. In some embodiments, histidine is present in the formulation at a concentration of 25-125 mM. In some embodiments, histidine is present in the formulation at a concentration of 30-100 mM. In some embodiments, histidine is present in the formulation at a concentration of 50-75 mM. In some embodiments, histidine is present in the formulation at a concentration of 50-100 mM. In some embodiments, histidine is present in the formulation at a concentration of 25-80 mM.

In some embodiments, histidine is present in the formulation at a concentration of 150 mM. In some embodiments, histidine is present in the formulation at a concentration of 125 mM. In some embodiments, histidine is present in the formulation at a concentration of 120 mM. In some embodiments, histidine is present in the formulation at a concentration of 110 mM. In some embodiments, histidine is present in the formulation at a concentration of 100 mM. In some embodiments, histidine acid is present in the formulation at a concentration of 90 mM. In some embodiments, histidine is present in the formulation at a concentration of 80 mM. In some embodiments, histidine is present in the formulation at a concentration of 75 mM. In some embodiments, histidine is present in the formulation at a concentration of 70 mM. In some embodiments, histidine is present in the formulation at a concentration of 65 mM. In some embodiments, histidine is present in the formulation at a concentration of 60 mM. In some embodiments, histidine is present in the formulation at a concentration of 55 mM. In some embodiments, histidine is present in the formulation at a concentration of 50 mM. In some embodiments, histidine is present in the formulation at a concentration of 40 mM. In some embodiments, histidine is present in the formulation at a concentration of 30 mM. In some embodiments, histidine is present in the formulation at a concentration of 25 mM. In some embodiments, histidine is present in the formulation at a concentration of 20 mM. In some embodiments, histidine is present in the formulation at a concentration of 15 mM. In some embodiments, histidine is present in the formulation at a concentration of 10 mM. In some embodiments, a formulation is substantially free of histidine.

In some embodiments, histidine is present in the formulation at a concentration of less than 150 mM. In some embodiments, histidine is present in the formulation at a concentration of less than 125 mM. In some embodiments, histidine is present in the formulation at a concentration of less than 120 mM. In some embodiments, histidine is present in the formulation at a concentration of less than 110 mM. In some embodiments, histidine is present in the formulation at a concentration of less than 100 mM. In some embodiments, histidine acid is present in the formulation at a concentration of less than 90 mM. In some embodiments, histidine is present in the formulation at a concentration of less than 80 mM. In some embodiments, histidine is present in the formulation at a concentration of less than 75 mM. In some embodiments, histidine is present in the formulation at a concentration of less than 70 mM. In some embodiments, histidine is present in the formulation at a concentration of less than 65 mM. In some embodiments, histidine is present in the formulation at a concentration of less than 60 mM. In some embodiments, histidine is present in the formulation at a concentration of less than 55 mM. In some embodiments, histidine is present in the formulation at a concentration of less than 50 mM. In some embodiments, histidine is present in the formulation at a concentration of less than 40 mM. In some embodiments, histidine is present in the formulation at a concentration of less than 30 mM. In some embodiments, histidine is present in the formulation at a concentration of less than 25 mM. In some embodiments, a formulation is substantially free of histidine.

Acidic Amino Acid

In some embodiments, a formulation comprises an acidic amino acid. In some embodiments, an acidic amino acid is glutamate. In some embodiments, an acidic amino acid is aspartate.

In some embodiments, an acidic amino acid is present in the formulation at a concentration of 10-500 mM. In some embodiments, an acidic amino acid is present in the formulation at a concentration of 10-300 mM. In some embodiments, an acidic amino acid is present in the formulation at a concentration of 25-250 mM. In some embodiments, an acidic amino acid is present in the formulation at a concentration of 50-150 mM. In some embodiments, an acidic amino acid is present in the formulation at a concentration of 50-100 mM. In some embodiments, an acidic amino acid is present in the formulation at a concentration of 25-75 mM. In some embodiments, an acidic amino acid is present in the formulation at a concentration of 50-75 mM.

In some embodiments, an acidic amino acid is present in the formulation at a concentration of 10 mM. In some embodiments, an acidic amino acid is present in the formulation at a concentration of 15 mM. In some embodiments, an acidic amino acid is present in the formulation at a concentration of 20 mM. In some embodiments, an acidic amino acid is present in the formulation at a concentration of 25 mM. In some embodiments, an acidic amino acid is present in the formulation at a concentration of 30 mM. In some embodiments, an acidic amino acid is present in the formulation at a concentration of 35 mM. In some embodiments, an acidic amino acid is present in the formulation at a concentration of 40 mM. In some embodiments, an acidic amino acid is present in the formulation at a concentration of 45 mM. In some embodiments, an acidic amino acid is present in the formulation at a concentration of 50 mM. In some embodiments, an acidic amino acid is present in the formulation at a concentration of 55 mM. In some embodiments, an acidic amino acid is present in the formulation at a concentration of 60 mM. In some embodiments, an acidic amino acid is present in the formulation at a concentration of 65 mM. In some embodiments, an acidic amino acid is present in the formulation at a concentration of 70 mM. In some embodiments, an acidic amino acid is present in the formulation at a concentration of 75 mM. In some embodiments, an acidic amino acid is present in the formulation at a concentration of 80 mM. In some embodiments, an acidic amino acid is present in the formulation at a concentration of 85 mM. In some embodiments, an acidic amino acid is present in the formulation at a concentration of 90 mM. In some embodiments, an acidic amino acid is present in the formulation at a concentration of 95 mM. In some embodiments, an acidic amino acid is present in the formulation at a concentration of 100 mM. In some embodiments, an acidic amino acid is present in the formulation at a concentration of 110 mM. In some embodiments, an acidic amino acid is present in the formulation at a concentration of 120 mM. In some embodiments, an acidic amino acid is present in the formulation at a concentration of 125 mM. In some embodiments, an acidic amino acid is present in the formulation at a concentration of 130 mM. In some embodiments, an acidic amino acid is present in the formulation at a concentration of 140 mM. In some embodiments, an acidic amino acid is present in the formulation at a concentration of 150 mM. In some embodiments, an acidic amino acid is present in the formulation at a concentration of 160 mM. In some embodiments, an acidic amino acid is present in the formulation at a concentration of 170 mM. In some embodiments, an acidic amino acid is present in the formulation at a concentration of 175 mM. In some embodiments, an acidic amino acid is present in the formulation at a concentration of 180 mM. In some embodiments, an acidic amino acid is present in the formulation at a concentration of 190 mM. In some embodiments, an acidic amino acid is present in the formulation at a concentration of 200 mM. In some embodiments, an acidic amino acid is present in the formulation at a concentration of 225 mM. In some embodiments, an acidic amino acid is present in the formulation at a concentration of 250 mM. In some embodiments, a formulation is substantially free of an acidic amino acid.

In some embodiments, an acidic amino acid is present in the formulation at a concentration of less than 150 mM. In some embodiments, an acidic amino acid is present in the formulation at a concentration of less than 125 mM. In some embodiments, an acidic amino acid is present in the formulation at a concentration of less than 120 mM. In some embodiments, an acidic amino acid is present in the formulation at a concentration of less than 110 mM. In some embodiments, an acidic amino acid is present in the formulation at a concentration of less than 100 mM. In some embodiments, an acidic amino acid is present in the formulation at a concentration of less than 90 mM. In some embodiments, an acidic amino acid is present in the formulation at a concentration of less than 80 mM. In some embodiments, an acidic amino acid is present in the formulation at a concentration of less than 75 mM. In some embodiments, an acidic amino acid is present in the formulation at a concentration of less than 70 mM. In some embodiments, an acidic amino acid is present in the formulation at a concentration of less than 65 mM. In some embodiments, an acidic amino acid is present in the formulation at a concentration of less than 60 mM. In some embodiments, an acidic amino acid is present in the formulation at a concentration of less than 55 mM. In some embodiments, an acidic amino acid is present in the formulation at a concentration of less than 50 mM. In some embodiments, an acidic amino acid is present in the formulation at a concentration of less than 40 mM. In some embodiments, an acidic amino acid is present in the formulation at a concentration of less than 30 mM. In some embodiments, an acidic amino acid is present in the formulation at a concentration of less than 25 mM. In some embodiments, an acidic amino acid is present in the formulation at a concentration of less than 20 mM. In some embodiments, an acidic amino acid is present in the formulation at a concentration of less than 15 mM. In some embodiments, an acidic amino acid is present in the formulation at a concentration of less than 10 mM.

In some embodiments, glutamate is present in the formulation at a concentration of 5-300 mM. In some embodiments, glutamate is present in the formulation at a concentration of 10-250 mM. In some embodiments, glutamate is present in the formulation at a concentration of 20-150 mM. In some embodiments, glutamate is present in the formulation at a concentration of 25-125 mM. In some embodiments, glutamate is present in the formulation at a concentration of 30-100 mM. In some embodiments, glutamate is present in the formulation at a concentration of 50-75 mM. In some embodiments, glutamate is present in the formulation at a concentration of 50-100 mM. In some embodiments, glutamate is present in the formulation at a concentration of 25-80 mM.

In some embodiments, glutamate is present in the formulation at a concentration of 150 mM. In some embodiments, glutamate is present in the formulation at a concentration of 125 mM. In some embodiments, glutamate is present in the formulation at a concentration of 120 mM. In some embodiments, glutamate is present in the formulation at a concentration of 110 mM. In some embodiments, glutamate is present in the formulation at a concentration of 100 mM. In some embodiments, glutamate is present in the formulation at a concentration of 90 mM. In some embodiments, glutamate is present in the formulation at a concentration of 80 mM. In some embodiments, glutamate is present in the formulation at a concentration of 75 mM. In some embodiments, glutamate is present in the formulation at a concentration of 70 mM. In some embodiments, glutamate is present in the formulation at a concentration of 65 mM. In some embodiments, glutamate is present in the formulation at a concentration of 60 mM. In some embodiments, glutamate is present in the formulation at a concentration of 55 mM. In some embodiments, glutamate is present in the formulation at a concentration of 50 mM. In some embodiments, glutamate is present in the formulation at a concentration of 40 mM. In some embodiments, glutamate is present in the formulation at a concentration of 30 mM. In some embodiments, glutamate is present in the formulation at a concentration of 25 mM. In some embodiments, glutamate is present in the formulation at a concentration of 20 mM. In some embodiments, glutamate is present in the formulation at a concentration of 15 mM. In some embodiments, glutamate is present in the formulation at a concentration of 10 mM. In some embodiments, a formulation is substantially free of glutamate.

In some embodiments, glutamate is present in the formulation at a concentration of less than 150 mM. In some embodiments, glutamate is present in the formulation at a concentration of less than 125 mM. In some embodiments, glutamate is present in the formulation at a concentration of less than 120 mM. In some embodiments, glutamate is present in the formulation at a concentration of less than 110 mM. In some embodiments, glutamate is present in the formulation at a concentration of less than 100 mM. In some embodiments, glutamate acid is present in the formulation at a concentration of less than 90 mM. In some embodiments, glutamate is present in the formulation at a concentration of less than 80 mM. In some embodiments, glutamate is present in the formulation at a concentration of less than 75 mM. In some embodiments, glutamate is present in the formulation at a concentration of less than 70 mM. In some embodiments, glutamate is present in the formulation at a concentration of less than 65 mM. In some embodiments, glutamate is present in the formulation at a concentration of less than 60 mM. In some embodiments, glutamate is present in the formulation at a concentration of less than 55 mM. In some embodiments, glutamate is present in the formulation at a concentration of less than 50 mM. In some embodiments, glutamate is present in the formulation at a concentration of less than 40 mM. In some embodiments, glutamate is present in the formulation at a concentration of less than 30 mM. In some embodiments, glutamate is present in the formulation at a concentration of less than 25 mM. In some embodiments, glutamate is present in the formulation at a concentration of less than 20 mM. In some embodiments, glutamate is present in the formulation at a concentration of less than 15 mM. In some embodiments, glutamate is present in the formulation at a concentration of less than 10 mM.

In some embodiments, aspartate is present in the formulation at a concentration of 5-300 mM. In some embodiments, aspartate is present in the formulation at a concentration of 10-250 mM. In some embodiments, aspartate is present in the formulation at a concentration of 20-150 mM.

In some embodiments, aspartate is present in the formulation at a concentration of 25-125 mM. In some embodiments, aspartate is present in the formulation at a concentration of 30-100 mM. In some embodiments, aspartate is present in the formulation at a concentration of 50-75 mM. In some embodiments, aspartate is present in the formulation at a concentration of 50-100 mM. In some embodiments, aspartate is present in the formulation at a concentration of 25-80 mM.

In some embodiments, aspartate is present in the formulation at a concentration of 150 mM. In some embodiments, aspartate is present in the formulation at a concentration of 125 mM. In some embodiments, aspartate is present in the formulation at a concentration of 120 mM. In some embodiments, aspartate is present in the formulation at a concentration of 110 mM. In some embodiments, aspartate is present in the formulation at a concentration of 100 mM. In some embodiments, aspartate is present in the formulation at a concentration of 90 mM. In some embodiments, aspartate is present in the formulation at a concentration of 80 mM. In some embodiments, aspartate is present in the formulation at a concentration of 75 mM. In some embodiments, aspartate is present in the formulation at a concentration of 70 mM. In some embodiments, aspartate is present in the formulation at a concentration of 65 mM. In some embodiments, aspartate is present in the formulation at a concentration of 60 mM. In some embodiments, aspartate is present in the formulation at a concentration of 55 mM. In some embodiments, aspartate is present in the formulation at a concentration of 50 mM. In some embodiments, aspartate is present in the formulation at a concentration of 40 mM. In some embodiments, aspartate is present in the formulation at a concentration of 30 mM. In some embodiments, aspartate is present in the formulation at a concentration of 25 mM. In some embodiments, aspartate is present in the formulation at a concentration of 20 mM. In some embodiments, aspartate is present in the formulation at a concentration of 15 mM. In some embodiments, aspartate is present in the formulation at a concentration of 10 mM. In some embodiments, a formulation is substantially free of aspartate.

In some embodiments, aspartate is present in the formulation at a concentration of less than 150 mM. In some embodiments, aspartate is present in the formulation at a concentration of less than 125 mM. In some embodiments, aspartate is present in the formulation at a concentration of less than 120 mM. In some embodiments, aspartate is present in the formulation at a concentration of less than 110 mM. In some embodiments, aspartate is present in the formulation at a concentration of less than 100 mM. In some embodiments, aspartate acid is present in the formulation at a concentration of less than 90 mM. In some embodiments, aspartate is present in the formulation at a concentration of less than 80 mM. In some embodiments, aspartate is present in the formulation at a concentration of less than 75 mM. In some embodiments, aspartate is present in the formulation at a concentration of less than 70 mM. In some embodiments, aspartate is present in the formulation at a concentration of less than 65 mM. In some embodiments, aspartate is present in the formulation at a concentration of less than 60 mM. In some embodiments, aspartate is present in the formulation at a concentration of less than 55 mM. In some embodiments, aspartate is present in the formulation at a concentration of less than 50 mM. In some embodiments, aspartate is present in the formulation at a concentration of less than 40 mM. In some embodiments, aspartate is present in the formulation at a concentration of less than 30 mM. In some embodiments, aspartate is present in the formulation at a concentration of less than 25 mM. In some embodiments, aspartate is present in the formulation at a concentration of less than 20 mM. In some embodiments, aspartate is present in the formulation at a concentration of less than 15 mM. In some embodiments, aspartate is present in the formulation at a concentration of less than 10 mM.

Other Amino Acids

In some embodiments, a formulation comprises proline. In some embodiments, a formulation comprises methionine. In some embodiments, a formulation comprises glycine. In some embodiments, a formulation comprises asparagine.

In some embodiments, proline is present in the formulation at a concentration of 5-300 mM. In some embodiments, proline is present in the formulation at a concentration of 10-250 mM. In some embodiments, proline is present in the formulation at a concentration of 50-250 mM. In some embodiments, proline is present in the formulation at a concentration of 75-225 mM. In some embodiments, proline is present in the formulation at a concentration of 20-150 mM. In some embodiments, proline is present in the formulation at a concentration of 25-125 mM. In some embodiments, proline is present in the formulation at a concentration of 30-100 mM. In some embodiments, proline is present in the formulation at a concentration of 50-75 mM. In some embodiments, proline is present in the formulation at a concentration of 50-100 mM. In some embodiments, proline is present in the formulation at a concentration of 25-80 mM.

In some embodiments, proline is present in the formulation at a concentration of 150 mM. In some embodiments, proline is present in the formulation at a concentration of 125 mM. In some embodiments, proline is present in the formulation at a concentration of 120 mM. In some embodiments, proline is present in the formulation at a concentration of 110 mM. In some embodiments, proline is present in the formulation at a concentration of 100 mM. In some embodiments, proline acid is present in the formulation at a concentration of 90 mM. In some embodiments, proline is present in the formulation at a concentration of 80 mM. In some embodiments, proline is present in the formulation at a concentration of 75 mM. In some embodiments, proline is present in the formulation at a concentration of 70 mM. In some embodiments, proline is present in the formulation at a concentration of 65 mM. In some embodiments, proline is present in the formulation at a concentration of 60 mM. In some embodiments, proline is present in the formulation at a concentration of 55 mM. In some embodiments, proline is present in the formulation at a concentration of 50 mM. In some embodiments, proline is present in the formulation at a concentration of 40 mM. In some embodiments, proline is present in the formulation at a concentration of 30 mM. In some embodiments, proline is present in the formulation at a concentration of 25 mM. In some embodiments, proline is present in the formulation at a concentration of 20 mM. In some embodiments, proline is present in the formulation at a concentration of 15 mM. In some embodiments, proline is present in the formulation at a concentration of 10 mM. In some embodiments, a formulation is substantially free of proline.

In some embodiments, proline is present in the formulation at a concentration of less than 150 mM. In some embodiments, proline is present in the formulation at a concentration of less than 125 mM. In some embodiments, proline is present in the formulation at a concentration of less than 120 mM. In some embodiments, proline is present in the formulation at a concentration of less than 110 mM. In some embodiments, proline is present in the formulation at a concentration of less than 100 mM. In some embodiments, proline acid is present in the formulation at a concentration of less than 90 mM. In some embodiments, proline is present in the formulation at a concentration of less than 80 mM. In some embodiments, proline is present in the formulation at a concentration of less than 75 mM. In some embodiments, proline is present in the formulation at a concentration of less than 70 mM. In some embodiments, proline is present in the formulation at a concentration of less than 65 mM. In some embodiments, proline is present in the formulation at a concentration of less than 60 mM. In some embodiments, proline is present in the formulation at a concentration of less than 55 mM. In some embodiments, proline is present in the formulation at a concentration of less than 50 mM. In some embodiments, proline is present in the formulation at a concentration of less than 40 mM. In some embodiments, proline is present in the formulation at a concentration of less than 30 mM. In some embodiments, proline is present in the formulation at a concentration of less than 25 mM. In some embodiments, proline is present in the formulation at a concentration of less than 20 mM. In some embodiments, proline is present in the formulation at a concentration of less than 15 mM. In some embodiments, proline is present in the formulation at a concentration of less than 10 mM.

In some embodiments, methionine is present in the formulation at a concentration of 5-300 mM. In some embodiments, methionine is present in the formulation at a concentration of 10-250 mM. In some embodiments, methionine is present in the formulation at a concentration of 20-150 mM. In some embodiments, methionine is present in the formulation at a concentration of 25-125 mM. In some embodiments, methionine is present in the formulation at a concentration of 30-100 mM. In some embodiments, methionine is present in the formulation at a concentration of 50-75 mM. In some embodiments, aspartate is present in the formulation at a concentration of 50-100 mM. In some embodiments, methionine is present in the formulation at a concentration of 25-80 mM.

In some embodiments, methionine is present in the formulation at a concentration of 150 mM. In some embodiments, methionine is present in the formulation at a concentration of 125 mM. In some embodiments, methionine is present in the formulation at a concentration of 120 mM. In some embodiments, methionine is present in the formulation at a concentration of 110 mM. In some embodiments, methionine is present in the formulation at a concentration of 100 mM. In some embodiments, methionine acid is present in the formulation at a concentration of 90 mM. In some embodiments, methionine is present in the formulation at a concentration of 80 mM. In some embodiments, methionine is present in the formulation at a concentration of 75 mM. In some embodiments, methionine is present in the formulation at a concentration of less than 70 mM. In some embodiments, methionine is present in the formulation at a concentration of less than 65 mM. In some embodiments, methionine is present in the formulation at a concentration of less than 60 mM. In some embodiments, methionine is present in the formulation at a concentration of less than 55 mM. In some embodiments, methionine is present in the formulation at a concentration of 50 mM. In some embodiments, methionine is present in the formulation at a concentration of 40 mM. In some embodiments, methionine is present in the formulation at a concentration of 30 mM. In some embodiments, methionine is present in the formulation at a concentration of 25 mM. In some embodiments, methionine is present in the formulation at a concentration of 20 mM. In some embodiments, methionine is present in the formulation at a concentration of 15 mM. In some embodiments, methionine is present in the formulation at a concentration of 10 mM. In some embodiments, a formulation is substantially free of methionine.

In some embodiments, glycine is present in the formulation at a concentration of 5-300 mM. In some embodiments, glycine is present in the formulation at a concentration of 10-250 mM. In some embodiments, glycine is present in the formulation at a concentration of 20-150 mM. In some embodiments, glycine is present in the formulation at a concentration of 25-125 mM. In some embodiments, glycine is present in the formulation at a concentration of 30-100 mM. In some embodiments, glycine is present in the formulation at a concentration of 50-75 mM. In some embodiments, aspartate is present in the formulation at a concentration of 50-100 mM. In some embodiments, glycine is present in the formulation at a concentration of 25-80 mM.

In some embodiments, glycine is present in the formulation at a concentration of 150 mM. In some embodiments, glycine is present in the formulation at a concentration of 125 mM. In some embodiments, glycine is present in the formulation at a concentration of 120 mM. In some embodiments, glycine is present in the formulation at a concentration of 110 mM. In some embodiments, glycine is present in the formulation at a concentration of 100 mM. In some embodiments, glycine acid is present in the formulation at a concentration of 90 mM. In some embodiments, glycine is present in the formulation at a concentration of 80 mM. In some embodiments, glycine is present in the formulation at a concentration of 75 mM. In some embodiments, glycine is present in the formulation at a concentration of less than 70 mM. In some embodiments, glycine is present in the formulation at a concentration of less than 65 mM. In some embodiments, glycine is present in the formulation at a concentration of less than 60 mM. In some embodiments, glycine is present in the formulation at a concentration of less than 55 mM. In some embodiments, glycine is present in the formulation at a concentration of 50 mM. In some embodiments, glycine is present in the formulation at a concentration of 40 mM. In some embodiments, glycine is present in the formulation at a concentration of 30 mM. In some embodiments, glycine is present in the formulation at a concentration of 25 mM. In some embodiments, glycine is present in the formulation at a concentration of 20 mM. In some embodiments, glycine is present in the formulation at a concentration of 15 mM. In some embodiments, glycine is present in the formulation at a concentration of 10 mM. In some embodiments, a formulation is substantially free of glycine.

In some embodiments, asparagine is present in the formulation at a concentration of 5-300 mM. In some embodiments, asparagine is present in the formulation at a concentration of 10-250 mM. In some embodiments, asparagine is present in the formulation at a concentration of 20-150 mM. In some embodiments, asparagine is present in the formulation at a concentration of 25-125 mM. In some embodiments, asparagine is present in the formulation at a concentration of 30-100 mM. In some embodiments, asparagine is present in the formulation at a concentration of 50-75 mM. In some embodiments, asparagine is present in the formulation at a concentration of 50-100 mM. In some embodiments, asparagine is present in the formulation at a concentration of 25-80 mM.

In some embodiments, asparagine is present in the formulation at a concentration of 150 mM. In some embodiments, asparagine is present in the formulation at a concentration of 125 mM. In some embodiments, asparagine is present in the formulation at a concentration of 120 mM. In some embodiments, asparagine is present in the formulation at a concentration of 110 mM. In some embodiments, asparagine is present in the formulation at a concentration of 100 mM. In some embodiments, asparagine acid is present in the formulation at a concentration of 90 mM. In some embodiments, asparagine is present in the formulation at a concentration of 80 mM. In some embodiments, asparagine is present in the formulation at a concentration of 75 mM. In some embodiments, asparagine is present in the formulation at a concentration of 70 mM. In some embodiments, asparagine is present in the formulation at a concentration of 65 mM. In some embodiments, asparagine is present in the formulation at a concentration of 60 mM. In some embodiments, asparagine is present in the formulation at a concentration of 55 mM. In some embodiments, asparagine is present in the formulation at a concentration of 50 mM. In some embodiments, asparagine is present in the formulation at a concentration of 40 mM. In some embodiments, asparagine is present in the formulation at a concentration of 30 mM. In some embodiments, asparagine is present in the formulation at a concentration of 25 mM. In some embodiments, asparagine is present in the formulation at a concentration of 20 mM. In some embodiments, asparagine is present in the formulation at a concentration of 15 mM. In some embodiments, asparagine is present in the formulation at a concentration of 10 mM. In some embodiments, a formulation is substantially free of asparagine.

In some embodiments, asparagine is present in the formulation at a concentration of less than 150 mM. In some embodiments, asparagine is present in the formulation at a concentration of less than 125 mM. In some embodiments, asparagine is present in the formulation at a concentration of less than 120 mM. In some embodiments, asparagine is present in the formulation at a concentration of less than 110 mM. In some embodiments, asparagine is present in the formulation at a concentration of less than 100 mM. In some embodiments, asparagine acid is present in the formulation at a concentration of less than 90 mM. In some embodiments, asparagine is present in the formulation at a concentration of less than 80 mM. In some embodiments, asparagine is present in the formulation at a concentration of less than 75 mM. In some embodiments, asparagine is present in the formulation at a concentration of less than 70 mM. In some embodiments, asparagine is present in the formulation at a concentration of less than 65 mM. In some embodiments, asparagine is present in the formulation at a concentration of less than 60 mM. In some embodiments, asparagine is present in the formulation at a concentration of less than 55 mM. In some embodiments, asparagine is present in the formulation at a concentration of less than 50 mM. In some embodiments, asparagine is present in the formulation at a concentration of less than 40 mM. In some embodiments, asparagine is present in the formulation at a concentration of less than 30 mM. In some embodiments, asparagine is present in the formulation at a concentration of less than 25 mM. In some embodiments, a formulation is substantially free of asparagine.

Antibody Concentration

In some embodiments, the stable formulation comprises the anti-IL1R1 antibody at a concentration of 50-200 mg/ml. In some embodiments, the stable formulation comprises the anti-IL1R1 antibody at a concentration of 50-195 mg/ml. In some embodiments, the stable formulation comprises the anti-IL1R1 antibody at a concentration of 50-190 mg/ml. In some embodiments, the stable formulation comprises the anti-IL1R1 antibody at a concentration of 50-185 mg/ml. In some embodiments, the stable formulation comprises the anti-IL1R1 antibody at a concentration of 50-180 mg/ml. In some embodiments, the stable formulation comprises the anti-IL1R1 antibody at a concentration of 50-175 mg/ml. In some embodiments, the stable formulation comprises the anti-IL1R1 antibody at a concentration of 50-170 mg/ml. In some embodiments, the stable formulation comprises the anti-IL1R1 antibody at a concentration of 50-165 mg/ml. In some embodiments, the stable formulation comprises the anti-IL1R1 antibody at a concentration of 50-160 mg/ml. In some embodiments, the stable formulation comprises the anti-IL1R1 antibody at a concentration of 50-155 mg/ml. In some embodiments, the stable formulation comprises the anti-IL1R1 antibody at a concentration of 50-150 mg/ml. In some embodiments, the stable formulation comprises the anti-IL1R1 antibody at a concentration of 50-125 mg/ml. In some embodiments, the stable formulation comprises the anti-IL1R1 antibody at a concentration of 50-100 mg/ml. In some embodiments, the stable formulation comprises the anti-IL1R1 antibody at a concentration of 50-190 mg/ml. In some embodiments, the stable formulation comprises the anti-IL1R1 antibody at a concentration of 55-190 mg/ml. In some embodiments, the stable formulation comprises the anti-IL1R1 antibody at a concentration of 60-190 mg/ml. In some embodiments, the stable formulation comprises the anti-IL1R1 antibody at a concentration of 65-190 mg/ml. In some embodiments, the stable formulation comprises the anti-IL1R1 antibody at a concentration of 70-190 mg/ml. In some embodiments, the stable formulation comprises the anti-IL1R1 antibody at a concentration of 75-190 mg/ml. In some embodiments, the stable formulation comprises the anti-IL1R1 antibody at a concentration of 80-190 mg/ml. In some embodiments, the stable formulation comprises the anti-IL1R1 antibody at a concentration of 85-190 mg/ml. In some embodiments, the stable formulation comprises the anti-IL1R1 antibody at a concentration of 90-190 mg/ml. In some embodiments, the stable formulation comprises the anti-IL1R1 antibody at a concentration of 95-190 mg/ml. In some embodiments, the stable formulation comprises the anti-IL1R1 antibody at a concentration of 100-190 mg/ml. In some embodiments, the stable formulation comprises the anti-IL1R1 antibody at a concentration of 105-190 mg/ml. In some embodiments, the stable formulation comprises the anti-IL1R1 antibody at a concentration of 110-190 mg/ml. In some embodiments, the stable formulation comprises the anti-IL1R1 antibody at a concentration of 115-190 mg/ml. In some embodiments, the stable formulation comprises the anti-IL1R1 antibody at a concentration of 120-190 mg/ml. In some embodiments, the stable formulation comprises the anti-IL1R1 antibody at a concentration of 125-190 mg/ml. In some embodiments, the stable formulation comprises the anti-IL1R1 antibody at a concentration of 130-190 mg/ml. In some embodiments, the stable formulation comprises the anti-IL1R1 antibody at a concentration of 135-190 mg/ml. In some embodiments, the stable formulation comprises the anti-IL1R1 antibody at a concentration of 140-190 mg/ml. In some embodiments, the stable formulation comprises the anti-IL1R1 antibody at a concentration of 145-190 mg/ml. In some embodiments, the stable formulation comprises the anti-IL1R1 antibody at a concentration of 150-190 mg/ml. In some embodiments, the stable formulation comprises the anti-IL1R1 antibody at a concentration of 100-150 mg/ml. In some embodiments, the stable formulation comprises the anti-IL1R1 antibody at a concentration of 100-160 mg/ml. In some embodiments, the stable formulation comprises the anti-IL1R1 antibody at a concentration of 100-165 mg/ml. In some embodiments, the stable formulation comprises the anti-IL1R1 antibody at a concentration of 150-160 mg/ml. In some embodiments, the stable formulation comprises the anti-IL1R1 antibody at a concentration of 150-165 mg/ml. In some embodiments, the stable formulation comprises the anti-IL1R1 antibody at a concentration of 135 mg/mL to 165 mg/mL. In some embodiments, the stable formulation comprises the anti-IL1R1 antibody at a concentration of 145 mg/mL to 160 mg/mL.

In some embodiments, the anti-IL1R1 antibody is present at a concentration of 50 mg/mL. In some embodiments, the anti-IL1R1 antibody is present at a concentration of 60 mg/mL. In some embodiments, the anti-IL1R1 antibody is present at a concentration of 70 mg/mL. In some embodiments, the anti-IL1R1 antibody is present at a concentration of 80 mg/mL. In some embodiments, the anti-IL1R1 antibody is present at a concentration of 100 mg/mL. In some embodiments, the anti-IL1R1 antibody is present at a concentration of 110 mg/mL. In some embodiments, the anti-IL1R1 antibody is present at a concentration of 120 mg/mL. In some embodiments, the anti-IL1R1 antibody is present at a concentration of 125 mg/mL. In some embodiments, the anti-IL1R1 antibody is present at a concentration of 130 mg/mL. In some embodiments, the anti-IL1R1 antibody is present at a concentration of 135 mg/mL. In some embodiments, the anti-IL1R1 antibody is present at a concentration of 140 mg/mL. In some embodiments, the anti-IL1R1 antibody is present at a concentration of 145 mg/mL. In some embodiments, the anti-IL1R1 antibody is present at a concentration of 150 mg/mL. In some embodiments, the anti-IL1R1 antibody is present at a concentration of 155 mg/mL. In some embodiments, the anti-IL1R1 antibody is present at a concentration of 160 mg/mL. In some embodiments, the anti-IL1R1 antibody is present at a concentration of 165 mg/mL. In some embodiments, the anti-IL1R1 antibody is present at a concentration of 170 mg/mL. In some embodiments, the anti-IL1R1 antibody is present at a concentration of 175 mg/mL. In some embodiments, the anti-IL1R1 antibody is present at a concentration of 180 mg/mL. In some embodiments, the anti-IL1R1 antibody is present at a concentration of 185 mg/mL. In some embodiments, the anti-IL1R1 antibody is present at a concentration of 190 mg/mL. In some embodiments, the anti-IL1R1 antibody is present at a concentration of 200 mg/mL. In some embodiments, the anti-IL1R1 antibody is present at a concentration of 225 mg/mL. In some embodiments, the anti-IL1R1 antibody is present at a concentration of 25° mg/mL. In some embodiments, the anti-IL1R1 antibody is present at a concentration of 275 mg/mL. In some embodiments, the anti-IL1R1 antibody is present at a concentration of 300 mg/mL.

In some embodiments, the stable formulation comprises the anti-IL1R1 antibody at a concentration of greater than 50 mg/ml. In some embodiments, the stable formulation comprises the anti-IL1R1 antibody at a concentration of greater than 60 mg/ml. In some embodiments, the stable formulation comprises the anti-IL1R1 antibody at a concentration of greater than 70 mg/ml. In some embodiments, the stable formulation comprises the anti-IL1R1 antibody at a concentration of greater than 80 mg/ml. In some embodiments, the stable formulation comprises the anti-IL1R1 antibody at a concentration of greater than 90 mg/ml. In some embodiments, the stable formulation comprises the anti-IL1R1 antibody at a concentration of greater than 100 mg/ml. In some embodiments, the stable formulation comprises the anti-IL1R1 antibody at a concentration of greater than 110 mg/ml. In some embodiments, the stable formulation comprises the anti-IL1R1 antibody at a concentration of greater than 120 mg/ml. In some embodiments, the stable formulation comprises the anti-IL1R1 antibody at a concentration of greater than 125 mg/ml. In some embodiments, the stable formulation comprises the anti-IL1R1 antibody at a concentration of greater than 130 mg/ml. In some embodiments, the stable formulation comprises the anti-IL1R1 antibody at a concentration of greater than 135 mg/ml. In some embodiments, the stable formulation comprises the anti-IL1R1 antibody at a concentration of greater than 140 mg/ml. In some embodiments, the stable formulation comprises the anti-IL1R1 antibody at a concentration of greater than 145 mg/ml. In some embodiments, the stable formulation comprises the anti-IL1R1 antibody at a concentration of greater than 150 mg/ml. In some embodiments, the stable formulation comprises the anti-IL1R1 antibody at a concentration of greater than 155 mg/ml. In some embodiments, the stable formulation comprises the anti-IL1R1 antibody at a concentration of greater than 160 mg/ml. In some embodiments, the stable formulation comprises the anti-IL1R1 antibody at a concentration of greater than 165 mg/ml. In some embodiments, the stable formulation comprises the anti-IL1R1 antibody at a concentration of greater than 170 mg/ml. In some embodiments, the stable formulation comprises the anti-IL1R1 antibody at a concentration of greater than 175 mg/ml. In some embodiments, the stable formulation comprises the anti-IL1R1 antibody at a concentration of greater than 180 mg/ml. In some embodiments, the stable formulation comprises the anti-IL1R1 antibody at a concentration of greater than 185 mg/ml. In some embodiments, the stable formulation comprises the anti-IL1R1 antibody at a concentration of greater than 190 mg/ml. In some embodiments, the stable formulation comprises the anti-IL1R1 antibody at a concentration of greater than 195 mg/ml. In some embodiments, the stable formulation comprises the anti-IL1R1 antibody at a concentration of greater than 200 mg/ml.

Buffers

In some embodiments of the invention, a formulation comprises a buffer to control pH. Suitable buffers include, for example, acetate, citrate, histidine, phosphate, succinate, tris(hydroxymethyl)aminomethane ("Tris") and other organic acids.

In some embodiments, the formulation comprises a buffer at a concentration ranging from 5 mM to 100 mM. In some embodiments, the formulation comprises a buffer at a concentration ranging from 5 mM to 75 mM. In some embodiments, the formulation comprises a buffer at a concentration ranging from 5 mM to 60 mM. In some embodiments, the formulation comprises a buffer at a concentration ranging from 25 mM to 50 mM. In some embodiments, the formulation comprises a buffer at a concentration ranging from 10 mM to 100 mM. In some embodiments, the formulation comprises a buffer at a concentration ranging from 20 mM to 100 mM. In some embodiments, the formulation comprises a buffer at a concentration ranging from 30 mM to 100 mM. In some embodiments, the formulation comprises a buffer at a concentration ranging from 40 mM to 100 mM. In some embodiments, the formulation comprises a buffer at a concentration ranging from 50 mM to 100 mM. In some embodiments, the formulation comprises a buffer at a concentration ranging from 75 mM to 100 mM. In some embodiments, the formulation comprises a buffer at a concentration ranging from 10 mM to 200 mM. In some embodiments, the formulation comprises a buffer at a concentration of 10 mM. In some embodiments, the formulation comprises a buffer at a concentration of 20 mM. In some embodiments, the formulation comprises a buffer at a concentration of 25 mM. In some embodiments, the formulation comprises a buffer at a concentration of 30 mM. In some embodiments, the formulation comprises a buffer at a concentration of 35 mM. In some embodiments, the formulation comprises a buffer at a concentration of 40 mM. In some embodiments, the formulation comprises a buffer at a concentration of 45 mM. In some embodiments, the formulation comprises a buffer at a concentration of 50 mM. In some embodiments, the formulation comprises a buffer at a concentration of 55 mM. In some embodiments, the formulation comprises a buffer at a concentration of 60 mM. In some embodiments, the formulation comprises a buffer at a concentration of 65 mM. In some embodiments, the formulation comprises a buffer at a concentration of 70 mM. In some embodiments, the formulation comprises a buffer at a concentration of 75 mM. In some embodiments, the formulation comprises a buffer at a concentration of 80 mM. In some embodiments, the formulation comprises a buffer at a concentration of 90 mM. In some embodiments, the formulation comprises a buffer at a concentration of 100 mM.

In some embodiments, the formulation comprises acetate. In some embodiments, the formulation comprises acetate at a concentration ranging from 5 mM to 100 mM. In some embodiments, the formulation comprises acetate at a concentration ranging from 5 mM to 90 mM. In some embodiments, the formulation comprises acetate at a concentration ranging from 15 mM to 80 mM. In some embodiments, the formulation comprises acetate at a concentration ranging from 20 mM to 75 mM. In some embodiments, the formulation comprises acetate at a concentration ranging from 25 mM to 50 mM. In some embodiments, the formulation comprises acetate at a concentration of 5 mM. In some embodiments, the formulation comprises acetate at a concentration of 10 mM. In some embodiments, the formulation comprises acetate at a concentration of 15 mM. In some embodiments, the formulation comprises acetate at a concentration of 20 mM. In some embodiments, the formulation comprises acetate at a concentration of 25 mM. In some embodiments, the formulation comprises acetate at a concentration of 30 mM. In some embodiments, the formulation comprises acetate at a concentration of 35 mM. In some embodiments, the formulation comprises acetate at a concentration of 40 mM. In some embodiments, the formulation comprises acetate at a concentration of 45 mM. In some embodiments, the formulation comprises acetate at a concentration of 50 mM. In some embodiments, the formulation comprises acetate at a concentration of 55 mM. In some embodiments, the formulation comprises acetate at a concentration of 60 mM. In some embodiments, the formulation comprises acetate at a concentration of 65 mM. In some embodiments, the formulation comprises acetate at a concentration of 70 mM. In some embodiments, the formulation comprises acetate at a concentration of 75 mM. In some embodiments, the formulation comprises acetate at a concentration of 80 mM. In some embodiments, the formulation comprises acetate at a concentration of 85 mM. In some embodiments, the formulation comprises acetate at a concentration of 90 mM. In some embodiments, the formulation comprises acetate at a concentration of 100 mM. In some embodiments the buffer is sodium acetate.

In some embodiments, the formulation comprises histidine. In some embodiments, the formulation comprises histidine at a concentration ranging from 5 mM to 100 mM. In some embodiments, the formulation comprises histidine at a concentration ranging from 5 mM to 90 mM. In some embodiments, the formulation comprises histidine at a concentration ranging from 15 mM to 80 mM. In some embodiments, the formulation comprises histidine at a concentration ranging from 20 mM to 75 mM. In some embodiments, the formulation comprises histidine at a concentration ranging from 25 mM to 50 mM. In some embodiments, the formulation comprises histidine at a concentration of 5 mM. In some embodiments, the formulation comprises histidine at a concentration of 10 mM. In some embodiments, the formulation comprises histidine at a concentration of 15 mM. In some embodiments, the formulation comprises histidine at a concentration of 20 mM. In some embodiments, the formulation comprises histidine at a concentration of 25 mM. In some embodiments, the formulation comprises histidine at a concentration of 30 mM. In some embodiments, the formulation comprises histidine at a concentration of 35 mM. In some embodiments, the formulation comprises histidine at a concentration of 40 mM. In some embodiments, the formulation comprises histidine at a concentration of 45 mM. In some embodiments, the formulation comprises histidine at a concentration of 50 mM. In some embodiments, the formulation comprises histidine at a concentration of 55 mM. In some embodiments, the formulation comprises histidine at a concentration of 60 mM. In some embodiments, the formulation comprises histidine at a concentration of 65 mM. In some embodiments, the formulation comprises histidine at a concentration of 70 mM. In some embodiments, the formulation comprises histidine at a concentration of 75 mM. In some embodiments, the formulation comprises histidine at a concentration of 80 mM. In some embodiments, the formulation comprises histidine at a concentration of 85 mM. In some embodiments, the formulation comprises histidine at a concentration of 90 mM. In some embodiments, the formulation comprises histidine at a concentration of 100 mM.

In some embodiments, the formulation comprises succinate. In some embodiments, the formulation comprises succinate at a concentration ranging from 5 mM to 100 mM. In some embodiments, the formulation comprises succinate at a concentration ranging from 5 mM to 90 mM. In some embodiments, the formulation comprises succinate at a concentration ranging from 15 mM to 80 mM. In some embodiments, the formulation comprises succinate at a concentration ranging from 20 mM to 75 mM. In some embodiments, the formulation comprises succinate at a concentration ranging from 25 mM to 50 mM. In some embodiments, the formulation comprises succinate at a concentration of 5 mM. In some embodiments, the formulation comprises succinate at a concentration of 10 mM. In some embodiments, the formulation comprises succinate at a concentration of 15 mM. In some embodiments, the formulation comprises succinate at a concentration of 20 mM. In some embodiments, the formulation comprises succinate at a concentration of 25 mM. In some embodiments, the formulation comprises succinate at a concentration of 30 mM. In some embodiments, the formulation comprises succinate at a concentration of 35 mM. In some embodiments, the formulation comprises succinate at a concentration of 40 mM. In some embodiments, the formulation comprises succinate at a concentration of 45 mM. In some embodiments, the formulation comprises succinate at a concentration of 50 mM. In some embodiments, the formulation comprises succinate at a concentration of 55 mM. In some embodiments, the formulation comprises succinate at a concentration of 60 mM. In some embodiments, the formulation comprises succinate at a concentration of 65 mM. In some embodiments, the formulation comprises succinate at a concentration of 70 mM. In some embodiments, the formulation comprises succinate at a concentration of 75 mM. In some embodiments, the formulation comprises succinate at a concentration of 80 mM. In some embodiments, the formulation comprises succinate at a concentration of 85 mM. In some embodiments, the formulation comprises succinate at a concentration of 90 mM. In some embodiments, the formulation comprises succinate at a concentration of 100 mM.

In some embodiments, the formulation comprises phosphate. In some embodiments, the formulation comprises phosphate at a concentration ranging from 5 mM to 100 mM. In some embodiments, the formulation comprises phosphate at a concentration ranging from 5 mM to 90 mM. In some embodiments, the formulation comprises phosphate at a concentration ranging from 15 mM to 80 mM. In some embodiments, the formulation comprises phosphate at a concentration ranging from 20 mM to 75 mM. In some embodiments, the formulation comprises phosphate at a concentration ranging from 25 mM to 50 mM. In some embodiments, the formulation comprises phosphate at a concentration of 5 mM. In some embodiments, the formulation comprises phosphate at a concentration of 10 mM. In some embodiments, the formulation comprises phosphate at a concentration of 15 mM. In some embodiments, the formulation comprises phosphate at a concentration of 20 mM. In some embodiments, the formulation comprises phosphate at a concentration of 25 mM. In some embodiments, the formulation comprises phosphate at a concentration of 30 mM. In some embodiments, the formulation comprises phosphate at a concentration of 35 mM. In some embodiments, the formulation comprises phosphate at a concentration of 40 mM. In some embodiments, the formulation comprises phosphate at a concentration of 45 mM. In some embodiments, the formulation comprises phosphate at a concentration of 50 mM. In some embodiments, the formulation comprises phosphate at a concentration of 55 mM. In some embodiments, the formulation comprises phosphate at a concentration of 60 mM. In some embodiments, the formulation comprises phosphate at a concentration of 65 mM. In some embodiments, the formulation comprises phosphate at a concentration of 70 mM. In some embodiments, the formulation comprises phosphate at a concentration of 75 mM. In some embodiments, the formulation comprises phosphate at a concentration of 80 mM. In some embodiments, the formulation comprises phosphate at a concentration of 85 mM. In some embodiments, the formulation comprises phosphate at a concentration of 90 mM. In some embodiments, the formulation comprises phosphate at a concentration of 100 mM.

In some embodiments, the formulation comprises citrate. In some embodiments, the formulation comprises citrate at a concentration ranging from 5 mM to 100 mM. In some embodiments, the formulation comprises citrate at a concentration ranging from 5 mM to 90 mM. In some embodiments, the formulation comprises citrate at a concentration ranging from 15 mM to 80 mM. In some embodiments, the formulation comprises citrate at a concentration ranging from 20 mM to 75 mM. In some embodiments, the formulation comprises citrate at a concentration ranging from 25 mM to 50 mM. In some embodiments, the formulation comprises citrate at a concentration of 5 mM. In some embodiments, the formulation comprises citrate at a concentration of 10 mM. In some embodiments, the formulation comprises citrate at a concentration of 15 mM. In some embodiments, the formulation comprises citrate at a concentration of 20 mM. In some embodiments, the formulation comprises citrate at a concentration of 25 mM. In some embodiments, the formulation comprises citrate at a concentration of 30 mM. In some embodiments, the formulation comprises citrate at a concentration of 35 mM. In some embodiments, the formulation comprises citrate at a concentration of 40 mM. In some embodiments, the formulation comprises citrate at a concentration of 45 mM. In some embodiments, the formulation comprises citrate at a concentration of 50 mM. In some embodiments, the formulation comprises citrate at a concentration of 55 mM. In some embodiments, the formulation comprises citrate at a concentration of 60 mM. In some embodiments, the formulation comprises citrate at a concentration of 65 mM. In some embodiments, the formulation comprises citrate at a concentration of 70 mM. In some embodiments, the formulation comprises citrate at a concentration of 75 mM. In some embodiments, the formulation comprises citrate at a concentration of 80 mM. In some embodiments, the formulation comprises citrate at a concentration of 85 mM. In some embodiments, the formulation comprises citrate at a concentration of 90 mM. In some embodiments, the formulation comprises citrate at a concentration of 100 mM.

In some embodiments, the formulation comprises Tris. In some embodiments, the formulation comprises Tris at a concentration ranging from 5 mM to 100 mM. In some embodiments, the formulation comprises Tris at a concentration ranging from 5 mM to 90 mM. In some embodiments, the formulation comprises Tris at a concentration ranging from 15 mM to 80 mM. In some embodiments, the formulation comprises Tris at a concentration ranging from 20 mM to 75 mM. In some embodiments, the formulation comprises Tris at a concentration ranging from 25 mM to 50 mM. In some embodiments, the formulation comprises Tris at a concentration of 5 mM. In some embodiments, the formulation comprises Tris at a concentration of 10 mM. In some embodiments, the formulation comprises Tris at a concentration of 15 mM. In some embodiments, the formulation comprises Tris at a concentration of 20 mM. In some embodiments, the formulation comprises Tris at a concentration of 25 mM. In some embodiments, the formulation comprises Tris at a concentration of 30 mM. In some embodiments, the formulation comprises Tris at a concentration of 35 mM. In some embodiments, the formulation comprises Tris at a concentration of 40 mM. In some embodiments, the formulation comprises Tris at a concentration of 45 mM. In some embodiments, the formulation comprises Tris at a concentration of 50 mM. In some embodiments, the formulation comprises Tris at a concentration of 55 mM. In some embodiments, the formulation comprises Tris at a concentration of 60 mM. In some embodiments, the formulation comprises Tris at a concentration of 65 mM. In some embodiments, the formulation comprises Tris at a concentration of 70 mM. In some embodiments, the formulation comprises Tris at a concentration of 75 mM. In some embodiments, the formulation comprises Tris at a concentration of 80 mM. In some embodiments, the formulation comprises Tris at a concentration of 85 mM. In some embodiments, the formulation comprises Tris at a concentration of 90 mM. In some embodiments, the formulation comprises Tris at a concentration of 100 mM.

pH

When considering any antibody formulation, the pH range of the solution is vital to formulation since antibodies are stable against chemical modifications and aggregation over a narrow pH range. Stabilizing buffers for antibodies should be rationally selected, as reactions leading to physicochemical instability are primarily driven by pH and ionic strength of the buffer.

In some embodiments, a formulation comprises a pH of 4.0 to 7.0. In some embodiments, a formulation comprises a pH of 4.0 to 7.4. In some embodiments, a formulation comprises a pH of 4.3 to 6.5. In some embodiments, a formulation comprises a pH of 4.5 to 6.1. In some embodiments, a formulation comprises a pH of 4.3 to 4.6. In some embodiments, a formulation comprises a pH of 4.5 to 5.5. In some embodiments, a formulation comprises a pH of 4.4 to 5.7. In some embodiments, a formulation comprises a pH of 4.4 to 5.4. In some embodiments, a formulation comprises a pH of 4.6 to 5.2. In some embodiments, a formulation comprises a pH of 4.7 to 5.1. In some embodiments, a formulation comprises a pH of 4.7 to 5.7. In some embodiments, a formulation comprises a pH of 5.0 to 5.4. In some embodiments, a formulation comprises a pH of 4.8 to 5.8. In some embodiments, a formulation comprises a pH of 4.5 to 5.0. In some embodiments, a formulation comprises a pH of 5.0 to 5.2. In some embodiments, a formulation comprises a pH of 5.0 to 5.6. In some embodiments, a formulation comprises a pH of 5.5 to 6.5. In some embodiments, a formulation comprises a pH of 5.2 to 6.2. In some embodiments, a formulation comprises a pH of 5.2 to 5.6. In some embodiments, a formulation comprises a pH of 4.9 to 5.2.

In some embodiments, a formulation comprises a pH of 4.0. In some embodiments, a formulation comprises a pH of 4.1. In some embodiments, a formulation comprises a pH of 4.2. In some embodiments, a formulation comprises a pH of 4.3. In some embodiments, a formulation comprises a pH of 4.4. In some embodiments, a formulation comprises a pH of 4.5. In some embodiments, a formulation comprises a pH of 4.6. In some embodiments, a formulation comprises a pH of 4.7. In some embodiments, a formulation comprises a pH of 4.8. In some embodiments, a formulation comprises a pH of 4.9. In some embodiments, a formulation comprises a pH of 5.0. In some embodiments, a formulation comprises a pH of 5.1. In some embodiments, a formulation comprises a pH of 5.2. In some embodiments, a formulation comprises a pH of 5.3. In some embodiments, a formulation comprises a pH of 5.4. In some embodiments, a formulation comprises a pH of 5.5. In some embodiments, a formulation comprises a pH of 5.6. In some embodiments, a formulation comprises a pH of 5.7. In some embodiments, a formulation comprises a pH of 5.8. In some embodiments, a formulation comprises a pH of 5.9. In some embodiments, a formulation comprises a pH of 6.0. In some embodiments, a formulation comprises a pH of 6.1. In some embodiments, a formulation comprises a pH of 6.2. In some embodiments, a formulation comprises a pH of 6.3. In some embodiments, a formulation comprises a pH of 6.4. In some embodiments, a formulation comprises a pH of 6.5. In some embodiments, a formulation comprises a pH of 6.6. In some embodiments, a formulation comprises a pH of 6.7. In some embodiments, a formulation comprises a pH of 6.8. In some embodiments, a formulation comprises a pH of 6.9. In some embodiments, a formulation comprises a pH of 7.0.

In some embodiments, a formulation comprises acetate and a pH of 4.0 to 5.6. In some embodiments, a formulation comprises acetate and a pH of 3.5 to 6.0. In some embodiments, a formulation comprises acetate and a pH of 3.8 to 5.8. In some embodiments, a formulation comprises acetate and a pH of 4.8 to 5.8. In some embodiments, a formulation comprises acetate and a pH of 4.0 to 5.8. In some embodiments, a formulation comprises acetate and a pH of 4.5 to 5.2. In some embodiments, a formulation comprises acetate and a pH of 4.4 to 5.7. In some embodiments, a formulation comprises acetate and a pH of 4.4 to 5.4. In some embodiments, a formulation comprises acetate and a pH of 4.6 to 5.2. In some embodiments, a formulation comprises acetate and a pH of 4.7 to 5.1. In some embodiments, a formulation comprises acetate and a pH of 4.7 to 5.7. In some embodiments, a formulation comprises acetate and a pH of 5.0 to 5.4. In some embodiments, a formulation comprises acetate and a pH of 4.9 to 5.2. In some embodiments, a formulation comprises acetate and a pH of 4.0. In some embodiments, a formulation comprises acetate and a pH of 4.1. In some embodiments, a formulation comprises acetate and a pH of 4.2. In some embodiments, a formulation comprises acetate and a pH of 4.3. In some embodiments, a formulation comprises acetate and a pH of 4.4. In some embodiments, a formulation comprises acetate and a pH of 4.5. In some embodiments, a formulation comprises acetate and a pH of 4.6. In some embodiments, a formulation comprises acetate and a pH of 4.7. In some embodiments, a formulation comprises acetate and a pH of 4.8. In some embodiments, a formulation comprises acetate and a pH of 4.9. In some embodiments, a formulation comprises acetate and a pH of 5.0. In some embodiments, a formulation comprises acetate and a pH of 5.1. In some embodiments, a formulation comprises acetate and a pH of 5.2. In some embodiments, a formulation comprises acetate and a pH of 5.3. In some embodiments, a formulation comprises acetate and a pH of 5.4. In some embodiments, a formulation comprises acetate and a pH of 5.5. In some embodiments, a formulation comprises acetate and a pH of 5.6. In some embodiments, a formulation comprises acetate and a pH of 5.7.

In some embodiments, a formulation comprises succinate and a pH of 4.5 to 6.0. In some embodiments, a formulation comprises succinate and a pH of 3.0 to 7.0. In some embodiments, a formulation comprises succinate and a pH of 3.0 to 6.8. In some embodiments, a formulation comprises succinate and a pH of 3.2 to 6.6. In some embodiments, a formulation comprises succinate and a pH of 4.0 to 7.0. In some embodiments, a formulation comprises succinate and a pH of 5.0 to 5.8. In some embodiments, a formulation comprises succinate and a pH of 5.4 to 5.8. In some embodiments, a formulation comprises succinate and a pH of 4.4. In some embodiments, a formulation comprises succinate and a pH of 4.5. In some embodiments, a formulation comprises succinate and a pH of 4.6. In some embodiments, a formulation comprises succinate and a pH of 4.7. In some embodiments, a formulation comprises succinate and a pH of 4.8. In some embodiments, a formulation comprises succinate and a pH of 4.9. In some embodiments, a formulation comprises succinate and a pH of 5.0. In some embodiments, a formulation comprises succinate and a pH of 5.1. In some embodiments, a formulation comprises succinate and a pH of 5.2. In some embodiments, a formulation comprises succinate and a pH of 5.3. In some embodiments, a formulation comprises succinate and a pH of 5.4. In some embodiments, a formulation comprises succinate and a pH of 5.5. In some embodiments, a formulation comprises succinate and a pH of 5.6. In some embodiments, a formulation comprises succinate and a pH of 5.7. In some embodiments, a formulation comprises succinate and a pH of 5.8. In some embodiments, a formulation comprises succinate and a pH of 5.9. In some embodiments, a formulation comprises succinate and a pH of 6.0. In some embodiments, a formulation comprises succinate and a pH of 6.1. In some embodiments, a formulation comprises succinate and a pH of 6.2.

In some embodiments, a formulation comprises histidine and a pH of 5.3 to 7.5. In some embodiments, a formulation comprises histidine and a pH of 4.5 to 7.5. In some embodiments, a formulation comprises histidine and a pH of 5.0 to 7.0. In some embodiments, a formulation comprises histidine and a pH of 5.5 to 7.4. In some embodiments, a formulation comprises histidine and a pH of 5.8 to 6.3. In some embodiments, a formulation comprises histidine and a pH of 5.0. In some embodiments, a formulation comprises histidine and a pH of 5.1. In some embodiments, a formulation comprises histidine and a pH of 5.2. In some embodiments, a formulation comprises histidine and a pH of 5.3. In some embodiments, a formulation comprises histidine and a pH of 5.4. In some embodiments, a formulation comprises histidine and a pH of 5.5. In some embodiments, a formulation comprises histidine and a pH of 5.6. In some embodiments, a formulation comprises histidine and a pH of 5.7. In some embodiments, a formulation comprises histidine and a pH of 5.8. In some embodiments, a formulation comprises histidine and a pH of 5.9. In some embodiments, a formulation comprises histidine and a pH of 6.0. In some embodiments, a formulation comprises histidine and a pH of 6.1. In some embodiments, a formulation comprises histidine and a pH of 6.2. In some embodiments, a formulation comprises histidine and a pH of 6.3. In some embodiments, a formulation comprises histidine and a pH of 6.4. In some embodiments, a formulation comprises histidine and a pH of 6.5. In some embodiments, a formulation comprises histidine and a pH of 6.6. In some embodiments, a formulation comprises histidine and a pH of 6.7. In some embodiments, a formulation comprises histidine and a pH of 6.8. In some embodiments, a formulation comprises histidine and a pH of 6.9. In some embodiments, a formulation comprises histidine and a pH of 7.0. In some embodiments, a formulation comprises histidine and a pH of 7.1. In some embodiments, a formulation comprises histidine and a pH of 7.2.

Salts

In some embodiments of the invention, a formulation further comprises a salt. Suitable salts include, for example, sodium chloride, potassium chloride, sodium sulfate, sodium acetate, and magnesium chloride. In some embodiments, the formulation comprises a halide. In some embodiments, the halide comprises an alkali metal halide.

In some embodiments, the salt is sodium chloride (NaCl). In some embodiments, the formulation comprises NaCl at a concentration ranging from 10 mM to 250 mM. In some embodiments, the salt is sodium chloride (NaCl). In some embodiments, the formulation comprises NaCl at a concentration ranging from 10 mM to 175 mM. In some embodiments, the formulation comprises NaCl at a concentration ranging from 25 mM to 150 mM. In some embodiments, the formulation comprises NaCl at a concentration ranging from 50 mM to 125 mM. In some embodiments, the formulation comprises NaCl at a concentration ranging from 50 mM to 100 mM. In some embodiments, the formulation comprises NaCl at a concentration ranging from 55 mM to 100 mM. In some embodiments, the formulation comprises NaCl at a concentration ranging from 75 mM to 125 mM. In some embodiments, the formulation comprises NaCl at a concentration ranging from 80 mM to 110 mM.

In some embodiments the formulation comprises 10 mM of sodium chloride. In some embodiments the formulation comprises 15 mM of sodium chloride. In some embodiments the formulation comprises 20 mM of sodium chloride. In some embodiments the formulation comprises 25 mM of sodium chloride. In some embodiments the formulation comprises 30 mM of sodium chloride. In some embodiments the formulation comprises 35 mM of sodium chloride. In some embodiments the formulation comprises 40 mM of sodium chloride. In some embodiments the formulation comprises 45 mM of sodium chloride. In some embodiments the formulation comprises 50 mM of sodium chloride. In some embodiments the formulation comprises 55 mM of sodium chloride. In some embodiments the formulation comprises 60 mM of sodium chloride. In some embodiments the formulation comprises 10 mM of sodium chloride. In some embodiments the formulation comprises 65 mM of sodium chloride. In some embodiments the formulation comprises 70 mM of sodium chloride. In some embodiments the formulation comprises 75 mM of sodium chloride. In some embodiments the formulation comprises 80 mM of sodium chloride. In some embodiments the formulation comprises 85 mM of sodium chloride. In some embodiments the formulation comprises 90 mM of sodium chloride. In some embodiments the formulation comprises 95 mM of sodium chloride. In some embodiments the formulation comprises 100 mM of sodium chloride. In some embodiments the formulation comprises 110 mM of sodium chloride. In some embodiments the formulation comprises 120 mM of sodium chloride. In some embodiments the formulation comprises 125 mM of sodium chloride. In some embodiments the formulation comprises 130 mM of sodium chloride. In some embodiments the formulation comprises 140 mM of sodium chloride. In some embodiments the formulation comprises 150 mM of sodium chloride. In some embodiments the formulation comprises 160 mM of sodium chloride. In some embodiments the formulation comprises 170 mM of sodium chloride. In some embodiments the formulation comprises 175 mM of sodium chloride. In some embodiments the formulation comprises 180 mM of sodium chloride. In some embodiments the formulation comprises 190 mM of sodium chloride. In some embodiments the formulation comprises 200 mM of sodium chloride. In some embodiments the formulation comprises 225 mM of sodium chloride. In some embodiments the formulation comprises 250 mM of sodium chloride.

In some embodiments, the salt is magnesium chloride ($MgCl_2$). In some embodiments, the formulation comprises $MgCl_2$ at a concentration ranging from 10 mM to 250 mM. In some embodiments, the salt is magnesium chloride ($MgCl_2$). In some embodiments, the formulation comprises $MgCl_2$ at a concentration ranging from 10 mM to 175 mM. In some embodiments, the formulation comprises $MgCl_2$ at a concentration ranging from 25 mM to 150 mM. In some embodiments, the formulation comprises $MgCl_2$ at a concentration ranging from 50 mM to 125 mM. In some embodiments, the formulation comprises $MgCl_2$ at a concentration ranging from 50 mM to 100 mM. In some embodiments, the formulation comprises $MgCl_2$ at a concentration ranging from 75 mM to 125 mM. In some embodiments, the formulation comprises $MgCl_2$ at a concentration ranging from 80 mM to 110 mM.

In some embodiments, the formulation comprises 10 mM of magnesium chloride. In some embodiments the formulation comprises 15 mM of magnesium chloride. In some embodiments, the formulation comprises 20 mM of magnesium chloride. In some embodiments, the formulation comprises 25 mM of magnesium chloride. In some embodiments, the formulation comprises 30 mM of magnesium chloride. In some embodiments, the formulation comprises 35 mM of magnesium chloride. In some embodiments, the formulation comprises 40 mM of magnesium chloride. In some embodiments, the formulation comprises 45 mM of magnesium chloride. In some embodiments, the formulation comprises 50 mM of magnesium chloride. In some embodiments, the formulation comprises 55 mM of magnesium chloride. In some embodiments, the formulation comprises 60 mM of magnesium chloride. In some embodiments the formulation comprises 10 mM of magnesium chloride. In some embodiments, the formulation comprises 65 mM of magnesium chloride. In some embodiments, the formulation comprises 70 mM of magnesium chloride. In some embodiments, the formulation comprises 75 mM of magnesium chloride. In some embodiments, the formulation comprises 80 mM of magnesium chloride. In some embodiments, the formulation comprises 90 mM of magnesium chloride. In some embodiments, the formulation comprises 100 mM of magnesium chloride. In some embodiments the formulation comprises 110 mM of magnesium chloride. In some embodiments, the formulation comprises 120 mM of magnesium chloride. In some embodiments, the formulation comprises 125 mM of magnesium chloride. In some embodiments, the formulation comprises 130 mM of magnesium chloride. In some embodiments, the formulation comprises 140 mM of magnesium chloride. In some embodiments, the formulation comprises 150 mM of magnesium chloride. In some embodiments, the formulation comprises 160 mM of magnesium chloride. In some embodiments, the formulation comprises 170 mM of magnesium chloride. In some embodiments, the formulation comprises 175 mM of magnesium chloride. In some embodiments, the formulation comprises 180 mM of magnesium chloride. In some embodiments, the formulation comprises 190 mM of magnesium chloride. In some embodiments, the formulation comprises 200 mM of magnesium chloride. In some embodiments, the formulation comprises 225 mM of magnesium chloride. In some embodiments the formulation comprises 250 mM of magnesium chloride.

In some embodiments, the salt is potassium chloride (KCl). In some embodiments, the formulation comprises KCl at a concentration ranging from 10 mM to 250 mM. In some embodiments, the salt is potassium chloride (KCl). In some embodiments, the formulation comprises KCl at a concentration ranging from 10 mM to 175 mM. In some embodiments, the formulation comprises KCl at a concentration ranging from 25 mM to 150 mM. In some embodiments, the formulation comprises KCl at a concentration ranging from 50 mM to 125 mM. In some embodiments, the formulation comprises KCl at a concentration ranging from 50 mM to 100 mM. In some embodiments, the formulation comprises KCl at a concentration ranging from 75 mM to 125 mM. In some embodiments, the formulation comprises KCl at a concentration ranging from 80 mM to 110 mM.

In some embodiments, the formulation comprises 10 mM of potassium chloride. In some embodiments the formulation comprises 15 mM of potassium chloride. In some embodiments, the formulation comprises 20 mM of potassium chloride. In some embodiments, the formulation comprises 25 mM of potassium chloride. In some embodiments, the formulation comprises 30 mM of potassium chloride. In some embodiments, the formulation comprises 35 mM of potassium chloride. In some embodiments, the formulation comprises 40 mM of potassium chloride. In some embodiments, the formulation comprises 45 mM of potassium chloride. In some embodiments, the formulation comprises 50 mM of potassium chloride. In some embodiments the formulation comprises 55 mM of potassium chloride. In some embodiments, the formulation comprises 60 mM of potassium chloride. In some embodiments, the formulation comprises 10 mM of potassium chloride. In some embodiments, the formulation comprises 65 mM of potassium chloride. In some embodiments, the formulation comprises 70 mM of potassium chloride. In some embodiments, the formulation comprises 75 mM of potassium chloride. In some embodiments, the formulation comprises 80 mM of potassium chloride. In some embodiments, the formulation comprises 90 mM of potassium chloride. In some embodiments, the formulation comprises 100 mM of potassium chloride. In some embodiments, the formulation comprises 110 mM of potassium chloride. In some embodiments, the formulation comprises 120 mM of potassium chloride. In some embodiments, the formulation comprises 125 mM of potassium chloride. In some embodiments, the formulation comprises 130 mM of potassium chloride. In some embodiments, the formulation comprises 140 mM of potassium chloride. In some embodiments, the formulation comprises 150 mM of potassium chloride. In some embodiments, the formulation comprises 160 mM of potassium chloride. In some embodiments, the formulation comprises 170 mM of potassium chloride. In some embodiments, the formulation comprises 175 mM of potassium chloride. In some embodiments, the formulation comprises 180 mM of potassium chloride. In some embodiments, the formulation comprises 190 mM of potassium chloride. In some embodiments, the formulation comprises 200 mM of potassium chloride. In some embodiments, the formulation comprises 225 mM of potassium chloride. In some embodiments, the formulation comprises 250 mM of potassium chloride.

In some embodiments, the salt is sodium sulfate. In some embodiments, the formulation comprises sodium sulfate at a concentration ranging from 10 mM to 250 mM. In some embodiments, the salt is sodium sulfate. In some embodiments, the formulation comprises sodium sulfate at a concentration ranging from 10 mM to 175 mM. In some embodiments, the formulation comprises sodium sulfate at a concentration ranging from 25 mM to 150 mM. In some embodiments, the formulation comprises sodium sulfate at a concentration ranging from 50 mM to 125 mM. In some embodiments, the formulation comprises sodium sulfate at a concentration ranging from 50 mM to 100 mM. In some embodiments, the formulation comprises sodium sulfate at a concentration ranging from 75 mM to 125 mM. In some embodiments, the formulation comprises sodium sulfate at a concentration ranging from 80 mM to 110 mM.

In some embodiments, the formulation comprises 10 mM of sodium sulfate. In some embodiments the formulation comprises 15 mM of sodium sulfate. In some embodiments, the formulation comprises 20 mM of sodium sulfate. In some embodiments, the formulation comprises 25 mM of sodium sulfate. In some embodiments, the formulation comprises 30 mM of sodium sulfate. In some embodiments, the formulation comprises 35 mM of sodium sulfate. In some embodiments the formulation comprises 40 mM of sodium sulfate. In some embodiments, the formulation comprises 45 mM of sodium sulfate. In some embodiments, the formulation comprises 50 mM of sodium sulfate. In some embodiments, the formulation comprises 55 mM of sodium sulfate. In some embodiments, the formulation comprises 60 mM of sodium sulfate. In some embodiments the formulation comprises 10 mM of sodium sulfate. In some embodiments, the formulation comprises 65 mM of sodium sulfate. In some embodiments, the formulation comprises 70 mM of sodium sulfate. In some embodiments, the formulation comprises 75 mM of sodium sulfate. In some embodiments, the formulation comprises 80 mM of sodium sulfate. In some embodiments, the formulation comprises 90 mM of sodium sulfate. In some embodiments the formulation comprises 100 mM of sodium sulfate. In some embodiments, the formulation comprises 110 mM of sodium sulfate. In some embodiments, the formulation comprises 120 mM of sodium sulfate. In some embodiments, the formulation comprises 125 mM of sodium sulfate. In some embodiments, the formulation comprises 130 mM of sodium sulfate. In some embodiments, the formulation comprises 140 mM of sodium sulfate. In some embodiments, the formulation comprises 150 mM of sodium sulfate. In some embodiments, the formulation comprises 160 mM of sodium sulfate. In some embodiments the formulation comprises 170 mM of sodium sulfate. In some embodiments the formulation comprises 175 mM of sodium sulfate. In some embodiments, the formulation comprises 180 mM of sodium sulfate. In some embodiments, the formulation comprises 190 mM of sodium sulfate. In some embodiments, the formulation comprises 200 mM of sodium sulfate. In some embodiments, the formulation comprises 225 mM of sodium sulfate. In some embodiments the formulation comprises 250 mM of sodium sulfate.

In some embodiments, the salt is sodium acetate. In some embodiments, the formulation comprises sodium acetate. In some embodiments, the formulation comprises sodium acetate at a concentration ranging from 5 mM to 100 mM. In some embodiments, the formulation comprises sodium acetate at a concentration ranging from 5 mM to 90 mM. In some embodiments, the formulation comprises sodium acetate at a concentration ranging from 15 mM to 80 mM. In some embodiments, the formulation comprises sodium acetate at a concentration ranging from 20 mM to 75 mM. In some embodiments, the formulation comprises sodium acetate at a concentration ranging from 25 mM to 50 mM. In some embodiments, the formulation comprises sodium acetate at a concentration ranging from 10 mM to 250 mM. In some embodiments, the salt is sodium acetate. In some embodiments, the formulation comprises sodium acetate at a concentration ranging from 10 mM to 175 mM. In some embodiments, the formulation comprises sodium acetate at a concentration ranging from 25 mM to 150 mM. In some embodiments, the formulation comprises sodium acetate at a concentration ranging from 50 mM to 125 mM. In some embodiments, the formulation comprises sodium acetate at a concentration ranging from 50 mM to 100 mM. In some embodiments, the formulation comprises sodium acetate at a concentration ranging from 75 mM to 125 mM. In some embodiments, the formulation comprises sodium acetate at a concentration ranging from 80 mM to 110 mM.

In some embodiments, the formulation comprises 5 mM of sodium acetate. In some embodiments, the formulation comprises 10 mM of sodium acetate. In some embodiments the formulation comprises 15 mM of sodium acetate. In some embodiments, the formulation comprises 20 mM of sodium acetate. In some embodiments, the formulation comprises 25 mM of sodium acetate. In some embodiments, the formulation comprises 30 mM of sodium acetate. In some embodiments, the formulation comprises 35 mM of sodium sulfate. In some embodiments, the formulation comprises 40 mM of sodium acetate. In some embodiments, the formulation comprises 45 mM of sodium acetate. In some embodiments, the formulation comprises 50 mM of sodium acetate. In some embodiments, the formulation comprises 55 mM of sodium acetate. In some embodiments, the formulation comprises 60 mM of sodium acetate. In some embodiments, the formulation comprises 65 mM of sodium acetate. In some embodiments, the formulation comprises 70 mM of sodium acetate. In some embodiments, the formulation comprises 75 mM of sodium acetate. In some embodiments, the formulation comprises 80 mM of sodium acetate. In some embodiments, the formulation comprises 85 mM of sodium acetate. In some embodiments, the formulation comprises 90 mM of sodium acetate. In some embodiments, the formulation comprises 95 mM of sodium acetate. In some embodiments, the formulation comprises 100 mM of sodium acetate. In some embodiments, the formulation comprises 110 mM of sodium acetate. In some embodiments, the formulation comprises 120 mM of sodium acetate. In some embodiments, the formulation comprises 125 mM of sodium acetate. In some embodiments, the formulation comprises 130 mM of sodium acetate. In some embodiments, the formulation comprises 140 mM of sodium acetate. In some embodiments, the formulation comprises 150 mM of sodium acetate. In some embodiments, the formulation comprises 160 mM of sodium acetate. In some embodiments, the formulation comprises 170 mM of sodium acetate. In some embodiments, the formulation comprises 175 mM of sodium acetate. In some embodiments, the formulation comprises 180 mM of sodium acetate. In some embodiments, the formulation comprises 190 mM of sodium acetate. In some embodiments, the formulation comprises 200 mM of sodium acetate. In some embodiments, the formulation comprises 225 mM of sodium acetate. In some embodiments, the formulation comprises 250 mM of sodium acetate.

Osmolyte

In some embodiments, a formulation comprises an osmolyte. In some embodiments, osmolytes provide stability to the folded, functional form of an antibody and alter the folding balance away from aggregation and/or degradation of the antibody. In some embodiments, an osmolyte is a tonicity agent. In some embodiments, an osmolyte is a sugar or polyol stabilizers.

In some embodiments, a formulation comprises a sugar. In some embodiments, a sugar is sucrose. In some embodiments, a sugar is trehalose. In some embodiments, a sugar is maltose. In some embodiments, a sugar is a disaccharide.

In some embodiments, a formulation comprises 0.5-20% (w/v) sugar. In some embodiments, the concentration of sugar is expressed in mg/ml. For example, 35 mg/ml of sugar is equivalent to 3.5% (w/v).

In some embodiments, a formulation comprises 1-15% (w/v) sugar. In some embodiments, a formulation comprises 3-12% (w/v) sugar. In some embodiments, a formulation comprises 3.5-7% (w/v) sugar. In some embodiments, a formulation comprises 4-8% (w/v) sugar. In some embodiments, a formulation comprises 5-7% (w/v) sugar. In some embodiments, a formulation comprises 5-8% (w/v) sugar. In some embodiments, a formulation comprises 1% (w/v) sugar. In some embodiments, a formulation comprises 2% (w/v) sugar. In some embodiments, a formulation comprises 3% (w/v) sugar. In some embodiments, a formulation comprises 3.5% (w/v) sugar. In some embodiments, a formulation comprises 4% (w/v) sugar. In some embodiments, a formulation comprises 5% (w/v) sugar. In some embodiments, a formulation comprises 6% (w/v) sugar. In some embodiments, a formulation comprises 7% (w/v) sugar. In some embodiments, a formulation comprises 8% (w/v) sugar. In some embodiments, a formulation comprises 9% (w/v) sugar. In some embodiments, a formulation comprises 10% (w/v) sugar. In some embodiments, a formulation comprises 11% (w/v) sugar. In some embodiments, a formulation comprises 12% (w/v) sugar. In some embodiments, a formulation comprises 13% (w/v) sugar. In some embodiments, a formulation comprises 14% (w/v) sugar. In some embodiments, a formulation comprises 15% (w/v) sugar. In some embodiments, a formulation comprises 16% (w/v) sugar. In some embodiments, a formulation comprises 17% (w/v) sugar. In some embodiments, a formulation comprises 18% (w/v) sugar. In some embodiments, a formulation comprises 19% (w/v) sugar. In some embodiments, a formulation comprises 20% (w/v) sugar.

In some embodiments, a formulation comprises 1-15% (w/v) sucrose. In some embodiments, a formulation comprises 3-12% (w/v) sucrose. In some embodiments, a formulation comprises 3.5-7% (w/v) sucrose. In some embodiments, a formulation comprises 4-8% (w/v) sucrose. In some embodiments, a formulation comprises 5-7% (w/v) sucrose. In some embodiments, a formulation comprises 5-8% (w/v) sucrose. In some embodiments, a formulation comprises 1% (w/v) sucrose. In some embodiments, a formulation comprises 2% (w/v) sucrose. In some embodiments, a formulation comprises 3% (w/v) sucrose. In some embodiments, a formulation comprises 3.5% (w/v) sucrose. In some embodiments, a formulation comprises 4% (w/v) sucrose. In some embodiments, a formulation comprises 5% (w/v) sucrose. In some embodiments, a formulation comprises 6% (w/v) sucrose. In some embodiments, a formulation comprises 7% (w/v) sucrose. In some embodiments, a formulation comprises 8% (w/v) sucrose. In some embodiments, a formulation comprises 9% (w/v) sucrose. In some embodiments, a formulation comprises 10% (w/v) sucrose. In some embodiments, a formulation comprises 11% (w/v) sucrose. In some embodiments, a formulation comprises 12% (w/v) sucrose. In some embodiments, a formulation comprises 13% (w/v) sucrose. In some embodiments, a formulation comprises 14% (w/v) sucrose. In some embodiments, a formulation comprises 15% (w/v) sucrose. In some embodiments, a formulation comprises 16% (w/v) sucrose. In some embodiments, a formulation comprises 17% (w/v) sucrose. In some embodiments, a formulation comprises 18% (w/v) sucrose. In some embodiments, a formulation comprises 19% (w/v) sucrose. In some embodiments, a formulation comprises 20% (w/v) sucrose.

In some embodiments, a formulation comprises 1-15% (w/v) trehalose. In some embodiments, a formulation comprises 3-12% (w/v) trehalose. In some embodiments, a formulation comprises 4-8% (w/v) trehalose. In some embodiments, a formulation comprises 5-7% (w/v) trehalose. In some embodiments, a formulation comprises 1% (w/v) trehalose. In some embodiments, a formulation comprises 2% (w/v) trehalose. In some embodiments, a formulation comprises 3% (w/v) trehalose. In some embodiments, a formulation comprises 4% (w/v) trehalose. In some embodiments, a formulation comprises 5% (w/v) trehalose. In some embodiments, a formulation comprises 6% (w/v) trehalose. In some embodiments, a formulation comprises 7% (w/v) trehalose. In some embodiments, a formulation comprises 8% (w/v) trehalose. In some embodiments, a formulation comprises 9% (w/v) trehalose. In some embodiments, a formulation comprises 10% (w/v) trehalose. In some embodiments, a formulation comprises 11% (w/v) trehalose. In some embodiments, a formulation comprises 12% (w/v) trehalose. In some embodiments, a formulation comprises 13% (w/v) trehalose. In some embodiments, a formulation comprises 14% (w/v) trehalose. In some embodiments, a formulation comprises 15% (w/v) trehalose. In some embodiments, a formulation comprises 16% (w/v) trehalose. In some embodiments, a formulation comprises 17% (w/v) trehalose. In some embodiments, a formulation comprises 18% (w/v) trehalose. In some embodiments, a formulation comprises 19% (w/v) trehalose. In some embodiments, a formulation comprises 20% (w/v) trehalose.

In some embodiments, a formulation comprises 1-15% (w/v) maltose. In some embodiments, a formulation comprises 3-12% (w/v) maltose. In some embodiments, a formulation comprises 4-8% (w/v) maltose. In some embodiments, a formulation comprises 5-7% (w/v) maltose. In some embodiments, a formulation comprises 1% (w/v)

maltose. In some embodiments, a formulation comprises 2% (w/v) maltose. In some embodiments, a formulation comprises 3% (w/v) maltose. In some embodiments, a formulation comprises 4% (w/v) maltose. In some embodiments, a formulation comprises 5% (w/v) maltose. In some embodiments, a formulation comprises 6% (w/v) maltose. In some embodiments, a formulation comprises 7% (w/v) maltose. In some embodiments, a formulation comprises 8% (w/v) maltose. In some embodiments, a formulation comprises 9% (w/v) maltose. In some embodiments, a formulation comprises 10% (w/v) maltose. In some embodiments, a formulation comprises 11% (w/v) maltose. In some embodiments, a formulation comprises 12% (w/v) maltose. In some embodiments, a formulation comprises 13% (w/v) maltose. In some embodiments, a formulation comprises 14% (w/v) maltose. In some embodiments, a formulation comprises 15% (w/v) maltose. In some embodiments, a formulation comprises 16% (w/v) maltose. In some embodiments, a formulation comprises 17% (w/v) maltose. In some embodiments, a formulation comprises 18% (w/v) maltose. In some embodiments, a formulation comprises 19% (w/v) maltose. In some embodiments, a formulation comprises 20% (w/v) maltose.

In some embodiments, a formulation comprises 1-15% (w/v) polyol. In some embodiments, a formulation comprises 3-12% (w/v) polyol. In some embodiments, a formulation comprises 4-8% (w/v) polyol. In some embodiments, a formulation comprises 5-7% (w/v) polyol. In some embodiments, a formulation comprises 1% (w/v) polyol. In some embodiments, a formulation comprises 2% (w/v) polyol. In some embodiments, a formulation comprises 3% (w/v) polyol. In some embodiments, a formulation comprises 4% (w/v) polyol. In some embodiments, a formulation comprises 5% (w/v) polyol. In some embodiments, a formulation comprises 6% (w/v) polyol. In some embodiments, a formulation comprises 7% (w/v) polyol. In some embodiments, a formulation comprises 8% (w/v) polyol. In some embodiments, a formulation comprises 9% (w/v) polyol. In some embodiments, a formulation comprises 10% (w/v) polyol. In some embodiments, a formulation comprises 11% (w/v) polyol. In some embodiments, a formulation comprises 12% (w/v) polyol. In some embodiments, a formulation comprises 13% (w/v) polyol. In some embodiments, a formulation comprises 14% (w/v) polyol. In some embodiments, a formulation comprises 15% (w/v) polyol. In some embodiments, a formulation comprises 16% (w/v) polyol. In some embodiments, a formulation comprises 17% (w/v) polyol. In some embodiments, a formulation comprises 18% (w/v) polyol. In some embodiments, a formulation comprises 19% (w/v) polyol. In some embodiments, a formulation comprises 20% (w/v) polyol. In some embodiments, a polyol is sorbitol. In some embodiments, a polyol is mannitol. In some embodiments, a polyol is glycerol.

Surfactants

In some embodiments, a formulation comprises a surfactant. In some embodiments, a surfactant is a polysorbate-20. In some embodiments, a surfactant is a polysorbate-80. In some embodiments, a surfactant is a poloxamer 188.

In some embodiments, a formulation comprises 0.005-2% (w/v) surfactant. In some embodiments, the concentration of surfactant is expressed in mg/ml. One of a person skilled in the art would be able to convert mg/ml to w/v %.

In some embodiments, a formulation comprises 0.01-1.0% (w/v) surfactant. In some embodiments, a formulation comprises 0.02-0.5% (w/v) surfactant. In some embodiments, a formulation comprises 0.02-0.1% (w/v) surfactant. In some embodiments, a formulation comprises 0.01-0.1%

(w/v) surfactant. In some embodiments, a formulation comprises 0.01-0.05% (w/v) surfactant. In some embodiments, a formulation comprises 0.02-0.05% (w/v) surfactant. In some embodiments, a formulation comprises 0.005% (w/v) surfactant. In some embodiments, a formulation comprises 0.01% (w/v) surfactant. In some embodiments, a formulation comprises 0.015% (w/v) surfactant. In some embodiments, a formulation comprises 0.02% (w/v) surfactant. In some embodiments, a formulation comprises 0.03% (w/v) surfactant. In some embodiments, a formulation comprises 0.04% (w/v) surfactant. In some embodiments, a formulation comprises 0.05% (w/v) surfactant. In some embodiments, a formulation comprises 0.06% (w/v) surfactant. In some embodiments, a formulation comprises 0.07% (w/v) surfactant. In some embodiments, a formulation comprises 0.08% (w/v) surfactant. In some embodiments, a formulation comprises 0.09% (w/v) surfactant. In some embodiments, a formulation comprises 0.10% (w/v) surfactant. In some embodiments, a formulation comprises 0.11% (w/v) surfactant. In some embodiments, a formulation comprises 0.12% (w/v) surfactant. In some embodiments, a formulation comprises 0.13% (w/v) surfactant. In some embodiments, a formulation comprises 0.14% (w/v) surfactant. In some embodiments, a formulation comprises 0.15% (w/v) surfactant. In some embodiments, a formulation comprises 0.16% (w/v) surfactant. In some embodiments, a formulation comprises 0.17% (w/v) surfactant. In some embodiments, a formulation comprises 0.18% (w/v) surfactant. In some embodiments, a formulation comprises 0.19% (w/v) surfactant. In some embodiments, a formulation comprises 0.2% (w/v) surfactant. In some embodiments, a formulation comprises 0.25% (w/v) surfactant. In some embodiments, a formulation comprises 0.3% (w/v) surfactant. In some embodiments, a formulation comprises 0.4% (w/v) surfactant. In some embodiments, a formulation comprises 0.5% (w/v) surfactant. In some embodiments, a formulation comprises 0.6% (w/v) surfactant. In some embodiments, a formulation comprises 0.7% (w/v) surfactant. In some embodiments, a formulation comprises 0.8% (w/v) surfactant. In some embodiments, a formulation comprises 0.9% (w/v) surfactant. In some embodiments, a formulation comprises 1.0% (w/v) surfactant. In some embodiments, a formulation comprises 1.2% (w/v) surfactant. In some embodiments, a formulation comprises 1.5% (w/v) surfactant. In some embodiments, a formulation comprises 1.8% (w/v) surfactant. In some embodiments, a formulation comprises 2.0% (w/v) surfactant.

In some embodiments, a formulation comprises 0.01-1.0% (w/v) polysorbate-20. In some embodiments, a formulation comprises 0.02-0.5% (w/v) polysorbate-20. In some embodiments, a formulation comprises 0.02-0.1% (w/v) polysorbate-20. In some embodiments, a formulation comprises 0.01-0.1% (w/v) polysorbate-20. In some embodiments, a formulation comprises 0.01-0.05% (w/v) polysorbate-20. In some embodiments, a formulation comprises 0.02-0.05% (w/v) polysorbate-20. In some embodiments, a formulation comprises 0.005% (w/v) polysorbate-20. In some embodiments, a formulation comprises 0.01% (w/v) polysorbate-20. In some embodiments, a formulation comprises 0.015% (w/v) polysorbate-20. In some embodiments, a formulation comprises 0.02% (w/v) polysorbate-20. In some embodiments, a formulation comprises 0.03% (w/v) polysorbate-20. In some embodiments, a formulation comprises 0.04% (w/v) polysorbate-20. In some embodiments, a formulation comprises 0.05% (w/v) polysorbate-20. In some embodiments, a formulation comprises 0.06% (w/v) polysorbate-20. In some embodiments, a formulation comprises 0.07% (w/v) polysorbate-20. In some embodiments, a formulation comprises 0.08% (w/v) polysorbate-20. In some embodiments, a formulation comprises 0.09% (w/v) polysorbate-20. In some embodiments, a formulation comprises 0.10% (w/v) polysorbate-20. In some embodiments, a formulation comprises 0.11% (w/v) polysorbate-20. In some embodiments, a formulation comprises 0.12% (w/v) polysorbate-20. In some embodiments, a formulation comprises 0.13% (w/v) polysorbate-20. In some embodiments, a formulation comprises 0.14% (w/v) polysorbate-20. In some embodiments, a formulation comprises 0.15% (w/v) polysorbate-20. In some embodiments, a formulation comprises 0.16% (w/v) polysorbate-20. In some embodiments, a formulation comprises 0.17% (w/v) polysorbate-20. In some embodiments, a formulation comprises 0.18% (w/v) polysorbate-20. In some embodiments, a formulation comprises 0.19% (w/v) polysorbate-20. In some embodiments, a formulation comprises 0.2% (w/v) polysorbate-20. In some embodiments, a formulation comprises 0.25% (w/v) polysorbate-20. In some embodiments, a formulation comprises 0.3% (w/v) polysorbate-20. In some embodiments, a formulation comprises 0.4% (w/v) polysorbate-20. In some embodiments, a formulation comprises 0.5% (w/v) polysorbate-20. In some embodiments, a formulation comprises 0.6% (w/v) polysorbate-20. In some embodiments, a formulation comprises 0.7% (w/v) polysorbate-20. In some embodiments, a formulation comprises 0.8% (w/v) polysorbate-20. In some embodiments, a formulation comprises 0.9% (w/v) polysorbate-20. In some embodiments, a formulation comprises 1.0% (w/v) polysorbate-20. In some embodiments, a formulation comprises 1.2% (w/v) polysorbate-20. In some embodiments, a formulation comprises 1.5% (w/v) polysorbate-20. In some embodiments, a formulation comprises 1.8% (w/v) polysorbate-20. In some embodiments, a formulation comprises 2.0% (w/v) polysorbate-20.

In some embodiments, a formulation comprises 0.01-1.0% (w/v) polysorbate-80. In some embodiments, a formulation comprises 0.02-0.5% (w/v) polysorbate-80. In some embodiments, a formulation comprises 0.02-0.1% (w/v) polysorbate-80. In some embodiments, a formulation comprises 0.01-0.1% (w/v) polysorbate-80. In some embodiments, a formulation comprises 0.01-0.05% (w/v) polysorbate-80. In some embodiments, a formulation comprises 0.02-0.05% (w/v) polysorbate-80. In some embodiments, a formulation comprises 0.005% (w/v) polysorbate-80. In some embodiments, a formulation comprises 0.01% (w/v) polysorbate-80. In some embodiments, a formulation comprises 0.015% (w/v) polysorbate-80. In some embodiments, a formulation comprises 0.02% (w/v) polysorbate-80. In some embodiments, a formulation comprises 0.03% (w/v) polysorbate-80. In some embodiments, a formulation comprises 0.04% (w/v) polysorbate-80. In some embodiments, a formulation comprises 0.05% (w/v) polysorbate-80. In some embodiments, a formulation comprises 0.06% (w/v) polysorbate-80. In some embodiments, a formulation comprises 0.07% (w/v) polysorbate-80. In some embodiments, a formulation comprises 0.08% (w/v) polysorbate-80. In some embodiments, a formulation comprises 0.09% (w/v) polysorbate-80. In some embodiments, a formulation comprises 0.10% (w/v) polysorbate-80. In some embodiments, a formulation comprises 0.11% (w/v) polysorbate-80. In some embodiments, a formulation comprises 0.12% (w/v) polysorbate-80. In some embodiments, a formulation comprises 0.13% (w/v) polysorbate-80. In some embodiments, a formulation comprises 0.14% (w/v) polysorbate-20. In some embodiments, a formulation comprises 0.15% (w/v) polysorbate-80. In some embodiments, a formulation comprises 0.16% (w/v) polysorbate-80. In some embodiments, a formulation comprises 0.17% (w/v) polysorbate-80. In some embodiments, a formulation comprises 0.18% (w/v) polysorbate-80. In some embodiments, a formulation comprises 0.19% (w/v) polysorbate-80. In some embodiments, a formulation comprises 0.2% (w/v) polysorbate-80. In some embodiments, a formulation comprises 0.25% (w/v) polysorbate-80. In some embodiments, a formulation comprises 0.3% (w/v) polysorbate-80. In some embodiments, a formulation comprises 0.4% (w/v) polysorbate-80. In some embodiments, a formulation comprises 0.5% (w/v) polysorbate-80. In some embodiments, a formulation comprises 0.6% (w/v) polysorbate-80. In some embodiments, a formulation comprises 0.7% (w/v) polysorbate-80. In some embodiments, a formulation comprises 0.8% (w/v) polysorbate-80. In some embodiments, a formulation comprises 0.9% (w/v) polysorbate-80. In some embodiments, a formulation comprises 1.0% (w/v) polysorbate-80. In some embodiments, a formulation comprises 1.2% (w/v) polysorbate-80. In some embodiments, a formulation comprises 1.5% (w/v) polysorbate-80. In some embodiments, a formulation comprises 1.8% (w/v) polysorbate-80. In some embodiments, a formulation comprises 2.0% (w/v) polysorbate-80.

In some embodiments, a formulation comprises 0.01-1.0% (w/v) poloxamer-188. In some embodiments, a formulation comprises 0.02-0.5% (w/v) poloxamer-188. In some embodiments, a formulation comprises 0.02-0.1% (w/v) poloxamer-188. In some embodiments, a formulation comprises 0.01-0.1% (w/v) poloxamer-188. In some embodiments, a formulation comprises 0.01-0.05% (w/v) poloxamer-188. In some embodiments, a formulation comprises 0.02-0.05% (w/v) poloxamer-188. In some embodiments, a formulation comprises 0.005% (w/v) poloxamer-188. In some embodiments, a formulation comprises 0.01% (w/v) poloxamer-188. In some embodiments, a formulation comprises 0.015% (w/v) poloxamer-188. In some embodiments, a formulation comprises 0.02% (w/v) poloxamer-188. In some embodiments, a formulation comprises 0.03% (w/v) poloxamer-188. In some embodiments, a formulation comprises 0.04% (w/v) poloxamer-188. In some embodiments, a formulation comprises 0.05% (w/v) poloxamer-188. In some embodiments, a formulation comprises 0.06% (w/v) poloxamer-188. In some embodiments, a formulation comprises 0.07% (w/v) poloxamer-188. In some embodiments, a formulation comprises 0.08% (w/v) poloxamer-188. In some embodiments, a formulation comprises 0.09% (w/v) poloxamer-188. In some embodiments, a formulation comprises 0.10% (w/v) poloxamer-188. In some embodiments, a formulation comprises 0.11% (w/v) poloxamer-188. In some embodiments, a formulation comprises 0.12% (w/v) poloxamer-188. In some embodiments, a formulation comprises 0.13% (w/v) poloxamer-188. In some embodiments, a formulation comprises 0.14% (w/v) poloxamer-188. In some embodiments, a formulation comprises 0.15% (w/v) poloxamer-188. In some embodiments, a formulation comprises 0.16% (w/v) poloxamer-188. In some embodiments, a formulation comprises 0.17% (w/v) poloxamer-188. In some embodiments, a formulation comprises 0.18% (w/v) poloxamer-188. In some embodiments, a formulation comprises 0.19% (w/v) poloxamer-188. In some embodiments, a formulation comprises 0.2% (w/v) poloxamer-188. In some embodiments, a formulation comprises 0.25% (w/v) poloxamer-188. In some embodiments, a formulation comprises 0.3% (w/v) poloxamer-188. In some embodiments, a formulation comprises 0.4% (w/v) poloxamer-188. In some embodiments, a formulation comprises 0.5% (w/v) polox-amer-188. In some embodiments, a formulation comprises 0.6% (w/v) poloxamer-188. In some embodiments, a for-mulation comprises 0.7% (w/v) poloxamer-188. In some embodiments, a formulation comprises 0.8% (w/v) polox-amer-188. In some embodiments, a formulation comprises 0.9% (w/v) poloxamer-188. In some embodiments, a for-mulation comprises 1.0% (w/v) poloxamer-188. In some embodiments, a formulation comprises 1.2% (w/v) polox-amer-188. In some embodiments, a formulation comprises 1.5% (w/v) poloxamer-188. In some embodiments, a for-mulation comprises 1.8% (w/v) poloxamer-188. In some embodiments, a formulation comprises 2.0% (w/v) polox-amer-188.

Stability and Properties of Antibody Formulation

In some embodiments of the invention, formulations were optimized in order to increase stability. The stability of an antibody formulation can be quantified in several ways. In some embodiments, stability of an antibody formulation is characterized by the amount of HMW species of an anti-IL1R1 antibody or the rate of increase of the amount of HMW species of an anti-IL1R1 antibody. In certain embodi-ments, the rate of increase of HMW species is determined at 2, 4, 6 or 8 weeks in storage and at approximately 5° C., 25° C. or 40° C. In some embodiments, stability of an antibody formulation is characterized by charge distribution, e.g., a change in the amount of the charge variant peaks of the antibody. In some embodiments, stability of an antibody formulation is characterized by dynamic light scattering, analytical ultracentrifugation (AUC), field flow fraction-ation (FFF), isoelectric focusing and ion exchange chroma-tography (IEX). In some embodiments, stability of an anti-body formulation is characterized by partial dissociation as measured by sodium-dodecyl sulfate capillary electropho-resis (CE-SDS) and/or sodium-dodecyl sulfate polyacrylam-ide gel electrophoresis (SDS-PAGE).

The stability of an anti-IL1R1 antibody, and the capability of the formulation to maintain stability of the anti-IL1R1 antibody, may be assessed over extended periods of time (e.g., weeks or months). In the context of a formulation, a stable formulation is one in which the antibody therein essentially retains its physical and/or chemical integrity and biological activity upon storage and during processes such as freeze/thaw, mechanical mixing and lyophilization. Anti-body stability can be measured by formation of high molecular weight (HMW) aggregates, shift of charge pro-files, and change in particle size.

Stability of an antibody may be assessed relative to the biological activity or physiochemical integrity of the anti-body over extended periods of time. For example, stability at a given time point may be compared against stability at an earlier time point (e.g., upon formulation day 0), against unformulated antibody, or against a differently formulated antibody and the results of this comparison expressed as a percentage. Preferably, the antibody formulations of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the antibody's biological activity, physiochemical integrity, and/or particle size over an extended period of time (e.g., as measured over at least about 1, 2, 3, 4, 5, 6, 7, 8, 9, 10, 11, 12, 18, 24, or 36 months, at room temperature or under accelerated storage conditions). In some embodiments, the percent values indi-cating protein levels as disclosed herein or throughout the specification, are expressed relative to the total protein in the formulation. In some embodiments, the relative values of any particular species of the product, as disclosed herein or throughout the specification, such as the monomeric IgG form or species, or the high molecular weight (HMW) form, or the aggregated forms, are expressed in relation to the total value of the total product.

High-Molecular Weight (HMW) Species

In some embodiments, less than 55%, 50%, 40%, 30%, 20%, 10%, 9%, 8%, 7%, 6%, 5%, 4%, 3%, 2%, 1.5%, 1%, or 0.5% of an anti-IL1R1 antibody exists as HMW species in a formulation upon storage at 5° C. for at least 4 weeks, at least 6 weeks, at least 2 months, at least 3 months, at least 4 months, at least 6 months, at least 8 months, at least 10 months, or at least 12 months. In some embodiments, less than 10% of an anti-IL1R1 antibody exists as HMW species in a formulation upon storage at 5° C. for at least 4 weeks. In some embodiments, less than 8% of an anti-IL1R1 antibody exists as HMW species in a formulation upon storage at 5° C. for at least 4 weeks. In some embodiments, less than 6% of an anti-IL1R1 antibody exists as HMW species in a formulation upon storage at 5° C. for at least 4 weeks. In some embodiments, less than 5% of an anti-IL1R1 antibody exists as HMW species in a formulation upon storage at 5° C. for at least 4 weeks. In some embodiments, less than 4% of an anti-IL1R1 antibody exists as HMW species in a formulation upon storage at 5° C. for at least 4 weeks. In some embodiments, less than 3% of an anti-IL1R1 antibody exists as HMW species in a formulation upon storage at 5° C. for at least 4 weeks. In some embodiments, less than 2.6% of an anti-IL1R1 antibody exists as HMW species in a formulation upon storage at 5° C. for at least 4 weeks. In some embodiments, less than 2.5% of an anti-IL1R1 antibody exists as HMW species in a formulation upon storage at 5° C. for at least 4 weeks. In some embodi-ments, less than 2.4% of an anti-IL1R1 antibody exists as HMW species in a formulation upon storage at 5° C. for at least 4 weeks. In some embodiments, less than 2.3% of an anti-IL1R1 antibody exists as HMW species in a formula-tion upon storage at 5° C. for at least 4 weeks. In some embodiments, less than 2.2% of an anti-IL1R1 antibody exists as HMW species in a formulation upon storage at 5° C. for at least 4 weeks. In some embodiments, less than 2.1% of an anti-IL1R1 antibody exists as HMW species in a formulation upon storage at 5° C. for at least 4 weeks. In some embodiments, less than 2% of an anti-IL1R1 antibody exists as HMW species in a formulation upon storage at 5° C. for at least 4 weeks. In some embodiments, less than 1.5% of an anti-IL1R1 antibody exists as HMW species in a formulation upon storage at 5° C. for at least 4 weeks. In some embodiments, less than 1% of an anti-IL1R1 antibody exists as HMW species in a formulation upon storage at 5° C. for at least 4 weeks. In some embodiments, less than 0.5% of an anti-IL1R1 antibody exists as HMW species in a formulation upon storage at 5° C. for at least 4 weeks. In some embodiments, less than 0.4% of an anti-IL1R1 anti-body exists as HMW species in a formulation upon storage at 5° C. for at least 4 weeks. In some embodiments, less than 0.3% of an anti-IL1R1 antibody exists as HMW species in a formulation upon storage at 5° C. for at least 4 weeks. In some embodiments, less than 0.2% of an anti-IL1R1 anti-body exists as HMW species in a formulation upon storage at 5° C. for at least 4 weeks. In some embodiments, less than 0.1% of an anti-IL1R1 antibody exists as HMW species in a formulation upon storage at 5° C. for at least 4 weeks. In some embodiments, the formulation is substantially free of HMW species upon storage at 5° C. for at least 4 weeks.

In some embodiments, less than 10% of an anti-IL1R1 antibody exists as HMW species in a formulation upon storage at 5° C. for at least 2 months. In some embodiments, less than 8% of an anti-IL1R1 antibody exists as HMW species in a formulation upon storage at 5° C. for at least 2 months. In some embodiments, less than 6% of an anti-IL1R1 antibody exists as HMW species in a formulation upon storage at 5° C. for at least 2 months. In some embodiments, less than 5% of an anti-IL1R1 antibody exists as HMW species in a formulation upon storage at 5° C. for at least 2 months. In some embodiments, less than 4% of an anti-IL1R1 antibody exists as HMW species in a formulation upon storage at 5° C. for at least 2 months. In some embodiments, less than 3% of an anti-IL1R1 antibody exists as HMW species in a formulation upon storage at 5° C. for at least 2 months. In some embodiments, less than 2.9% of an anti-IL1R1 antibody exists as HMW species in a formulation upon storage at 5° C. for at least 2 months. In some embodiments, less than 2.8% of an anti-IL1R1 antibody exists as HMW species in a formulation upon storage at 5° C. for at least 2 months. In some embodiments, less than 2.7% of an anti-IL1R1 antibody exists as HMW species in a formulation upon storage at 5° C. for at least 2 months. In some embodiments, less than 2.6% of an anti-IL1R1 antibody exists as HMW species in a formulation upon storage at 5° C. for at least 2 months. In some embodiments, less than 2.5% of an anti-IL1R1 antibody exists as HMW species in a formulation upon storage at 5° C. for at least 2 months. In some embodiments, less than 2.4% of an anti-IL1R1 antibody exists as HMW species in a formulation upon storage at 5° C. for at least 2 months. In some embodiments, less than 2.3% of an anti-IL1R1 antibody exists as HMW species in a formulation upon storage at 5° C. for at least 2 months. In some embodiments, less than 2.2% of an anti-IL1R1 antibody exists as HMW species in a formulation upon storage at 5° C. for at least 2 months. In some embodiments, less than 2.1% of an anti-IL1R1 antibody exists as HMW species in a formulation upon storage at 5° C. for at least 2 months. In some embodiments, less than 2% of an anti-IL1R1 antibody exists as HMW species in a formulation upon storage at 5° C. for at least 2 months. In some embodiments, less than 1% of an anti-IL1R1 antibody exists as HMW species in a formulation upon storage at 5° C. for at least 2 months. In some embodiments, less than 0.5% of an anti-IL1R1 antibody exists as HMW species in a formulation upon storage at 5° C. for at least 2 months. In some embodiments, less than 0.4% of an anti-IL1R1 antibody exists as HMW species in a formulation upon storage at 5° C. for at least 2 months. In some embodiments, less than 0.3% of an anti-IL1R1 antibody exists as HMW species in a formulation upon storage at 5° C. for at least 2 months. In some embodiments, less than 0.2% of an anti-IL1R1 antibody exists as HMW species in a formulation upon storage at 5° C. for at least 2 months. In some embodiments, less than 0.1% of an anti-IL1R1 antibody exists as HMW species in a formulation upon storage at 5° C. for at least 2 months. In some embodiments, the formulation is substantially free of HMW species upon storage at 5° C. for at least 2 months.

In some embodiments, 5% or less of an anti-IL1R1 antibody exists as HMW species in a formulation upon storage at 5° C. for 3 months. In some embodiments, 4% or less of an anti-IL1R1 antibody exists as HMW species in a formulation upon storage at 5° C. for 3 months. In some embodiments, 4% or less of an anti-IL1R1 antibody exists as HMW species in a formulation upon storage at 5° C. for 3 months. In some embodiments, 3% or less of an anti-IL1R1 antibody exists as HMW species in a formulation upon storage at 5° C. for 3 months. In some embodiments, 2% or less of an anti-IL1R1 antibody exists as HMW species in a formulation upon storage at 5° C. for 3 months. In some embodiments, 1.5% or less of an anti-IL1R1 antibody exists as HMW species in a formulation upon storage at 5° C. for 3 months. In some embodiments, 1% or less of an anti-IL1R1 antibody exists as HMW species in a formulation upon storage at 5° C. for 3 months.

In some embodiments, 5% or less of an anti-IL1R1 antibody exists as HMW species in a formulation upon storage at 5° C. for 6 months. In some embodiments, 4% or less of an anti-IL1R1 antibody exists as HMW species in a formulation upon storage at 5° C. for 6 months. In some embodiments, 3% or less of an anti-IL1R1 antibody exists as HMW species in a formulation upon storage at 5° C. for 6 months. In some embodiments, less than 2% of an anti-IL1R1 antibody exists as HMW species in a formulation upon storage at 5° C. for 6 months. In some embodiments, 1% or less of an anti-IL1R1 antibody exists as HMW species in a formulation upon storage at 5° C. for 6 months.

In some embodiments, less than 10%, 8%, 5%, 4%, 3%, 2.5%, 2%, 1%, or 0.5% of an anti-IL1R1 antibody exists as HMW species in a formulation upon storage at 25° C. for at least 4 weeks, at least 6 weeks, at least 2 months, at least 3 months, at least 4 months, at least 6 months, at least 8 months, at least 10 months, or at least 12 months. In some embodiments, less than 10% of an anti-IL1R1 antibody exists as HMW species in a formulation upon storage at 25° C. for at least 4 weeks. In some embodiments, less than 8% of an anti-IL1R1 antibody exists as HMW species in a formulation upon storage at 25° C. for at least 4 weeks. In some embodiments, less than 6% of an anti-IL1R1 antibody exists as HMW species in a formulation upon storage at 25° C. for at least 4 weeks. In some embodiments, less than 5% of an anti-IL1R1 antibody exists as HMW species in a formulation upon storage at 25° C. for at least 4 weeks. In some embodiments, less than 4% of an anti-IL1R1 antibody exists as HMW species in a formulation upon storage at 25° C. for at least 4 weeks. In some embodiments, less than 3.5% of an anti-IL1R1 antibody exists as HMW species in a formulation upon storage at 25° C. for at least 4 weeks. In some embodiments, less than 3.4% of an anti-IL1R1 antibody exists as HMW species in a formulation upon storage at 25° C. for at least 4 weeks. In some embodiments, less than 3.3% of an anti-IL1R1 antibody exists as HMW species in a formulation upon storage at 25° C. for at least 4 weeks. In some embodiments, less than 3.2% of an anti-IL1R1 antibody exists as HMW species in a formulation upon storage at 25° C. for at least 4 weeks. In some embodiments, less than 3.1% of an anti-IL1R1 antibody exists as HMW species in a formulation upon storage at 25° C. for at least 4 weeks. In some embodiments, less than 3% of an anti-IL1R1 antibody exists as HMW species in a formulation upon storage at 25° C. for at least 4 weeks. In some embodiments, less than 2.9% of an anti-IL1R1 antibody exists as HMW species in a formulation upon storage at 25° C. for at least 4 weeks. In some embodiments, less than 2.8% of an anti-IL1R1 antibody exists as HMW species in a formulation upon storage at 25° C. for at least 4 weeks. In some embodiments, less than 2.7% of an anti-IL1R1 antibody exists as HMW species in a formulation upon storage at 25° C. for at least 4 weeks. In some embodiments, less than 2.6% of an anti-IL1R1 antibody exists as HMW species in a formulation upon storage at 25° C. for at least 4 weeks. In some embodiments, less than 2.5% of an anti-IL1R1 antibody exists as HMW species in a formulation upon storage at 25° C. for at least 4 weeks. In some embodiments, less than 2.4% of an anti-IL1R1 antibody exists as HMW species in a formulation upon storage at 25° C. for at least 4 weeks. In some embodiments, less than 2.3% of an anti-IL1R1 antibody exists as HMW species in a formulation upon storage at 25° C. for at least 4 weeks. In some embodiments, less than 2.2% of an anti-IL1R1 antibody exists as HMW species in a formulation upon storage at 25° C. for at least 4 weeks. In some embodiments, less than 2.1% of an anti-IL1R1 antibody exists as HMW species in a formulation upon storage at 25° C. for at least 4 weeks. In some embodiments, less than 2% of an anti-IL1R1 antibody exists as HMW species in a formulation upon storage at 25° C. for at least 4 weeks. In some embodiments, less than 1.8% of an anti-IL1R1 antibody exists as HMW species in a formulation upon storage at 25° C. for at least 4 weeks. In some embodiments, less than 1.5% of an anti-IL1R1 antibody exists as HMW species in a formulation upon storage at 25° C. for at least 4 weeks. In some embodiments, less than 1% of an anti-IL1R1 antibody exists as HMW species in a formulation upon storage at 25° C. for at least 4 weeks. In some embodiments, less than 0.5% of an anti-IL1R1 antibody exists as HMW species in a formulation upon storage at 25° C. for at least 4 weeks. In some embodiments, less than 0.4% of an anti-IL1R1 antibody exists as HMW species in a formulation upon storage at 25° C. for at least 4 weeks. In some embodiments, less than 0.3% of an anti-IL1R1 antibody exists as HMW species in a formulation upon storage at 25° C. for at least 4 weeks. In some embodiments, less than 0.2% of an anti-IL1R1 antibody exists as HMW species in a formulation upon storage at 25° C. for at least 4 weeks. In some embodiments, less than 0.1% of an anti-IL1R1 antibody exists as HMW species in a formulation upon storage at 25° C. for at least 4 weeks. In some embodiments, the formulation is substantially free of HMW species upon storage at 25° C. for at least 4 weeks.

In some embodiments, less than 10% of an anti-IL1R1 antibody exists as HMW species in a formulation upon storage at 25° C. for at least 2 months. In some embodiments, less than 8% of an anti-IL1R1 antibody exists as HMW species in a formulation upon storage at 25° C. for at least 2 months. In some embodiments, less than 6% of an anti-IL1R1 antibody exists as HMW species in a formulation upon storage at 25° C. for at least 2 months. In some embodiments, less than 5% of an anti-IL1R1 antibody exists as HMW species in a formulation upon storage at 25° C. for at least 2 months. In some embodiments, less than 4.5% of an anti-IL1R1 antibody exists as HMW species in a formulation upon storage at 25° C. for at least 2 months. In some embodiments, less than 4.4% of an anti-IL1R1 antibody exists as HMW species in a formulation upon storage at 25° C. for at least 2 months. In some embodiments, less than 4.3% of an anti-IL1R1 antibody exists as HMW species in a formulation upon storage at 25° C. for at least 2 months. In some embodiments, less than 4.2% of an anti-IL1R1 antibody exists as HMW species in a formulation upon storage at 25° C. for at least 2 months. In some embodiments, less than 4.1% of an anti-IL1R1 antibody exists as HMW species in a formulation upon storage at 25° C. for at least 2 months. In some embodiments, less than 4% of an anti-IL1R1 antibody exists as HMW species in a formulation upon storage at 25° C. for at least 2 months. In some embodiments, less than 3.9% of an anti-IL1R1 antibody exists as HMW species in a formulation upon storage at 25° C. for at least 2 months. In some embodiments, less than 3.8% of an anti-IL1R1 antibody exists as HMW species in a formulation upon storage at 25° C. for at least 2 months. In some embodiments, less than 3.7% of an anti-IL1R1 antibody exists as HMW species in a formulation upon storage at 25° C. for at least 2 months. In some embodiments, less than 3.6% of an anti-IL1R1 antibody exists as HMW species in a formulation upon storage at 25° C. for at least 2 months. In some embodiments, less than 3.5% of an anti-IL1R1 antibody exists as HMW species in a formulation upon storage at 25° C. for at least 2 months. In some embodiments, less than 3.4% of an anti-IL1R1 antibody exists as HMW species in a formulation upon storage at 25° C. for at least 2 months. In some embodiments, less than 3.3% of an anti-IL1R1 antibody exists as HMW species in a formulation upon storage at 25° C. for at least 2 months. In some embodiments, less than 3.2% of an anti-IL1R1 antibody exists as HMW species in a formulation upon storage at 25° C. for at least 2 months. In some embodiments, less than 3.1% of an anti-IL1R1 antibody exists as HMW species in a formulation upon storage at 25° C. for at least 2 months. In some embodiments, less than 3% of an anti-IL1R1 antibody exists as HMW species in a formulation upon storage at 25° C. for at least 2 months. In some embodiments, less than 2.9% of an anti-IL1R1 antibody exists as HMW species in a formulation upon storage at 25° C. for at least 2 months. In some embodiments, less than 2.8% of an anti-IL1R1 antibody exists as HMW species in a formulation upon storage at 25° C. for at least 2 months. In some embodiments, less than 2.7% of an anti-IL1R1 antibody exists as HMW species in a formulation upon storage at 25° C. for at least 2 months. In some embodiments, less than 2.6% of an anti-IL1R1 antibody exists as HMW species in a formulation upon storage at 25° C. for at least 2 months. In some embodiments, less than 2.5% of an anti-IL1R1 antibody exists as HMW species in a formulation upon storage at 25° C. for at least 2 months. In some embodiments, less than 2.4% of an anti-IL1R1 antibody exists as HMW species in a formulation upon storage at 25° C. for at least 2 months. In some embodiments, less than 2.3% of an anti-IL1R1 antibody exists as HMW species in a formulation upon storage at 25° C. for at least 2 months. In some embodiments, less than 2.2% of an anti-IL1R1 antibody exists as HMW species in a formulation upon storage at 25° C. for at least 2 months. In some embodiments, less than 2.1% of an anti-IL1R1 antibody exists as HMW species in a formulation upon storage at 25° C. for at least 2 months. In some embodiments, less than 2% of an anti-IL1R1 antibody exists as HMW species in a formulation upon storage at 25° C. for at least 2 months. In some embodiments, less than 1% of an anti-IL1R1 antibody exists as HMW species in a formulation upon storage at 25° C. for at least 2 months. In some embodiments, less than 0.5% of an anti-IL1R1 antibody exists as HMW species in a formulation upon storage at 25° C. for at least 2 months. In some embodiments, less than 0.4% of an anti-IL1R1 antibody exists as HMW species in a formulation upon storage at 25° C. for at least 2 months. In some embodiments, less than 0.3% of an anti-IL1R1 antibody exists as HMW species in a formulation upon storage at 25° C. for at least 2 months. In some embodiments, less than 0.2% of an anti-IL1R1 antibody exists as HMW species in a formulation upon storage at 25° C. for at least 2 months. In some embodiments, less than 0.1% of an anti-IL1R1 antibody exists as HMW species in a formulation upon storage at 25° C. for at least 2 months. In some embodiments, the formulation is substantially free of HMW species upon storage at 25° C. for at least 2 months.

In some embodiments, 5% or less of an anti-IL1R1 antibody exists as HMW species in a formulation upon storage at 25° C. for 3 months. In some embodiments, 4% or less of an anti-IL1R1 antibody exists as HMW species in a formulation upon storage at 25° C. for 3 months. In some embodiments, 3% or less of an anti-IL1R1 antibody exists as HMW species in a formulation upon storage at 25° C. for 3 months. In some embodiments, 2.5% or less of an anti-IL1R1 antibody exists as HMW species in a formulation upon storage at 25° C. for 3 months. In some embodiments, 2% or less of an anti-IL1R1 antibody exists as HMW species in a formulation upon storage at 25° C. for 3 months. In some embodiments, 1% or less of an anti-IL1R1 antibody exists as HMW species in a formulation upon storage at 25° C. for 3 months.

In some embodiments, 5% or less of an anti-IL1R1 antibody exists as HMW species in a formulation upon storage at 25° C. for 6 months. In some embodiments, 4% or less of an anti-IL1R1 antibody exists as HMW species in a formulation upon storage at 25° C. for 6 months. In some embodiments, less than 3% of an anti-IL1R1 antibody exists as HMW species in a formulation upon storage at 25° C. for 6 months. In some embodiments, 2.5% or less of an anti-IL1R1 antibody exists as HMW species in a formulation upon storage at 25° C. for 6 months. In some embodiments, 2% or less of an anti-IL1R1 antibody exists as HMW species in a formulation upon storage at 25° C. for 6 months. In some embodiments, 1% or less of an anti-IL1R1 antibody exists as HMW species in a formulation upon storage at 25° C. for 6 months.

In some embodiments, less than 10%, 8%, 5%, 4%, 3%, 2%, 1%, or 0.5% of an anti-IL1R1 antibody exists as HMW species in a formulation upon storage at 40° C. for at least 4 weeks, at least 6 weeks, at least 2 months, at least 3 months, at least 4 months, at least 6 months, at least 8 months, at least 10 months, or at least 12 months. In some embodiments, less than 50% of an anti-IL1R1 antibody exists as HMW species in a formulation upon storage at 40° C. for at least 4 weeks. In some embodiments, less than 40% of an anti-IL1R1 antibody exists as HMW species in a formulation upon storage at 40° C. for at least 4 weeks. In some embodiments, less than 39% of an anti-IL1R1 antibody exists as HMW species in a formulation upon storage at 40° C. for at least 4 weeks. In some embodiments, less than 38% of an anti-IL1R1 antibody exists as HMW species in a formulation upon storage at 40° C. for at least 4 weeks. In some embodiments, less than 37% of an anti-IL1R1 antibody exists as HMW species in a formulation upon storage at 40° C. for at least 4 weeks. In some embodiments, less than 36% of an anti-IL1R1 antibody exists as HMW species in a formulation upon storage at 40° C. for at least 4 weeks. In some embodiments, less than 35% of an anti-IL1R1 antibody exists as HMW species in a formulation upon storage at 40° C. for at least 4 weeks. In some embodiments, less than 30% of an anti-IL1R1 antibody exists as HMW species in a formulation upon storage at 40° C. for at least 4 weeks. In some embodiments, less than 25% of an anti-IL1R1 antibody exists as HMW species in a formulation upon storage at 40° C. for at least 4 weeks. In some embodiments, less than 20% of an anti-IL1R1 antibody exists as HMW species in a formulation upon storage at 40° C. for at least 4 weeks. In some embodiments, less than 15% of an anti-IL1R1 antibody exists as HMW species in a formulation upon storage at 40° C. for at least 4 weeks. In some embodiments, less than 14% of an anti-IL1R1 antibody exists as HMW species in a formulation upon storage at 40° C. for at least 4 weeks. In some embodiments, less than 13% of an anti-IL1R1 antibody exists as HMW species in a formulation upon storage at 40° C. for at least 4 weeks. In some embodiments, less than 12% of an anti-IL1R1 antibody exists as HMW species in a formulation upon storage at 40° C. for at least 4 weeks. In some embodiments, less than 11% of an anti-IL1R1 antibody exists as HMW species in a formulation upon storage at 40° C. for at least 4 weeks. In some embodiments, less than 10% of an anti-IL1R1 antibody exists as HMW species in a formulation upon storage at 40° C. for at least 4 weeks. In some embodiments, less than 9% of an anti-IL1R1 antibody exists as HMW species in a formulation upon storage at 40° C. for at least 4 weeks. In some embodiments, less than 8% of an anti-IL1R1 antibody exists as HMW species in a formulation upon storage at 40° C. for at least 4 weeks. In some embodiments, less than 8% of an anti-IL1R1 antibody exists as HMW species in a formulation upon storage at 40° C. for at least 4 weeks. In some embodiments, less than 7% of an anti-IL1R1 antibody exists as HMW species in a formulation upon storage at 40° C. for at least 4 weeks. In some embodiments, less than 6% of an anti-IL1R1 antibody exists as HMW species in a formulation upon storage at 40° C. for at least 4 weeks. In some embodiments, less than 5% of an anti-IL1R1 antibody exists as HMW species in a formulation upon storage at 40° C. for at least 4 weeks. In some embodiments, less than 4% of an anti-IL1R1 antibody exists as HMW species in a formulation upon storage at 40° C. for at least 4 weeks. In some embodiments, less than 3% of an anti-IL1R1 antibody exists as HMW species in a formulation upon storage at 40° C. for at least 4 weeks. In some embodiments, less than 2% of an anti-IL1R1 antibody exists as HMW species in a formulation upon storage at 40° C. for at least 4 weeks. In some embodiments, less than 1.5% of an anti-IL1R1 antibody exists as HMW species in a formulation upon storage at 40° C. for at least 4 weeks. In some embodiments, less than 1% of an anti-IL1R1 antibody exists as HMW species in a formulation upon storage at 40° C. for at least 4 weeks. In some embodiments, less than 0.5% of an anti-IL1R1 antibody exists as HMW species in a formulation upon storage at 40° C. for at least 4 weeks. In some embodiments, less than 0.5% of an anti-IL1R1 antibody exists as HMW species in a formulation upon storage at 40° C. for at least 4 weeks. In some embodiments, less than 0.3% of an anti-IL1R1 antibody exists as HMW species in a formulation upon storage at 40° C. for at least 4 weeks. In some embodiments, less than 0.2% of an anti-IL1R1 antibody exists as HMW species in a formulation upon storage at 40° C. for at least 4 weeks. In some embodiments, less than 0.1% of an anti-IL1R1 antibody exists as HMW species in a formulation upon storage at 40° C. for at least 4 weeks.

In some embodiments, less than 60% of an anti-IL1R1 antibody exists as HMW species in a formulation upon storage at 40° C. for at least 2 months. In some embodiments, less than 58% of an anti-IL1R1 antibody exists as HMW species in a formulation upon storage at 40° C. for at least 2 months. In some embodiments, less than 57% of an anti-IL1R1 antibody exists as HMW species in a formulation upon storage at 40° C. for at least 2 months. In some embodiments, less than 56% of an anti-IL1R1 antibody exists as HMW species in a formulation upon storage at 40° C. for at least 2 months. In some embodiments, less than 55% of an anti-IL1R1 antibody exists as HMW species in a formulation upon storage at 40° C. for at least 2 months. In some embodiments, less than 50% of an anti-IL1R1 antibody exists as HMW species in a formulation upon storage at 40° C. for at least 2 months. In some embodiments, less than 45% of an anti-IL1R1 antibody exists as HMW species in a formulation upon storage at 40° C. for at least 2 months. In some embodiments, less than 40% of an anti-IL1R1 antibody exists as HMW species in a formulation upon storage at 40° C. for at least 2 months. In some embodiments, less than 35% of an anti-IL1R1 antibody exists as HMW species in a formulation upon storage at 40° C. for at least 2 months. In some embodiments, less than 30% of an anti-IL1R1 antibody exists as HMW species in a formulation upon storage at 40° C. for at least 42 months. In some embodiments, less than 25% of an anti-IL1R1 antibody exists as HMW species in a formulation upon storage at 40° C. for at least 2 months. In some embodiments, less than 24% of an anti-IL1R1 antibody exists as HMW species in a formulation upon storage at 40° C. for at least 2 months. In some embodiments, less than 23% of an anti-IL1R1 antibody exists as HMW species in a formulation upon storage at 40° C. for at least 2 months. In some embodiments, less than 22% of an anti-IL1R1 antibody exists as HMW species in a formulation upon storage at 40° C. for at least 2 months. In some embodiments, less than 21% of an anti-IL1R1 antibody exists as HMW species in a formulation upon storage at 40° C. for at least 2 months. In some embodiments, less than 20% of an anti-IL1R1 antibody exists as HMW species in a formulation upon storage at 40° C. for at least 2 months. In some embodiments, less than 15% of an anti-IL1R1 antibody exists as HMW species in a formulation upon storage at 40° C. for at least 2 months. In some embodiments, less than 14% of an anti-IL1R1 antibody exists as HMW species in a formulation upon storage at 40° C. for at least 2 months. In some embodiments, less than 13% of an anti-IL1R1 antibody exists as HMW species in a formulation upon storage at 40° C. for at least 2 months. In some embodiments, less than 12% of an anti-IL1R1 antibody exists as HMW species in a formulation upon storage at 40° C. for at least 2 months. In some embodiments, less than 11% of an anti-IL1R1 antibody exists as HMW species in a formulation upon storage at 40° C. for at least 2 months. In some embodiments, less than 10% of an anti-IL1R1 antibody exists as HMW species in a formulation upon storage at 40° C. for at least 2 months. In some embodiments, less than 9% of an anti-IL1R1 antibody exists as HMW species in a formulation upon storage at 40° C. for at least 2 months. In some embodiments, less than 8% of an anti-IL1R1 antibody exists as HMW species in a formulation upon storage at 40° C. for at least 2 months. In some embodiments, less than 7% of an anti-IL1R1 antibody exists as HMW species in a formulation upon storage at 40° C. for at least 2 months. In some embodiments, less than 6% of an anti-IL1R1 antibody exists as HMW species in a formulation upon storage at 40° C. for at least 2 months. In some embodiments, less than 5% of an anti-IL1R1 antibody exists as HMW species in a formulation upon storage at 40° C. for at least 2 months. In some embodiments, less than 4% of an anti-IL1R1 antibody exists as HMW species in a formulation upon storage at 40° C. for at least 2 months. In some embodiments, less than 3% of an anti-IL1R1 antibody exists as HMW species in a formulation upon storage at 40° C. for at least 2 months. In some embodiments, less than 2% of an anti-IL1R1 antibody exists as HMW species in a formulation upon storage at 40° C. for at least 2 months. In some embodiments, less than 1% of an anti-IL1R1 antibody exists as HMW species in a formulation upon storage at 40° C. for at least 2 months.

In some embodiments, less than 5% of an anti-IL1R1 antibody exists as HMW species in a formulation upon storage at 40° C. for 3 months. In some embodiments, less than 4.5% of an anti-IL1R1 antibody exists as HMW species in a formulation upon storage at 40° C. for 3 months.

In some embodiments, less than 15% of an anti-IL1R1 antibody exists as HMW species in a formulation upon storage at 40° C. for 6 months. In some embodiments, less than 11% of an anti-IL1R1 antibody exists as HMW species in a formulation upon storage at 40° C. for 6 months. In some embodiments, less than 10% of an anti-IL1R1 antibody exists as HMW species in a formulation upon storage at 40° C. for 6 months. In some embodiments, the percentage of HMW species that exists in the formulation is evaluated by size exclusion chromatography (SEC). In some embodiments, the percentage of higher molecular weight species in the formulation (ΔHMW %) is evaluated at 60% relative humidity. In some embodiments, the percentage of higher molecular weight species in the formulation (ΔHMW %) is evaluated at 75% relative humidity.

In some embodiments, the amount of HMW species in a formulation increases less than 10%, 9%, 8%, 7%, 6%, 5%, 4%, 3%, 2%, 1%, 0.5%, 0.4%, 0.2% or 0.1% upon storage at 5° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 5° C. for 4 weeks, the amount of HMW species in the formulation does not substantially increase. In some embodiments, upon storage at 5° C. for 4 weeks, the amount of HMW species in the formulation increases less than 10%. In some embodiments, upon storage at 5° C. for 4 weeks, the amount of HMW species in the formulation increases 8% or less. In some embodiments, upon storage at 5° C. for 4 weeks, the amount of HMW species in the formulation increases less than 5%. In some embodiments, upon storage at 5° C. for 4 weeks, the amount of HMW species in the formulation increases less than 4%. In some embodiments, upon storage at 5° C. for 4 weeks, the amount of HMW species in the formulation increases less than 3%. In some embodiments, upon storage at 5° C. for 4 weeks, the amount of HMW species in the formulation increases less than 2%. In some embodiments, upon storage at 5° C. for 4 weeks, the amount of HMW species in the formulation increases less than 1.5%. In some embodiments, upon storage at 5° C. for 4 weeks, the amount of HMW species in the formulation increases less than 1.0%. In some embodiments, upon storage at 5° C. for 4 weeks, the amount of HMW species in the formulation increases less than 0.8%. In some embodiments, upon storage at 5° C. for 4 weeks, the amount of HMW species in the formulation increases less than 0.6%. In some embodiments, upon storage at 5° C. for 4 weeks, the amount of HMW species in the formulation increases less than 0.5%. In some embodiments, upon storage at 5° C. for 4 weeks, the amount of HMW species in the formulation increases less than 0.4%. In some embodiments, upon storage at 5° C. for 4 weeks, the amount of HMW species in the formulation increases less than 0.3%. In some embodiments, upon storage at 5° C. for 4 weeks, the amount of HMW species in the formulation increases less than 0.2%. In some embodiments, upon storage at 5° C. for 4 weeks, the amount of HMW species in the formulation increases less than 0.1%.

In some embodiments, upon storage at 5° C. for 2 months, the amount of HMW species in the formulation does not substantially increase. In some embodiments, upon storage at 5° C. for 2 months, the amount of HMW species in the formulation increases less than 5%. In some embodiments, upon storage at 5° C. for 2 months, the amount of HMW species in the formulation increases less than 4%. In some embodiments, upon storage at 5° C. for 2 months, the amount of HMW species in the formulation increases less than 3%. In some embodiments, upon storage at 5° C. for 2 months, the amount of HMW species in the formulation increases less than 2%. In some embodiments, upon storage at 5° C. for 2 months, the amount of HMW species in the formulation increases less than 1.5%. In some embodiments, upon storage at 5° C. for 2 months, the amount of HMW species in the formulation increases less than 1.0%. In some embodiments, upon storage at 5° C. for 2 months, the amount of HMW species in the formulation increases less than 0.8%. In some embodiments, upon storage at 5° C. for 2 months, the amount of HMW species in the formulation increases less than 0.6%. In some embodiments, upon storage at 5° C. for 2 months, the amount of HMW species in the formulation increases less than 0.5%. In some embodiments, upon storage at 5° C. for 2 months, the amount of HMW species in the formulation increases less than 0.4%. In some embodiments, upon storage at 5° C. for 2 months, the amount of HMW species in the formulation increases less than 0.3%. In some embodiments, upon storage at 5° C. for 2 months, the amount of HMW species in the formulation increases less than 0.2%. In some embodiments, upon storage at 5° C. for 2 months, the amount of HMW species in the formulation increases less than 0.1%.

In some embodiments, upon storage at 5° C. for 3 months, the amount of HMW species in the formulation increases less than 20%. In some embodiments, upon storage at 5° C. for 3 months, the amount of HMW species in the formulation increases less than 16%. In some embodiments, upon storage at 5° C. for 3 months, the amount of HMW species in the formulation increases 15% or less. In some embodiments, upon storage at 5° C. for 3 months, the amount of HMW species in the formulation increases less than 10%.

In some embodiments, upon storage at 5° C. for 6 months, the amount of HMW species in the formulation increases less than 30%. In some embodiments, upon storage at 5° C. for 6 months, the amount of HMW species in the formulation increases less than 25%. In some embodiments, upon storage at 5° C. for 6 months, the amount of HMW species in the formulation increases 23% or less.

In some embodiments, the amount of HMW species in a formulation increases less than 80%, 70%, 60%, 50%, 40%, 30%, 20%, 10%, 5%, 4%, 3%, 2%, 1%, 0.5%, 0.4%, 0.2% or 0.1% upon storage at 25° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 25° C. for 4 weeks, the amount of HMW species in the formulation does not substantially increase. In some embodiments, upon storage at 25° C. for 4 weeks, the amount of HMW species in the formulation increases less than 35%. In some embodiments, upon storage at 25° C. for 4 weeks, the amount of HMW species in the formulation increases less than 34%. In some embodiments, upon storage at 25° C. for 4 weeks, the amount of HMW species in the formulation increases less than 33%. In some embodiments, upon storage at 25° C. for 4 weeks, the amount of HMW species in the formulation increases less than 32%. In some embodiments, upon storage at 25° C. for 4 weeks, the amount of HMW species in the formulation increases less than 31%. In some embodiments, upon storage at 25° C. for 4 weeks, the amount of HMW species in the formulation increases 30% or less. In some embodiments, upon storage at 25° C. for 4 weeks, the amount of HMW species in the formulation increases 25% or less. In some embodiments, upon storage at 25° C. for 4 weeks, the amount of HMW species in the formulation increases less than 20%. In some embodiments, upon storage at 25° C. for 4 weeks, the amount of HMW species in the formulation increases less than 15%. In some embodiments, upon storage at 25° C. for 4 weeks, the amount of HMW species in the formulation increases less than 10%. In some embodiments, upon storage at 25° C. for 4 weeks, the amount of HMW species in the formulation increases less than 5%. In some embodiments, upon storage at 25° C. for 4 weeks, the amount of HMW species in the formulation increases less than 4%. In some embodiments, upon storage at 25° C. for 4 weeks, the amount of HMW species in the formulation increases less than 3%. In some embodiments, upon storage at 25° C. for 4 weeks, the amount of HMW species in the formulation increases less than 2%. In some embodiments, upon storage at 25° C. for 4 weeks, the amount of HMW species in the formulation increases less than 1.5%. In some embodiments, upon storage at 25° C. for 4 weeks, the amount of HMW species in the formulation increases less than 1.0%. In some embodiments, upon storage at 25° C. for 4 weeks, the amount of HMW species in the formulation increases less than 0.9%. In some embodiments, upon storage at 25° C. for 4 weeks, the amount of HMW species in the formulation increases less than 0.8%. In some embodiments, upon storage at 25° C. for 4 weeks, the amount of HMW species in the formulation increases less than 0.7%. In some embodiments, upon storage at 25° C. for 4 weeks, the amount of HMW species in the formulation increases less than 0.6%. In some embodiments, upon storage at 25° C. for 4 weeks, the amount of HMW species in the formulation increases less than 0.5%. In some embodiments, upon storage at 25° C. for 4 weeks, the amount of HMW species in the formulation increases less than 0.4%. In some embodiments, upon storage at 25° C. for 4 weeks, the amount of HMW species in the formulation increases less than 0.3%. In some embodiments, upon storage at 25° C. for 4 weeks, the amount of HMW species in the formulation increases less than 0.2%. In some embodiments, upon storage at 25° C. for 4 weeks, the amount of HMW species in the formulation increases less than 0.1%.

In some embodiments, upon storage at 25° C. for 2 months, the amount of HMW species in the formulation does not substantially increase. In some embodiments, upon storage at 25° C. for 2 months, the amount of HMW species in the formulation increases less than 5%. In some embodiments, upon storage at 25° C. for 2 months, the amount of HMW species in the formulation increases less than 4%. In some embodiments, upon storage at 25° C. for 2 months, the amount of HMW species in the formulation increases less than 3%. In some embodiments, upon storage at 25° C. for 2 months, the amount of HMW species in the formulation increases less than 2%. In some embodiments, upon storage at 25° C. for 2 months, the amount of HMW species in the formulation increases less than 1.9%. In some embodiments, upon storage at 25° C. for 2 months, the amount of HMW species in the formulation increases less than 1.8%. In some embodiments, upon storage at 25° C. for 2 months, the amount of HMW species in the formulation increases less than 1.7%. In some embodiments, upon storage at 25° C. for 2 months, the amount of HMW species in the formulation increases less than 1.6%. In some embodiments, upon storage at 25° C. for 2 months, the amount of HMW species in the formulation increases less than 1.5%. In some embodiments, upon storage at 25° C. for 2 months, the amount of HMW species in the formulation increases less than 1.4%. In some embodiments, upon storage at 25° C. for 2 months, the amount of HMW species in the formulation increases less than 1.3%. In some embodiments, upon storage at 25° C. for 2 months, the amount of HMW species in the formulation increases less than 1.2%. In some embodiments, upon storage at 25° C. for 2 months, the amount of HMW species in the formulation increases less than 1.1%. In some embodiments, upon storage at 25° C. for 2 months, the amount of HMW species in the formulation increases less than 1.0%. In some embodiments, upon storage at 25° C. for 2 months, the amount of HMW species in the formulation increases less than 0.9%. In some embodiments, upon storage at 25° C. for 2 months, the amount of HMW species in the formulation increases less than 0.8%. In some embodiments, upon storage at 25° C. for 2 months, the amount of HMW species in the formulation increases less than 0.7%. In some embodiments, upon storage at 25° C. for 2 months, the amount of HMW species in the formulation increases less than 0.6%. In some embodiments, upon storage at 25° C. for 2 months, the amount of HMW species in the formulation increases less than 0.5%. In some embodiments, upon storage at 25° C. for 2 months, the amount of HMW species in the formulation increases less than 0.4%. In some embodiments, upon storage at 25° C. for 2 months, the amount of HMW species in the formulation increases less than 0.3%. In some embodiments, upon storage at 25° C. for 2 months, the amount of HMW species in the formulation increases less than 0.2%. In some embodiments, upon storage at 25° C. for 2 months, the amount of HMW species in the formulation increases less than 0.1%.

In some embodiments, upon storage at 25° C. for 3 months, the amount of HMW species in the formulation increases less than 60%. In some embodiments, upon storage at 25° C. for 3 months, the amount of HMW species in the formulation increases less than 55%. In some embodiments, upon storage at 25° C. for 3 months, the amount of HMW species in the formulation increases less than 54%. In some embodiments, upon storage at 25° C. for 3 months, the amount of HMW species in the formulation increases 53% or less. In some embodiments, upon storage at 25° C. for 3 months, the amount of HMW species in the formulation increases less than 50%.

In some embodiments, upon storage at 25° C. for 6 months, the amount of HMW species in the formulation increases less than 80%. In some embodiments, upon storage at 25° C. for 6 months, the amount of HMW species in the formulation increases less than 79%. In some embodiments, upon storage at 25° C. for 6 months, the amount of HMW species in the formulation increases less than 78%. In some embodiments, upon storage at 25° C. for 6 months, the amount of HMW species in the formulation increases less than 77%. In some embodiments, upon storage at 25° C. for 6 months, the amount of HMW species in the formulation increases less than 76%. In some embodiments, upon storage at 25° C. for 6 months, the amount of HMW species in the formulation increases less than 75%.

In some embodiments, the amount of HMW species in a formulation increases less than 735%, 255%, 200%, 100%, 75%, 55%, 50%, 45%, 40%, 38%, 35% 30%, 25%, 20%, 15%, 10%, 5%, 4%, 3%, 2%, 1%, or 0.5% upon storage at 40° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 40° C. for 4 weeks, the amount of HMW species in the formulation increases less than 255%. In some embodiments, upon storage at 40° C. for 4 weeks, the amount of HMW species in the formulation increases less than 250%. In some embodiments, upon storage at 40° C. for 4 weeks, the amount of HMW species in the formulation increases less than 100%. In some embodiments, upon storage at 40° C. for 4 weeks, the amount of HMW species in the formulation increases less than 50%. In some embodiments, upon storage at 40° C. for 4 weeks, the amount of HMW species in the formulation increases less than 45%. In some embodiments, upon storage at 40° C. for 4 weeks, the amount of HMW species in the formulation increases less than 40%. In some embodiments, upon storage at 40° C. for 4 weeks, the amount of HMW species in the formulation increases less than 39%. In some embodiments, upon storage at 40° C. for 4 weeks, the amount of HMW species in the formulation increases less than 38%. In some embodiments, upon storage at 40° C. for 4 weeks, the amount of HMW species in the formulation increases less than 37%. In some embodiments, upon storage at 40° C. for 4 weeks, the amount of HMW species in the formulation increases less than 36%. In some embodiments, upon storage at 40° C. for 4 weeks, the amount of HMW species in the formulation increases less than 35%. In some embodiments, upon storage at 40° C. for 4 weeks, the amount of HMW species in the formulation increases less than 30%. In some embodiments, upon storage at 40° C. for 4 weeks, the amount of HMW species in the formulation increases less than 25%. In some embodiments, upon storage at 40° C. for 4 weeks, the amount of HMW species in the formulation increases less than 20%. In some embodiments, upon storage at 40° C. for 4 weeks, the amount of HMW species in the formulation increases less than 15%. In some embodiments, upon storage at 40° C. for 4 weeks, the amount of HMW species in the formulation increases less than 14%. In some embodiments, upon storage at 40° C. for 4 weeks, the amount of HMW species in the formulation increases less than 13%. In some embodiments, upon storage at 40° C. for 4 weeks, the amount of HMW species in the formulation increases less than 12%. In some embodiments, upon storage at 40° C. for 4 weeks, the amount of HMW species in the formulation increases less than 11%. In some embodiments, upon storage at 40° C. for 4 weeks, the amount of HMW species in the formulation increases less than 10%. In some embodiments, upon storage at 40° C. for 4 weeks, the amount of HMW species in the formulation increases less than 9%. In some embodiments, upon storage at 40° C. for 4 weeks, the amount of HMW species in the formulation increases less than 8%. In some embodiments, upon storage at 40° C. for 4 weeks, the amount of HMW species in the formulation increases less than 7%. In some embodiments, upon storage at 40° C. for 4 weeks, the amount of HMW species in the formulation increases less than 6%. In some embodiments, upon storage at 40° C. for 4 weeks, the amount of HMW species in the formulation increases less than 5%. In some embodiments, upon storage at 40° C. for 4 weeks, the amount of HMW species in the formulation increases less than 4.8%. In some embodiments, upon storage at 40° C. for 4 weeks, the amount of HMW species in the formulation increases less than 4.5%. In some embodiments, upon storage at 40° C. for 4 weeks, the amount of HMW species in the formulation increases less than 4%. In some embodiments, upon storage at 40° C. for 4 weeks, the amount of HMW species in the formulation increases less than 3%. In some embodiments, upon storage at 40° C. for 4 weeks, the amount of HMW species in the formulation increases less than 2.5%. In some embodiments, upon storage at 40° C. for 4 weeks, the amount of HMW species in the formulation increases less than 2%. In some embodiments, upon storage at 40° C. for 4 weeks, the amount of HMW species in the formulation increases less than 1.5%. In some embodiments, upon storage at 40° C. for 4 weeks, the amount of HMW species in the formulation increases less than 1.0%. In some embodiments, upon storage at 40° C. for 4 weeks, the amount of HMW species in the formulation increases less than 0.8%. In some embodiments, upon storage at 40° C. for 4 weeks, the amount of HMW species in the formulation increases less than 0.6%. In some embodiments, upon storage at 40° C. for 4 weeks, the amount of HMW species in the formulation increases less than 0.5%.

In some embodiments, upon storage at 40° C. for 2 months, the amount of HMW species in the formulation increases less than 60%. In some embodiments, upon storage at 40° C. for 2 months, the amount of HMW species in the formulation increases less than 59%. In some embodiments, upon storage at 40° C. for 2 months, the amount of HMW species in the formulation increases less than 58%. In some embodiments, upon storage at 40° C. for 2 months, the amount of HMW species in the formulation increases less than 57%. In some embodiments, upon storage at 40° C. for 2 months, the amount of HMW species in the formulation increases less than 56%. In some embodiments, upon storage at 40° C. for 2 months, the amount of HMW species in the formulation increases less than 55%. In some embodiments, upon storage at 40° C. for 2 months, the amount of HMW species in the formulation increases less than 54%. In some embodiments, upon storage at 40° C. for 2 months, the amount of HMW species in the formulation increases less than 53%. In some embodiments, upon storage at 40° C. for 2 months, the amount of HMW species in the formulation increases less than 52%. In some embodiments, upon storage at 40° C. for 2 months, the amount of HMW species in the formulation increases less than 51%. In some embodiments, upon storage at 40° C. for 2 months, the amount of HMW species in the formulation increases less than 50%. In some embodiments, upon storage at 40° C. for 2 months, the amount of HMW species in the formulation increases less than 45%. In some embodiments, upon storage at 40° C. for 2 months, the amount of HMW species in the formulation increases less than 40%. In some embodiments, upon storage at 40° C. for 2 months, the amount of HMW species in the formulation increases less than 35%. In some embodiments, upon storage at 40° C. for 2 months, the amount of HMW species in the formulation increases less than 30%. In some embodiments, upon storage at 40° C. for 2 months, the amount of HMW species in the formulation increases less than 25%. In some embodiments, upon storage at 40° C. for 2 months, the amount of HMW species in the formulation increases less than 24%. In some embodiments, upon storage at 40° C. for 2 months, the amount of HMW species in the formulation increases less than 23%. In some embodiments, upon storage at 40° C. for 2 months, the amount of HMW species in the formulation increases less than 22%. In some embodiments, upon storage at 40° C. for 2 months, the amount of HMW species in the formulation increases less than 21%. In some embodiments, upon storage at 40° C. for 2 months, the amount of HMW species in the formulation increases less than 20%. In some embodiments, upon storage at 40° C. for 2 months, the amount of HMW species in the formulation increases less than 15%. In some embodiments, upon storage at 40° C. for 2 months, the amount of HMW species in the formulation increases less than 10%. In some embodiments, upon storage at 40° C. for 2 months, the amount of HMW species in the formulation increases less than 9%. In some embodiments, upon storage at 40° C. for 2 months, the amount of HMW species in the formulation increases less than 8%. In some embodiments, upon storage at 40° C. for 2 months, the amount of HMW species in the formulation increases less than 7%. In some embodiments, upon storage at 40° C. for 2 months, the amount of HMW species in the formulation increases less than 6%. In some embodiments, upon storage at 40° C. for 2 months, the amount of HMW species in the formulation increases less than 5%. In some embodiments, upon storage at 40° C. for 2 months, the amount of HMW species in the formulation increases less than 4%. In some embodiments, upon storage at 40° C. for 2 months, the amount of HMW species in the formulation increases less than 3%. In some embodiments, upon storage at 40° C. for 2 months, the amount of HMW species in the formulation increases less than 2%. In some embodiments, upon storage at 40° C. for 2 months, the amount of HMW species in the formulation increases less than 1.0%.

In some embodiments, upon storage at 40° C. for 3 months, the amount of HMW species in the formulation increases less than 735%. In some embodiments, upon storage at 40° C. for 3 months, the amount of HMW species in the formulation increases 730% or less. In some embodiments, the percent increase in higher molecular weight species in the formulation ($\Delta$HMW %) is evaluated by size exclusion chromatography (SEC). In some embodiments, the percentage of higher molecular weight species in the formulation ($\Delta$HMW %) is evaluated at 60% relative humidity. In some embodiments, the percentage of higher molecular weight species in the formulation ($\Delta$HMW %) is evaluated at 75% relative humidity.

Monomer

In some embodiments, at least 80%, 85%, 90%, 95%, or 98% of an anti-IL1R1 antibody exists as monomers in a formulation upon storage at 5° C. for at least 4 weeks, at least 6 weeks, at least 2 months, at least 3 months, at least 4 months, at least 6 months, at least 8 months, at least 10 months, or at least 12 months. In some embodiments, at least 90% of an anti-IL1R1 antibody exists as monomers in a formulation upon storage at 5° C. for at least 4 weeks. In some embodiments, at least 91% of an anti-IL1R1 antibody exists as monomer in a formulation upon storage at 5° C. for at least 4 weeks. In some embodiments, at least 92% of an anti-IL1R1 antibody exists as monomers in a formulation upon storage at 5° C. for at least 4 weeks. In some embodiments, at least 93% of an anti-IL1R1 antibody exists as monomers in a formulation upon storage at 5° C. for at least 4 weeks. In some embodiments, at least 94% of an anti-IL1R1 antibody exists as monomers in a formulation upon storage at 5° C. for at least 4 weeks. In some embodiments, at least 95% of an anti-IL1R1 antibody exists as monomers in a formulation upon storage at 5° C. for at least 4 weeks. In some embodiments, at least 96% of an anti-IL1R1 antibody exists as monomers in a formulation upon storage at 5° C. for at least 4 weeks. In some embodiments, at least 97% of an anti-IL1R1 antibody exists as monomers in a formulation upon storage at 5° C. for at least 4 weeks. In some embodiments, at least 98% of an anti-IL1R1 antibody exists as monomers in a formulation upon storage at 5° C. for at least 4 weeks. In some embodiments, at least 99% of an anti-IL1R1 antibody exists as monomers in a formulation upon storage at 5° C. for at least 4 weeks.

In some embodiments, at least 90% of an anti-IL1R1 antibody exists as monomers in a formulation upon storage at 5° C. for at least 2 months. In some embodiments, at least 91% of an anti-IL1R1 antibody exists as monomers in a formulation upon storage at 5° C. for at least 2 months. In some embodiments, at least 92% of an anti-IL1R1 antibody exists as monomers in a formulation upon storage at 5° C. for at least 2 months. In some embodiments, at least 93% of an anti-IL1R1 antibody exists as monomers in a formulation upon storage at 5° C. for at least 2 months. In some embodiments, at least 94% of an anti-IL1R1 antibody exists as monomers in a formulation upon storage at 5° C. for at least 2 months. In some embodiments, at least 95% of an anti-IL1R1 antibody exists as monomers in a formulation upon storage at 5° C. for at least 2 months. In some embodiments, at least 96% of an anti-IL1R1 antibody exists as monomers in a formulation upon storage at 5° C. for at least 2 months. In some embodiments, at least 97% of an anti-IL1R1 antibody exists as monomers in a formulation upon storage at 5° C. for at least 2 months. In some embodiments, at least 98% of an anti-IL1R1 antibody exists as monomers in a formulation upon storage at 5° C. for at least 2 months. In some embodiments, at least 99% of an anti-IL1R1 antibody exists as monomers in a formulation upon storage at 5° C. for at least 2 months.

In some embodiments, at least 80%, 85%, 90%, 95%, or 98% of an anti-IL1R1 antibody exists as monomers in a formulation upon storage at 25° C. for at least 4 weeks, at least 6 weeks, at least 2 months, at least 3 months, at least 4 months, at least 6 months, at least 8 months, at least 10 months, or at least 12 months. In some embodiments, at least 90% of an anti-IL1R1 antibody exists as monomers in a formulation upon storage at 25° C. for at least 4 weeks. In some embodiments, at least 91% of an anti-IL1R1 antibody exists as monomers in a formulation upon storage at 25° C. for at least 4 weeks. In some embodiments, at least 92% of an anti-IL1R1 antibody exists as monomers in a formulation upon storage at 25° C. for at least 4 weeks. In some embodiments, at least 93% of an anti-IL1R1 antibody exists as monomers in a formulation upon storage at 25° C. for at least 4 weeks. In some embodiments, at least 94% of an anti-IL1R1 antibody exists as monomers in a formulation upon storage at 25° C. for at least 4 weeks. In some embodiments, at least 95% of an anti-IL1R1 antibody exists as monomers in a formulation upon storage at 25° C. for at least 4 weeks. In some embodiments, at least 96% of an anti-IL1R1 antibody exists as monomers in a formulation upon storage at 25° C. for at least 4 weeks. In some embodiments, at least 97% of an anti-IL1R1 antibody exists as monomers in a formulation upon storage at 25° C. for at least 4 weeks. In some embodiments, at least 98% of an anti-IL1R1 antibody exists as monomers in a formulation upon storage at 25° C. for at least 4 weeks. In some embodiments, at least 99% of an anti-IL1R1 antibody exists as monomers in a formulation upon storage at 25° C. for at least 4 weeks.

In some embodiments, at least 90% of an anti-IL1R1 antibody exists as monomers in a formulation upon storage at 25° C. for at least 2 months. In some embodiments, at least 91% of an anti-IL1R1 antibody exists as monomers in a formulation upon storage at 25° C. for at least 2 months. In some embodiments, at least 92% of an anti-IL1R1 antibody exists as monomers in a formulation upon storage at 25° C. for at least 2 months. In some embodiments, at least 93% of an anti-IL1R1 antibody exists as monomers in a formulation upon storage at 25° C. for at least 2 months. In some embodiments, at least 94% of an anti-IL1R1 antibody exists as monomers in a formulation upon storage at 25° C. for at least 2 months. In some embodiments, at least 95% of an anti-IL1R1 antibody exists as monomers in a formulation upon storage at 25° C. for at least 2 months. In some embodiments, at least 96% of an anti-IL1R1 antibody exists as monomers in a formulation upon storage at 25° C. for at least 2 months. In some embodiments, at least 97% of an anti-IL1R1 antibody exists as monomers in a formulation upon storage at 25° C. for at least 2 months. In some embodiments, at least 98% of an anti-IL1R1 antibody exists as monomers in a formulation upon storage at 25° C. for at least 2 months. In some embodiments, at least 99% of an anti-IL1R1 antibody exists as monomers in a formulation upon storage at 25° C. for at least 2 months.

In some embodiments, at least 50%, 55%, 60% 80%, 85%, 90%, 95%, or 98% of an anti-IL1R1 antibody exists as monomers in a formulation upon storage at 40° C. for at least 4 weeks, at least 6 weeks, at least 2 months, at least 3 months, at least 4 months, at least 6 months, at least 8 months, at least 10 months, or at least 12 months. In some embodiments, at least 55% of an anti-IL1R1 antibody exists as monomers in a formulation upon storage at 40° C. for at least 4 weeks. In some embodiments, at least 56% of an anti-IL1R1 antibody exists as monomers in a formulation upon storage at 40° C. for at least 4 weeks. In some embodiments, at least 57% of an anti-IL1R1 antibody exists as monomers in a formulation upon storage at 40° C. for at least 4 weeks. In some embodiments, at least 58% of an anti-IL1R1 antibody exists as monomers in a formulation upon storage at 40° C. for at least 4 weeks. In some embodiments, at least 59% of an anti-IL1R1 antibody exists as monomers in a formulation upon storage at 40° C. for at least 4 weeks. In some embodiments, at least 60% of an anti-IL1R1 antibody exists as monomers in a formulation upon storage at 40° C. for at least 4 weeks. In some embodiments, at least 61% of an anti-IL1R1 antibody exists as monomers in a formulation upon storage at 40° C. for at least 4 weeks. In some embodiments, at least 62% of an anti-IL1R1 antibody exists as monomers in a formulation upon storage at 40° C. for at least 4 weeks. In some embodiments, at least 63% of an anti-IL1R1 antibody exists as monomers in a formulation upon storage at 40° C. for at least 4 weeks. In some embodiments, at least 64% of an anti-IL1R1 antibody exists as monomers in a formulation upon storage at 40° C. for at least 4 weeks. In some embodiments, at least 65% of an anti-IL1R1 antibody exists as monomers in a formulation upon storage at 40° C. for at least 4 weeks. In some embodiments, at least 70% of an anti-IL1R1 antibody exists as monomers in a formulation upon storage at 40° C. for at least 4 weeks. In some embodiments, at least 80% of an anti-IL1R1 antibody exists as monomers in a formulation upon storage at 40° C. for at least 4 weeks. In some embodiments, at least 85% of an anti-IL1R1 antibody exists as monomers in a formulation upon storage at 40° C. for at least 4 weeks. In some embodiments, at least 86% of an anti-IL1R1 antibody exists as monomers in a formulation upon storage at 40° C. for at least 4 weeks. In some embodiments, at least 87% of an anti-IL1R1 antibody exists as monomers in a formulation upon storage at 40° C. for at least 4 weeks. In some embodiments, at least 88% of an anti-IL1R1 antibody exists as monomers in a formulation upon storage at 40° C. for at least 4 weeks. In some embodiments, at least 89% of an anti-IL1R1 antibody exists as monomers in a formulation upon storage at 40° C. for at least 4 weeks. In some embodiments, at least 90% of an anti-IL1R1 antibody exists as monomers in a formulation upon storage at 40° C. for at least 4 weeks. In some embodiments, at least 91% of an anti-IL1R1 antibody exists as monomers in a formulation upon storage at 40° C. for at least 4 weeks. In some embodiments, at least 92% of an anti-IL1R1 antibody exists as monomers in a formulation upon storage at 40° C. for at least 4 weeks. In some embodiments, at least 93% of an anti-IL1R1 antibody exists as monomers in a formulation upon storage at 40° C. for at least 4 weeks. In some embodiments, at least 94% of an anti-IL1R1 antibody exists as monomers in a formulation upon storage at 40° C. for at least 4 weeks. In some embodiments, at least 95% of an anti-IL1R1 antibody exists as monomers in a formulation upon storage at 40° C. for at least 4 weeks. In some embodiments, at least 96% of an anti-IL1R1 antibody exists as monomers in a formulation upon storage at 40° C. for at least 4 weeks. In some embodiments, at least 97% of an anti-IL1R1 antibody exists as monomers in a formulation upon storage at 40° C. for at least 4 weeks. In some embodiments, at least 98% of an anti-IL1R1 antibody exists as monomers in a formulation upon storage at 40° C. for at least 4 weeks. In some embodiments, at least 99% of an anti-IL1R1 antibody exists as monomers in a formulation upon storage at 40° C. for at least 4 weeks. In some embodiments, a formulation comprising an anti-IL1R1 antibody does not gel upon storage at 40° C. for at least 4 weeks.

In some embodiments, at least 40% of an anti-IL1R1 antibody exists as monomers in a formulation upon storage at 40° C. for at least 2 months. In some embodiments, at least 41% of an anti-IL1R1 antibody exists as monomers in a formulation upon storage at 40° C. for at least 2 months. In some embodiments, at least 42% of an anti-IL1R1 antibody exists as monomers in a formulation upon storage at 40° C. for at least 2 months. In some embodiments, at least 43% of an anti-IL1R1 antibody exists as monomers in a formulation upon storage at 40° C. for at least 2 months. In some embodiments, at least 44% of an anti-IL1R1 antibody exists as monomers in a formulation upon storage at 40° C. for at least 2 months. In some embodiments, at least 45% of an anti-IL1R1 antibody exists as monomers in a formulation upon storage at 40° C. for at least 2 months. In some embodiments, at least 50% of an anti-IL1R1 antibody exists as monomers in a formulation upon storage at 40° C. for at least 2 months. In some embodiments, at least 55% of an anti-IL1R1 antibody exists as monomers in a formulation upon storage at 40° C. for at least 2 months. In some embodiments, at least 56% of an anti-IL1R1 antibody exists as monomers in a formulation upon storage at 40° C. for at least 2 months. In some embodiments, at least 57% of an anti-IL1R1 antibody exists as monomers in a formulation upon storage at 40° C. for at least 2 months. In some embodiments, at least 58% of an anti-IL1R1 antibody exists as monomers in a formulation upon storage at 40° C. for at least 2 months. In some embodiments, at least 59% of an anti-IL1R1 antibody exists as monomers in a formulation upon storage at 40° C. for at least 2 months. In some embodiments, at least 60% of an anti-IL1R1 antibody exists as monomers in a formulation upon storage at 40° C. for at least 2 months. In some embodiments, at least 61% of an anti-IL1R1 antibody exists as monomers in a formulation upon storage at 40° C. for at least 2 months. In some embodiments, at least 62% of an anti-IL1R1 antibody exists as monomers in a formulation upon storage at 40° C. for at least 2 months. In some embodiments, at least 63% of an anti-IL1R1 antibody exists as monomers in a formulation upon storage at 40° C. for at least 2 months. In some embodiments, at least 64% of an anti-IL1R1 antibody exists as monomers in a formulation upon storage at 40° C. for at least 2 months. In some embodiments, at least 65% of an anti-IL1R1 antibody exists as monomers in a formulation upon storage at 40° C. for at least 2 months. In some embodiments, at least 70% of an anti-IL1R1 antibody exists as monomers in a formulation upon storage at 40° C. for at least 2 months. In some embodiments, at least 75% of an anti-IL1R1 antibody exists as monomers in a formulation upon storage at 40° C. for at least 2 months. In some embodiments, at least 76% of an anti-IL1R1 antibody exists as monomers in a formulation upon storage at 40° C. for at least 2 months. In some embodiments, at least 77% of an anti-IL1R1 antibody exists as monomers in a formulation upon storage at 40° C. for at least 2 months. In some embodiments, at least 78% of an anti-IL1R1 antibody exists as monomers in a formulation upon storage at 40° C. for at least 2 months. In some embodiments, at least 79% of an anti-IL1R1 antibody exists as monomers in a formulation upon storage at 40° C. for at least 2 months. In some embodiments, at least 80% of an anti-IL1R1 antibody exists as monomers in a formulation upon storage at 40° C. for at least 2 months. In some embodiments, at least 85% of an anti-IL1R1 antibody exists as monomers in a formulation upon storage at 40° C. for at least 2 months. In some embodiments, at least 86% of an anti-IL1R1 antibody exists as monomers in a formulation upon storage at 40° C. for at least 2 months. In some embodiments, at least 87% of an anti-IL1R1 antibody exists as monomers in a formulation upon storage at 40° C. for at least 2 months. In some embodiments, at least 88% of an anti-IL1R1 antibody exists as monomers in a formulation upon storage at 40° C. for at least 2 months. In some embodiments, at least 89% of an anti-IL1R1 antibody exists as monomers in a formulation upon storage at 40° C. for at least 2 months. In some embodiments, at least 90% of an anti-IL1R1 antibody exists as monomers in a formulation upon storage at 40° C. for at least 2 months. In some embodiments, at least 91% of an anti-IL1R1 antibody exists as monomers in a formulation upon storage at 40° C. for at least 2 months. In some embodiments, at least 92% of an anti-IL1R1 antibody exists as monomers in a formulation upon storage at 40° C. for at least 2 months. In some embodiments, at least 93% of an anti-IL1R1 antibody exists as monomers in a formulation upon storage at 40° C. for at least 2 months. In some embodiments, at least 94% of an anti-IL1R1 antibody exists as monomers in a formulation upon storage at 40° C. for at least 2 months. In some embodiments, at least 95% of an anti-IL1R1 antibody exists as monomers in a formulation upon storage at 40° C. for at least 2 months. In some embodiments, at least 96% of an anti-IL1R1 antibody exists as monomers in a formulation upon storage at 40° C. for at least 2 months. In some embodiments, at least 97% of an anti-IL1R1 antibody exists as monomers in a formulation upon storage at 40° C. for at least 2 months. In some embodiments, at least 98% of an anti-IL1R1 antibody exists as monomers in a formulation upon storage at 40° C. for at least 2 months. In some embodiments, at least 99% of an anti-IL1R1 antibody exists as monomers in a formulation upon storage at 40° C. for at least 2 months. In some embodiments, a formulation comprising an anti-IL1R1 antibody does not gel upon storage at 40° C. for at least 2 months.

In some embodiments, the amount of monomer in a formulation decreases less than 55%, 50%, 45%, 40%, 38%, 35% 30%, 25%, 20%, 15%, 10%, 5%, 4%, 3%, 2%, 1%, 0.5%, 0.4%, 0.2% or 0.1% upon storage at 5° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 5° C. for 4 weeks, the amount of monomer in the formulation does not substantially decrease. In some embodiments, upon storage at 5° C. for 4 weeks, the amount of monomer in the formulation decreases less than 5%. In some embodiments, upon storage at 5° C. for 4 weeks, the amount of monomer in the formulation decreases less than 4%. In some embodiments, upon storage at 5° C. for 4 weeks, the amount of monomer in the formulation decreases less than 3%. In some embodiments, upon storage at 5° C.

for 4 weeks, the amount of monomer in the formulation decreases less than 2%. In some embodiments, upon storage at 5° C. for 4 weeks, the amount of monomer in the formulation decreases less than 1.5%. In some embodiments, upon storage at 5° C. for 4 weeks, the amount of monomer in the formulation decreases less than 1.0%. In some embodiments, upon storage at 5° C. for 4 weeks, the amount of monomer in the formulation decreases less than 0.8%. In some embodiments, upon storage at 5° C. for 4 weeks, the amount of monomer in the formulation decreases less than 0.6%. In some embodiments, upon storage at 5° C. for 4 weeks, the amount of monomer in the formulation decreases less than 0.5%. In some embodiments, upon storage at 5° C. for 4 weeks, the amount of monomer in the formulation decreases less than 0.4%. In some embodiments, upon storage at 5° C. for 4 weeks, the amount of monomer in the formulation decreases less than 0.3%. In some embodiments, upon storage at 5° C. for 4 weeks, the amount of monomer in the formulation decreases less than 0.2%. In some embodiments, upon storage at 5° C. for 4 weeks, the amount of monomer in the formulation decreases less than 0.1%.

In some embodiments, upon storage at 5° C. for 2 months, the amount of monomer in the formulation decreases less than 5%. In some embodiments, upon storage at 5° C. for 2 months, the amount of monomer in the formulation decreases less than 4%. In some embodiments, upon storage at 5° C. for 2 months, the amount of monomer in the formulation decreases less than 3%. In some embodiments, upon storage at 5° C. for 2 months, the amount of monomer in the formulation decreases less than 2%. In some embodiments, upon storage at 5° C. for 2 months, the amount of monomer in the formulation decreases less than 1.5%. In some embodiments, upon storage at 5° C. for 2 months, the amount of monomer in the formulation decreases less than 1.0%. In some embodiments, upon storage at 5° C. for 2 months, the amount of monomer in the formulation decreases less than 0.8%. In some embodiments, upon storage at 5° C. for 2 months, the amount of monomer in the formulation decreases less than 0.6%. In some embodiments, upon storage at 5° C. for 2 months, the amount of monomer in the formulation decreases less than 0.5%. In some embodiments, upon storage at 5° C. for 2 months, the amount of monomer in the formulation decreases less than 0.4%. In some embodiments, upon storage at 5° C. for 2 months, the amount of monomer in the formulation decreases less than 0.3%. In some embodiments, upon storage at 5° C. for 2 months, the amount of monomer in the formulation decreases less than 0.2%. In some embodiments, upon storage at 5° C. for 2 months, the amount of monomer in the formulation decreases less than 0.1%.

In some embodiments, the amount of monomer in a formulation decreases less than 5%, 4%, 3%, 2%, 1%, 0.5%, 0.4%, 0.2% or 0.1% upon storage at 25° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 25° C. for 4 weeks, the amount of monomer in the formulation does not substantially increase. In some embodiments, upon storage at 25° C. for 4 weeks, the amount of monomer in the formulation decreases less than 5%. In some embodiments, upon storage at 25° C. for 4 weeks, the amount of monomer in the formulation decreases less than 4%. In some embodiments, upon storage at 25° C. for 4 weeks, the amount of monomer in the formulation decreases less than 3%. In some embodiments, upon storage at 25° C. for 4 weeks, the amount of monomer in the formulation decreases less than 2%. In some embodiments, upon storage at 25° C. for 4 weeks, the amount of monomer in the formulation decreases less than 1.5%. In some embodiments, upon storage at 25° C. for 4 weeks, the amount of monomer in the formulation decreases less than 1.0%. In some embodiments, upon storage at 25° C. for 4 weeks, the amount of monomer in the formulation decreases less than 0.8%. In some embodiments, upon storage at 25° C. for 4 weeks, the amount of monomer in the formulation decreases less than 0.6%. In some embodiments, upon storage at 25° C. for 4 weeks, the amount of monomer in the formulation decreases less than 0.5%. In some embodiments, upon storage at 25° C. for 4 weeks, the amount of monomer in the formulation decreases less than 0.4%. In some embodiments, upon storage at 25° C. for 4 weeks, the amount of monomer in the formulation decreases less than 0.3%. In some embodiments, upon storage at 25° C. for 4 weeks, the amount of monomer in the formulation decreases less than 0.2%. In some embodiments, upon storage at 25° C. for 4 weeks, the amount of monomer in the formulation decreases less than 0.1%.

In some embodiments, upon storage at 25° C. for 2 months, the amount of monomer in the formulation decreases less than 5%. In some embodiments, upon storage at 25° C. for 2 months, the amount of monomer in the formulation decreases less than 4%. In some embodiments, upon storage at 25° C. for 2 months, the amount of monomer in the formulation decreases less than 3%. In some embodiments, upon storage at 25° C. for 2 months, the amount of monomer in the formulation decreases less than 2%. In some embodiments, upon storage at 25° C. for 2 months, the amount of monomer in the formulation decreases less than 1.9%. In some embodiments, upon storage at 25° C. for 2 months, the amount of monomer in the formulation decreases less than 1.8%. In some embodiments, upon storage at 25° C. for 2 months, the amount of monomer in the formulation decreases less than 1.7%. In some embodiments, upon storage at 25° C. for 2 months, the amount of monomer in the formulation decreases less than 1.6%. In some embodiments, upon storage at 25° C. for 2 months, the amount of monomer in the formulation decreases less than 1.5%. In some embodiments, upon storage at 25° C. for 2 months, the amount of monomer in the formulation decreases less than 1.4%. In some embodiments, upon storage at 25° C. for 2 months, the amount of monomer in the formulation decreases less than 1.3%. In some embodiments, upon storage at 25° C. for 2 months, the amount of monomer in the formulation decreases less than 1.2%. In some embodiments, upon storage at 25° C. for 2 months, the amount of monomer in the formulation decreases less than 1.1%. In some embodiments, upon storage at 25° C. for 2 months, the amount of monomer in the formulation decreases less than 1.0%. In some embodiments, upon storage at 25° C. for 2 months, the amount of monomer in the formulation decreases less than 0.9%. In some embodiments, upon storage at 25° C. for 2 months, the amount of monomer in the formulation decreases less than 0.8%. In some embodiments, upon storage at 25° C. for 2 months, the amount of monomer in the formulation decreases less than 0.7%. In some embodiments, upon storage at 25° C. for 2 months, the amount of monomer in the formulation decreases less than 0.6%. In some embodiments, upon storage at 25° C. for 2 months, the amount of monomer in the formulation decreases less than 0.5%. In some embodiments, upon storage at 25° C. for 2 months, the amount of monomer in the formulation decreases less than 0.4%. In some embodiments, upon storage at 25° C. for 2 months, the amount of monomer in the formulation decreases less than 0.3%. In some embodiments, upon storage at 25° C. for 2 months, the amount of monomer in the formulation decreases less than 0.2%. In some embodiments, upon storage at 25° C. for 2 months, the amount of monomer in the formulation decreases less than 0.1%.

In some embodiments, the amount of monomer in a formulation decreases less than 50%, 45%, 40%, 38%, 35% 30%, 25%, 20%, 15%, 10%, 5%, 4%, 3%, 2%, 1%, or 0.5% upon storage at 40° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 40° C. for 4 weeks, the amount of monomer in the formulation decreases less than 50%. In some embodiments, upon storage at 40° C. for 4 weeks, the amount of monomer in the formulation decreases less than 45%. In some embodiments, upon storage at 40° C. for 4 weeks, the amount of monomer in the formulation decreases less than 40%. In some embodiments, upon storage at 40° C. for 4 weeks, the amount of monomer in the formulation decreases less than 38%. In some embodiments, upon storage at 40° C. for 4 weeks, the amount of monomer in the formulation decreases less than 35%. In some embodiments, upon storage at 40° C. for 4 weeks, the amount of monomer in the formulation decreases less than 30%. In some embodiments, upon storage at 40° C. for 4 weeks, the amount of monomer in the formulation decreases less than 25%. In some embodiments, upon storage at 40° C. for 4 weeks, the amount of monomer in the formulation decreases less than 20%. In some embodiments, upon storage at 40° C. for 4 weeks, the amount of monomer in the formulation decreases less than 15%. In some embodiments, upon storage at 40° C. for 4 weeks, the amount of monomer in the formulation decreases less than 14%. In some embodiments, upon storage at 40° C. for 4 weeks, the amount of monomer in the formulation decreases less than 13%. In some embodiments, upon storage at 40° C. for 4 weeks, the amount of monomer in the formulation decreases less than 12%. In some embodiments, upon storage at 40° C. for 4 weeks, the amount of monomer in the formulation decreases less than 11%. In some embodiments, upon storage at 40° C. for 4 weeks, the amount of monomer in the formulation decreases less than 10%. In some embodiments, upon storage at 40° C. for 4 weeks, the amount of monomer in the formulation decreases less than 9%. In some embodiments, upon storage at 40° C. for 4 weeks, the amount of monomer in the formulation decreases less than 8%. In some embodiments, upon storage at 40° C. for 4 weeks, the amount of monomer in the formulation decreases less than 7%. In some embodiments, upon storage at 40° C. for 4 weeks, the amount of monomer in the formulation decreases less than 6%. In some embodiments, upon storage at 40° C. for 4 weeks, the amount of monomer in the formulation decreases less than 5%. In some embodiments, upon storage at 40° C. for 4 weeks, the amount of monomer in the formulation decreases less than 4.8%. In some embodiments, upon storage at 40° C. for 4 weeks, the amount of monomer in the formulation decreases less than 4.5%. In some embodiments, upon storage at 40° C. for 4 weeks, the amount of monomer in the formulation decreases less than 4%. In some embodiments, upon storage at 40° C. for 4 weeks, the amount of monomer in the formulation decreases less than 3%. In some embodiments, upon storage at 40° C. for 4 weeks, the amount of monomer in the formulation decreases less than 2.5%. In some embodiments, upon storage at 40°

C. for 4 weeks, the amount of monomer in the formulation decreases less than 2%. In some embodiments, upon storage at 40° C. for 4 weeks, the amount of monomer in the formulation decreases less than 1.5%. In some embodiments, upon storage at 40° C. for 4 weeks, the amount of monomer in the formulation decreases less than 1.0%. In some embodiments, upon storage at 40° C. for 4 weeks, the amount of monomer in the formulation decreases less than 0.8%. In some embodiments, upon storage at 40° C. for 4 weeks, the amount of monomer in the formulation decreases less than 0.6%. In some embodiments, upon storage at 40° C. for 4 weeks, the amount of monomer in the formulation decreases less than 0.5%.

In some embodiments, upon storage at 40° C. for 2 months, the amount of monomer in the formulation decreases less than 55%. In some embodiments, upon storage at 40° C. for 2 months, the amount of monomer in the formulation decreases less than 50%. In some embodiments, upon storage at 40° C. for 2 months, the amount of monomer in the formulation decreases less than 45%. In some embodiments, upon storage at 40° C. for 2 months, the amount of monomer in the formulation decreases less than 40%. In some embodiments, upon storage at 40° C. for 2 months, the amount of monomer in the formulation decreases less than 35%. In some embodiments, upon storage at 40° C. for 2 months, the amount of monomer in the formulation decreases less than 30%. In some embodiments, upon storage at 40° C. for 2 months, the amount of monomer in the formulation decreases less than 25%. In some embodiments, upon storage at 40° C. for 2 months, the amount of monomer in the formulation decreases less than 24%. In some embodiments, upon storage at 40° C. for 2 months, the amount of monomer in the formulation decreases less than 23%. In some embodiments, upon storage at 40° C. for 2 months, the amount of monomer in the formulation decreases less than 22%. In some embodiments, upon storage at 40° C. for 2 months, the amount of monomer in the formulation decreases less than 21%. In some embodiments, upon storage at 40° C. for 2 months, the amount of monomer in the formulation decreases less than 20%. In some embodiments, upon storage at 40° C. for 2 months, the amount of monomer in the formulation decreases less than 15%. In some embodiments, upon storage at 40° C. for 2 months, the amount of monomer in the formulation decreases less than 10%. In some embodiments, upon storage at 40° C. for 2 months, the amount of monomer in the formulation decreases less than 9%. In some embodiments, upon storage at 40° C. for 2 months, the amount of monomer in the formulation decreases less than 8%. In some embodiments, upon storage at 40° C. for 2 months, the amount of monomer in the formulation decreases less than 7%. In some embodiments, upon storage at 40° C. for 2 months, the amount of monomer in the formulation decreases less than 6%. In some embodiments, upon storage at 40° C. for 2 months, the amount of monomer in the formulation decreases less than 5%. In some embodiments, upon storage at 40° C. for 2 months, the amount of monomer in the formulation decreases less than 4%. In some embodiments, upon storage at 40° C. for 2 months, the amount of monomer in the formulation decreases less than 3%. In some embodiments, upon storage at 40° C. for 2 months, the amount of monomer in the formulation decreases less than 2%. In some embodiments, upon storage at 40° C. for 2 months, the amount of monomer in the formulation decreases less than 1.0%.

In some embodiments, the percentage of monomers that exists in the formulation is evaluated by size exclusion chromatography (SEC).

Low Molecular Weight (LMW) Species

In some embodiments, less than 10%, 8%, 5%, 4%, 3%, 2%, 1%, or 0.5% of an anti-IL1R1 antibody exists as LMW species in a formulation upon storage at 5° C. for at least 4 weeks, at least 6 weeks, at least 2 months, at least 3 months, at least 4 months, at least 6 months, at least 8 months, at least 10 months, or at least 12 months. In some embodiments, less than 5% of an anti-IL1R1 antibody exists as LMW species in a formulation upon storage at 5° C. for at least 4 weeks. In some embodiments, less than 4% of an anti-IL1R1 antibody exists as LMW species in a formulation upon storage at 5° C. for at least 4 weeks. In some embodiments, less than 3% of an anti-IL1R1 antibody exists as LMW species in a formulation upon storage at 5° C. for at least 4 weeks. In some embodiments, less than 2% of an anti-IL1R1 antibody exists as LMW species in a formulation upon storage at 5° C. for at least 4 weeks. In some embodiments, less than 1% of an anti-IL1R1 antibody exists as LMW species in a formulation upon storage at 5° C. for at least 4 weeks. In some embodiments, less than 0.5% of an anti-IL1R1 antibody exists as LMW species in a formulation upon storage at 5° C. for at least 4 weeks. In some embodiments, less than 0.4% of an anti-IL1R1 antibody exists as LMW species in a formulation upon storage at 5° C. for at least 4 weeks. In some embodiments, less than 0.3% of an anti-IL1R1 antibody exists as LMW species in a formulation upon storage at 5° C. for at least 4 weeks. In some embodiments, less than 0.2% of an anti-IL1R1 antibody exists as LMW species in a formulation upon storage at 5° C. for at least 4 weeks. In some embodiments, less than 0.1% of an anti-IL1R1 antibody exists as LMW species in a formulation upon storage at 5° C. for at least 4 weeks. In some embodiments, the formulation is substantially free of LMW species upon storage at 5° C. for at least 4 weeks.

In some embodiments, less than 5% of an anti-IL1R1 antibody exists as LMW species in a formulation upon storage at 5° C. for at least 2 months. In some embodiments, less than 4% of an anti-IL1R1 antibody exists as LMW species in a formulation upon storage at 5° C. for at least 2 months. In some embodiments, less than 3% of an anti-IL1R1 antibody exists as LMW species in a formulation upon storage at 5° C. for at least 2 months. In some embodiments, less than 2% of an anti-IL1R1 antibody exists as LMW species in a formulation upon storage at 5° C. for at least 2 months. In some embodiments, less than 1% of an anti-IL1R1 antibody exists as LMW species in a formulation upon storage at 5° C. for at least 2 months. In some embodiments, less than 0.5% of an anti-IL1R1 antibody exists as LMW species in a formulation upon storage at 5° C. for at least 2 months. In some embodiments, less than 0.4% of an anti-IL1R1 antibody exists as LMW species in a formulation upon storage at 5° C. for at least 2 months. In some embodiments, less than 0.3% of an anti-IL1R1 antibody exists as LMW species in a formulation upon storage at 5° C. for at least 2 months. In some embodiments, less than 0.2% of an anti-IL1R1 antibody exists as LMW species in a formulation upon storage at 5° C. for at least 2 months. In some embodiments, less than 0.1% of an anti-IL1R1 antibody exists as LMW species in a formulation upon storage at 5° C. for at least 2 months. In some embodiments, the formulation is substantially free of LMW species upon storage at 5° C. for at least 2 months.

In some embodiments, less than 10%, 8%, 5%, 4%, 3%, 2%, 1%, or 0.5% of an anti-IL1R1 antibody exists as LMW species in a formulation upon storage at 25° C. for at least 4 weeks, at least 6 weeks, at least 2 months, at least 3 months, at least 4 months, at least 6 months, at least 8 months, at least 10 months, or at least 12 months. In some embodiments, less than 5% of an anti-IL1R1 antibody exists as LMW species in a formulation upon storage at 25° C. for at least 4 weeks. In some embodiments, less than 4% of an anti-IL1R1 antibody exists as LMW species in a formulation upon storage at 25° C. for at least 4 weeks. In some embodiments, less than 3% of an anti-IL1R1 antibody exists as LMW species in a formulation upon storage at 25° C. for at least 4 weeks. In some embodiments, less than 2% of an anti-IL1R1 antibody exists as LMW species in a formulation upon storage at 25° C. for at least 4 weeks. In some embodiments, less than 1% of an anti-IL1R1 antibody exists as LMW species in a formulation upon storage at 25° C. for at least 4 weeks. In some embodiments, less than 0.5% of an anti-IL1R1 antibody exists as LMW species in a formulation upon storage at 25° C. for at least 4 weeks. In some embodiments, less than 0.4% of an anti-IL1R1 antibody exists as LMW species in a formulation upon storage at 25° C. for at least 4 weeks. In some embodiments, less than 0.3% of an anti-IL1R1 antibody exists as LMW species in a formulation upon storage at 25° C. for at least 4 weeks. In some embodiments, less than 0.2% of an anti-IL1R1 antibody exists as LMW species in a formulation upon storage at 25° C. for at least 4 weeks. In some embodiments, less than 0.1% of an anti-IL1R1 antibody exists as LMW species in a formulation upon storage at 25° C. for at least 4 weeks. In some embodiments, the formulation is substantially free of LMW species upon storage at 25° C. for at least 4 weeks.

In some embodiments, less than 5% of an anti-IL1R1 antibody exists as LMW species in a formulation upon storage at 25° C. for at least 2 months. In some embodiments, less than 4% of an anti-IL1R1 antibody exists as LMW species in a formulation upon storage at 25° C. for at least 2 months. In some embodiments, less than 3% of an anti-IL1R1 antibody exists as LMW species in a formulation upon storage at 25° C. for at least 2 months. In some embodiments, less than 2% of an anti-IL1R1 antibody exists as LMW species in a formulation upon storage at 25° C. for at least 2 months. In some embodiments, less than 1% of an anti-IL1R1 antibody exists as LMW species in a formulation upon storage at 25° C. for at least 2 months. In some embodiments, less than 0.5% of an anti-IL1R1 antibody exists as LMW species in a formulation upon storage at 25° C. for at least 2 months. In some embodiments, less than 0.4% of an anti-IL1R1 antibody exists as LMW species in a formulation upon storage at 25° C. for at least 2 months. In some embodiments, less than 0.3% of an anti-IL1R1 antibody exists as LMW species in a formulation upon storage at 25° C. for at least 2 months. In some embodiments, less than 0.2% of an anti-IL1R1 antibody exists as LMW species in a formulation upon storage at 25° C. for at least 2 months. In some embodiments, less than 0.1% of an anti-IL1R1 antibody exists as LMW species in a formulation upon storage at 25° C. for at least 2 months. In some embodiments, the formulation is substantially free of LMW species upon storage at 25° C. for at least 2 months.

In some embodiments, less than 10%, 8%, 5%, 4%, 3%, 2%, 1%, or 0.5% of an anti-IL1R1 antibody exists as LMW species in a formulation upon storage at 40° C. for at least 4 weeks, at least 6 weeks, at least 2 months, at least 3 months, at least 4 months, at least 6 months, at least 8 months, at least 10 months, or at least 12 months. In some embodiments, less than 5% of an anti-IL1R1 antibody exists as LMW species in a formulation upon storage at 40° C. for at least 4 weeks. In some embodiments, less than 4% of an anti-IL1R1 antibody exists as LMW species in a formulation upon storage at 40° C. for at least 4 weeks. In some embodiments, less than 3% of an anti-IL1R1 antibody exists as LMW species in a formulation upon storage at 40° C. for at least 4 weeks. In some embodiments, less than 2% of an anti-IL1R1 antibody exists as LMW species in a formulation upon storage at 40° C. for at least 4 weeks. In some embodiments, less than 1% of an anti-IL1R1 antibody exists as LMW species in a formulation upon storage at 40° C. for at least 4 weeks. In some embodiments, less than 0.5% of an anti-IL1R1 antibody exists as LMW species in a formulation upon storage at 40° C. for at least 4 weeks. In some embodiments, less than 0.4% of an anti-IL1R1 antibody exists as LMW species in a formulation upon storage at 40° C. for at least 4 weeks. In some embodiments, less than 0.3% of an anti-IL1R1 antibody exists as LMW species in a formulation upon storage at 40° C. for at least 4 weeks. In some embodiments, less than 0.2% of an anti-IL1R1 antibody exists as LMW species in a formulation upon storage at 40° C. for at least 4 weeks. In some embodiments, less than 0.1% of an anti-IL1R1 antibody exists as LMW species in a formulation upon storage at 40° C. for at least 4 weeks. In some embodiments, the formulation is substantially free of LMW species upon storage at 40° C. for at least 4 weeks.

In some embodiments, less than 5% of an anti-IL1R1 antibody exists as LMW species in a formulation upon storage at 40° C. for at least 2 months. In some embodiments, less than 4% of an anti-IL1R1 antibody exists as LMW species in a formulation upon storage at 40° C. for at least 2 months. In some embodiments, less than 3% of an anti-IL1R1 antibody exists as LMW species in a formulation upon storage at 40° C. for at least 2 months. In some embodiments, less than 2% of an anti-IL1R1 antibody exists as LMW species in a formulation upon storage at 40° C. for at least 2 months. In some embodiments, less than 1% of an anti-IL1R1 antibody exists as LMW species in a formulation upon storage at 40° C. for at least 2 months. In some embodiments, less than 0.5% of an anti-IL1R1 antibody exists as LMW species in a formulation upon storage at 40° C. for at least 2 months. In some embodiments, less than 0.4% of an anti-IL1R1 antibody exists as LMW species in a formulation upon storage at 40° C. for at least 2 months. In some embodiments, less than 0.3% of an anti-IL1R1 antibody exists as LMW species in a formulation upon storage at 40° C. for at least 2 months. In some embodiments, less than 0.2% of an anti-IL1R1 antibody exists as LMW species in a formulation upon storage at 40° C. for at least 2 months. In some embodiments, less than 0.1% of an anti-IL1R1 antibody exists as LMW species in a formulation upon storage at 40° C. for at least 2 months. In some embodiments, the formulation is substantially free of LMW species upon storage at 40° C. for at least 2 months.

In some embodiments, the percentage of LMW species that exists in the formulation is evaluated by size exclusion chromatography (SEC).

Fragmentation

Fragmentation is a well-characterized degradation pathway of therapeutic antibodies and is usually monitored by capillary electrophoresis-sodium dodecyl sulfate (CE-SDS). In some embodiments, stability of an antibody formulation is assessed by non-reducing CE-SDS (NR-CD-SDS).

In some embodiments, less than 5%, 4%, 3%, 2%, 1%, 0.5%, 0.4%, 0.3%, 0.2% or 0.1% of an anti-IL1R1 antibody exists as fragments upon storage at 5° C. for at least 2 weeks, 4 weeks, 6 weeks, 2 months, 4, months, 6 months, 8 months, 10 months, or 12 months. In some embodiments, less than 5% of an anti-IL1R1 antibody exists as fragments upon storage at 5° C. for at least 4 weeks. In some embodiments, less than 4% of an anti-IL1R1 antibody exists as fragments upon storage at 5° C. for at least 4 weeks. In some embodiments, less than 3% of an anti-IL1R1 antibody exists as fragments upon storage at 5° C. for at least 4 weeks. In some embodiments, less than 2% of an anti-IL1R1 antibody exists as fragments upon storage at 5° C. for at least 4 weeks. In some embodiments, less than 1.9% of an anti-IL1R1 antibody exists as fragments upon storage at 5° C. for at least 4 weeks. In some embodiments, less than 1.8% of an anti-IL1R1 antibody exists as fragments upon storage at 5° C. for at least 4 weeks. In some embodiments, less than 1.7% of an anti-IL1R1 antibody exists as fragments upon storage at 5° C. for at least 4 weeks. In some embodiments, less than 1.6% of an anti-IL1R1 antibody exists as fragments upon storage at 5° C. for at least 4 weeks. In some embodiments, less than 1.5% of an anti-IL1R1 antibody exists as fragments upon storage at 5° C. for at least 4 weeks. In some embodiments, less than 1.4% of an anti-IL1R1 antibody exists as fragments upon storage at 5° C. for at least 4 weeks. In some embodiments, less than 1.3% of an anti-IL1R1 antibody exists as fragments upon storage at 5° C. for at least 4 weeks. In some embodiments, less than 1.2% of an anti-IL1R1 antibody exists as fragments upon storage at 5° C. for at least 4 weeks. In some embodiments, less than 1.1% of an anti-IL1R1 antibody exists as fragments upon storage at 5° C. for at least 4 weeks. In some embodiments, less than 1% of an anti-IL1R1 antibody exists as fragments upon storage at 5° C. for at least 4 weeks. In some embodiments, less than 0.5% of an anti-IL1R1 antibody exists as fragments upon storage at 5° C. for at least 4 weeks. In some embodiments, less than 0.4% of an anti-IL1R1 antibody exists as fragments upon storage at 5° C. for at least 4 weeks. In some embodiments, less than 0.3% of an anti-IL1R1 antibody exists as fragments upon storage at 5° C. for at least 4 weeks. In some embodiments, less than 0.2% of an anti-IL1R1 antibody exists as fragments upon storage at 5° C. for at least 4 weeks. In some embodiments, less than 0.1% of an anti-IL1R1 antibody exists as fragments upon storage at 5° C. for at least 4 weeks. In some embodiments, the formulation is substantially free of fragments upon storage at 5° C. for at least 4 weeks. In some embodiments, upon storage at 5° C. for at least 4 weeks, the amount of fragments in the formulation does not substantially increase.

In some embodiments, less than 5% of an anti-IL1R1 antibody exists as fragments upon storage at 5° C. for at least 2 months. In some embodiments, less than 4% of an anti-IL1R1 antibody exists as fragments upon storage at 5° C. for at least 2 months. In some embodiments, less than 3% of an anti-IL1R1 antibody exists as fragments upon storage at 5° C. for at least 2 months. In some embodiments, less than 2% of an anti-IL1R1 antibody exists as fragments upon storage at 5° C. for at least 2 months. In some embodiments, less than 1.9% of an anti-IL1R1 antibody exists as fragments upon storage at 5° C. for at least 2 months. In some embodiments, less than 1.8% of an anti-IL1R1 antibody exists as fragments upon storage at 5° C. for at least 2 months. In some embodiments, less than 1.7% of an anti-IL1R1 antibody exists as fragments upon storage at 5° C. for at least 2 months. In some embodiments, less than 1.6% of an anti-IL1R1 antibody exists as fragments upon storage at 5° C. for at least 2 months. In some embodiments, less than 1.5% of an anti-IL1R1 antibody exists as fragments upon storage at 5° C. for at least 2 months. In some embodiments, less than 1.4% of an anti-IL1R1 antibody exists as fragments upon storage at 5° C. for at least 2 months. In some embodiments, less than 1.3% of an anti-IL1R1 antibody exists as fragments upon storage at 5° C. for at least 2 months. In some embodiments, less than 1.2% of an anti- IL1R1 antibody exists as fragments upon storage at 5° C. for at least 2 months. In some embodiments, less than 1.1% of an anti-IL1R1 antibody exists as fragments upon storage at 5° C. for at least 2 months. In some embodiments, less than 1% of an anti-IL1R1 antibody exists as fragments upon storage at 5° C. for at least 2 months. In some embodiments, less than 0.5% of an anti-IL1R1 antibody exists as fragments upon storage at 5° C. for at least 2 months. In some embodiments, less than 0.4% of an anti-IL1R1 antibody exists as fragments upon storage at 5° C. for at least 2 months. In some embodiments, less than 0.3% of an anti-IL1R1 antibody exists as fragments upon storage at 5° C. for at least 2 months. In some embodiments, less than 0.2% of an anti-IL1R1 antibody exists as fragments upon storage at 5° C. for at least 2 months. In some embodiments, less than 0.1% of an anti-IL1R1 antibody exists as fragments upon storage at 5° C. for at least 2 months. In some embodiments, the formulation is substantially free of fragments upon storage at 5° C. for at least 2 months.

In some embodiments, less than 2% of an anti-IL1R1 antibody exists as fragments upon storage at 5° C. for at least 3 months. In some embodiments, less than 1.7% of an anti-IL1R1 antibody exists as fragments upon storage at 5° C. for at least 3 months.

In some embodiments, less than 2% of an anti-IL1R1 antibody exists as fragments upon storage at 5° C. for at least 6 months. In some embodiments, less than 1.6% of an anti-IL1R1 antibody exists as fragments upon storage at 5° C. for at least 6 months.

In some embodiments, less than 5%, 4%, 3%, 2%, 1%, 0.5%, 0.4%, 0.3%, 0.2% or 0.1% of an anti-IL1R1 antibody exists as fragments upon storage at 25° C. for at least 2 weeks, 4 weeks, 6 weeks, 2 months, 4, months, 6 months, 8 months, 10 months, or 12 months. In some embodiments, less than 5% of an anti-IL1R1 antibody exists as fragments upon storage at 25° C. for at least 4 weeks. In some embodiments, the amount of fragments in the formulation is less than 4% of an anti-IL1R1 antibody exists as fragments upon storage at 25° C. for at least 4 weeks. In some embodiments, less than 3% of an anti-IL1R1 antibody exists as fragments upon storage at 25° C. for at least 4 weeks. In some embodiments, less than 2% of an anti-IL1R1 antibody exists as fragments upon storage at 25° C. for at least 4 weeks. In some embodiments, less than 1.9% of an anti-IL1R1 antibody exists as fragments upon storage at 25° C. for at least 4 weeks. In some embodiments, less than 1.8% of an anti-IL1R1 antibody exists as fragments upon storage at 25° C. for at least 4 weeks. In some embodiments, less than 1.7% of an anti-IL1R1 antibody exists as fragments upon storage at 25° C. for at least 4 weeks. In some embodiments, less than 1.6% of an anti-IL1R1 antibody exists as fragments upon storage at 25° C. for at least 4 weeks. In some embodiments, less than 1.5% of an anti-IL1R1 antibody exists as fragments upon storage at 25° C. for at least 4 weeks. In some embodiments, less than 1.4% of an anti-IL1R1 antibody exists as fragments upon storage at 25° C. for at least 4 weeks. In some embodiments, less than 1.3% of an anti-IL1R1 antibody exists as fragments upon storage at 25° C. for at least 4 weeks. In some embodiments, less than 1.2% of an anti-IL1R1 antibody exists as fragments upon storage at 25° C. for at least 4 weeks. In some embodiments, less than 1.1% of an anti-IL1R1 antibody exists as fragments upon storage at 25° C. for at least 4 weeks. In some embodiments, less than 1% of an anti-IL1R1 antibody exists as fragments upon storage at 25° C. for at least 4 weeks. In some embodiments, less than 0.5% of an anti-IL1R1 antibody exists as fragments upon storage at 25° C. for at least 4 weeks. In some embodiments, less than 0.4% of an anti-IL1R1 antibody exists as fragments upon storage at 25° C. for at least 4 weeks. In some embodiments, less than 0.3% of an anti-IL1R1 antibody exists as fragments upon storage at 25° C. for at least 4 weeks. In some embodiments, less than 0.2% of an anti-IL1R1 antibody exists as fragments upon storage at 25° C. for at least 4 weeks. In some embodiments, less than 0.1% of an anti-IL1R1 antibody exists as fragments upon storage at 25° C. for at least 4 weeks. In some embodiments, the formulation is substantially free of fragments upon storage at 25° C. for at least 4 weeks.

In some embodiments, less than 5% of an anti-IL1R1 antibody exists as fragments upon storage at 5° C. for at least 2 months. In some embodiments, less than 4% of an anti-IL1R1 antibody exists as fragments upon storage at 25° C. for at least 2 months. In some embodiments, less than 3% of an anti-IL1R1 antibody exists as fragments upon storage at 25° C. for at least 2 months. In some embodiments, less than 2% of an anti-IL1R1 antibody exists as fragments upon storage at 25° C. for at least 2 months. In some embodiments, less than 1.9% of an anti-IL1R1 antibody exists as fragments upon storage at 25° C. for at least 2 months. In some embodiments, less than 1.8% of an anti-IL1R1 antibody exists as fragments upon storage at 25° C. for at least 2 months. In some embodiments, less than 1.7% of an anti-IL1R1 antibody exists as fragments upon storage at 25° C. for at least 2 months. In some embodiments, less than 1.6% of an anti-IL1R1 antibody exists as fragments upon storage at 25° C. for at least 2 months. In some embodiments, less than 1.5% of an anti-IL1R1 antibody exists as fragments upon storage at 25° C. for at least 2 months. In some embodiments, less than 1.4% of an anti-IL1R1 antibody exists as fragments upon storage at 25° C. for at least 2 months. In some embodiments, less than 1.3% of an anti-IL1R1 antibody exists as fragments upon storage at 25° C. for at least 2 months. In some embodiments, less than 1.2% of an anti-IL1R1 antibody exists as fragments upon storage at 25° C. for at least 2 months. In some embodiments, less than 1.1% of an anti-IL1R1 antibody exists as fragments upon storage at 25° C. for at least 2 months. In some embodiments, less than 1% of an anti-IL1R1 antibody exists as fragments upon storage at 25° C. for at least 2 months. In some embodiments, less than 0.5% of an anti-IL1R1 antibody exists as fragments upon storage at 25° C. for at least 2 months. In some embodiments, less than 0.4% of an anti-IL1R1 antibody exists as fragments upon storage at 25° C. for at least 2 months. In some embodiments, less than 0.3% of an anti-IL1R1 antibody exists as fragments upon storage at 25° C. for at least 2 months. In some embodiments, less than 0.2% of an anti-IL1R1 antibody exists as fragments upon storage at 25° C. for at least 2 months. In some embodiments, less than 0.1% of an anti-IL1R1 antibody exists as fragments upon storage at 25° C. for at least 2 months. In some embodiments, the formulation is substantially free of fragments upon storage at 25° C. for at least 2 months.

In some embodiments, less than 2% of an anti-IL1R1 antibody exists as fragments upon storage at 25° C. for at least 3 months. In some embodiments, less than 2.5% of an anti-IL1R1 antibody exists as fragments upon storage at 25° C. for at least 6 months. In some embodiments, less than 2.3% of an anti-IL1R1 antibody exists as fragments upon storage at 25° C. for at least 6 months.

In some embodiments, less than 5%, 4%, 3%, 2%, 1%, 0.5%, 0.4%, 0.3%, 0.2% or 0.1% of an anti-IL1R1 antibody exists as fragments upon storage at 40° C. for at least 2 weeks, 4 weeks, 6 weeks, 2 months, 4, months, 6 months, 8 months, 10 months, or 12 months. In some embodiments, less than 5% of an anti-IL1R1 antibody exists as fragments upon storage at 40° C. for at least 4 weeks. In some embodiments, less than 4% of an anti-IL1R1 antibody exists as fragments upon storage at 40° C. for at least 4 weeks. In some embodiments, less than 3.9% of an anti-IL1R1 antibody exists as fragments upon storage at 40° C. for at least 4 weeks. In some embodiments, less than 3.8% of an anti-IL1R1 antibody exists as fragments upon storage at 40° C. for at least 4 weeks. In some embodiments, less than 3.7% of an anti-IL1R1 antibody exists as fragments upon storage at 40° C. for at least 4 weeks. In some embodiments, less than 3.6% of an anti-IL1R1 antibody exists as fragments upon storage at 40° C. for at least 4 weeks. In some embodiments, less than 3.5% of an anti-IL1R1 antibody exists as fragments upon storage at 40° C. for at least 4 weeks. In some embodiments, less than 3.4% of an anti-IL1R1 antibody exists as fragments upon storage at 40° C. for at least 4 weeks. In some embodiments, less than 3.3% of an anti-IL1R1 antibody exists as fragments upon storage at 40° C. for at least 4 weeks. In some embodiments, less than 3.2% of an anti-IL1R1 antibody exists as fragments upon storage at 40° C. for at least 4 weeks. In some embodiments, less than 3.1% of an anti-IL1R1 antibody exists as fragments upon storage at 40° C. for at least 4 weeks. In some embodiments, less than 3% of an anti-IL1R1 antibody exists as fragments upon storage at 40° C. for at least 4 weeks. In some embodiments, less than 2.9% of an anti-IL1R1 antibody exists as fragments upon storage at 40° C. for at least 4 weeks. In some embodiments, less than 2.8% of an anti-IL1R1 antibody exists as fragments upon storage at 40° C. for at least 4 weeks. In some embodiments, less than 2.7% of an anti-IL1R1 antibody exists as fragments upon storage at 40° C. for at least 4 weeks. In some embodiments, less than 2.6% of an anti-IL1R1 antibody exists as fragments upon storage at 40° C. for at least 4 weeks. In some embodiments, less than 2.5% of an anti-IL1R1 antibody exists as fragments upon storage at 40° C. for at least 4 weeks. In some embodiments, less than 2.4% of an anti-IL1R1 antibody exists as fragments upon storage at 40° C. for at least 4 weeks. In some embodiments, less than 2.3% of an anti-IL1R1 antibody exists as fragments upon storage at 40° C. for at least 4 weeks. In some embodiments, less than 2.2% of an anti-IL1R1 antibody exists as fragments upon storage at 40° C. for at least 4 weeks. In some embodiments, less than 2.1% of an anti-IL1R1 antibody exists as fragments upon storage at 40° C. for at least 4 weeks. In some embodiments, less than 2% of an anti-IL1R1 antibody exists as fragments upon storage at 40° C. for at least 4 weeks. In some embodiments, less than 1.8% of an anti-IL1R1 antibody exists as fragments upon storage at 40° C. for at least 4 weeks. In some embodiments, less than 1.5% of an anti-IL1R1 antibody exists as fragments upon storage at 40° C. for at least 4 weeks. In some embodiments, less than 1.2% of an anti-IL1R1 antibody exists as fragments upon storage at 40° C. for at least 4 weeks. In some embodiments, less than 1.0% of an anti-IL1R1 antibody exists as fragments upon storage at 40° C. for at least 4 weeks. In some embodiments, less than 0.8% of an anti-IL1R1 antibody exists as fragments upon storage at 40° C. for at least 4 weeks. In some embodiments, less than 0.5% of an anti-IL1R1 antibody exists as fragments upon storage at 40° C. for at least 4 weeks.

In some embodiments, less than 10% of an anti-IL1R1 antibody exists as fragments upon storage at 40° C. for at least 2 months. In some embodiments, less than 8% of an anti-IL1R1 antibody exists as fragments upon storage at 40° C. for at least 2 months. In some embodiments, less than 7% of an anti-IL1R1 antibody exists as fragments upon storage at 40° C. for at least 2 months. In some embodiments, less than 6% of an anti-IL1R1 antibody exists as fragments upon storage at 40° C. for at least 2 months. In some embodiments, less than 5.9% of an anti-IL1R1 antibody exists as fragments upon storage at 40° C. for at least 2 months. In some embodiments, less than 5.8% of an anti-IL1R1 antibody exists as fragments upon storage at 40° C. for at least 2 months. In some embodiments, less than 5.7% of an anti-IL1R1 antibody exists as fragments upon storage at 40° C. for at least 2 months. In some embodiments, less than 5.6% of an anti-IL1R1 antibody exists as fragments upon storage at 40° C. for at least 2 months. In some embodiments, less than 5.5% of an anti-IL1R1 antibody exists as fragments upon storage at 40° C. for at least 2 months. In some embodiments, less than 5.4% of an anti-IL1R1 antibody exists as fragments upon storage at 40° C. for at least 2 months. In some embodiments, less than 5.3% of an anti-IL1R1 antibody exists as fragments upon storage at 40° C. for at least 2 months. In some embodiments, less than 5.2% of an anti-IL1R1 antibody exists as fragments upon storage at 40° C. for at least 2 months. In some embodiments, less than 5.1% of an anti-IL1R1 antibody exists as fragments upon storage at 40° C. for at least 2 months. In some embodiments, less than 5% of an anti-IL1R1 antibody exists as fragments upon storage at 40° C. for at least 2 months. In some embodiments, less than 4.9% of an anti-IL1R1 antibody exists as fragments upon storage at 40° C. for at least 2 months. In some embodiments, less than 4.8% of an anti-IL1R1 antibody exists as fragments upon storage at 40° C. for at least 2 months. In some embodiments, less than 4.7% of an anti-IL1R1 antibody exists as fragments upon storage at 40° C. for at least 2 months. In some embodiments, less than 4.6% of an anti-IL1R1 antibody exists as fragments upon storage at 40° C. for at least 2 months. In some embodiments, less than 4.5% of an anti-IL1R1 antibody exists as fragments upon storage at 40° C. for at least 2 months. In some embodiments, less than 4% of an anti-IL1R1 antibody exists as fragments upon storage at 40° C. for at least 2 months. In some embodiments, less than 3.9% of an anti-IL1R1 antibody exists as fragments upon storage at 40° C. for at least 2 months. In some embodiments, less than 3.8% of an anti-IL1R1 antibody exists as fragments upon storage at 40° C. for at least 2 months. In some embodiments, less than 3.7% of an anti-IL1R1 antibody exists as fragments upon storage at 40° C. for at least 2 months. In some embodiments, less than 3.6% of an anti-IL1R1 antibody exists as fragments upon storage at 40° C. for at least 2 months. In some embodiments, less than 3.5% of an anti-IL1R1 antibody exists as fragments upon storage at 40° C. for at least 2 months. In some embodiments, less than 3.4% of an anti-IL1R1 antibody exists as fragments upon storage at 40° C. for at least 2 months. In some embodiments, less than 3.3% of an anti-IL1R1 antibody exists as fragments upon storage at 40° C. for at least 2 months. In some embodiments, less than 3.2% of an anti-IL1R1 antibody exists as fragments upon storage at 40° C. for at least 2 months. In some embodiments, less than 3.1% of an anti-IL1R1 antibody exists as fragments upon storage at 40° C. for at least 2 months. In some embodiments, less than 3% of an anti-IL1R1 antibody exists as fragments upon storage at 40° C. for at least 2 months. In some embodiments, less than 2.9% of an anti-IL1R1 antibody exists as fragments upon storage at 40° C. for at least 2 months. In some embodiments, less than 2.8% of an anti-IL1R1 antibody exists as fragments upon storage at 40° C. for at least 2 months. In some embodiments, less than 2.7% of an anti-IL1R1 antibody exists as fragments upon storage at 40° C. for at least 2 months. In some embodiments, less than 2.6% of an anti-IL1R1 antibody exists as fragments upon storage at 40° C. for at least 2 months. In some embodiments, less than 2.5% of an anti-IL1R1 antibody exists as fragments upon storage at 40° C. for at least 2 months. In some embodiments, less than 2.4% of an anti-IL1R1 antibody exists as fragments upon storage at 40° C. for at least 2 months. In some embodiments, less than 2.3% of an anti-IL1R1 antibody exists as fragments upon storage at 40° C. for at least 2 months. In some embodiments, less than 2.2% of an anti-IL1R1 antibody exists as fragments upon storage at 40° C. for at least 2 months. In some embodiments, less than 2.1% of an anti-IL1R1 antibody exists as fragments upon storage at 40° C. for at least 2 months. In some embodiments, less than 2% of an anti-IL1R1 antibody exists as fragments upon storage at 40° C. for at least 2 months. In some embodiments, less than 1.8% of an anti-IL1R1 antibody exists as fragments upon storage at 40° C. for at least 2 months. In some embodiments, less than 1.5% of an anti-IL1R1 antibody exists as fragments upon storage at 40° C. for at least 2 months. In some embodiments, less than 1.2% of an anti-IL1R1 antibody exists as fragments upon storage at 40° C. for at least 2 months. In some embodiments, less than 1.0% of an anti-IL1R1 antibody exists as fragments upon storage at 40° C. for at least 2 months. In some embodiments, less than 0.8% of an anti-IL1R1 antibody exists as fragments upon storage at 40° C. for at least 2 months. In some embodiments, less than 0.5% of an anti-IL1R1 antibody exists as fragments upon storage at 40° C. for at least 2 months.

In some embodiments, less than 5% of an anti-IL1R1 antibody exists as fragments upon storage at 40° C. for at least 3 months. In some embodiments, less than 4.5% of an anti-IL1R1 antibody exists as fragments upon storage at 40° C. for at least 3 months. In some embodiments, less than 4.2% of an anti-IL1R1 antibody exists as fragments upon storage at 40° C. for at least 3 months.

In some embodiments, the amount of fragments in the formulation is evaluated by non-reducing capillary electrophoresis sodium dodecyl sulphate (NR-CE-SDS).

In some embodiments, the amount of fragments in a formulation increases less than 20%, 15%, 14%, 13%, 12%, 11%, 10%, 9%, 8%, 7%, 6%, 5%, 4%, 3%, 2%, 1%, 0.5%, 0.4%, 0.2% or 0.1% upon storage at 5° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 5° C. for 4 weeks, the amount of fragments in the formulation does not substantially increase. In some embodiments, upon storage at 5° C. for 4 weeks, the amount of fragments in the formulation increases less than 15%. In some embodiments, upon storage at 5° C. for 4 weeks, the amount of fragments in the formulation increases less than 14%. In some embodiments, upon storage at 5° C. for 4 weeks, the amount of fragments in the formulation increases less than 13%. In some embodiments, upon storage at 5° C. for 4 weeks, the amount of fragments in the formulation increases less than 12%. In some embodiments, upon storage at 5° C. for 4 weeks, the amount of fragments in the formulation increases less than 11%. In some embodiments, upon storage at 5° C. for 4 weeks, the amount of fragments in the formulation increases less than 10%. In some embodiments, upon storage at 5° C. for 4 weeks, the amount of fragments in the formulation increases less than 5%. In some embodiments, upon storage at 5° C. for 4 weeks, the amount of fragments in the formulation increases less than 4%. In some embodiments, upon storage at 5° C. for 4 weeks, the amount of fragments in the formulation increases less than 3%. In some embodiments, upon storage at 5° C. for 4 weeks, the amount of fragments in the formulation increases less than 2%. In some embodiments, upon storage at 5° C. for 4 weeks, the amount of fragments in the formulation increases less than 1.5%. In some embodiments, upon storage at 5° C. for 4 weeks, the amount of fragments in the formulation increases less than 1.0%. In some embodiments, upon storage at 5° C. for 4 weeks, the amount of fragments in the formulation increases less than 0.8%. In some embodiments, upon storage at 5° C. for 4 weeks, the amount of fragments in the formulation increases less than 0.6%. In some embodiments, upon storage at 5° C. for 4 weeks, the amount of fragments in the formulation increases less than 0.5%. In some embodiments, upon storage at 5° C. for 4 weeks, the amount of fragments in the formulation increases less than 0.4%. In some embodiments, upon storage at 5° C. for 4 weeks, the amount of fragments in the formulation increases less than 0.3%. In some embodiments, upon storage at 5° C. for 4 weeks, the amount of fragments in the formulation increases less than 0.2%. In some embodiments, upon storage at 5° C. for 4 weeks, the amount of fragments in the formulation increases less than 0.1%. In some embodiments, upon storage at 5° C., for 4 weeks the amount of fragments in the formulation does not substantially increase.

In some embodiments, upon storage at 5° C. for 3 months, the amount of fragments in the formulation increases less than 20%. In some embodiments, upon storage at 5° C. for 3 months, the amount of fragments in the formulation increases less than 15%. In some embodiments, upon storage at 5° C., for 3 months, the amount of fragments in the formulation does not substantially increase. In some embodiments, upon storage at 5° C. for 6 months, the amount of fragments in the formulation increases less than 20%. In some embodiments, upon storage at 5° C. for 6 months, the amount of fragments in the formulation increases less than 15%. In some embodiments, upon storage at 5° C. for 6 months, the amount of fragments in the formulation increases less than 10%. In some embodiments, upon storage at 5° C. for 6 months, the amount of fragments in the formulation increases less than 8%. In some embodiments, upon storage at 5° C., for 6 months, the amount of fragments in the formulation does not substantially increase.

In some embodiments, the amount of fragments in a formulation increases less than 60%, 55%, 50%, 45%, 40%, 35%, 30%, 25%, 24%, 23%, 22%, 21%, 20%, 15%, 10%, 5%, 4%, 3%, 2%, 1%, 0.5%, 0.4%, 0.2% or 0.1% upon storage at 25° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 25° C. for 4 weeks, the amount of fragments in the formulation does not substantially increase. In some embodiments, upon storage at 25° C. for 4 weeks, the amount of fragments in the formulation increases less than 25%. In some embodiments, upon storage at 25° C. for 4 weeks, the amount of fragments in the formulation increases less than 22%. In some embodiments, upon storage at 25° C. for 4 weeks, the amount of fragments in the formulation increases less than 20%. In some embodiments, upon storage at 25° C. for 4 weeks, the amount of fragments in the formulation increases less than 10%. In some embodiments, upon storage at 25° C. for 4 weeks, the amount of fragments in the formulation increases less than 5%. In some embodiments, upon storage at 25° C. for 4 weeks, the amount of fragments in the formulation increases less than 4%. In some embodiments, upon storage at 25° C. for 4 weeks, the amount of fragments in the formulation increases less than 3%. In some embodiments, upon storage at 25° C. for 4 weeks, the amount of fragments in the formulation increases less than 2%. In some embodiments, upon storage at 25° C. for 4 weeks, the amount of fragments in the formulation increases less than 1.5%. In some embodiments, upon storage at 25° C. for 4 weeks, the amount of fragments in the formulation increases less than 1.0%. In some embodiments, upon storage at 25° C. for 4 weeks, the amount of fragments in the formulation increases less than 0.8%. In some embodiments, upon storage at 25° C. for 4 weeks, the amount of fragments in the formulation increases less than 0.6%. In some embodiments, upon storage at 25° C. for 4 weeks, the amount of fragments in the formulation increases less than 0.5%. In some embodiments, upon storage at 25° C. for 4 weeks, the amount of fragments in the formulation increases less than 0.4%. In some embodiments, upon storage at 25° C. for 4 weeks, the amount of fragments in the formulation increases less than 0.3%. In some embodiments, upon storage at 25° C. for 4 weeks, the amount of fragments in the formulation increases less than 0.2%. In some embodiments, upon storage at 25° C. for 4 weeks, the amount of fragments in the formulation increases less than 0.1%. In some embodiments, upon storage at 25° C., for 4 weeks the amount of fragments in the formulation does not substantially increase.

In some embodiments, upon storage at 25° C. for 3 months, the amount of fragments in the formulation increases less than 45%. In some embodiments, upon storage at 25° C. for 3 months, the amount of fragments in the formulation increases less than 40%. In some embodiments, upon storage at 25° C. for 3 months, the amount of fragments in the formulation increases less than 38%. In some embodiments, upon storage at 25° C. for 3 months, the amount of fragments in the formulation increases less than 36%. In some embodiments, upon storage at 25° C. for 3 months, the amount of fragments in the formulation increases less than 34%. In some embodiments, upon storage at 25° C. for 3 months, the amount of fragments in the formulation increases less than 32%. In some embodiments, upon storage at 25° C. for 3 months, the amount of fragments in the formulation increases less than 30%.

In some embodiments, upon storage at 25° C. for 6 months, the amount of fragments in the formulation increases less than 65%. In some embodiments, upon storage at 25° C. for 6 months, the amount of fragments in the formulation increases less than 60%. In some embodiments, upon storage at 25° C. for 6 months, the amount of fragments in the formulation increases less than 58%. In some embodiments, upon storage at 25° C. for 6 months, the amount of fragments in the formulation increases less than 55%.

In some embodiments, the amount of fragments in a formulation increases less than 200%, 150%, 100%, 90%, 50%, 25%, 20%, 15%, 10%, 8%, 5%, 4%, 3%, 2%, 1%, 0.5%, 0.4%, 0.2% or 0.1% upon storage at 40° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 40° C. for 4 weeks, the amount of fragments in the formulation does not substantially increase. In some embodiments, upon storage at 40° C. for 4 weeks, the amount of fragments in the formulation increases less than 90%. In some embodiments, upon storage at 40° C. for 4 weeks, the amount of fragments in the formulation increases less than 86%. In some embodiments, upon storage at 40° C. for 4 weeks, the amount of fragments in the formulation increases less than 80%. In some embodiments, upon storage at 40° C. for 4 weeks, the amount of fragments in the formulation increases less than 60%. In some embodiments, upon storage at 40° C. for 4 weeks, the amount of fragments in the formulation increases less than 40%. In some embodiments, upon storage at 40° C. for 4 weeks, the amount of fragments in the formulation increases less than 20%. In some embodiments, upon storage at 40° C. for 4 weeks, the amount of fragments in the formulation increases less than 10%. In some embodiments, upon storage at 40° C. for 4 weeks, the amount of fragments in the formulation increases less than 5%. In some embodiments, upon storage at 40° C. for 4 weeks, the amount of fragments in the formulation increases less than 4%. In some embodiments, upon storage at 40° C. for 4 weeks, the amount of fragments in the formulation increases less than 3%. In some embodiments, upon storage at 40° C. for 4 weeks, the amount of fragments in the formulation increases less than 2.5%. In some embodiments, upon storage at 40° C. for 4 weeks, the amount of fragments in the formulation increases less than 2%. In some embodiments, upon storage at 40° C. for 4 weeks, the amount of fragments in the formulation increases less than 1.9%. In some embodiments, upon storage at 40° C. for 4 weeks, the amount of fragments in the formulation increases less than 1.8%. In some embodiments, upon storage at 40° C. for 4 weeks, the amount of fragments in the formulation increases less than 1.7%. In some embodiments, upon storage at 40° C. for 4 weeks, the amount of fragments in the formulation increases less than 1.6%. In some embodiments, upon storage at 40° C. for 4 weeks, the amount of fragments in the formulation increases less than 1.5%. In some embodiments, upon storage at 40° C. for 4 weeks, the amount of fragments in the formulation increases less than 1.4%. In some embodiments, upon storage at 40° C. for 4 weeks, the amount of fragments in the formulation increases less than 1.3%. In some embodiments, upon storage at 40° C. for 4 weeks, the amount of fragments in the formulation increases less than 1.2%. In some embodiments, upon storage at 40° C. for 4 weeks, the amount of fragments in the formulation increases less than 1.1%. In some embodiments, upon storage at 40° C. for 4 weeks, the amount of fragments in the formulation increases less than 1.0%. In some embodiments, upon storage at 40° C. for 4 weeks, the amount of fragments in the formulation increases less than 0.8%. In some embodiments, upon storage at 40° C. for 4 weeks, the amount of fragments in the formulation increases less than 0.6%. In some embodiments, upon storage at 40° C. for 4 weeks, the amount of fragments in the formulation increases less than 0.5%. In some embodiments, upon storage at 40° C. for 4 weeks, the amount of fragments in the formulation increases less than 0.4%. In some embodiments, upon storage at 40° C. for 4 weeks, the amount of fragments in the formulation increases less than 0.3%. In some embodiments, upon storage at 40° C. for 4 weeks, the amount of fragments in the formulation increases less than 0.2%. In some embodiments, upon storage at 40° C. for 4 weeks, the amount of fragments in the formulation increases less than 0.1%. In some embodiments, upon storage at 40° C., for 4 weeks the amount of fragments in the formulation does not substantially increase.

In some embodiments, upon storage at 40° C. for 3 months, the amount of fragments in the formulation increases less than 225%. In some embodiments, upon storage at 40° C. for 3 months, the amount of fragments in the formulation increases less than 200%. In some embodiments, upon storage at 40° C. for 3 months, the amount of fragments in the formulation increases less than 193%. In some embodiments, upon storage at 40° C. for 3 months, the amount of fragments in the formulation increases less than 185%. In some embodiments, upon storage at 40° C. for 3 months, the amount of fragments in the formulation increases less than 175%. In some embodiments, the percent increase of fragments in the formulation (ΔFragment %) is evaluated by non-reducing capillary electrophoresis sodium dodecyl sulphate (NR-CE-SDS).

Acidic Species

In some embodiments, less than 55%, 50%, 45%, 44%, 43%, 42%, 41%, 40%, 39%, 38%, 37%, 36%, 35%, 34%, 33%, 32%, 31%, 30%, 20%, 10%, 8%, 5%, 4%, 3%, 2%, 1%, or 0.5% of an anti-IL1R1 antibody exists as acidic species in a formulation upon storage at 5° C. for at least 4 weeks, at least 6 weeks, at least 2 months, at least 3 months, at least 4 months, at least 6 months, at least 8 months, at least 10 months, or at least 12 months. In some embodiments, less than 50% of an anti-IL1R1 antibody exists as acidic species in a formulation upon storage at 5° C. for at least 4 weeks. In some embodiments, less than 45% of an anti-IL1R1 antibody exists as acidic species in a formulation upon storage at 5° C. for at least 4 weeks. In some embodiments, less than 44.5% of an anti-IL1R1 antibody exists as acidic species in a formulation upon storage at 5° C. for at least 4 weeks. In some embodiments, less than 44.4% of an anti-IL1R1 antibody exists as acidic species in a formulation upon storage at 5° C. for at least 4 weeks. In some embodiments, less than 44.3% of an anti-IL1R1 antibody exists as acidic species in a formulation upon storage at 5° C. for at least 4 weeks. In some embodiments, less than 44.2% of an anti-IL1R1 antibody exists as acidic species in a formulation upon storage at 5° C. for at least 4 weeks. In some embodiments, less than 44.1% of an anti-IL1R1 antibody exists as acidic species in a formulation upon storage at 5° C. for at least 4 weeks. In some embodiments, less than 44% of an anti-IL1R1 antibody exists as acidic species in a formulation upon storage at 5° C. for at least 4 weeks. In some embodiments, less than 43.5% of an anti-IL1R1 antibody exists as acidic species in a formulation upon storage at 5° C. for at least 4 weeks. In some embodiments, less than 42% of an anti-IL1R1 antibody exists as acidic species in a formulation upon storage at 5° C. for at least 4 weeks. In some embodiments, less than 41% of an anti-IL1R1 antibody exists as acidic species in a formulation upon storage at 5° C. for at least 4 weeks. In some embodiments, less than 40% of an anti-IL1R1 antibody exists as acidic species in a formulation upon storage at 5° C. for at least 4 weeks. In some embodiments, less than 39% of an anti-IL1R1 antibody exists as acidic species in a formulation upon storage at 5° C. for at least 4 weeks. In some embodiments, less than 38% of an anti-IL1R1 antibody exists as acidic species in a formulation upon storage at 5° C. for at least 4 weeks. In some embodiments, less than 37% of an anti-IL1R1 antibody exists as acidic species in a formulation upon storage at 5° C. for at least 4 weeks. In some embodiments, less than 36% of an anti-IL1R1 antibody exists as acidic species in a formulation upon storage at 5° C. for at least 4 weeks. In some embodiments, less than 35% of an anti-IL1R1 antibody exists as acidic species in a formulation upon storage at 5° C. for at least 4 weeks. In some embodiments, 34.5% or less of an anti-IL1R1 antibody exists as acidic species in a formulation upon storage at 5° C. for at least 4 weeks. In some embodiments, less than 34% of an anti-IL1R1 antibody exists as acidic species in a formulation upon storage at 5° C. for at least 4 weeks. In some embodiments, less than 30% of an anti-IL1R1 antibody exists as acidic species in a formulation upon storage at 5° C. for at least 4 weeks. In some embodiments, less than 20% of an anti-IL1R1 antibody exists as acidic species in a formulation upon storage at 5° C. for at least 4 weeks. In some embodiments, less than 10% of an anti-IL1R1 antibody exists as acidic species in a formulation upon storage at 5° C. for at least 4 weeks.

In some embodiments, less than 50% of an anti-IL1R1 antibody exists as acidic species in a formulation upon storage at 5° C. for at least 2 months. In some embodiments, less than 45% of an anti-IL1R1 antibody exists as acidic species in a formulation upon storage at 5° C. for at least 2 months. In some embodiments, less than 44% of an anti-IL1R1 antibody exists as acidic species in a formulation upon storage at 5° C. for at least 2 months. In some embodiments, less than 43% of an anti-IL1R1 antibody exists as acidic species in a formulation upon storage at 5° C. for at least 2 months. In some embodiments, less than 42.5% of an anti-IL1R1 antibody exists as acidic species in a formulation upon storage at 5° C. for at least 2 months. In some embodiments, less than 42.4% of an anti-IL1R1 antibody exists as acidic species in a formulation upon storage at 5° C. for at least 2 months. In some embodiments, less than 42.3% of an anti-IL1R1 antibody exists as acidic species in a formulation upon storage at 5° C. for at least 2 months. In some embodiments, less than 42.2% of an anti-IL1R1 antibody exists as acidic species in a formulation upon storage at 5° C. for at least 2 months. In some embodiments, less than 42.1% of an anti-IL1R1 antibody exists as acidic species in a formulation upon storage at 5° C. for at least 2 months. In some embodiments, less than 42% of an anti-IL1R1 antibody exists as acidic species in a formulation upon storage at 5° C. for at least 2 months. In some embodiments, less than 41.5% of an anti-IL1R1 antibody exists as acidic species in a formulation upon storage at 5° C. for at least 2 months. In some embodiments, less than 41% of an anti-IL1R1 antibody exists as acidic species in a formulation upon storage at 5° C. for at least 2 months. In some embodiments, less than 40% of an anti-IL1R1 antibody exists as acidic species in a formulation upon storage at 5° C. for at least 2 months. In some embodiments, less than 30% of an anti-IL1R1 antibody exists as acidic species in a formulation upon storage at 5° C. for at least 2 months. In some embodiments, less than 20% of an anti-IL1R1 antibody exists as acidic species in a formulation upon storage at 5° C. for at least 2 months. In some embodiments, less than 10% of an anti-IL1R1 antibody exists as acidic species in a formulation upon storage at 5° C. for at least 2 months.

In some embodiments, less than 40% of an anti-IL1R1 antibody exists as acidic species in a formulation upon storage at 5° C. for at least 3 months. In some embodiments, less than 39% of an anti-IL1R1 antibody exists as acidic species in a formulation upon storage at 5° C. for at least 3 months. In some embodiments, less than 38% of an anti-IL1R1 antibody exists as acidic species in a formulation upon storage at 5° C. for at least 3 months. In some embodiments, less than 37% of an anti-IL1R1 antibody exists as acidic species in a formulation upon storage at 5° C. for at least 3 months. In some embodiments, less than 36% of an anti-IL1R1 antibody exists as acidic species in a formulation upon storage at 5° C. for at least 3 months. In some embodiments, less than 35% of an anti-IL1R1 antibody exists as acidic species in a formulation upon storage at 5° C. for at least 3 months.

In some embodiments, less than 45% of an anti-IL1R1 antibody exists as acidic species in a formulation upon storage at 5° C. for at least 6 months. In some embodiments, less than 44% of an anti-IL1R1 antibody exists as acidic species in a formulation upon storage at 5° C. for at least 6 months. In some embodiments, less than 43% of an anti-IL1R1 antibody exists as acidic species in a formulation upon storage at 5° C. for at least 6 months. In some embodiments, less than 42% of an anti-IL1R1 antibody exists as acidic species in a formulation upon storage at 5° C. for at least 6 months. In some embodiments, less than 41% of an anti-IL1R1 antibody exists as acidic species in a formulation upon storage at 5° C. for at least 6 months. In some embodiments, less than 40% of an anti-IL1R1 antibody exists as acidic species in a formulation upon storage at 5° C. for at least 6 months.

In some embodiments, less than 55%, 50%, 45%, 44%, 43%, 42%, 41%, 40%, 39%, 38%, 37%, 36%, 35%, 34%, 33%, 32%, 31%, 30%, 20%, 10%, 8%, 5%, 4%, 3%, 2%, 1%, or 0.5% of an anti-IL1R1 antibody exists as acidic species in a formulation upon storage at 25° C. for at least 4 weeks, at least 6 weeks, at least 2 months, at least 3 months, at least 4 months, at least 6 months, at least 8 months, at least 10 months, or at least 12 months. In some embodiments, less than 50% of an anti-IL1R1 antibody exists as acidic species in a formulation upon storage at 25° C. for at least 4 weeks. In some embodiments, less than 45% of an anti-IL1R1 antibody exists as acidic species in a formulation upon storage at 25° C. for at least 4 weeks. In some embodiments, less than 44.5% of an anti-IL1R1 antibody exists as acidic species in a formulation upon storage at 25° C. for at least 4 weeks. In some embodiments, less than 44% of an anti-IL1R1 antibody exists as acidic species in a formulation upon storage at 25° C. for at least 4 weeks. In some embodiments, less than 43.9% of an anti-IL1R1 antibody exists as acidic species in a formulation upon storage at 25° C. for at least 4 weeks. In some embodiments, less than 43.8% of an anti-IL1R1 antibody exists as acidic species in a formulation upon storage at 25° C. for at least 4 weeks. In some embodiments, less than 43.7% of an anti-IL1R1 antibody exists as acidic species in a formulation upon storage at 25° C. for at least 4 weeks. In some embodiments, less than 43.6% of an anti-IL1R1 antibody exists as acidic species in a formulation upon storage at 25° C. for at least 4 weeks. In some embodiments, less than 43.5% of an anti-IL1R1 antibody exists as acidic species in a formulation upon storage at 25° C. for at least 4 weeks. In some embodiments, less than 43% of an anti-IL1R1 antibody exists as acidic species in a formulation upon storage at 25° C. for at least 4 weeks. In some embodiments, less than 42% of an anti-IL1R1 antibody exists as acidic species in a formulation upon storage at 25° C. for at least 4 weeks. In some embodiments, less than 41% of an anti-IL1R1 antibody exists as acidic species in a formulation upon storage at 25° C. for at least 4 weeks. In some embodiments, less than 40% of an anti-IL1R1 antibody exists as acidic species in a formulation upon storage at 25° C. for at least 4 weeks. In some embodiments, less than 35% of an anti-IL1R1 antibody exists as acidic species in a formulation upon storage at 25° C. for at least 4 weeks. In some embodiments, less than 30% of an anti-IL1R1 antibody exists as acidic species in a formulation upon storage at 25° C. for at least 4 weeks. In some embodiments, less than 20% of an anti-IL1R1 antibody exists as acidic species in a formulation upon storage at 25° C. for at least 4 weeks. In some embodiments, less than 10% of an anti-IL1R1 antibody exists as acidic species in a formulation upon storage at 25° C. for at least 4 weeks.

In some embodiments, less than 50% of an anti-IL1R1 antibody exists as acidic species in a formulation upon storage at 25° C. for at least 2 months. In some embodiments, less than 45% of an anti-IL1R1 antibody exists as acidic species in a formulation upon storage at 25° C. for at least 2 months. In some embodiments, less than 44.5% of an anti-IL1R1 antibody exists as acidic species in a formulation upon storage at 25° C. for at least 2 months. In some embodiments, less than 44% of an anti-IL1R1 antibody exists as acidic species in a formulation upon storage at 25° C. for at least 2 months. In some embodiments, less than 43.9% of an anti-IL1R1 antibody exists as acidic species in a formulation upon storage at 25° C. for at least 2 months. In some embodiments, less than 43.8% of an anti-IL1R1 antibody exists as acidic species in a formulation upon storage at 25° C. for at least 2 months. In some embodiments, less than 43.7% of an anti-IL1R1 antibody exists as acidic species in a formulation upon storage at 25° C. for at least 2 months. In some embodiments, less than 43.6% of an anti-IL1R1 antibody exists as acidic species in a formulation upon storage at 25° C. for at least 2 months. In some embodiments, less than 43.5% of an anti-IL1R1 antibody exists as acidic species in a formulation upon storage at 25° C. for at least 2 months. In some embodiments, less than 43% of an anti-IL1R1 antibody exists as acidic species in a formulation upon storage at 25° C. for at least 2 months. In some embodiments, less than 42% of an anti-IL1R1 antibody exists as acidic species in a formulation upon storage at 25° C. for at least 2 months. In some embodiments, less than 41% of an anti-IL1R1 antibody exists as acidic species in a formulation upon storage at 25° C. for at least 2 months. In some embodiments, less than 40% of an anti-IL1R1 antibody exists as acidic species in a formulation upon storage at 25° C. for at least 2 months. In some embodiments, less than 30% of an anti-IL1R1 antibody exists as acidic species in a formulation upon storage at 25° C. for at least 2 months. In some embodiments, less than 20% of an anti-IL1R1 antibody exists as acidic species in a formulation upon storage at 25° C. for at least 2 months. In some embodiments, less than 10% of an anti-IL1R1 antibody exists as acidic species in a formulation upon storage at 25° C. for at least 2 months.

In some embodiments, less than 40% of an anti-IL1R1 antibody exists as acidic species in a formulation upon storage at 25° C. for at least 3 months. In some embodiments, less than 36% of an anti-IL1R1 antibody exists as acidic species in a formulation upon storage at 25° C. for at least 3 months.

In some embodiments, less than 45% of an anti-IL1R1 antibody exists as acidic species in a formulation upon storage at 25° C. for at least 6 months. In some embodiments, less than 41% of an anti-IL1R1 antibody exists as acidic species in a formulation upon storage at 25° C. for at least 6 months.

In some embodiments, less than 85%, 80%, 75%, 70%, 65%, 64%, 63%, 62%, 61%, 60%, 55%, 50%, 45%, 44%, 43%, 42%, 41%, 40%, 39%, 38%, 37%, 36%, 35%, 34%, 33%, 32%, 31%, 30%, 20%, 10%, 8%, 5%, 4%, 3%, 2%, 1%, or 0.5% of an anti-IL1R1 antibody exists as acidic species in a formulation upon storage at 40° C. for at least 4 weeks, at least 6 weeks, at least 2 months, at least 3 months, at least 4 months, at least 6 months, at least 8 months, at least 10 months, or at least 12 months. In some embodiments, less than 70% of an anti-IL1R1 antibody exists as acidic species in a formulation upon storage at 40° C. for at least 4 weeks. In some embodiments, less than 69.9% of an anti-IL1R1 antibody exists as acidic species in a formulation upon storage at 40° C. for at least 4 weeks. In some embodiments, less than 69.8% of an anti-IL1R1 antibody exists as acidic species in a formulation upon storage at 40° C. for at least 4 weeks. In some embodiments, less than 69.7% of an anti-IL1R1 antibody exists as acidic species in a formulation upon storage at 40° C. for at least 4 weeks. In some embodiments, less than 69.6% of an anti-IL1R1 antibody exists as acidic species in a formulation upon storage at 40° C. for at least 4 weeks. In some embodiments, less than 69.5% of an anti-IL1R1 antibody exists as acidic species in a formulation upon storage at 40° C. for at least 4 weeks. In some embodiments, less than 68% of an anti-IL1R1 antibody exists as acidic species in a formulation upon storage at 40° C. for at least 4 weeks. In some embodiments, less than 67% of an anti-IL1R1 antibody exists as acidic species in a formulation upon storage at 40° C. for at least 4 weeks. In some embodiments, less than 66% of an anti-IL1R1 antibody exists as acidic species in a formulation upon storage at 40° C. for at least 4 weeks. In some embodiments, less than 65% of an anti-IL1R1 antibody exists as acidic species in a formulation upon storage at 40° C. for at least 4 weeks. In some embodiments, less than 60% of an anti-IL1R1 antibody exists as acidic species in a formulation upon storage at 40° C. for at least 4 weeks. In some embodiments, less than 55% of an anti-IL1R1 antibody exists as acidic species in a formulation upon storage at 40° C. for at least 4 weeks. In some embodiments, less than 54% of an anti-IL1R1 antibody exists as acidic species in a formulation upon storage at 40° C. for at least 4 weeks. In some embodiments, less than 53% of an anti-IL1R1 antibody exists as acidic species in a formulation upon storage at 40° C. for at least 4 weeks. In some embodiments, less than 52% of an anti-IL1R1 antibody exists as acidic species in a formulation upon storage at 40° C. for at least 4 weeks. In some embodiments, less than 51.5% of an anti-IL1R1 antibody exists as acidic species in a formulation upon storage at 40° C. for at least 4 weeks. In some embodiments, less than 51% of an anti-IL1R1 antibody exists as acidic species in a formulation upon storage at 40° C. for at least 4 weeks. In some embodiments, less than 50.5% of an anti-IL1R1 antibody exists as acidic species in a formulation upon storage at 40° C. for at least 4 weeks. In some embodiments, less than 50% of an anti-IL1R1 antibody exists as acidic species in a formulation upon storage at 40° C. for at least 4 weeks. In some embodiments, less than 45% of an anti-IL1R1 antibody exists as acidic species in a formulation upon storage at 40° C. for at least 4 weeks. In some embodiments, less than 44% of an anti-IL1R1 antibody exists as acidic species in a formulation upon storage at 40° C. for at least 4 weeks. In some embodiments, less than 43% of an anti-IL1R1 antibody exists as acidic species in a formulation upon storage at 40° C. for at least 4 weeks. In some embodiments, less than 42% of an anti-IL1R1 antibody exists as acidic species in a formulation upon storage at 40° C. for at least 4 weeks. In some embodiments, less than 41% of an anti-IL1R1 antibody exists as acidic species in a formulation upon storage at 40° C. for at least 4 weeks. In some embodiments, less than 40% of an anti-IL1R1 antibody exists as acidic species in a formulation upon storage at 40° C. for at least 4 weeks. In some embodiments, less than 30% of an anti-IL1R1 antibody exists as acidic species in a formulation upon storage at 40° C. for at least 4 weeks. In some embodiments, less than 20% of an anti-IL1R1 antibody exists as acidic species in a formulation upon storage at 40° C. for at least 4 weeks. In some embodiments, less than 10% of an anti-IL1R1 antibody exists as acidic species in a formulation upon storage at 40° C. for at least 4 weeks.

In some embodiments, less than 85% of an anti-IL1R1 antibody exists as acidic species in a formulation upon storage at 40° C. for at least 2 months. In some embodiments, less than 81% of an anti-IL1R1 antibody exists as acidic species in a formulation upon storage at 40° C. for at least 2 months. In some embodiments, less than 80.9% of an anti-IL1R1 antibody exists as acidic species in a formulation upon storage at 40° C. for at least 2 months. In some embodiments, less than 80.8% of an anti-IL1R1 antibody exists as acidic species in a formulation upon storage at 40° C. for at least 2 months. In some embodiments, less than 80.7% of an anti-IL1R1 antibody exists as acidic species in a formulation upon storage at 40° C. for at least 2 months. In some embodiments, less than 80.6% of an anti-IL1R1 antibody exists as acidic species in a formulation upon storage at 40° C. for at least 2 months. In some embodiments, less than 80.5% of an anti-IL1R1 antibody exists as acidic species in a formulation upon storage at 40° C. for at least 2 months. In some embodiments, less than 80% of an anti-IL1R1 antibody exists as acidic species in a formulation upon storage at 40° C. for at least 2 months. In some embodiments, less than 75% of an anti-IL1R1 antibody exists as acidic species in a formulation upon storage at 40° C. for at least 2 months. In some embodiments, less than 70% of an anti-IL1R1 antibody exists as acidic species in a formulation upon storage at 40° C. for at least 2 months. In some embodiments, less than 69% of an anti-IL1R1 antibody exists as acidic species in a formulation upon storage at 40° C. for at least 2 months. In some embodiments, less than 68% of an anti-IL1R1 antibody exists as acidic species in a formulation upon storage at 40° C. for at least 2 months. In some embodiments, less than 67% of an anti-IL1R1 antibody exists as acidic species in a formulation upon storage at 40° C. for at least 2 months. In some embodiments, less than 66% of an anti-IL1R1 antibody exists as acidic species in a formulation upon storage at 40° C. for at least 2 months. In some embodiments, less than 65% of an anti-IL1R1 antibody exists as acidic species in a formulation upon storage at 40° C. for at least 2 months. In some embodiments, less than 64% of an anti-IL1R1 antibody exists as acidic species in a formulation upon storage at 40° C. for at least 2 months. In some embodiments, less than 63% of an anti-IL1R1 antibody exists as acidic species in a formulation upon storage at 40° C. for at least 2 months. In some embodiments, less than 62% of an anti-IL1R1 antibody exists as acidic species in a formulation upon storage at 40° C. for at least 2 months. In some embodiments, less than 61% of an anti-IL1R1 antibody exists as acidic species in a formulation upon storage at 40° C. for at least 2 months. In some embodiments, less than 60% of an anti-IL1R1 antibody exists as acidic species in a formulation upon storage at 40° C. for at least 2 months. In some embodiments, less than 50% of an anti-IL1R1 antibody exists as acidic species in a formulation upon storage at 40° C. for at least 2 months. In some embodiments, less than 40% of an anti-IL1R1 antibody exists as acidic species in a formulation upon storage at 40° C. for at least 2 months. In some embodiments, less than 30% of an anti-IL1R1 antibody exists as acidic species in a formulation upon storage at 40° C. for at least 2 months. In some embodiments, less than 20% of an anti-IL1R1 antibody exists as acidic species in a formulation upon storage at 40° C. for at least 2 months. In some embodiments, less than 10% of an anti-IL1R1 antibody exists as acidic species in a formulation upon storage at 40° C. for at least 2 months.

In some embodiments, less than 65% of an anti-IL1R1 antibody exists as acidic species in a formulation upon storage at 40° C. for at least 3 months. In some embodiments, less than 64% of an anti-IL1R1 antibody exists as acidic species in a formulation upon storage at 40° C. for at least 3 months. In some embodiments, less than 63% of an anti-IL1R1 antibody exists as acidic species in a formulation upon storage at 40° C. for at least 3 months. In some embodiments, less than 62% of an anti-IL1R1 antibody exists as acidic species in a formulation upon storage at 40° C. for at least 3 months. In some embodiments, less than 61% of an anti-IL1R1 antibody exists as acidic species in a formulation upon storage at 40° C. for at least 3 months. In some embodiments, less than 60% of an anti-IL1R1 antibody exists as acidic species in a formulation upon storage at 40° C. for at least 3 months. In some embodiments, the percentage of acidic species that exists in the formulation is evaluated by imaged capillary isoelectric focusing (icIEF). In some embodiments, the percentage of acidic species that exists in the formulation is evaluated at 60% relative humidity. In some embodiments, the percentage of acidic species that exists in the formulation is evaluated at 75% relative humidity.

In some embodiments, the amount of acidic species in a formulation increases less than 5%, 4%, 3%, 2%, 1%, 0.5%, 0.4%, 0.2% or 0.1% upon storage at 5° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 5° C. for 4 weeks, the amount of acidic species in the formulation does not substantially increase. In some embodiments, upon storage at 5° C. for 4 weeks, the amount of acidic species in the formulation increases less than 1%. In some embodiments, upon storage at 5° C. for 4 weeks, the amount of acidic species in the formulation increases less than 0.5%. In some embodiments, upon storage at 5° C. for 4 weeks, the amount of acidic species in the formulation increases less than 0.4%. In some embodiments, upon storage at 5° C. for 4 weeks, the amount of acidic species in the formulation increases less than 0.3%. In some embodiments, upon storage at 5° C. for 4 weeks, the amount of acidic species in the formulation increases less than 0.2%. In some embodiments, upon storage at 5° C. for 4 weeks, the amount of acidic species in the formulation increases less than 0.1%.

In some embodiments, upon storage at 5° C. for 2 months, the amount of acidic species in the formulation does not substantially increase. In some embodiments, upon storage at 5° C. for 2 months, the amount of acidic species in the formulation increases less than 1%. In some embodiments, upon storage at 5° C. for 2 months, the amount of acidic species in the formulation increases less than 0.5%. In some embodiments, upon storage at 5° C. for 2 months, the amount of acidic species in the formulation increases less than 0.4%. In some embodiments, upon storage at 5° C. for 2 months, the amount of acidic species in the formulation increases less than 0.3%. In some embodiments, upon storage at 5° C. for 2 months, the amount of acidic species in the formulation increases less than 0.2%. In some embodiments, upon storage at 5° C. for 2 months, the amount of acidic species in the formulation increases less than 0.1%.

In some embodiments, upon storage at 5° C. for 3 months, the amount of acidic species in the formulation does not substantially increase. In some embodiments, upon storage at 5° C. for 3 months, the amount of acidic species in the formulation increases less than 5%. In some embodiments, upon storage at 5° C. for 3 months, the amount of acidic species in the formulation increases less than 2%. In some embodiments, upon storage at 5° C. for 3 months, the amount of acidic species in the formulation increases less than 1.5%. In some embodiments, upon storage at 5° C. for 3 months, the amount of acidic species in the formulation increases less than 1.2%. In some embodiments, upon storage at 5° C. for 3 months, the amount of acidic species in the formulation increases less than 1%. In some embodiments, upon storage at 5° C. for 3 months, the amount of acidic species in the formulation increases less than 0.5%. In some embodiments, upon storage at 5° C. for 3 months, the amount of acidic species in the formulation increases less than 0.4%. In some embodiments, upon storage at 5° C. for 3 months, the amount of acidic species in the formulation increases less than 0.3%. In some embodiments, upon storage at 5° C. for 3 months, the amount of acidic species in the formulation increases less than 0.2%. In some embodiments, upon storage at 5° C. for 3 months, the amount of acidic species in the formulation increases less than 0.1%.

In some embodiments, upon storage at 5° C. for 6 months, the amount of acidic species in the formulation does not substantially increase. In some embodiments, upon storage at 5° C. for 6 months, the amount of acidic species in the formulation increases less than 5%. In some embodiments, upon storage at 5° C. for 6 months, the amount of acidic species in the formulation increases less than 4%. In some embodiments, upon storage at 5° C. for 6 months, the amount of acidic species in the formulation increases less than 3%. In some embodiments, upon storage at 5° C. for 6 months, the amount of acidic species in the formulation increases less than 2%. In some embodiments, upon storage at 5° C. for 6 months, the amount of acidic species in the formulation increases less than 1.8%. In some embodiments, upon storage at 5° C. for 6 months, the amount of acidic species in the formulation increases less than 1.5%.

In some embodiments, the amount of acidic species in a formulation increases less than 20%, 19%, 18%, 17%, 16%, 15%, 14%, 13%, 12%, 11%, 10%, 8%, 7%, 6%, 5%, 4%, 3%, 2%, 1%, 0.5%, 0.4%, 0.2% or 0.1% upon storage at 25° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 25° C. for 4 weeks, the amount of acidic species in the formulation does not substantially increase. In some embodiments, upon storage at 25° C. for 4 weeks, the amount of acidic species in the formulation increases less than 2%. In some embodiments, upon storage at 25° C. for 4 weeks, the amount of acidic species in the formulation increases less than 1.5%. In some embodiments, upon storage at 25° C. for 4 weeks, the amount of acidic species in the formulation increases less than 1.2%. In some embodiments, upon storage at 25° C. for 4 weeks, the amount of acidic species in the formulation increases less than 1%. In some embodiments, upon storage at 25° C. for 4 weeks, the amount of acidic species in the formulation increases less than 0.5%. In some embodiments, upon storage at 25° C. for 4 weeks, the amount of acidic species in the formulation increases less than 0.4%. In some embodiments, upon storage at 25° C. for 4 weeks, the amount of acidic species in the formulation increases less than 0.3%. In some embodiments, upon storage at 25° C. for 4 weeks, the amount of acidic species in the formulation increases less than 0.2%. In some embodiments, upon storage at 25° C. for 4 weeks, the amount of acidic species in the formulation increases less than 0.1%.

In some embodiments, upon storage at 25° C. for 2 months, the amount of acidic species in the formulation does not substantially increase. In some embodiments, upon storage at 25° C. for 2 months, the amount of acidic species in the formulation increases less than 1%. In some embodiments, upon storage at 25° C. for 2 months, the amount of acidic species in the formulation increases less than 0.5%. In some embodiments, upon storage at 25° C. for 2 months, the amount of acidic species in the formulation increases less than 0.4%. In some embodiments, upon storage at 25° C. for 2 months, the amount of acidic species in the formulation increases less than 0.3%. In some embodiments, upon storage at 25° C. for 2 months, the amount of acidic species in the formulation increases less than 0.2%. In some embodiments, upon storage at 25° C. for 2 months, the amount of acidic species in the formulation increases less than 0.1%.

In some embodiments, upon storage at 25° C. for 3 months, the amount of acidic species in the formulation does not substantially increase. In some embodiments, upon storage at 25° C. for 3 months, the amount of acidic species in the formulation increases less than 2%. In some embodiments, upon storage at 25° C. for 3 months, the amount of acidic species in the formulation increases less than 1.5%. In some embodiments, upon storage at 25° C. for 3 months, the amount of acidic species in the formulation increases less than 1.2%. In some embodiments, upon storage at 25° C. for 3 months, the amount of acidic species in the formulation increases less than 1%

In some embodiments, upon storage at 25° C. for 6 months, the amount of acidic species in the formulation does not substantially increase. In some embodiments, upon storage at 25° C. for 6 months, the amount of acidic species in the formulation increases less than 20%. In some embodiments, upon storage at 25° C. for 6 months, the amount of acidic species in the formulation increases less than 19%. In some embodiments, upon storage at 25° C. for 6 months, the amount of acidic species in the formulation increases less than 18%. In some embodiments, upon storage at 25° C. for 6 months, the amount of acidic species in the formulation increases less than 17%. In some embodiments, upon storage at 25° C. for 6 months, the amount of acidic species in the formulation increases less than 16%. In some embodiments, upon storage at 25° C. for 6 months, the amount of acidic species in the formulation increases less than 15%.

In some embodiments, the amount of acidic species in a formulation increases less than 75%, 70%, 65%, 60%, 55%, 50% 45%, 40%, 35%, 30%, 26%, 25%, 20%, 15%, 10%, 8%, 7%, 6%, 5%, 4%, 3%, 2%, 1% upon storage at 40° C. for more than 2 weeks, more than 4 weeks, more than 6 weeks, more than 2 months, more than 3 months, more than 4 months, more than 6 months, more than 8 months, more than 10 months, or more than 12 months. In some embodiments, upon storage at 40° C. for 4 weeks, the amount of acidic species in the formulation increases less than 30%. In some embodiments, upon storage at 40° C. for 4 weeks, the amount of acidic species in the formulation increases less than 28%. In some embodiments, upon storage at 40° C. for 4 weeks, the amount of acidic species in the formulation increases less than 26%. In some embodiments, upon storage at 40° C. for 4 weeks, the amount of acidic species in the formulation increases less than 25.9%. In some embodiments, upon storage at 40° C. for 4 weeks, the amount of acidic species in the formulation increases less than 25.8%. In some embodiments, upon storage at 40° C. for 4 weeks, the amount of acidic species in the formulation increases less than 25.7%. In some embodiments, upon storage at 40° C. for 4 weeks, the amount of acidic species in the formulation increases less than 25.6%. In some embodiments, upon storage at 40° C. for 4 weeks, the amount of acidic species in the formulation increases less than 25.5%. In some embodiments, upon storage at 40° C. for 4 weeks, the amount of acidic species in the formulation increases less than 25%. In some embodiments, upon storage at 40° C. for 4 weeks, the amount of acidic species in the formulation increases less than 20%. In some embodiments, upon storage at 40° C. for 4 weeks, the amount of acidic species in the formulation increases less than 15%. In some embodiments, upon storage at 40° C. for 4 weeks, the amount of acidic species in the formulation increases less than 10%. In some embodiments, upon storage at 40° C. for 4 weeks, the amount of acidic species in the formulation increases less than 9%. In some embodiments, upon storage at 40° C. for 4 weeks, the amount of acidic species in the formulation increases less than 8%. In some embodiments, upon storage at 40° C. for 4 weeks, the amount of acidic species in the formulation increases less than 7%. In some embodiments, upon storage at 40° C. for 4 weeks, the amount of acidic species in the formulation increases less than 6%. In some embodiments, upon storage at 40° C. for 4 weeks, the amount of acidic species in the formulation increases less than 5%.

In some embodiments, upon storage at 40° C. for 2 months, the amount of acidic species in the formulation increases less than 40%. In some embodiments, upon storage at 40° C. for 2 months, the amount of acidic species in the formulation increases less than 39% In some embodiments, upon storage at 40° C. for 2 months, the amount of acidic species in the formulation increases less than 38% In some embodiments, upon storage at 40° C. for 2 months, the amount of acidic species in the formulation increases less than 37% In some embodiments, upon storage at 40° C. for 2 months, the amount of acidic species in the formulation increases less than 36.9%. In some embodiments, upon storage at 40° C. for 2 months, the amount of acidic species in the formulation increases less than 36.8%. In some embodiments, upon storage at 40° C. for 2 months, the amount of acidic species in the formulation increases less than 36.7%. In some embodiments, upon storage at 40° C. for 2 months, the amount of acidic species in the formulation increases less than 36.6%. In some embodiments, upon storage at 40° C. for 2 months, the amount of acidic species in the formulation increases less than 36.5%. In some embodiments, upon storage at 40° C. for 2 months, the amount of acidic species in the formulation increases less than 36% In some embodiments, upon storage at 40° C. for 2 months, the amount of acidic species in the formulation increases less than 35% In some embodiments, upon storage at 40° C. for 2 months, the amount of acidic species in the formulation increases less than 30%. In some embodiments, upon storage at 40° C. for 2 months, the amount of acidic species in the formulation increases less than 25%. In some embodiments, upon storage at 40° C. for 2 months, the amount of acidic species in the formulation increases less than 20%. In some embodiments, upon storage at 40° C. for 2 months, the amount of acidic species in the formulation increases less than 19%. In some embodiments, upon storage at 40° C. for 2 months, the amount of acidic species in the formulation increases less than 18%. In some embodiments, upon storage at 40° C. for 2 months, the amount of acidic species in the formulation increases less than 17%.

In some embodiments, upon storage at 40° C. for 3 months, the amount of acidic species in the formulation increases less than 100%. In some embodiments, upon storage at 40° C. for 3 months, the amount of acidic species in the formulation increases less than 80%. In some embodiments, upon storage at 40° C. for 3 months, the amount of acidic species in the formulation increases less than 75%. In some embodiments, the percent increase in acidic species in the formulation (Δacidic %) is evaluated by image capillary isoelectric focusing (icIEF). In some embodiments, the percentage of acidic species that exists in the formulation is evaluated at 60% relative humidity. In some embodiments, the percentage of acidic species that exists in the formulation is evaluated at 75% relative humidity.

Freeze-Thaw Stability

In some embodiments, the formulation of the present invention is stable such that the formulation is able to withstand multiple freeze-thaw cycles without significant increase in HMW species.

In some embodiments, at least 95% of the anti-IL1R1 antibody exists as a monomer after 2 rounds of freeze and thaw cycles. In some embodiments, at least 95% of the anti-IL1R1 antibody exists as a monomer after 3 rounds of freeze and thaw cycles. In some embodiments, at least 95% of the anti-IL1R1 antibody exists as a monomer after 4 rounds of freeze and thaw cycles. In some embodiments, at least 95% of the anti-IL1R1 antibody exists as a monomer after 5 rounds of freeze and thaw cycles. In some embodiments, at least 95% of the anti-IL1R1 antibody exists as a monomer after 6 rounds of freeze and thaw cycles. In some embodiments, at least 95% of the anti-IL1R1 antibody exists as a monomer after 7 rounds of freeze and thaw cycles. In some embodiments, at least 95% of the anti-IL1R1 antibody exists as a monomer after 8 rounds of freeze and thaw cycles. In some embodiments, at least 95% of the anti-IL1R1 antibody exists as a monomer after 9 rounds of freeze and thaw cycles. In some embodiments, at least 95% of the anti-IL1R1 antibody exists as a monomer after 10 rounds of freeze and thaw cycles.

In some embodiments, at least 90% of the anti-IL1R1 antibody exists as a monomer after 3 rounds of freeze and thaw cycles. In some embodiments, at least 92% of the anti-IL1R1 antibody exists as a monomer after 3 rounds of freeze and thaw cycles. In some embodiments, at least 94% of the anti-IL1R1 antibody exists as a monomer after 3 rounds of freeze and thaw cycles. In some embodiments, at least 95% of the anti-IL1R1 antibody exists as a monomer after 3 rounds of freeze and thaw cycles. In some embodiments, at least 96% of the anti-IL1R1 antibody exists as a monomer after 3 rounds of freeze and thaw cycles. In some embodiments, at least 97% of the anti-IL1R1 antibody exists as a monomer after 3 rounds of freeze and thaw cycles. In some embodiments, at least 98% of the anti-IL1R1 antibody exists as a monomer after 3 rounds of freeze and thaw cycles. In some embodiments, at least 99% of the anti-IL1R1 antibody exists as a monomer after 3 rounds of freeze and thaw cycles. In some embodiments, at least 99.5% of the anti-IL1R1 antibody exists as a monomer after 3 rounds of freeze and thaw cycles. In some embodiments, at least 99.9% of the anti-IL1R1 antibody exists as a monomer after 3 rounds of freeze and thaw cycles. In some embodiments, substantially 100% of the anti-IL1R1 antibody exists as a monomer after 3 rounds of freeze and thaw cycles.

In some embodiments, at least 90% of the anti-IL1R1 antibody exists as a monomer after 6 rounds of freeze and thaw cycles. In some embodiments, at least 92% of the anti-IL1R1 antibody exists as a monomer after 6 rounds of freeze and thaw cycles. In some embodiments, at least 94% of the anti-IL1R1 antibody exists as a monomer after 6 rounds of freeze and thaw cycles. In some embodiments, at least 95% of the anti-IL1R1 antibody exists as a monomer after 3 rounds of freeze and thaw cycles. In some embodiments, at least 96% of the anti-IL1R1 antibody exists as a monomer after 6 rounds of freeze and thaw cycles. In some embodiments, at least 97% of the anti-IL1R1 antibody exists as a monomer after 6 rounds of freeze and thaw cycles. In some embodiments, at least 98% of the anti-IL1R1 antibody exists as a monomer after 6 rounds of freeze and thaw cycles. In some embodiments, at least 99% of the anti-IL1R1 antibody exists as a monomer after 6 rounds of freeze and thaw cycles. In some embodiments, at least 99.5% of the anti-IL1R1 antibody exists as a monomer after 6 rounds of freeze and thaw cycles. In some embodiments, at least 99.9% of the anti-IL1R1 antibody exists as a monomer after 6 rounds of freeze and thaw cycles. In some embodiments, substantially 100% of the anti-IL1R1 antibody exists as a monomer after 6 rounds of freeze and thaw cycles. In some embodiments, the amount of monomer that exist in the formulation is evaluated by size exclusion chromatography (SEC).

In some embodiments, the amount of monomer in a formulation decreases less than 10%, 8%, 5%, 4%, 3%, 2%, 1%, 0.5%, 0.4%, 0.2% or 0.1% after one or more rounds of freeze and thaw cycles. In some embodiments, the amount of monomer in a formulation decreases less than 10% after 3 rounds of freeze and thaw cycles. In some embodiments, the amount of monomer in a formulation decreases less than 9% after 3 rounds of freeze and thaw cycles. In some embodiments, the amount of monomer in a formulation decreases less than 8% after 3 rounds of freeze and thaw cycles. In some embodiments, the amount of monomer in a formulation decreases less than 7% after 3 rounds of freeze and thaw cycles. In some embodiments, the amount of monomer in a formulation decreases less than 6% after 3 rounds of freeze and thaw cycles. In some embodiments, the amount of monomer in a formulation decreases less than 5% after 3 rounds of freeze and thaw cycles. In some embodiments, the amount of monomer in a formulation decreases less than 4% after 3 rounds of freeze and thaw cycles. In some embodiments, the amount of monomer in a formulation decreases less than 3% after 3 rounds of freeze and thaw cycles. In some embodiments, the amount of monomer in a formulation decreases less than 2% after 3 rounds of freeze and thaw cycles. In some embodiments, the amount of monomer in a formulation decreases less than 1.8% after 3 rounds of freeze and thaw cycles. In some embodiments, the amount of monomer in a formulation decreases less than 1.6% after 3 rounds of freeze and thaw cycles. In some embodiments, the amount of monomer in a formulation decreases less than 1.5% after 3 rounds of freeze and thaw cycles. In some embodiments, the amount of monomer in a formulation decreases less than 1.4% after 3 rounds of freeze and thaw cycles. In some embodiments, the amount of monomer in a formulation decreases less than 1.3% after 3 rounds of freeze and thaw cycles. In some embodiments, the amount of monomer in a formulation decreases less than 1.2% after 3 rounds of freeze and thaw cycles. In some embodiments, the amount of monomer in a formulation decreases less than 1.1% after 3 rounds of freeze and thaw cycles. In some embodiments, the amount of monomer in a formulation decreases less than 1.0% after 3 rounds of freeze and thaw cycles. In some embodiments, the amount of monomer in a formulation decreases less than 0.9% after 3 rounds of freeze and thaw cycles. In some embodiments, the amount of monomer in a formulation decreases less than 0.8% after 3 rounds of freeze and thaw cycles. In some embodiments, the amount of monomer in a formulation decreases less than 0.7% after 3 rounds of freeze and thaw cycles. In some embodiments, the amount of monomer in a formulation decreases less than 0.6% after 3 rounds of freeze and thaw cycles. In some embodiments, the amount of monomer in a formulation decreases less than 0.5% after 3 rounds of freeze and thaw cycles. In some embodiments, the amount of monomer in a formulation decreases less than 0.4% after 3 rounds of freeze and thaw cycles. In some embodiments, the amount of monomer in a formulation decreases less than 0.3% after 3 rounds of freeze and thaw cycles. In some embodiments, the amount of monomer in a formulation decreases less than 0.2% after 3 rounds of freeze and thaw cycles. In some embodiments, the amount of monomer in a formulation decreases less than 0.1% after 3 rounds of freeze and thaw cycles.

In some embodiments, the amount of monomer in a formulation decreases less than 10% after 6 rounds of freeze and thaw cycles. In some embodiments, the amount of monomer in a formulation decreases less than 9% after 6 rounds of freeze and thaw cycles. In some embodiments, the amount of monomer in a formulation decreases less than 8% after 6 rounds of freeze and thaw cycles. In some embodiments, the amount of monomer in a formulation decreases less than 7% after 6 rounds of freeze and thaw cycles. In some embodiments, the amount of monomer in a formulation decreases less than 6% after 6 rounds of freeze and thaw cycles. In some embodiments, the amount of monomer in a formulation decreases less than 5% after 6 rounds of freeze and thaw cycles. In some embodiments, the amount of monomer in a formulation decreases less than 4% after 6 rounds of freeze and thaw cycles. In some embodiments, the amount of monomer in a formulation decreases less than 3% after 6 rounds of freeze and thaw cycles. In some embodiments, the amount of monomer in a formulation decreases less than 2% after 6 rounds of freeze and thaw cycles. In some embodiments, the amount of monomer in a formulation decreases less than 1.8% after 6 rounds of freeze and thaw cycles. In some embodiments, the amount of monomer in a formulation decreases less than 1.6% after 6 rounds of freeze and thaw cycles. In some embodiments, the amount of monomer in a formulation decreases less than 1.5% after 6 rounds of freeze and thaw cycles. In some embodiments, the amount of monomer in a formulation decreases less than 1.4% after 6 rounds of freeze and thaw cycles. In some embodiments, the amount of monomer in a formulation decreases less than 1.3% after 6 rounds of freeze and thaw cycles. In some embodiments, the amount of monomer in a formulation decreases less than 1.2% after 6 rounds of freeze and thaw cycles. In some embodiments, the amount of monomer in a formulation decreases less than 1.1% after 6 rounds of freeze and thaw cycles. In some embodiments, the amount of monomer in a formulation decreases less than 1.0% after 6 rounds of freeze and thaw cycles. In some embodiments, the amount of monomer in a formulation decreases less than 0.9% after 6 rounds of freeze and thaw cycles. In some embodiments, the amount of monomer in a formulation decreases less than 0.8% after 6 rounds of freeze and thaw cycles. In some embodiments, the amount of monomer in a formulation decreases less than 0.7% after 6 rounds of freeze and thaw cycles. In some embodiments, the amount of monomer in a formulation decreases less than 0.6% after 6 rounds of freeze and thaw cycles. In some embodiments, the amount of monomer in a formulation decreases less than 0.5% after 6 rounds of freeze and thaw cycles. In some embodiments, the amount of monomer in a formulation decreases less than 0.4% after 6 rounds of freeze and thaw cycles. In some embodiments, the amount of monomer in a formulation decreases less than 0.3% after 6 rounds of freeze and thaw cycles. In some embodiments, the amount of monomer in a formulation decreases less than 0.2% after 6 rounds of freeze and thaw cycles. In some embodiments, the amount of monomer in a formulation decreases less than 0.1% after 6 rounds of freeze and thaw cycles. In some embodiments, the percent decrease of monomer is evaluated by SEC.

In some embodiments, less than 10% of an anti-IL1R1 antibody exists as HMW species in a formulation after 2 rounds of freeze and thaw cycles. In some embodiments, less than 10% of an anti-IL1R1 antibody exists as HMW species in a formulation after 3 rounds of freeze and thaw cycles. In some embodiments, less than 10% of an anti-IL1R1 antibody exists as HMW species in a formulation after 4 rounds of freeze and thaw cycles. In some embodiments, less than 10% of an anti-IL1R1 antibody exists as HMW species in a formulation after 5 rounds of freeze and thaw cycles. In some embodiments, less than 10% of an anti-IL1R1 antibody exists as HMW species in a formulation after 6 rounds of freeze and thaw cycles. In some embodiments, less than 10% of an anti-IL1R1 antibody exists as HMW species in a formulation after 7 rounds of freeze and thaw cycles. In some embodiments, less than 10% of an anti-IL1R1 antibody exists as HMW species in a formulation after 8 rounds of freeze and thaw cycles. In some embodiments, less than 10% of an anti-IL1R1 antibody exists as HMW species in a formulation after 9 rounds of freeze and thaw cycles. In some embodiments, less than 10% of an anti-IL1R1 antibody exists as HMW species in a formulation after 10 rounds of freeze and thaw cycles.

In some embodiments, less than 10%, 8%, 5%, 4%, 3%, 2%, 1%, or 0.5% of an anti-IL1R1 antibody exists as HMW species in a formulation after 1, 2, 3, 4, 5, 6, 7, 8, 9, or 10 rounds of freeze and thaw cycles. In some embodiments, less than 15% of an anti-IL1R1 antibody exists as HMW species in a formulation after 3 rounds of freeze and thaw cycles. In some embodiments, less than 13% of an anti-IL1R1 antibody exists as HMW species in a formulation after 3 rounds of freeze and thaw cycles. In some embodiments, less than 12% of an anti-IL1R1 antibody exists as HMW species in a formulation after 3 rounds of freeze and thaw cycles. In some embodiments, less than 10% of an anti-IL1R1 antibody exists as HMW species in a formulation after 3 rounds of freeze and thaw cycles. In some embodiments, less than 9% of an anti-IL1R1 antibody exists as HMW species in a formulation after 3 rounds of freeze and thaw cycles. In some embodiments, less than 8% of an anti-IL1R1 antibody exists as HMW species in a formulation after 3 rounds of freeze and thaw cycles. In some embodiments, less than 7% of an anti-IL1R1 antibody exists as HMW species in a formulation after 3 rounds of freeze and thaw cycles. In some embodiments, less than 6% of an anti-IL1R1 antibody exists as HMW species in a formulation after 3 rounds of freeze and thaw cycles. In some embodiments, less than 5% of an anti-IL1R1 antibody exists as HMW species in a formulation after 3 rounds of freeze and thaw cycles. In some embodiments, less than 4% of an anti-IL1R1 antibody exists as HMW species in a formulation after 3 rounds of freeze and thaw cycles. In some embodiments, less than 3% of an anti-IL1R1 antibody exists as HMW species in a formulation after 3 rounds of freeze and thaw cycles. In some embodiments, less than 2.5% of an anti-IL1R1 antibody exists as HMW species in a formulation after 3 rounds of freeze and thaw cycles. In some embodiments, less than 2.4% of an anti-IL1R1 antibody exists as HMW species in a formulation after 3 rounds of freeze and thaw cycles. In some embodiments, less than 2.3% of an anti-IL1R1 antibody exists as HMW species in a formulation after 3 rounds of freeze and thaw cycles. In some embodiments, less than 2.2% of an anti-IL1R1 antibody exists as HMW species in a formulation after 3 rounds of freeze and thaw cycles. In some embodiments, less than 2.1% of an anti-IL1R1 antibody exists as HMW species in a formulation after 3 rounds of freeze and thaw cycles. In some embodiments, less than 2% after 3 rounds of freeze and thaw cycles. In some embodiments, less than 1.9% of an anti-IL1R1 antibody exists as HMW species in a formulation after 3 rounds of freeze and thaw cycles. In some embodiments, less than 1.8% of an anti-IL1R1 antibody exists as HMW species in a formulation after 3 rounds of freeze and thaw cycles. In some embodiments, less than 1.7% of an anti-IL1R1 antibody exists as HMW species in a formulation after 3 rounds of freeze and thaw cycles. In some embodiments, less than 1.6% of an anti-IL1R1 antibody exists as HMW species in a formulation after 3 rounds of freeze and thaw cycles. In some embodiments, less than 1.5% of an anti-IL1R1 antibody exists as HMW species in a formulation after 3 rounds of freeze and thaw cycles. In some embodiments, less than 1.4% of an anti-IL1R1 antibody exists as HMW species in a formulation after 3 rounds of freeze and thaw cycles. In some embodiments, less than 1.3% of an anti-IL1R1 antibody exists as HMW species in a formulation after 3 rounds of freeze and thaw cycles. In some embodiments, less than 1.2% of an anti-IL1R1 antibody exists as HMW species in a formulation after 3 rounds of freeze and thaw cycles. In some embodiments, less than 1.1% of an anti-IL1R1 antibody exists as HMW species in a formulation after 3 rounds of freeze and thaw cycles. In some embodiments, less than 1.0% of an anti-IL1R1 antibody exists as HMW species in a formulation after 3 rounds of freeze and thaw cycles. In some embodiments, less than 0.9% of an anti-IL1R1 antibody exists as HMW species in a formulation after 3 rounds of freeze and thaw cycles. In some embodiments, less than 0.8% of an anti-IL1R1 antibody exists as HMW species in a formulation after 3 rounds of freeze and thaw cycles. In some embodiments, less than 0.7% of an anti-IL1R1 antibody exists as HMW species in a formulation after 3 rounds of freeze and thaw cycles. In some embodiments, less than 0.6% of an anti-IL1R1 antibody exists as HMW species in a formulation after 3 rounds of freeze and thaw cycles. In some embodiments, less than 0.5% of an anti-IL1R1 antibody exists as HMW species in a formulation after 3 rounds of freeze and thaw cycles. In some embodiments, less than 0.4% of an anti-IL1R1 antibody exists as HMW species in a formulation after 3 rounds of freeze and thaw cycles. In some embodiments, less than 0.3% of an anti-IL1R1 antibody exists as HMW species in a formulation after 3 rounds of freeze and thaw cycles. In some embodiments, less than 0.2% of an anti-IL1R1 antibody exists as HMW species in a formulation after 3 rounds of freeze and thaw cycles. In some embodiments, less than 0.1% of an anti-IL1R1 antibody exists as HMW species in a formulation after 3 rounds of freeze and thaw cycles. In some embodiments, a formulation is substantially free of HMW species after 3 rounds of freeze and thaw cycles.

In some embodiments, less than 15% of an anti-IL1R1 antibody exists as HMW species in a formulation after 6 rounds of freeze and thaw cycles. In some embodiments, less than 13% of an anti-IL1R1 antibody exists as HMW species in a formulation after 6 rounds of freeze and thaw cycles. In some embodiments, less than 12% of an anti-IL1R1 antibody exists as HMW species in a formulation after 6 rounds of freeze and thaw cycles. In some embodiments, less than 10% of an anti-IL1R1 antibody exists as HMW species in a formulation after 6 rounds of freeze and thaw cycles. In some embodiments, less than 9% of an anti-IL1R1 antibody exists as HMW species in a formulation after 6 rounds of freeze and thaw cycles. In some embodiments, less than 8% of an anti-IL1R1 antibody exists as HMW species in a formulation after 6 rounds of freeze and thaw cycles. In some embodiments, less than 7% of an anti-IL1R1 antibody exists as HMW species in a formulation after 6 rounds of freeze and thaw cycles. In some embodiments, less than 6% of an anti-IL1R1 antibody exists as HMW species in a formulation after 6 rounds of freeze and thaw cycles. In some embodiments, less than 5% of an anti-IL1R1 antibody exists as HMW species in a formulation after 6 rounds of freeze and thaw cycles. In some embodiments, less than 4% of an anti-IL1R1 antibody exists as HMW species in a formulation after 6 rounds of freeze and thaw cycles. In some embodiments, less than 3.9% of an anti-IL1R1 antibody exists as HMW species in a formulation after 6 rounds of freeze and thaw cycles. In some embodiments, less than 3.8% of an anti-IL1R1 antibody exists as HMW species in a formulation after 6 rounds of freeze and thaw cycles. In some embodiments, less than 3.7% of an anti-IL1R1 antibody exists as HMW species in a formulation after 6 rounds of freeze and thaw cycles. In some embodiments, less than 3.6% of an anti-IL1R1 antibody exists as HMW species in a formulation after 6 rounds of freeze and thaw cycles. In some embodiments, less than 3.5% of an anti-IL1R1 antibody exists as HMW species in a formulation after 6 rounds of freeze and thaw cycles. In some embodiments, less than 3.4% of an anti-IL1R1 antibody exists as HMW species in a formulation after 6 rounds of freeze and thaw cycles. In some embodiments, less than 3.3% of an anti-IL1R1 antibody exists as HMW species in a formulation after 6 rounds of freeze and thaw cycles. In some embodiments, less than 3.2% of an anti-IL1R1 antibody exists as HMW species in a formulation after 6 rounds of freeze and thaw cycles. In some embodiments, less than 3.1% of an anti-IL1R1 antibody exists as HMW species in a formulation after 6 rounds of freeze and thaw cycles. In some embodiments, less than 3% of an anti-IL1R1 antibody exists as HMW species in a formulation after 6 rounds of freeze and thaw cycles. In some embodiments, less than 2.5% of an anti-IL1R1 antibody exists as HMW species in a formulation after 6 rounds of freeze and thaw cycles. In some embodiments, less than 2.4% of an anti-IL1R1 antibody exists as HMW species in a formulation after 6 rounds of freeze and thaw cycles. In some embodiments, less than 2.3% of an anti-IL1R1 antibody exists as HMW species in a formulation after 6 rounds of freeze and thaw cycles. In some embodiments, less than 2.2% of an anti-IL1R1 antibody exists as HMW species in a formulation after 6 rounds of freeze and thaw cycles. In some embodiments, less than 2.1% of an anti-IL1R1 antibody exists as HMW species in a formulation after 6 rounds of freeze and thaw cycles. In some embodiments, less than 2% of an anti-IL1R1 antibody exists as HMW species in a formulation after 6 rounds of freeze and thaw cycles. In some embodiments, less than 1.8% of an anti-IL1R1 antibody exists as HMW species in a formulation after 6 rounds of freeze and thaw cycles. In some embodiments, less than 1.5% of an anti-IL1R1 antibody exists as HMW species in a formulation after 6 rounds of freeze and thaw cycles. In some embodiments, less than 1.4% of an anti-IL1R1 antibody exists as HMW species in a formulation after 6 rounds of freeze and thaw cycles. In some embodiments, less than 1.3% of an anti-IL1R1 antibody exists as HMW species in a formulation after 6 rounds of freeze and thaw cycles. In some embodiments, less than 1.2% of an anti-IL1R1 antibody exists as HMW species in a formulation after 6 rounds of freeze and thaw cycles. In some embodiments, less than 1.1% of an anti-IL1R1 antibody exists as HMW species in a formulation after 6 rounds of freeze and thaw cycles. In some embodiments, less than 1.0% of an anti-IL1R1 antibody exists as HMW species in a formulation after 6 rounds of freeze and thaw cycles. In some embodiments, less than 0.9% of an anti-IL1R1 antibody exists as HMW species in a formulation after 6 rounds of freeze and thaw cycles. In some embodiments, less than 0.8% of an anti-IL1R1 antibody exists as HMW species in a formulation after 6 rounds of freeze and thaw cycles. In some embodiments, less than 0.7% of an anti-IL1R1 antibody exists as HMW species in a formulation after 6 rounds of freeze and thaw cycles. In some embodiments, less than 0.6% of an anti-IL1R1 antibody exists as HMW species in a formulation after 6 rounds of freeze and thaw cycles. In some embodiments, less than 0.5% of an anti-IL1R1 antibody exists as HMW species in a formulation after 6 rounds of freeze and thaw cycles. In some embodiments, less than 0.4% of an anti-IL1R1 antibody exists as HMW species in a formulation after 6 rounds of freeze and thaw cycles. In some embodiments, less than 0.3% of an anti-IL1R1 antibody exists as HMW species in a formulation after 6 rounds of freeze and thaw cycles. In some embodiments, less than 0.2% of an anti-IL1R1 antibody exists as HMW species in a formulation after 6 rounds of freeze and thaw cycles. In some embodiments, less than 0.1% of an anti-IL1R1 antibody exists as HMW species in a formulation after 6 rounds of freeze and thaw cycles. In some embodiments, a formulation is substantially free of HMW species after 6 rounds of freeze and thaw cycles. In some embodiments, the amount of HMW species that exists in the formulation is evaluated by SEC.

In some embodiments, the amount of HMW species in the formulation increases less than 3.0% after 3 rounds of freeze and thaw cycles. In some embodiments, the amount of HMW species in the formulation increases less than 2.5% after 3 rounds of freeze and thaw cycles. In some embodiments, the amount of HMW species in the formulation increases less than 2.0% after 3 rounds of freeze and thaw cycles. In some embodiments, the amount of HMW species in the formulation increases less than 1.8% after 3 rounds of freeze and thaw cycles. In some embodiments, the amount of HMW species in the formulation increases less than 1.5% after 3 rounds of freeze and thaw cycles. In some embodiments, the amount of HMW species in the formulation increases less than 1.3% after 3 rounds of freeze and thaw cycles. In some embodiments, the amount of HMW species in the formulation increases less than 1.2% after 3 rounds of freeze and thaw cycles. In some embodiments, the amount of HMW species in the formulation increases less than 1.0% after 3 rounds of freeze and thaw cycles. In some embodiments, the amount of HMW species in the formulation increases less than 0.8% after 3 rounds of freeze and thaw cycles. In some embodiments, the amount of HMW species in the formulation increases less than 0.6% after 3 rounds of freeze and thaw cycles. In some embodiments, the amount of HMW species in the formulation increases less than 0.5% after 3 rounds of freeze and thaw cycles. In some embodiments, the amount of HMW species in the formulation increases less than 0.4% after 3 rounds of freeze and thaw cycles. In some embodiments, the amount of HMW species in the formulation increases less than 0.3% after 3 rounds of freeze and thaw cycles. In some embodiments, the amount of HMW species in the formulation increases less than 0.2% after 3 rounds of freeze and thaw cycles. In some embodiments, the amount of HMW species in the formulation increases less than 0.1% after 3 rounds of freeze and thaw cycles. In some embodiments, the amount of HMW species in the formulation does not substantially increase after 3 rounds of freeze and thaw cycles.

In some embodiments, the amount of HMW species in the formulation increases less than 3.0% after 6 rounds of freeze and thaw cycles. In some embodiments, the amount of HMW species in the formulation increases less than 2.5% after 6 rounds of freeze and thaw cycles. In some embodiments, the amount of HMW species in the formulation increases less than 2.0% after 6 rounds of freeze and thaw cycles. In some embodiments, the amount of HMW species in the formulation increases less than 1.8% after 6 rounds of freeze and thaw cycles. In some embodiments, the amount of HMW species in the formulation increases less than 1.5% after 6 rounds of freeze and thaw cycles. In some embodiments, the amount of HMW species in the formulation increases less than 1.4% after 6 rounds of freeze and thaw cycles. In some embodiments, the amount of HMW species in the formulation increases less than 1.3% after 6 rounds of freeze and thaw cycles. In some embodiments, the amount of HMW species in the formulation increases less than 1.2% after 6 rounds of freeze and thaw cycles. In some embodiments, the amount of HMW species in the formulation increases less than 1.1% after 6 rounds of freeze and thaw cycles. In some embodiments, the amount of HMW species in the formulation increases less than 1.0% after 6 rounds of freeze and thaw cycles. In some embodiments, the amount of HMW species in the formulation increases less than 1.9% after 6 rounds of freeze and thaw cycles. In some embodiments, the amount of HMW species in the formulation increases less than 0.8% after 6 rounds of freeze and thaw cycles. In some embodiments, the amount of HMW species in the formulation increases less than 1.7% after 6 rounds of freeze and thaw cycles. In some embodiments, the amount of HMW species in the formulation increases less than 0.6% after 6 rounds of freeze and thaw cycles. In some embodiments, the amount of HMW species in the formulation increases less than 0.5% after 6 rounds of freeze and thaw cycles. In some embodiments, the amount of HMW species in the formulation increases less than 0.4% after 6 rounds of freeze and thaw cycles. In some embodiments, the amount of HMW species in the formulation increases less than 0.3% after 6 rounds of freeze and thaw cycles. In some embodiments, the amount of HMW species in the formulation increases less than 0.2% after 6 rounds of freeze and thaw cycles. In some embodiments, the amount of HMW species in the formulation increases less than 0.1% after 6 rounds of freeze and thaw cycles. In some embodiments, the amount of HMW species in the formulation does not substantially increase after 6 rounds of freeze and thaw cycles. In some embodiments, the percent increase in higher molecular weight species in the formulation ($\Delta$HMW %) is evaluated by size exclusion chromatography (SEC)

Second Viral Coefficient ($B_{22}$)

In some embodiments, stability of an antibody formulation is measured by second viral coefficients ($B_{22}$). In some embodiments, static light scattering (SLS) is used to determine $B_{22}$. Positive $B_{22}$ values indicate overall repulsive interactions, favoring protein solubility.

In some embodiments, a formulation has a positive $B_{22}$ value. In some embodiments, a formulation as a $B_{22}$ value of greater than 0 mol·ml/g². In some embodiments, a formulation has a $B_{22}$ value of −5 to 10 mol·ml/g². In some embodiments, a formulation has a $B_{22}$ value of greater than −5 mol·ml/g². In some embodiments, a formulation has a $B_{22}$ value of greater than −4 mol·ml/g².

Diffusion Interaction Parameter ($K_D$)

In some embodiments, stability of an antibody formulation is measured by diffusion interaction parameter ($K_D$). In some embodiments, $K_D$ value is measured by dynamic light scattering (DLS). Positive $K_D$ values generally indicate less self-association. In some embodiments, a formulation has a $K_D$ value of greater than −10 mL/g. In some embodiments, a formulation has a $K_D$ value of −10 mL/g to 10 mL/g. In some embodiments, a formulation has a $K_D$ value of greater than −8 mL/g. In some embodiments, a formulation has a $K_D$ value of greater than −6 mL/g. In some embodiments, a formulation has a $K_D$ value of greater than −5 mL/g. In some embodiments, a formulation has a $K_D$ value of greater than −3 mL/g. In some embodiments, a formulation has a $K_D$ value of greater than −2 mL/g. In some embodiments, a formulation has a $K_D$ value of greater than −1 mL/g. In some embodiments, a formulation has a $K_D$ value of greater than 0 mL/g. In some embodiments, a formulation has a positive $K_D$ value. In some embodiments, a formulation has a $K_D$ value of greater than 3 mL/g. In some embodiments, a formulation has a $K_D$ value of greater than 5 mL/g. In some embodiments, a formulation has a $K_D$ value of greater than 6 mL/g. In some embodiments, a formulation has a negative $B_{22}$ value and has a positive $K_D$ value. In some embodiments, a formulation has a $B_{22}$ value of greater than −12 mol·ml/g² and a positive $K_D$ value. In some embodiments, a formulation has a $B_{22}$ value of greater than −12 mol·ml/g² and a $K_D$ value greater than 6 mL/g.

Viscosity

In some embodiments of the invention, formulations were optimized in order to reduce viscosity, while maintaining high antibody concentration. In some embodiments, lower viscosity allows for increased injectability of a formulation or effective sample transfer and preparation during manufacturing.

In some embodiments, a viscosity is measured at an antibody concentration of 80 mg/ml. In some embodiments, a viscosity is measured at an antibody concentration of 100 mg/ml. In some embodiments, a viscosity is measured at an antibody concentration of 120 mg/ml. In some embodiments, a viscosity is measured at an antibody concentration of 140 mg/ml. In some embodiments, a viscosity is measured at an antibody concentration of 150 mg/ml. In some embodiments, a viscosity is measured at an antibody concentration of 160 mg/ml. In some embodiments, a viscosity is measured at an antibody concentration of 170 mg/ml. In some embodiments, a viscosity is measured at an antibody concentration of 180 mg/ml. In some embodiments, a viscosity is measured at an antibody concentration of 200 mg/ml.

In some embodiments, a formulation has a viscosity of less than 30 cP at 12° C. In some embodiments, a formulation has a viscosity of less than 25 cP at 12° C. In some embodiments, a formulation has a viscosity of less than 20 cP at 12° C. In some embodiments, a formulation has a viscosity of less than or equal to 15 cP at 12° C. In some embodiments, a formulation has a viscosity of less than 13 cP at 12° C. In some embodiments, a formulation has a viscosity of less than 10 cP at 12° C. In some embodiments, a formulation has a viscosity of less than 8 cP at 12° C. In some embodiments, a formulation has a viscosity of less than 5 cP at 12° C. In some embodiments, a formulation has a viscosity of less than 30 cP at 12° C.

In some embodiments, a formulation comprising an anti-IL-1R antibody at 180 mg/ml has a viscosity of 15 cp to 30 cP at 12° C. In some embodiments, a formulation comprising an anti-IL-1R antibody at 180 mg/ml has a viscosity of less than 30 cP at 12° C. In some embodiments, a formulation comprising an anti-IL-1R antibody at 180 mg/ml has a viscosity of less than 25 cP at 12° C. In some embodiments, a formulation comprising an anti-IL-1R antibody at 180 mg/ml has a viscosity of less than 20 cP at 12° C.

In some embodiments, a formulation comprising an anti-IL-1R antibody at 150 mg/ml has a viscosity of 5 cp to 20 cP at 12° C. In some embodiments, a formulation comprising an anti-IL-1R antibody at 150 mg/ml has a viscosity of 5 cp to 15 cP at 12° C. In some embodiments, a formulation comprising an anti-IL-1R antibody at 150 mg/ml has a viscosity of 8 cp to 15 cP at 12° C. In some embodiments, a formulation comprising an anti-IL-1R antibody at 150 mg/ml has a viscosity of 20 cp at 12° C. In some embodiments, a formulation comprising an anti-IL-1R antibody at 150 mg/ml has a viscosity of 15 cp at 12° C. In some embodiments, a formulation comprising an anti-IL-1R antibody at 150 mg/ml has a viscosity of 12 cp at 12° C. In some embodiments, a formulation comprising an anti-IL-1R antibody at 150 mg/ml has a viscosity of 10 cp at 12° C.

In some embodiments, a formulation comprising an anti-IL-1R antibody at 150 mg/ml has a viscosity of less than 20 cP at 12° C. In some embodiments, a formulation comprising an anti-IL-1R antibody at 150 mg/ml has a viscosity of less than 18 cP at 12° C. In some embodiments, a formulation comprising an anti-IL-1R antibody at 150 mg/ml has a viscosity of less than or equal to 15 cP at 12° C. In some embodiments, a formulation comprising an anti-IL-1R antibody at 150 mg/ml has a viscosity of less than 12 cP at 12° C. In some embodiments, a formulation comprising an anti-IL-1R antibody at 150 mg/ml has a viscosity of less than 10 cP at 12° C.

In some embodiments, a formulation comprising an anti-IL-1R antibody at 100 mg/ml has a viscosity of less than 10 cP at 12° C. In some embodiments, a formulation comprising an anti-IL-1R antibody at 100 mg/ml has a viscosity of less than 8 cP at 12° C. In some embodiments, a formulation comprising an anti-IL-1R antibody at 100 mg/ml has a viscosity of less than 6 cP at 12° C. In some embodiments, a formulation comprising an anti-IL-1R antibody at 100 mg/ml has a viscosity of less than 5 cP at 12° C.

In some embodiments, a formulation has a viscosity of less than 25 cP at 20° C. In some embodiments, a formulation has a viscosity of less than 20 cP at 20° C. In some embodiments, a formulation has a viscosity of less than or equal to 15 cP at 20° C. In some embodiments, a formulation has a viscosity of less than 13 cP at 20° C. In some embodiments, a formulation has a viscosity of less than 10 cP at 20° C. In some embodiments, a formulation has a viscosity of less than 8 cP at 20° C. In some embodiments, a formulation has a viscosity of less than 5 cP at 20° C. In some embodiments, a formulation has a viscosity of less than 30 cP at 20° C.

In some embodiments, a formulation comprising an anti-IL-1R antibody at 180 mg/ml has a viscosity of 10 cp to 20 cP at 20° C. In some embodiments, a formulation comprising an anti-IL-1R antibody at 180 mg/ml has a viscosity of 10 cp to 15 cP at 20° C. In some embodiments, a formulation comprising an anti-IL-1R antibody at 180 mg/ml has a viscosity of 12 cp to 15 cP at 20° C. In some embodiments, a formulation comprising an anti-IL-1R antibody at 180 mg/ml has a viscosity of less than 25 cP at 20° C. In some embodiments, a formulation comprising an anti-IL-1R antibody at 180 mg/ml has a viscosity of less than 20 cP at 20° C. In some embodiments, a formulation comprising an anti-IL-1R antibody at 180 mg/ml has a viscosity of less than or equal to 15 cP at 20° C. In some embodiments, a formulation comprising an anti-IL-1R antibody at 180 mg/ml has a viscosity of less than 10 cP at 20° C.

In some embodiments, a formulation comprising an anti-IL-1R antibody at 150 mg/ml has a viscosity of 5 cp to 20 cP at 20° C. In some embodiments, a formulation comprising an anti-IL-1R antibody at 150 mg/ml has a viscosity of 5 cp to 15 cP at 20° C. In some embodiments, a formulation comprising an anti-IL-1R antibody at 150 mg/ml has a viscosity of 5 cp to 10 cP at 20° C. In some embodiments, a formulation comprising an anti-IL-1R antibody at 150 mg/ml has a viscosity of 20 cp at 20° C. In some embodiments, a formulation comprising an anti-IL-1R antibody at 150 mg/ml has a viscosity of 15 cp at 20° C. In some embodiments, a formulation comprising an anti-IL-1R antibody at 150 mg/ml has a viscosity of 12 cp at 20° C. In some embodiments, a formulation comprising an anti-IL-1R antibody at 150 mg/ml has a viscosity of 10 cp at 20° C. In some embodiments, a formulation comprising an anti-IL-1R antibody at 150 mg/ml has a viscosity of 8 cp at 20° C. In some embodiments, a formulation comprising an anti-IL-1R antibody at 150 mg/ml has a viscosity of 5 cp at 20° C.

In some embodiments, a formulation comprising an anti-IL-1R antibody at 150 mg/ml has a viscosity of less than 20 cP at 20° C. In some embodiments, a formulation comprising an anti-IL-1R antibody at 150 mg/ml has a viscosity of less than 18 cP at 20° C. In some embodiments, a formulation comprising an anti-IL-1R antibody at 150 mg/ml has a viscosity of less than or equal to 15 cP at 20° C. In some embodiments, a formulation comprising an anti-IL-1R antibody at 150 mg/ml has a viscosity of less than 12 cP at 20° C. In some embodiments, a formulation comprising an anti-IL-1R antibody at 150 mg/ml has a viscosity of less than 10 cP at 20° C. In some embodiments, a formulation comprising an anti-IL-1R antibody at 150 mg/ml has a viscosity of less than 8 cP at 20° C. In some embodiments, a formulation comprising an anti-IL-1R antibody at 150 mg/ml has a viscosity of less than 5 cP at 20° C.

In some embodiments, a formulation comprising an anti-IL-1R antibody at 100 mg/ml has a viscosity of less than 10 cP at 20° C. In some embodiments, a formulation comprising an anti-IL-1R antibody at 100 mg/ml has a viscosity of less than 8 cP at 20° C. In some embodiments, a formulation comprising an anti-IL-1R antibody at 100 mg/ml has a viscosity of less than 6 cP at 20° C. In some embodiments, a formulation comprising an anti-IL-1R antibody at 100 mg/ml has a viscosity of less than 5 cP at 20° C. In some embodiments, a formulation comprising an anti-IL-1R antibody at 100 mg/mi has a viscosity of about 4 cp at 20° C.

Exemplary Anti-IL1R1 Antibody Formulations

In some embodiments, a stable formulation of the present invention comprises components shown in Table B. In some embodiments, a stable formulation of the present invention comprises components shown in Table C.

TABLE B

| | Exemplary Anti-IL1R1 Antibody Formulations | | | | | | |
|---|---|---|---|---|---|---|---|
| No. | Buffer | Basic AA | Acidic AA | Other AA | Osmolyte | Salt | pH |
| 1 | 50 mM Ac | 75 mM LYS | None | 75 mM PRO | 5% w/v Sucrose | None | 5.2 |
| 2 | 25 mM His | 75 mM ARG | None | None | 5% w/v Sucrose | None | 6.1 |
| 3 | 25 mM His | 75 mM ARG | 75 mM GLU | None | None | 100 mM NaCl | 6.1 |
| 4 | 50 mM Succ | 75 mM ARG | None | 75 mM PRO | None | None | 5.6 |
| 5 | 25 mM His | 75 mM LYS | 75 mM GLU | 75 mM PRO | None | 100 mM NaCl | 6.1 |
| 6 | 50 mM Succ | None | None | None | 5% w/v Sucrose | None | 5.6 |
| 7 | 50 mM Ac | 75 mM LYS | 75 mM GLU | None | 5% w/v Sucrose | 100 mM NaCl | 5.2 |
| 8 | 50 mM Ac | 75 mM LYS | None | None | None | 100 mM MgCl2 | 5.2 |
| 9 | 50 mM Succ | 75 mM LYS | None | 75 mM PRO | None | 100 mM MgCl2 | 5.6 |
| 10 | 50 mM Succ | 75 mM ARG | None | None | 5% w/v Sucrose | 100 mM MgCl2 | 5.6 |
| 11 | 25 mM His | None | 75 mM GLU | None | None | 100 mM MgCl2 | 6.1 |
| 12 | 50 mM Succ | None | 75 mM GLU | 75 mM PRO | 5% w/v Sucrose | 100 mM MgCl2 | 5.6 |
| 13 | 50 mM Succ | 75 mM ARG | 75 mM GLU | 75 mM PRO | 5% w/v Sucrose | 100 mM NaCl | 5.6 |
| 14 | 50 mM Succ | 75 mM LYS | 75 mM GLU | None | None | None | 5.6 |
| 15 | 25 mM His | 75 mM ARG | None | 75 mM PRO | None | 100 mM MgCl2 | 6.1 |
| 16 | 50 mM Ac | None | None | 75 mM PRO | 5% w/v Sucrose | 100 mM MgCl2 | 5.2 |
| 17 | 25 mM His | 75 mM LYS | None | None | None | None | 6.1 |
| 18 | 50 mM Ac | 75 mM ARG | 75 mM GLU | 75 mM PRO | None | None | 5.2 |
| 19 | 50 mM Ac | 75 mM ARG | 75 mM GLU | 75 mM PRO | 5% w/v Sucrose | 100 mM MgCl2 | 5.2 |
| 20 | 25 mM His | None | None | 75 mM PRO | 5% w/v Sucrose | 100 mM NaCl | 6.1 |
| 21 | 50 mM Succ | 75 mM LYS | None | None | 5% w/v Sucrose | 100 mM NaCl | 5.6 |
| 22 | 25 mM His | None | 75 mM GLU | 75 mM PRO | 5% w/v Sucrose | None | 6.1 |
| 23 | 25 mM His | 75 mM LYS | None | None | 5% w/v Sucrose | 100 mM MgCl2 | 6.1 |
| 24 | 50 mM Ac | None | 75 mM GLU | None | 5% w/v Sucrose | None | 5.2 |
| 25 | 50 mM Ac | None | 75 mM GLU | 75 mM PRO | None | 100 mM NaCl | 5.2 |
| 26 | 50 mM Ac | 75 mM ARG | None | None | 5% w/v Sucrose | 100 mM NaCl | 5.2 |
| 27 | 50 mM Succ | None | None | None | None | 100 mM NaCl | 5.6 |
| 28 | 25 mM His | None | None | None | 5% w/v Sucrose | 55 mM NaCl | 6.1 |
| 29 | 25 mM His | None | None | None | 8% w/v Sucrose | None | 6.1 |
| 30 | 25 mM Ac | None | None | None | 7% w/v Sucrose | None | 5.2 |

Ac = acetate;
Succ = succinate;
His = histidine;
LYS = lysine;
ARG = arginine;
GLU = glutamate;
PRO = proline

TABLE C

| | | | | Sodium | Amino | |
|----|---------------------|-----------|-------------------|----------------|------------------------|-----|
| No. | Ab Conc. (mg/ml) | Sucrose | Poly-sorbate 20 | acetate | acid | pH |
| F0 | 150 | 7% W/V | 0.02% W/V | 25 mM | | 5.2 |
| F1 | 150 | 7% W/V | 0.02% W/V | 25 mM | | 5.0 |
| F2 | 150 | 7% W/V | 0.02% W/V | 25 mM | | 4.5 |
| F3 | 150 | | 0.02% W/V | 25 mM | 25.9 mg/ml proline | 5.0 |
| F4 | 150 | 3.5% W/V | 0.02% W/V | 25 mM | 14.0 mg/ml Arg-HCl | 5.0 |
| F5 | 150 | | 0.02% W/V | 25 mM | 27.9 mg/mL Arg-HCl | 5.0 |

Delivery

In some embodiments of the invention, formulations comprise high anti-IL1R1 antibody concentrations suitable for subcutaneous, intradermal, intramuscular and/or intra-articular delivery. In some embodiments, a formulation comprises an anti-IL1R1 antibody at a concentration of about 50 mg/mL, 75 mg/ml, 100 mg/ml, 125 mg/ml, 150 mg/ml, 160 mg/ml, 165 mg/ml, 170 mg/ml, 175 mg/ml, 180 mg/ml, 185 mg/ml, 190 mg/ml, 195 mg/ml or 200 mg/ml. In some embodiments, a formulation comprises an anti-IL1R1 antibody at a concentration of 100 mg/ml. In some embodiments, a formulation comprises an anti-IL1R1 antibody at a concentration of 150 mg/ml. In some embodiments, a formulation comprises an anti-IL1R1 antibody at a concentration of 100 mg/ml to 200 mg/ml. In some embodiments, a formulation comprises an anti-IL1R1 antibody at a concentration of 100 mg/ml to 175 mg/ml. In some embodiments, a formulation comprises an anti-IL1R1 antibody at a concentration of 100 mg/ml to 160 mg/ml. In some embodiments, a formulation comprises an anti-IL1R1 antibody at a concentration of 100 mg/ml to 150 mg/ml. In some embodiments, a formulation comprises an anti-IL1R1 antibody at a concentration of 150 mg/ml to 165 mg/ml. In some embodiments, a formulation comprises an anti-IL1R1 antibody at a concentration of 150 mg/ml to 165 mg/ml. In some embodiments, a formulation comprises an anti-IL1R1 antibody at a concentration of at least approximately 50 mg/mL. In some embodiments, a formulation comprises an anti-IL1R1 antibody at a concentration of at least approximately 75 mg/mL. In some embodiments, a formulation comprises an anti-IL1R1 antibody at a concentration of at least approximately 100 mg/mL. In some embodiments, a formulation comprises an anti-IL1R1 antibody at a concentration of at least approximately 125 mg/mL. In some embodiments, a formulation comprises an anti-IL1R1 antibody at a concentration of at least approximately 150 mg/mL. In some embodiments, a formulation comprises an anti-IL1R1 antibody at a concentration of at least approximately 175 mg/mL. In some embodiments, a formulation comprises an anti-IL1R1 antibody at a concentration of at least approximately 200 mg/mL. In some embodiments, a formulation comprises an anti-IL1R1 antibody at a concentration of at least approximately 225 mg/mL. In some embodiments, a formulation comprises an anti-IL1R1 antibody at a concentration of at least approximately 25° mg/mL.

In some embodiments, the volume of an anti-IL1R1 antibody formulation delivered by subcutaneous, intradermal, intramuscular and/or intra-articular injection is 10 mL or less. In some embodiments, the volume of an anti-IL1R1 antibody formulation delivered by subcutaneous, intradermal, intramuscular and/or intra-articular injection is 5 mL or less. In some embodiments, the volume of an anti-IL1R1 antibody formulation delivered by subcutaneous, intradermal, intramuscular and/or intra-articular injection is 4 mL or less. In some embodiments, the volume of an anti-IL1R1 antibody formulation delivered by subcutaneous, intradermal, intramuscular and/or intra-articular injection is 3 mL or less. In some embodiments, the volume of an anti-IL1R1 antibody formulation delivered by subcutaneous, intradermal, intramuscular and/or intra-articular injection is 2 mL or less. In some embodiments, the volume of an anti-IL1R1 antibody formulation delivered by subcutaneous, intradermal, intramuscular and/or intra-articular injection is 1 mL or less. In some embodiments, the volume of an anti-IL1R1 antibody formulation delivered by subcutaneous, intradermal, intramuscular and/or intra-articular injection is 0.5 mL or less.

In some embodiments, the volume of an anti-IL1R1 antibody formulation delivered by subcutaneous injection is 10 mL or less. In some embodiments, the volume of an anti-IL1R1 antibody formulation delivered by subcutaneous injection is 5 mL or less. In some embodiments, the volume of an anti-IL1R1 antibody formulation delivered by subcutaneous injection is 4 mL or less. In some embodiments, the volume of an anti-IL1R1 antibody formulation delivered by subcutaneous injection is 3 mL or less. In some embodiments, the volume of an anti-IL1R1 antibody formulation delivered by subcutaneous injection is 2 mL or less. In some embodiments, the volume of an anti-IL1R1 antibody formulation delivered by subcutaneous injection is 1 mL or less. In some embodiments, the volume of an anti-IL1R1 antibody formulation delivered by subcutaneous injection is 0.5 mL or less. In some embodiments the volume of an anti-IL1R1 antibody formulation delivered by subcutaneous injection is 3 mL. In some embodiments the volume of an anti-IL1R1 antibody formulation delivered by subcutaneous injection is 2 mL. In some embodiments the volume of an anti-IL1R1 antibody formulation delivered by subcutaneous injection is 1.5 mL. In some embodiments the volume of an anti-IL1R1 antibody formulation delivered by subcutaneous injection is 1 mL. In some embodiments the volume of an anti-IL1R1 antibody formulation delivered by subcutaneous injection is 0.5 mL.

In some embodiments, subcutaneous injection of the anti-IL1R1 antibody formulation can be performed in the upper arm, the anterior surface of the thigh, the lower portion of the abdomen, the upper back or the upper area of the buttock. In some embodiments, the site of injection is rotated.

In some embodiments, formulations of the present invention may be designed for delivery by any suitable route, including but not limited to, subcutaneous, intradermal, intra-articular, oral, rectal, and vaginal, and by parenteral routes, including intravenous and intra-arterial injection, and intramuscular injection.

Kits

The present invention further provides kits or other articles of manufacture which contain the formulation of the present invention and provides instructions for its reconstitution (if lyophilized) and/or use. Kits or other articles of manufacture may include a container, a needle, and any other articles, devices or equipment useful in subcutaneous administration. Suitable containers include, for example, bottles, vials, syringes (e.g., pre-filled syringes and autoinjectors), subcutaneous pumps, ampules, cartridges, reservoirs, or lyo-jects. The container may be formed from a variety of materials such as glass or plastic. In some embodiments, a container is a prefilled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to antibody concentrations as described above. The label may further indicate that the formulation is useful or intended for, for example, subcutaneous administration. In some embodiments, a container may contain a single dose of a stable formulation containing a therapeutic antibody (e.g., an anti-IL1R1 antibody). In various embodiments, a single dose of the stable formulation is present in a volume of less than about 10 mL, 5.0 mL, 4.0 mL, 3.5 mL, 3.0 mL, 2.5 mL, 2.0 mL, 1.5 mL, 1.0 mL, or 0.5 mL.

Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final antibody concentration in the reconstituted formulation will generally be at least 150 mg/mL (e.g., at least 160 mg/mL, at least 170 mg/mL, at least 180 mg/mL, at least 190 mg/mL, at least 200 mg/mL). Kits or other articles of manufacture may further include other materials desirable from a commercial and user standpoint, including other buffers, diluents, preservatives, filters, needles, syringes, and package inserts with instructions for use.

EXAMPLES

Example 1. Conformational Stability Study Summary

The example herein describes a summary of the conformational stability studies for stable formulations of the anti-interleukin 1 (IL1) receptor antibody, Ab1. Ab1 comprises a heavy chain of SEQ ID NO: 1 and a light chain of SEQ ID NO: 2.

The pH was varied based on the isoelectric point of Ab1 (pI range=7.4 to 7.8; main=7.6) utilizing either acetate or histidine-based buffers. Stabilizers, such as sucrose and arginine, to control conformational stability and induce charge formation on the surface of proteins were tested. Selection criteria for conformational stability included high melting temperature $(T_m)$ and aggregation temperature assessed at 266 nm $(T_{agg-266\ nm})$. It was determined that pH 5.0 (acetate) and 6.1 (histidine) behaved the well based on statistical fits. Sucrose was selected as a buffer component for further study for stabilizing effect and use as a cryoprotectant. Further, the following base formulation buffers were explored for resistance to surface-induced denaturation and short-term shelf stability:

Formulation buffer A: 5% w/v Sucrose and 55 mM NaCl in 25 mM Histidine at pH 6.1;

Formulation buffer B: 8% w/v Sucrose in 25 mM Histidine at pH 6.1;

Formulation buffer C: 8% w/v Sucrose in 25 mM Sodium acetate at pH 5.2.

Example 2. Assessment of Susceptibility of Ab1 to Surface-Induced Degradation and Short-Term Shelf Stability This example outlines screening exemplary formulations to control surface-induced degradation of Ab1 and test short-term shelf life.

To assess susceptibility to surface-induced degradation, 10 mg/mL Ab1 was tested in three formulation buffers:

Formulation buffer A: 5% w/v Sucrose and 55 mM NaCl in 25 mM Histidine at pH 6.1;

Formulation buffer B: 8% w/v Sucrose in 25 mM Histidine at pH 6.1;

Formulation buffer C: 8% w/v Sucrose in 25 mM Sodium acetate at pH 5.2.

Polysorbate 20 (PS20) was added to all formulation buffers at concentrations of 0% w/v, 0.005% w/v, 0.010% w/v, 0.020% w/v and 0.050% w/v. The visual appearance and presence of subvisible particles were assessed under stress by the following methods:

1) Agitation by shaking
   a. Samples were agitated for 48 hours at 25° rpm in 3 mL vials with 1 mL fill while held horizontally.
2) Freeze-Thaw
   a. Samples were frozen at −70° C. for 24 hours;
   b. Underwent five freeze-thaw cycles under ambient conditions while protected from light.

Based on visual appearance, it was determined that formulations containing PS20 at concentrations greater than or equal to 0.01% w/v were sufficient to eliminate the formation of visible particles. With respect to sensitivity to agitation and freeze-thaw based on subvisible particle formation, Formulation C was determined to be the least sensitive, wherein PS20 concentrations of greater than or equal to 0.005% w/v were enough to suppress formation of subvisible particles.

Following the preceding study, short-term shelf-life stability of Ab1 was tested at a concentration of 100 mg/mL in the following formulation buffers:

Formulation buffer A: 5% w/v Sucrose, 0.02% w/v PS20 and 55 mM NaCl in 25 mM Histidine at pH 6.1;

Formulation buffer B: 5% w/v Sucrose, 0.02% w/v PS20 in 25 mM Histidine at pH 6.1;

Formulation buffer C: 8% w/v Sucrose, 0.02% w/v PS20 in 25 mM Sodium acetate at pH 5.2.

These formulations were stored at 25° C. and 40° C. and their visual appearances were evaluated for visible particle formation, color, and clarity. The visual appearances of representative samples are seen in FIG. 1, with their respective descriptions in Table 1.

TABLE 1

| Summary of Visual Appearance (Opalescence) | | | |
|---|---|---|---|
| Formulation | Clarity | Color | Visible Particles |
| A | Slightly opalescent | Slightly brownish-yellow | None |
| B | Slightly opalescent | Slightly brownish-yellow | None |
| C | Clear to slightly opalescent | Slightly brownish-yellow | None |

Based on the data presented above, Formulation C was determined to have the highest resistance to surface-induced degradation and is an attractive candidate for further stability studies as the pH is the furthest from the pI of Ab1 (pI=7.4 to 7.8; main=7.6).

Example 3. Biophysical Characterization of Formulations

This example highlights the biophysical characterization of the proposed formulations to identify the major factors affecting colloidal properties $(K_D$ and $B_{22})$ and thermal stability ($T_m$ and $T_{agg}$). As evidenced by Table 2, pH, total buffer concentration and type of buffer (Ac=Acetate, His=Histidine, Succ=Succinate), addition of charged amino acids (LYS=Lysine, ARG=Arginine, GLU=Glutamic Acid) or neutral amino acids (PRO=Proline) to inhibit aggregation, osmolyte concentration (5-8% w/v Sucrose), and salt for ionic strength (NaCl versus $MgCl_2$) were evaluated. A total of thirty formulation buffers were characterized.

Figure 2:
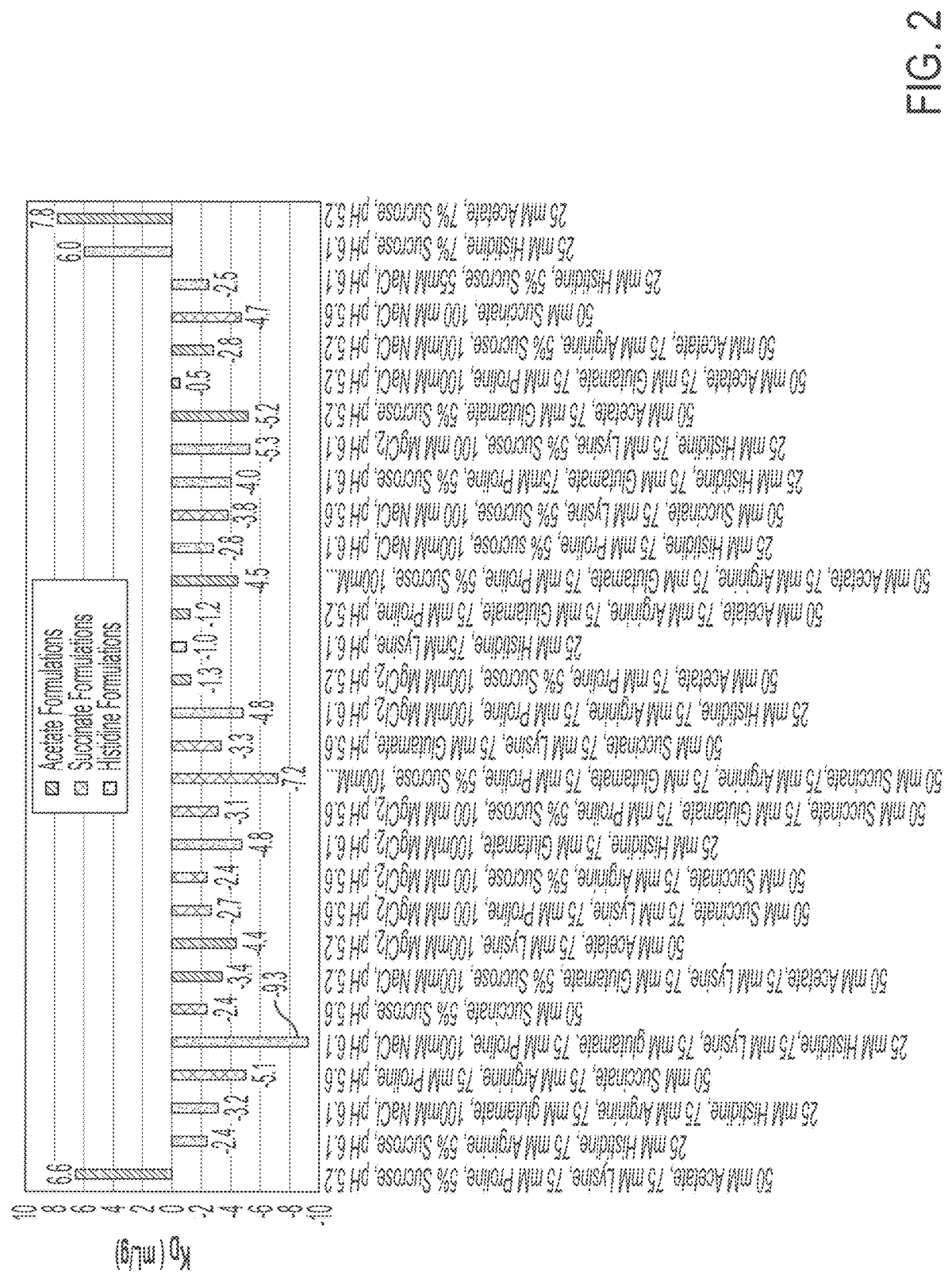

For $K_D$, experimentally determined values greater than or equal to 0 mL/g indicate less self-association. Three formulations were determined to have positive $K_D$ values. The rest of the formulations had $K_D$ values of greater than −10 mL/g, as shown in FIG. 2.

For $B_{22}$, experimentally determined values greater than or equal to 0 mol-mL/g$^2$ indicate repulsive interactions

TABLE 2

Drug Substance and Formulation Buffers

| No. | Buffer | Basic AA | Acidic AA | Other AA | Osmolyte | Salt | pH |
|---|---|---|---|---|---|---|---|
| 1 | 50 mM Ac | 75 mM LYS | None | 75 mM PRO | 5% w/v Sucrose | None | 5.2 |
| 2 | 25 mM His | 75 mM ARG | None | None | 5% w/v Sucrose | None | 6.1 |
| 3 | 25 mM His | 75 mM ARG | 75 mM GLU | None | None | 100 mM NaCl | 6.1 |
| 4 | 50 mM Succ | 75 mM ARG | None | 75 mM PRO | None | None | 5.6 |
| 5 | 25 mM His | 75 mM LYS | 75 mM GLU | 75 mM PRO | None | 100 mM NaCl | 6.1 |
| 6 | 50 mM Succ | None | None | None | 5% w/v Sucrose | None | 5.6 |
| 7 | 50 mM Ac | 75 mM LYS | 75 mM GLU | None | 5% w/v Sucrose | 100 mM NaCl | 5.2 |
| 8 | 50 mM Ac | 75 mM LYS | None | None | None | 100 mM MgCl2 | 5.2 |
| 9 | 50 mM Succ | 75 mM LYS | None | 75 mM PRO | None | 100 mM MgCl2 | 5.6 |
| 10 | 50 mM Succ | 75 mM ARG | None | None | 5% w/v Sucrose | 100 mM MgCl2 | 5.6 |
| 11 | 25 mM His | None | 75 mM GLU | None | None | 100 mM MgCl2 | 6.1 |
| 12 | 50 mM Succ | None | 75 mM GLU | 75 mM PRO | 5% w/v Sucrose | 100 mM MgCl2 | 5.6 |
| 13 | 50 mM Succ | 75 mM ARG | 75 mM GLU | 75 mM PRO | 5% w/v Sucrose | 100 mM NaCl | 5.6 |
| 14 | 50 mM Succ | 75 mM LYS | 75 mM GLU | None | None | None | 5.6 |
| 15 | 25 mM His | 75 mM ARG | None | 75 mM PRO | None | 100 mM MgCl2 | 6.1 |
| 16 | 50 mM Ac | None | None | 75 mM PRO | 5% w/v Sucrose | 100 mM MgCl2 | 5.2 |
| 17 | 25 mM His | 75 mM LYS | None | None | None | None | 6.1 |
| 18 | 50 mM Ac | 75 mM ARG | 75 mM GLU | 75 mM PRO | None | None | 5.2 |
| 19 | 50 mM Ac | 75 mM ARG | 75 mM GLU | 75 mM PRO | 5% w/v Sucrose | 100 mM MgCl2 | 5.2 |
| 20 | 25 mM His | None | None | 75 mM PRO | 5% w/v Sucrose | 100 mM NaCl | 6.1 |
| 21 | 50 mM Succ | 75 mM LYS | None | None | 5% w/v Sucrose | 100 mM NaCl | 5.6 |
| 22 | 25 mM His | None | 75 mM GLU | 75 mM PRO | 5% w/v Sucrose | None | 6.1 |
| 23 | 25 mM His | 75 mM LYS | None | None | 5% w/v Sucrose | 100 mM MgCl2 | 6.1 |
| 24 | 50 mM Ac | None | 75 mM GLU | None | 5% w/v Sucrose | None | 5.2 |
| 25 | 50 mM Ac | None | 75 mM GLU | 75 mM PRO | None | 100 mM NaCl | 5.2 |
| 26 | 50 mM Ac | 75 mM ARG | None | None | 5% w/v Sucrose | 100 mM NaCl | 5.2 |
| 27 | 50 mM Succ | None | None | None | None | 100 mM NaCl | 5.6 |
| 28 | 25 mM His | None | None | None | 5% w/v Sucrose | 55 mM NaCl | 6.1 |
| 29 | 25 mM His | None | None | None | 8% w/v Sucrose | None | 6.1 |
| 30 | 25 mM Ac | None | None | None | 7% w/v Sucrose | None | 5.2 |

Conformational Stability—Unfolding Temperature ($T_m$) and Aggregation Temperature ($T_{agg}$)

Five samples for each formulation buffer at Ab1 concentrations ranging from 1-10 mg/mL were tested to assess conformational stability ($T_m$ and $T_{agg}$; temperature range from 25 to 95° C. at a rate of 0.3° C./min). Ab1 exhibited good conformational stability with $T_m$ greater than or equal to 55° C. and $T_{agg}$ (260 nm) greater than or equal to 60° C., which suggests that there is a low risk of unfolding-driven aggregation.

Colloidal Property Testing ($K_D$, $B_{22}$)

Figure 3:
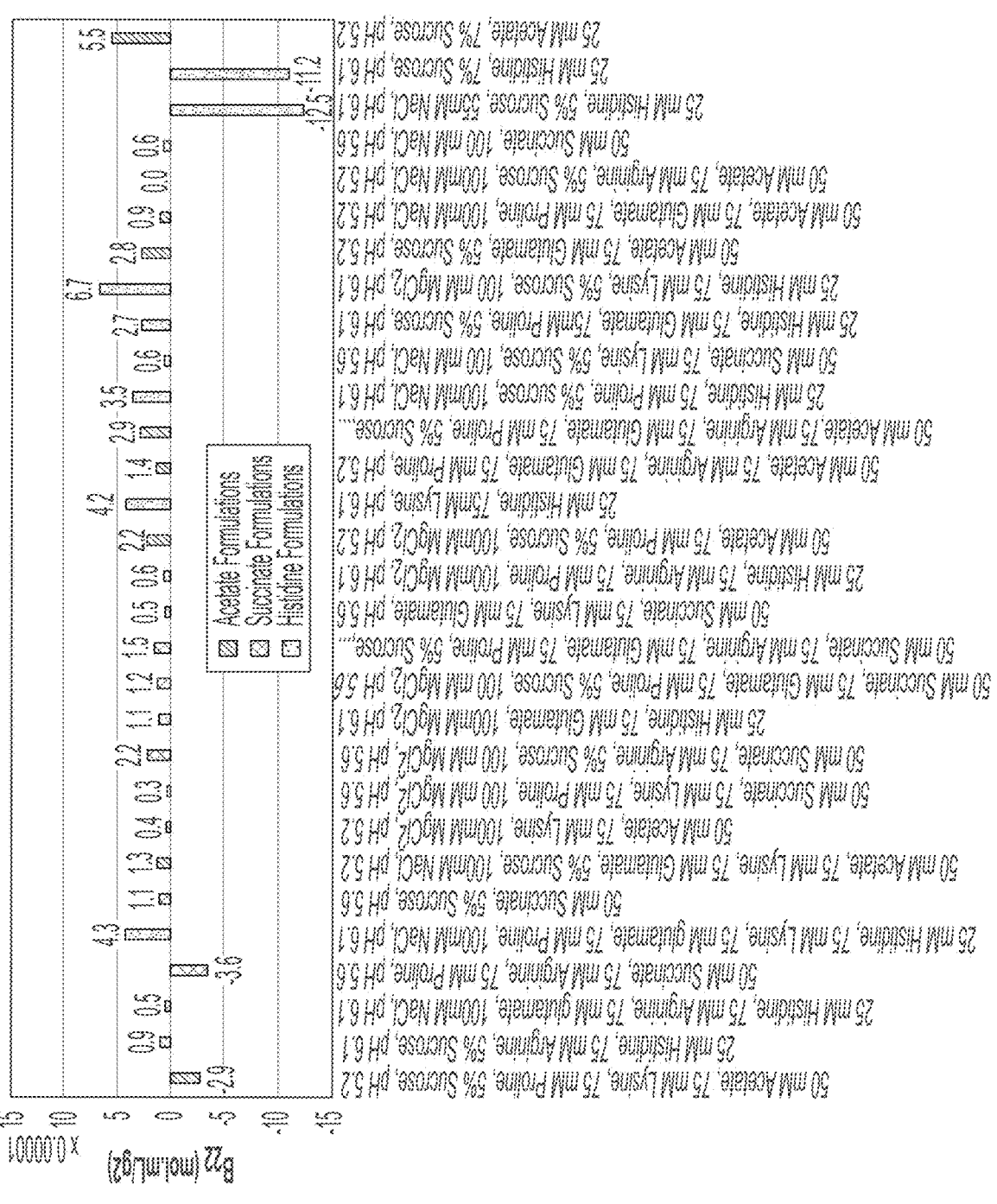
FIG. 3 depicts an exemplary bar graph of the experimentally determined second virial coefficients ($B_{22}$) for each formulation at an antibody concentration ranging from 1 mg/mL to 20 mg/mL.

The diffusion interaction parameter ($K_D$) and second virial coefficient ($B_{22}$; measures total protein-protein interaction) for each formulation was determined by dynamic and static light scattering, respectively. For each parameter, five samples for each formulation buffer at Ab1 concentrations ranging from 1-20 mg/mL at 25° C. were tested.

between protein molecules or more favorable interactions with solvent. Nearly all formulations exhibited positive $B_{22}$ values (FIG. 3).

Overall, Ab1 demonstrated good conformational stability in all formulations, however the explored excipients did not have a significant impact on the colloidal and thermal stability properties of each formulation.

Example 4. Viscosity and Solution Stability Studies

This example outlines the viscosity and solution stability studies for the best-behaved formulations of Ab1 from Example 3. The exemplary formulation compositions tested for viscosity and freeze-thaw stability are listed in Table 3, wherein F0 was the formulation with the desirable experimental $K_D$ and $B_{22}$ values from Example 3. Herein, the effects of varying pH, excipient type and concentration were explored for all exemplary formulations.

TABLE 3

Formulation Compositions for Viscosity and Solution Stability Studies

| No. | Formulation Composition |
|---|---|
| F0 | 150 mg/mL Ab1, 7% W/V Sucrose, 0.02% W/V Polysorbate 20 in 25 mM Sodium Acetate at pH 5.2 |
| F1 | 150 mg/mL Ab1, 7% W/V sucrose, 0.02% W/V Polysorbate 20 in 25 mM Sodium Acetate at pH 5.0 |

TABLE 3-continued

Formulation Compositions for Viscosity and Solution Stability Studies

| No. | Formulation Composition |
|-----|-------------------------|
| F2 | 150 mg/mL Ab1, 7% W/V sucrose, 0.02% W/V Polysorbate 20 in 25 mM Sodium Acetate at pH 4.5 |
| F3 | 150 mg/mL Ab1, 25.9 mg/mL proline, 0.02% W/V Polysorbate 20 in 25 mM Sodium Acetate at pH 5.0 |
| F4 | 150 mg/mL Ab1, 14.0 mg/mL Arg-HCl, 3.5% W/V sucrose, 0.02% W/V Polysorbate 20 in 25 mM Sodium Acetate at pH 5.0 |
| F5 | 150 mg/mL Ab1, 27.9 mg/mL Arg-HCl, 0.02% W/V Polysorbate 20 in 25 mM Sodium Acetate at pH 5.0 |

Briefly, viscosity of exemplary formulations was tested at Ab1 concentrations ranging from 100-180 mg/mL at 20° C. Solution stability of exemplary formulations was tested by freeze-thaw agitation (−80° C./room temperature) and storage at 5, 25 and 40° C. for 1 month, wherein stability was measured by the percent change in higher molecular weight species (ΔHMW %) as evaluated by size exclusion chromatography (SEC). This was further evaluated by image capillary isoelectric focusing (icIEF) and non-reducing capillary electrophoresis sodium dodecyl sulfate (NR-CE-SDS) to characterize charge variants and percent change in fragment (Δfragment %) for intact antibody, respectively.

Figure 4:
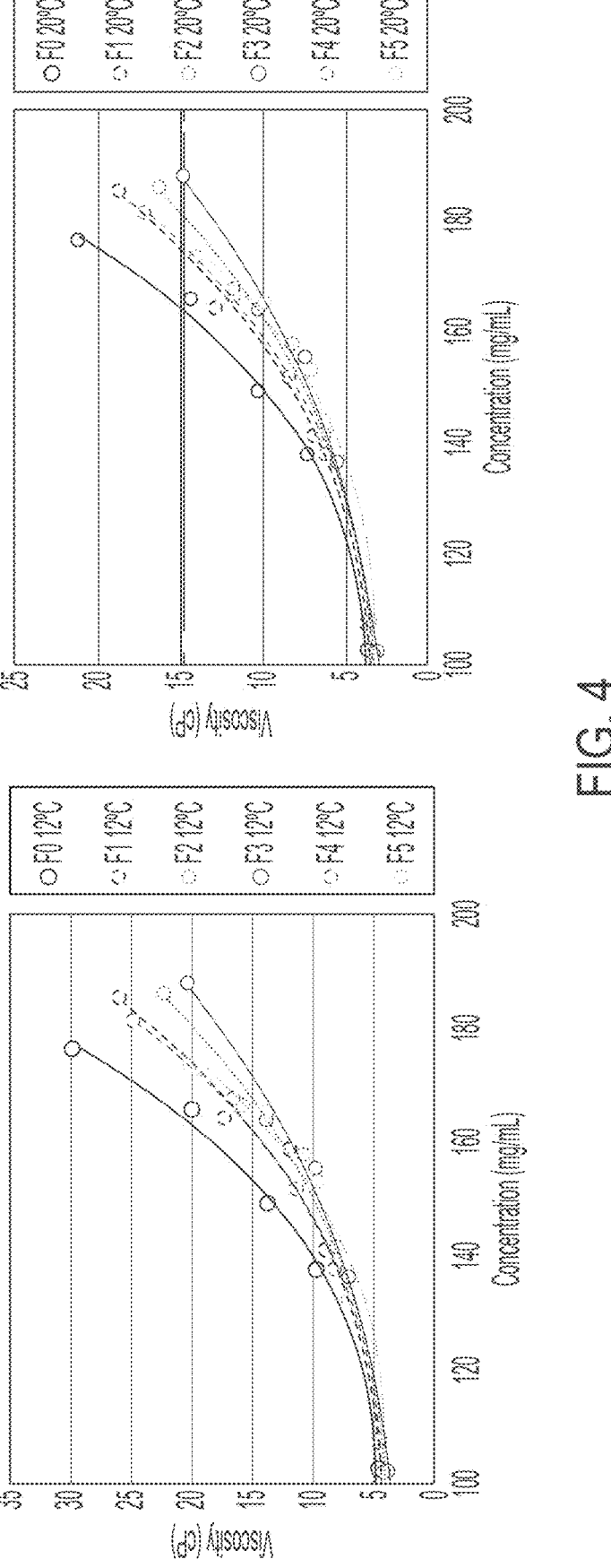
FIG. 4 depicts exemplary plots showing viscosity of the formulations versus antibody concentration, which ranges from 100 mg/mL to 180 mg/mL.

At 20° C., all exemplary formulations have a viscosity of less than or equal to 15 cP at Ab1 concentrations ranging from 100-150 mg/mL (see FIG. 4), making them attractive for manufacturing and progression-free survival and AI development. Formulations with lower pH (F1, F2), Proline (F3), and Arginine-HCl (F5, F6) have a significantly decreased viscosity relative to F0.

Formulations shown in Table 3 were tested for stability after 3 and 6 rounds of freeze thaw cycles. The percentages of HMW, monomer, and LMW species were determined by SEC. The results are shown in Table 4.

TABLE 4

Stability After 3 and 6 Rounds of Freeze and Thaw Cycles

| Formulation | Freeze/Thaw Cycles | % HMW | % Monomer | % LMW | Δ % HMW |
|-------------|--------------------|-------|-----------|-------|---------|
| F0 | 0 | 2.0 | 98.0 | 0.0 | 0.0 |
| F1 |   | 1.9 | 98.1 | 0.0 | 0.0 |
| F2 |   | 1.8 | 98.2 | 0.0 | 0.0 |
| F3 |   | 2.0 | 98.0 | 0.0 | 0.0 |
| F4 |   | 1.8 | 98.2 | 0.0 | 0.0 |
| F5 |   | 2.4 | 97.6 | 0.0 | 0.0 |
| F0 | 3 | 2.1 | 97.9 | 0.0 | 0.1 |
| F1 |   | 2.0 | 98.0 | 0.0 | 0.1 |
| F2 |   | 1.8 | 98.2 | 0.0 | 0.0 |
| F3 |   | 2.1 | 97.9 | 0.0 | 0.1 |
| F4 |   | 1.8 | 98.2 | 0.0 | 0.0 |
| F5 |   | 3.0 | 97.0 | 0.0 | 0.6 |
| F0 | 6 | 2.1 | 97.9 | 0.0 | 0.1 |
| F1 |   | 2.0 | 98.0 | 0.0 | 0.1 |
| F2 |   | 1.9 | 98.1 | 0.0 | 0.1 |
| F3 |   | 2.2 | 97.8 | 0.0 | 0.2 |
| F4 |   | 1.8 | 98.2 | 0.0 | 0.0 |
| F5 |   | 3.7 | 96.3 | 0.0 | 1.3 |

Figure 5:
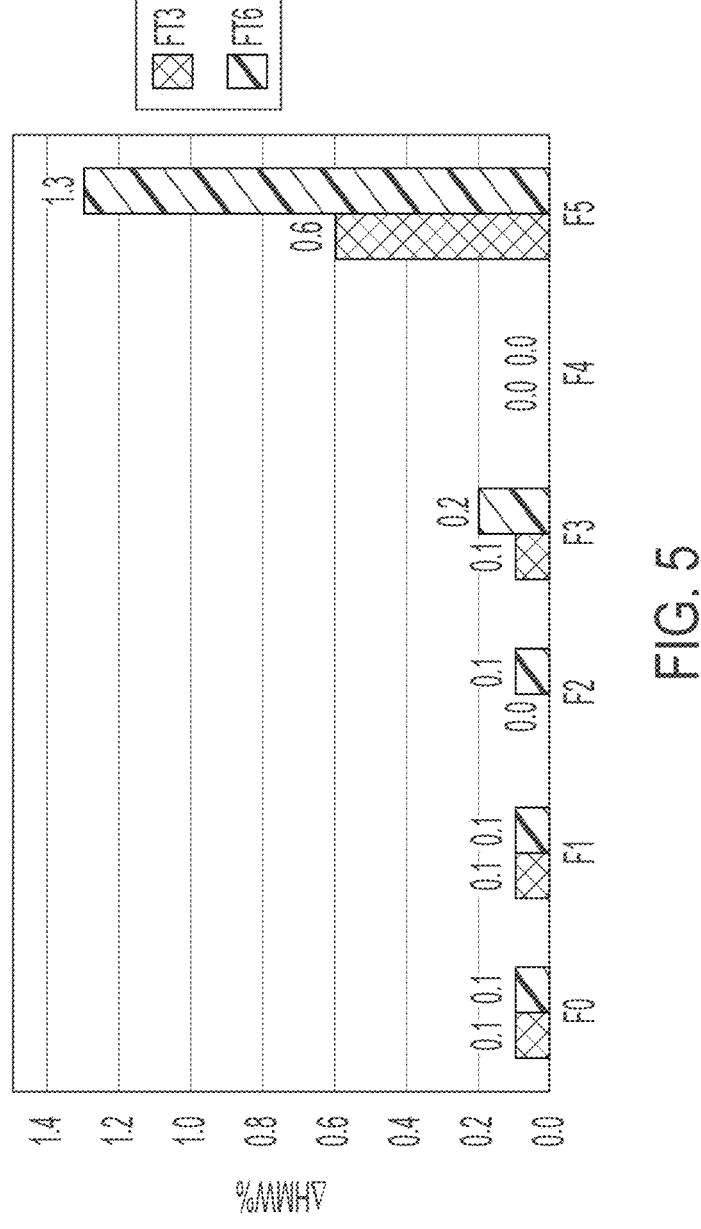
FIG. 5 depicts an exemplary bar chart showing the percent change in levels of high molecular weight species of antibody in formulations after three (FT3) or six (FT6) cycles of freeze/thaw agitation, wherein the antibody concentration is 150 mg/mL.

All formulations have good freeze-thaw stability after six freeze-thaw cycles, maintaining a ΔHMW % less than or equal to 1.5%, indicating little to no aggregate formation. F5, however, has significantly higher ΔHMW % than F0-F4 (FIG. 5).

The solution stability of the exemplary formulations was further tested by storing them at 5° C., 25° C. and 40° C. for 2 months and measuring the percentages of HMW, monomer, and low molecular weight (LMW) species by SEC after 1-month and 2-month time points, as shown in Table 5.

TABLE 5

Absolute % and Δ % of HMW, Monomer, and LMW Species

| Formulation | Temp (° C.) | Time (months) | % HMW | % Monomer | % LMW | Δ% HMW | Δ% Monomer | Δ% LMW |
|-------------|-------------|---------------|-------|-----------|-------|--------|------------|--------|
| F0 | −80 (reference) | 0 | 2.0 | 98.0 | 0.0 | 0.0 | 0.0 | 0.0 |
| F1 |   |   | 1.9 | 98.1 | 0.0 | 0.0 | 0.0 | 0.0 |
| F2 |   |   | 1.8 | 98.2 | 0.0 | 0.0 | 0.0 | 0.0 |
| F3 |   |   | 2.0 | 98.0 | 0.0 | 0.0 | 0.0 | 0.0 |
| F4 |   |   | 1.8 | 98.2 | 0.0 | 0.0 | 0.0 | 0.0 |
| F5 |   |   | 2.4 | 97.6 | 0.0 | 0.0 | 0.0 | 0.0 |
| F0 | 5 | 1 | 2.4 | 97.6 | 0.0 | 0.4 | −0.4 | 0.0 |
| F1 |   |   | 2.2 | 97.8 | 0.0 | 0.3 | −0.3 | 0.0 |
| F2 |   |   | 2.0 | 98.0 | 0.0 | 0.2 | −0.2 | 0.0 |
| F3 |   |   | 2.1 | 97.9 | 0.0 | 0.1 | −0.1 | 0.0 |
| F4 |   |   | 1.9 | 98.1 | 0.0 | 0.1 | −0.1 | 0.0 |
| F5 |   |   | 2.6 | 97.4 | 0.0 | 0.2 | −0.2 | 0.0 |
| F0 | 25 | 1 | 3.1 | 96.9 | 0.0 | 1.1 | −1.1 | 0.0 |
| F1 |   |   | 2.9 | 97.1 | 0.0 | 1.0 | −1.0 | 0.0 |
| F2 |   |   | 2.5 | 97.5 | 0.0 | 0.7 | −0.7 | 0.0 |
| F3 |   |   | 2.6 | 97.4 | 0.0 | 0.6 | −0.6 | 0.0 |
| F4 |   |   | 2.4 | 97.6 | 0.0 | 0.6 | −0.6 | 0.0 |
| F5 |   |   | 3.3 | 96.7 | 0.0 | 0.9 | −0.9 | 0.0 |
| F0 | 40 | 1 | 5.9 | 94.0 | 0.1 | 3.9 | −4.0 | 0.1 |
| F1 |   |   | 6.6 | 93.4 | 0.1 | 4.7 | −4.7 | 0.1 |
| F2 |   |   | 13.3 | 86.6 | 0.1 | 11.5 | −11.6 | 0.1 |
| F3 |   |   | 7.2 | 92.7 | 0.1 | 5.2 | −5.3 | 0.1 |
| F4 |   |   | 39.8 | 60.1 | 0.1 | 38.0 | −38.1 | 0.1 |
| F5 |   |   | Gelled |  |  |  |  |  |
| F0 | 5 | 2 | 2.6 | 97.4 | 0.0 | 0.6 | −0.6 | 0.0 |
| F1 |   |   | 2.4 | 97.6 | 0.0 | 0.5 | −0.5 | 0.0 |
| F2 |   |   | 2.1 | 97.9 | 0.0 | 0.3 | −0.3 | 0.0 |
| F3 |   |   | 2.3 | 97.7 | 0.0 | 0.3 | −0.3 | 0.0 |
| F4 |   |   | 2.0 | 98.0 | 0.0 | 0.2 | −0.2 | 0.0 |
| F5 |   |   | 2.6 | 97.4 | 0.0 | 0.2 | −0.2 | 0.0 |
| F0 | 25 | 2 | 3.5 | 96.5 | 0.0 | 1.5 | −1.5 | 0.0 |
| F1 |   |   | 3.3 | 96.7 | 0.0 | 1.4 | 1.4 | 0.0 |
| F2 |   |   | 3.0 | 97.0 | 0.0 | 1.2 | −1.2 | 0.0 |
| F3 |   |   | 2.9 | 97.1 | 0.0 | 0.9 | −0.9 | 0.0 |
| F4 |   |   | 2.9 | 97.1 | 0.0 | 1.1 | −1.1 | 0.0 |
| F5 |   |   | 4.1 | 95.9 | 0.0 | 1.7 | −1.7 | 0.0 |
| F0 | 40 | 2 | 9.0 | 90.9 | 0.1 | 7.0 | −7.1 | 0.1 |
| F1 |   |   | 10.8 | 89.1 | 0.1 | 8.9 | −9.0 | 0.1 |
| F2 |   |   | 22.0 | 77.9 | 0.1 | 20.2 | −20.3 | 0.1 |
| F3 |   |   | 11.8 | 88.0 | 0.1 | 9.8 | −10.0 | 0.1 |
| F4 |   |   | 56.4 | 43.6 | 0.1 | 54.6 | −54.6 | 0.1 |
| F5 |   |   | Gelled |  |  |  |  |  |

Figure 6:
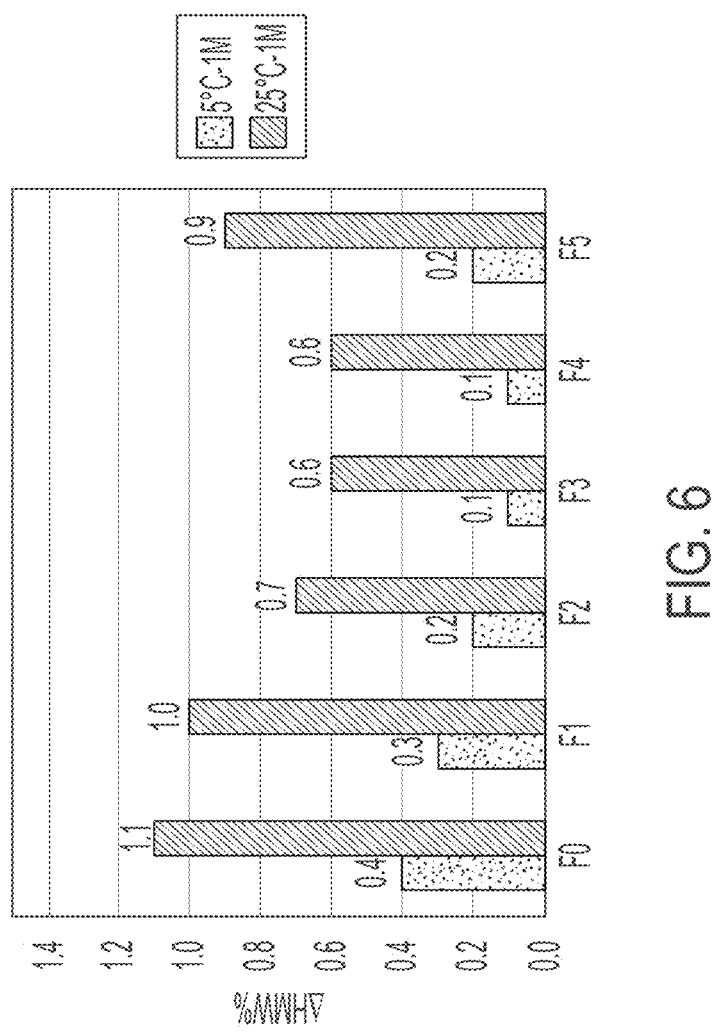
FIG. 6 depicts an exemplary bar chart showing the percent change in levels of high molecular weight species of antibody in formulations by SEC after a storage period of 1 month at 5° C. and 25° C., wherein the antibody concentration is 150 mg/mL.

Additionally, ΔHMW % upon storage at 5° C., 25° C. and 40° C. after 1 month was assessed. At 5 and 25° C., all formulations had less than 1.2% increase in HMW species suggesting stability of these formulations under these conditions (FIG. 6).

Figure 7:
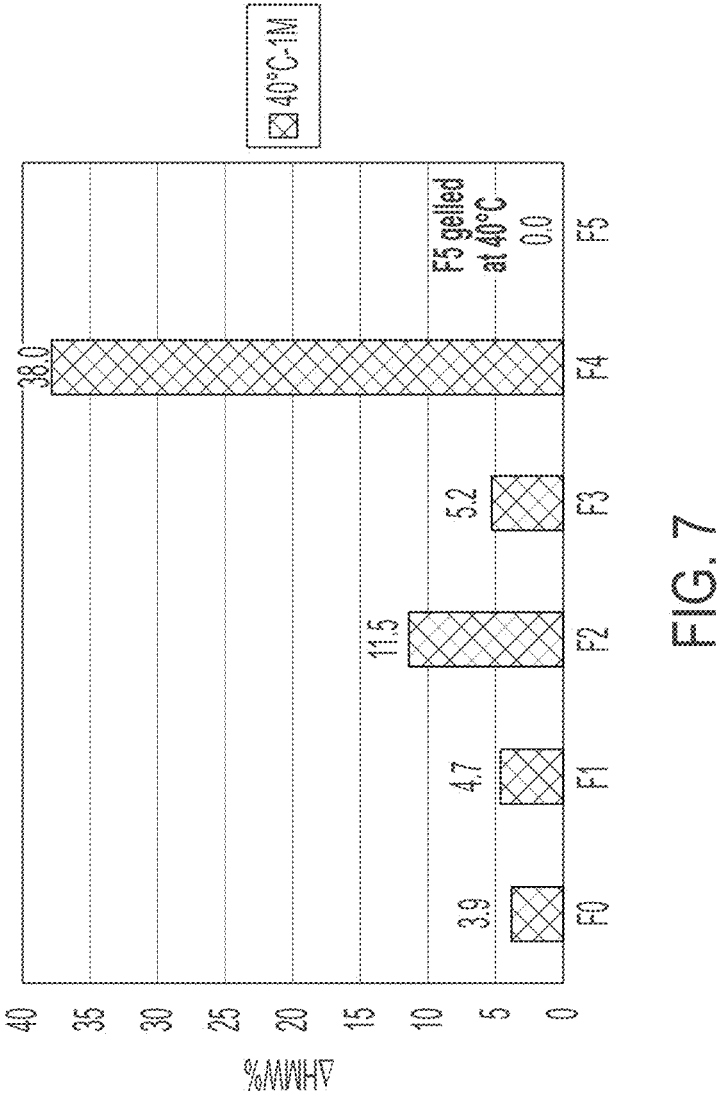
FIG. 7 depicts an exemplary bar chart showing the percent change in levels of high molecular weight species of antibody in in formulations by SEC after a storage period of 1 month at 40° C., wherein the antibody concentration is 150 mg/mL.

FIG. 7 shows the solution stability of each formulation at 40° C. after 1 month. The appearance of F0-F3 were clear, whereas F4 and F5 were opalescent in appearance, wherein F5 gelled. Notably, gel formation is indicative of excessively high levels of protein aggregation in the formulation. While F0 had the lowest ΔHMW % at 40° C. after 1 month, F1-F3 also had relatively low ΔHMW %.

Figure 8:
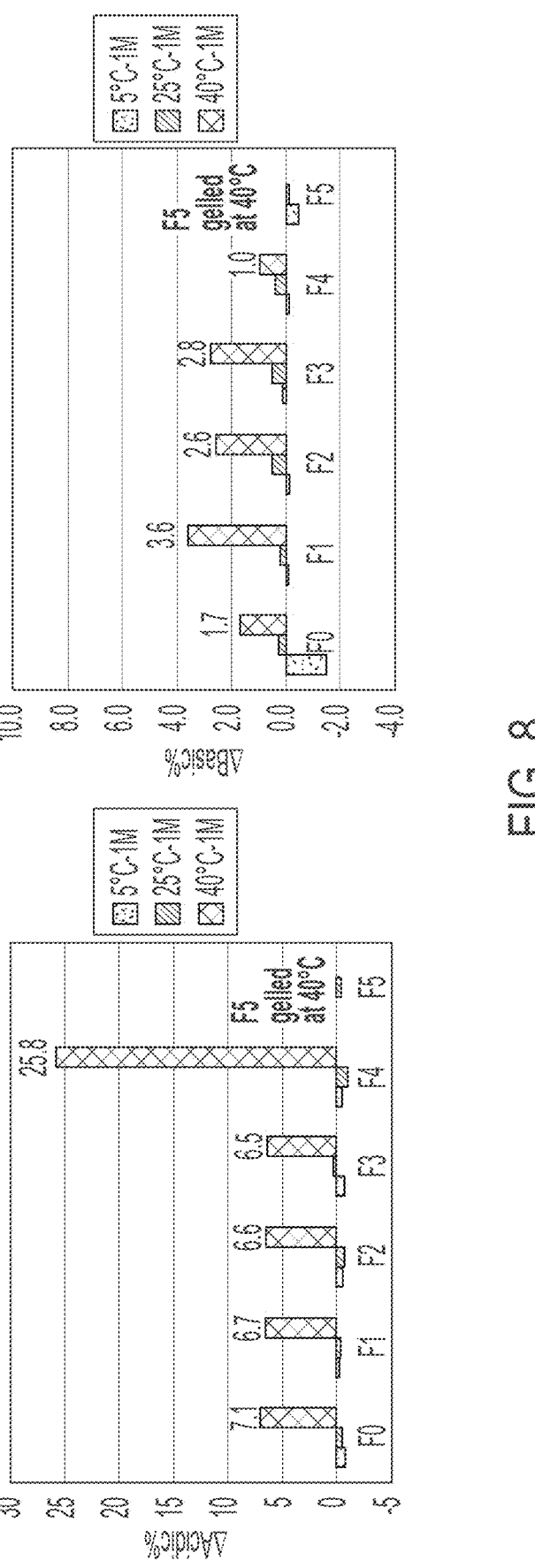
FIG. 8 depicts exemplary bar charts showing the percent change in levels of acidic and basic charge variants in formulations by iclEF after a storage period of 1 month at 5° C., 25° C., and 40° C., wherein the antibody concentration is 150 mg/mL.

Further, all six formulations were characterized by icIEF, a technique widely known in the art, which separates charge variants with differing isoelectric points (FIG. 8). The absolute percentages of acidic, main, and basic peaks were measured upon storage at 5° C., 25° C. and 40° C. for 1 or 2 months. The results are shown in Table 6.

TABLE 6

Absolute % and Δ % of Acidic, Main and Basic Peaks

| Formula-tion | Temp (° C.) | Time (months) | % Acidic | % Main | % Basic | Δ% Acidic | Δ% Main | Δ% Basic |
|---|---|---|---|---|---|---|---|---|
| F0 | −80 (reference) | 0 | 44.3 | 52.9 | 2.8 | 0.0 | 0.0 | 0.0 |
| F1 | | | 43.8 | 53.2 | 2.9 | 0.0 | 0.0 | 0.0 |
| F2 | | | 44.3 | 52.9 | 2.8 | 0.0 | 0.0 | 0.0 |
| F3 | | | 43.7 | 53.5 | 2.7 | 0.0 | 0.0 | 0.0 |
| F4 | | | 44 | 53.2 | 2.8 | 0.0 | 0.0 | 0.0 |
| F5 | | | 44.1 | 52.7 | 3.3 | 0.0 | 0.0 | 0.0 |
| F0 | 5 | 1 | 43.5 | 55.1 | 1.3 | −0.8 | 2.2 | −1.5 |
| F1 | | | 43.6 | 53.5 | 2.9 | −0.2 | 0.3 | 0.0 |
| F2 | | | 43.8 | 53.4 | 2.7 | −0.5 | 0.5 | −0.1 |
| F3 | | | 43 | 54.3 | 2.8 | −0.7 | 0.8 | 0.1 |
| F4 | | | 43.6 | 53.7 | 2.7 | −0.4 | 0.5 | −0.1 |
| F5 | | | 44.1 | 53.1 | 2.8 | 0 | 0.4 | −0.5 |
| F0 | 25 | 1 | 44 | 52.9 | 3.1 | −0.3 | 0 | 0.3 |
| F1 | | | 43.5 | 53.3 | 3.1 | −0.3 | 0.1 | 0.2 |
| F2 | | | 43.6 | 53 | 3.3 | −0.7 | 0.1 | 0.5 |
| F3 | | | 44.1 | 52.7 | 3.2 | 0.4 | −0.8 | 0.5 |
| F4 | | | 43 | 53.8 | 3.2 | −1 | 0.6 | 0.4 |
| F5 | | | 43.7 | 53.2 | 3.2 | −0.4 | 0.5 | −0.1 |
| F0 | 40 | 1 | 51.4 | 44.1 | 4.5 | 7.1 | −8.8 | 1.7 |
| F1 | | | 50.5 | 43 | 6.5 | 6.7 | −10.2 | 3.6 |
| F2 | | | 50.9 | 43.7 | 5.4 | 6.6 | −9.2 | 2.6 |
| F3 | | | 50.2 | 44.3 | 5.5 | 6.5 | −9.2 | 2.8 |
| F4 | | | 69.8 | 26.4 | 3.8 | 25.8 | −26.8 | 1.0 |
| F5 | | | Gelled | | | | | |
| F0 | 5 | 2 | 40.9 | 56.3 | 2.9 | −3.4 | 3.4 | 0.1 |
| F1 | | | 42.1 | 55.2 | 2.8 | −1.7 | 2.0 | −0.1 |
| F2 | | | 42.5 | 54.6 | 2.9 | −1.8 | 1.7 | 0.1 |
| F3 | | | 42.5 | 54.7 | 2.9 | −1.2 | 1.2 | 0.2 |
| F4 | | | 41.1 | 55.7 | 3.3 | −2.9 | 2.5 | 0.5 |
| F5 | | | 42.1 | 54.8 | 3.1 | −2.0 | 2.1 | −0.2 |
| F0 | 25 | 2 | 42.5 | 54.1 | 3.4 | −1.8 | 1.2 | 0.6 |
| F1 | | | 42.6 | 53.5 | 3.9 | −1.2 | 0.3 | 1.0 |
| F2 | | | 41.8 | 54.5 | 3.7 | −2.5 | 1.6 | 0.9 |
| F3 | | | 42.7 | 53.7 | 3.6 | −1.0 | 0.2 | 0.9 |
| F4 | | | 43.1 | 53.5 | 3.4 | −0.9 | 0.3 | 0.6 |
| F5 | | | 43.6 | 53.3 | 3.1 | −0.5 | 0.6 | −0.2 |
| F0 | 40 | 2 | 62.2 | 33.4 | 4.4 | 17.9 | −19.5 | 1.6 |
| F1 | | | 61.1 | 34.1 | 4.8 | 17.3 | −19.1 | 1.9 |
| F2 | | | 68.1 | 27 | 4.9 | 23.8 | −25.9 | 2.1 |
| F3 | | | 60.1 | 35 | 4.9 | 16.4 | −18.5 | 2.2 |
| F4 | | | 80.5 | 17.3 | 2.2 | 36.5 | −35.9 | −0.6 |
| F5 | | | Gelled | | | | | |

After storage at 5 and 25° C. for one month, all formulations show similar Δacidic % and Δbasic % peaks; whereas at 40° C. after one month, F4 has a significantly increased Δacidic % (FIG. 8 left) and F5 gelled.

As a last point of solution stability testing, the formulations were characterized by NR-CE-SDS to determine the percentage of intact Ab1 upon storage at 5° C., 25° C. and 40° C. for 1 or 2 months. The results are shown in Table 7.

TABLE 7

Absolute % and Δ % of Fragment

| Formulation | Temp (° C.) | Time (months) | % Fragment | Δ % Fragment |
|---|---|---|---|---|
| F0 | −80 (reference) | 0 | 1.2 | 0.0 |
| F1 | | | 1.3 | 0.0 |

TABLE 7-continued

Absolute % and Δ % of Fragment

| Formulation | Temp (° C.) | Time (months) | % Fragment | Δ % Fragment |
|---|---|---|---|---|
| F2 | | | 1.3 | 0.0 |
| F3 | | | 1.4 | 0.0 |
| F4 | | | 1.3 | 0.0 |
| F5 | | | 1.3 | 0.0 |
| F0 | 5 | 1 | 1.2 | 0.0 |
| F1 | | | 1.2 | −0.1 |
| F2 | | | 1.2 | −0.1 |
| F3 | | | 1.4 | 0.0 |
| F4 | | | 1.5 | 0.2 |
| F5 | | | 1.1 | −0.2 |
| F0 | 25 | 1 | 1.3 | 0.1 |
| F1 | | | 1.4 | 0.1 |
| F2 | | | 1.3 | 0.0 |
| F3 | | | 1.4 | 0.0 |
| F4 | | | 1.5 | 0.2 |
| F5 | | | 1.5 | 0.2 |
| F0 | 40 | 1 | 2.1 | 0.8 |
| F1 | | | 2.2 | 1.0 |
| F2 | | | 3.1 | 1.8 |
| F3 | | | 2.9 | 1.6 |
| F4 | | | 3.3 | 1.9 |
| F5 | | | Gelled | |
| F0 | 5 | 2 | 1.2 | 0.0 |
| F1 | | | 1.5 | 0.2 |
| F2 | | | 1.3 | 0.0 |
| F3 | | | 1.3 | −0.1 |
| F4 | | | 1.1 | −0.2 |
| F5 | | | 1.1 | −0.2 |
| F0 | 25 | 2 | 1.4 | 0.2 |
| F1 | | | 1.4 | 0.1 |
| F2 | | | 1.6 | 0.3 |
| F3 | | | 1.6 | 0.2 |
| F4 | | | 1.3 | 0.0 |
| F5 | | | 1.6 | 0.3 |
| F0 | 40 | 2 | 2.9 | 1.7 |
| F1 | | | 3.3 | 2.0 |
| F2 | | | 5.3 | 4.0 |
| F3 | | | 4.9 | 3.5 |
| F4 | | | 5.8 | 4.5 |
| F5 | | | Gelled | |

Figure 9:
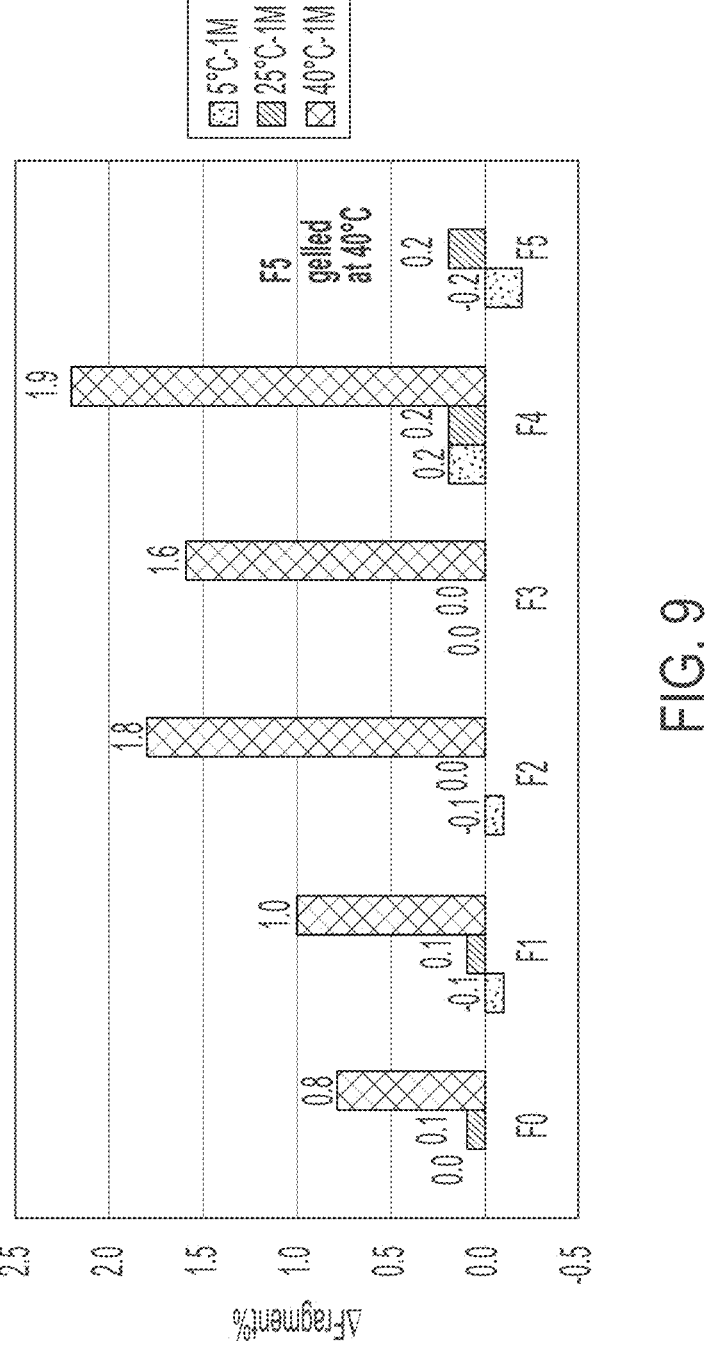
FIG. 9 depicts an exemplary bar chart showing the percent change in levels of antibody fragment as characterized by NR-CE-SDS after a storage period of 1 month at 5° C., 25° C., and 40° C., wherein the antibody concentration is 150 mg/mL.

After storage at 5° C. and 25° C. for one month, the Δfragment % was less than or equal to 0.2%, suggesting largely intact Ab1; even upon storage for one month at 40° C., the Δfragment % was below 2%, except for F5, which gelled (FIG. 9).

Example 5. IL-1R1 Antibody Stability Study

Figure 10:
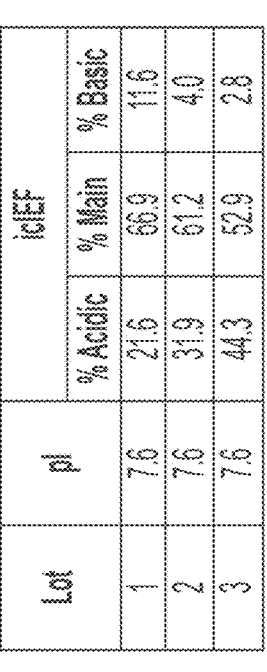
FIG. 10 depicts an exemplary graph showing the change in the % HMW species of Ab1 over time in samples with varying levels of acidic species at baseline.
Figure 10:
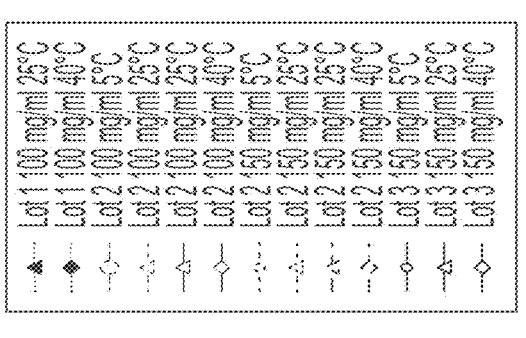
Figure 10:
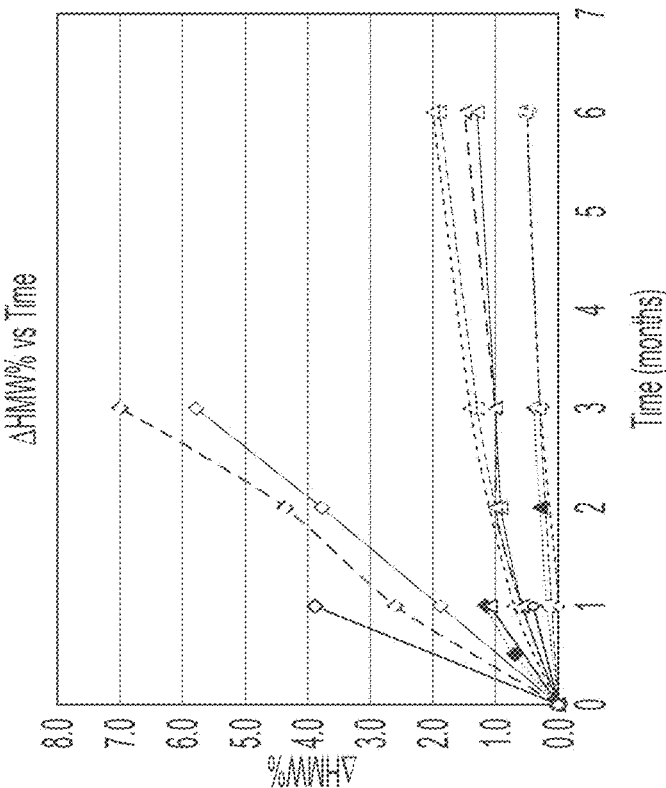

This Example describes the effect of acidic species on Ab1 stability (FIG. 10). Purified Ab1 drug substance was sourced from three different lots, each with varying levels of acidic species at baseline (level of acidic species in Lot 1<Lot 2<Lot 3). All samples of Ab1 drug substance were formulated in the same liquid formulation and the stability of Ab1 was tested by storing them at 5, 25 or 40° C. for 1 to 6 months at 100 mg/ml or 150 mg/ml (as indicated in FIG. 10), and assessed for the ΔHMW % by SEC. The formulation of Lot 1 was 100 mg/ml Ab1, 7% w/v sucrose, 0.02% w/v polysorbate 20, and 25 mM sodium acetate at pH 5.2. The formulation of Lot 2 was 100 mg/ml Ab1 or 150 mg/ml Ab1, 7% w/v sucrose, 0.02% w/v polysorbate 20, and 25 mM sodium acetate at pH 5.2. The formulation of Lot 3 was 150 mg/ml Ab1, 7% w/v sucrose, 0.02% w/v polysorbate 20, and 25 mM sodium acetate at pH 5.2. FIG. 10 shows the ΔHMW % in each sample over time. Notably, the results surprisingly demonstrate a positive correlation between the baseline level of acidic species in a sample and an increase in the amount of higher molecular weight aggregates of Ab1 that form over time. These data demonstrate the importance of maintaining an acceptable level, or preventing an increase, of acidic species in the formulation. Indeed, acidic species present in the formulation can be detrimental to product stability by promoting an increase in high molecular weight aggregates during long term storage.

Example 6. Long-Term Stability Study of IL-1R1 Antibody Formulation

To understand the long-term stability and support shelf-life, a representative drug product was prepared in a DP container closure systems with an exemplary formulation (150 mg/mL Ab1 in 25 mM sodium acetate, 25.9 mg/mL proline, 0.02% w/v PS20, pH4.9), and put on stability testing. The stability is monitored according to ICH Q5C: Quality of Biotechnological Products: Stability Testing of Biotechnological/Biological Products at three conditions:

1. Long-term storage condition (5° C.±3° C.) evaluates stability at the temperature at which the drug product is intended to be stored.
2. Accelerated condition (25° C.±2° C./60% relative humidity (RH)±5% RH) assesses effects, if any, of holding the drug product at room temperature.
3. Stressed condition (40° C.±2° C./75% RH±5% RH) assesses effects, if any, of unplanned temperature excursions during storage or shipping.

The samples were pulled out at the defined timepoints, and the quality attributes were measured per established analytical methods described below. The available stability data are summarized in Tables 8-10. These data demonstrate that the exemplary drug product formulation is stable at its intended long-term storage temperatures and could provide sufficient stability to support its use at room temperature and unplanned temperature excursion that could happen during the drug product handling.

TABLE 8

| Anti-IL1R1 Antibody Drug Product Stability Result (Long-Term Condition: 5° C. ± 3° C.) | | | | | | |
|---|---|---|---|---|---|---|
| | Test | Target | $T_0$ | 1 Month | 3 Months | 6 Months |
| Appearance | Color and State | Colorless to brownish yellow liquid | Slightly Brownish-Yellow Liquid | Slightly Brownish-Yellow Liquid | Slightly Brownish-Yellow Liquid | Slightly Brownish-Yellow Liquid |
| | Clarity | Clear to opalescent | Slightly Opalescent | Slightly Opalescent | Slightly Opalescent | Slightly Opalescent |
| | Visible Particles | Practically free of visible particles | Practically Free of Visible Particles | Practically Free of Visible Particles | Practically Free of Visible Particles | Practically Free of Visible Particles |
| | pH | 4.6-5.2 | 5.2 | 5.2 | 5.1 | 5.1 |
| Total Protein Concentration | (A280) | 135.0-165.0 mg/mL | 153.7 | 151.6 | 153.7 | 150.6 |
| SEC | HMW (%) | ≤5.0 | 1.3 | 1.4 | 1.5 | 1.6 |
| | Main (%) | ≥90.0 | 98.7 | 98.6 | 98.5 | 98.4 |
| | LMW (%) | — | 0.0 | 0.0 | 0.0 | 0.0 |
| icIEF | pl | — | 7.6 | 7.6 | 7.6 | 7.6 |
| | Acidic (%) | — | 35.1 | 34.5 | 34.6 | 35.7 |
| | Main (%) | — | 61.6 | 61.9 | 61.9 | 60.4 |
| | Basic (%) | — | 3.2 | 3.6 | 3.5 | 3.9 |
| NR-CE-SDS | Main (%) | ≥90.0 | 97.6 | 97.4 | 96.9 | 96.8 |
| | Aggregates (%) | — | 1.0 | 1.0 | 1.5 | 1.7 |
| | Fragments (%) | — | 1.4 | 1.6 | 1.6 | 1.5 |
| R-CE-SDS | LC + HC (%) | ≥90.0 | 96.1 | 95.5 | 96.4 | 95.9 |
| | NGHC (%) | — | 2.6 | 2.8 | 2.6 | 2.8 |
| | Impurities (%) | — | 1.2 | 1.7 | 1.1 | 1.4 |
| Binding - ELISA | Relative Potency | 50 to 150% | 98.0 | 97.0 | 97.0 | 98.0 |
| Subvisible Particulates- HIAC | ≥2 μm | — | 890 | N.A. | N.A. | N.A. |
| | ≥10 μm | ≤6000 particles/ container | 90 | N.A. | N.A. | N.A. |
| | ≥25 μm | ≤600 particles/ container | 8 | N.A. | N.A. | N.A. |

TABLE 9

| Anti-IL1R1 Antibody Stability Result (Accelerated Stability: 25° C. ± 2° C./60% ± 5% RH) | | | | | | |
|---|---|---|---|---|---|---|
| | Test | Target | $T_0$ | 1 Month | 3 Months | 6 Months |
| Appearance | Color and State | Colorless to brownish yellow liquid | Slightly Brownish-Yellow Liquid | Slightly Brownish-Yellow Liquid | Slightly Brownish-Yellow Liquid | Slightly Brownish-Yellow Liquid |

TABLE 9-continued

Anti-IL1R1 Antibody Stability Result (Accelerated Stability: 25° C. ± 2° C./60% ± 5% RH)

| | Test | Target | $T_0$ | 1 Month | 3 Months | 6 Months |
|---|---|---|---|---|---|---|
| | Clarity | Clear to opalescent | Slightly Opalescent | Slightly Opalescent | Slightly Opalescent | Slightly Opalescent |
| | Visible Particles | Practically free of visible particles | Practically Free of Visible Particles | Practically Free of Visible Particles | Practically Free of Visible Particles | Practically Free of Visible Particles |
| | pH | 4.6-5.2 | 5.2 | 5.2 | 5.1 | 5.1 |
| Total Protein Concentration | (A280) | 135.0-165.0 mg/mL | 153.7 | 152.5 | 153.6 | 151.5 |
| SEC | HMW (%) | ≤5.0% | 1.3 | 1.7 | 2.0 | 2.3 |
| | MAIN (%) | ≥90.0% | 98.7 | 98.3 | 98.0 | 97.7 |
| | LMW (%) | — | 0.0 | 0.0 | 0.0 | 0.0 |
| icIEF | pl | — | 7.6 | 7.6 | 7.6 | 7.6 |
| | Acidic (%) | — | 35.1 | 34.6 | 35.5 | 40.6 |
| | Main (%) | — | 61.6 | 61.6 | 59.3 | 54.9 |
| | Basic (%) | — | 3.2 | 3.7 | 4.3 | 4.6 |
| NR-CE-SDS | Main (%) | ≥90.0% | 97.6 | 96.8 | 95.9 | 95.2 |
| | Aggregates (%) | — | 1.0 | 1.5 | 2.1 | 2.6 |
| | Fragments (%) | — | 1.4 | 1.7 | 1.9 | 2.2 |
| R-CE-SDS | LC + HC (%) | ≥90.0% | 96.1 | 95.6 | 95.6 | 94.2 |
| | NGHC (%) | — | 2.6 | 2.7 | 2.7 | 3.0 |
| | Impurities (%) | — | 1.2 | 1.7 | 1.7 | 2.7 |
| Binding - ELISA | Relative Potency | 50 to 150% | 98.0 | 99.0 | 99.0 | 109.0 |
| Subvisible | ≥2 μm | — | 890.0 | N.A. | N.A. | N.A. |
| Particulates-HIAC | ≥10 μm | ≤6000 particles/container | 90.0 | N.A. | N.A. | N.A. |
| | ≥25 μm | ≤600 particles/container | 8.0 | N.A. | N.A. | N.A. |

TABLE 10

Anti-IL1R1 Antibody Stability Result (Stressed Stability: 40° C. ± 2° C./75% ± 5% RH)

| | Test | Target | $T_0$ | 1 Month | 3 Months |
|---|---|---|---|---|---|
| Appearance | Color and State | Colorless to brownish yellow liquid | Slightly Brownish-Yellow Liquid | Slightly Brownish-Yellow Liquid | Slightly Brownish-Yellow Liquid |
| | Clarity | Clear to opalescent | Slightly Opalescent | Slightly Opalescent | Slightly Opalescent |
| | Visible Particles | Practically free of visible particles | Practically Free of Visible Particles | Practically Free of Visible Particles | Practically Free of Visible Particles |
| | pH | 4.6-5.2 | 5.2 | 5.2 | 5.2 |
| Total Protein Concentration | (A280) | 135.0-165.0 mg/mL | 153.7 | 152.4 | 152.7 |
| SEC | HMW (%) | ≤5.0% | 1.3 | 4.6 | 10.8 |
| | MAIN (%) | ≥90.0% | 98.7 | 95.4 | 89.0 |
| | LMW (%) | — | 0 | 0 | 0 |
| icIEF | pl | — | 7.6 | 7.6 | 7.6 |
| | Acidic (%) | — | 35.1 | 42.1 | 61.2 |
| | Main (%) | — | 61.6 | 52.6 | 33.4 |
| | Basic (%) | — | 3.2 | 5.2 | 5.4 |
| NR-CE-SDS | Main (%) | ≥90.0% | 97.6 | 94.6 | 91.1 |
| | Aggregates (%) | — | 1.0 | 2.8 | 4.8 |
| | Fragments (%) | — | 1.4 | 2.6 | 4.1 |
| R-CE-SDS | LC + HC (%) | ≥90.0% | 96.1 | 94.6 | 91 |
| | NGHC (%) | — | 2.6 | 2.9 | 3.2 |
| | Impurities (%) | — | 1.2 | 2.5 | 5.8 |
| Binding - ELISA | Relative Potency | 50 to 150% | 98 | 106 | 114 |
| Subvisible | ≥2 μm | — | 890 | N.A. | 258 |
| Particulates-HIAC | ≥10 μm | ≤6000 particles/container | 90 | N.A. | 20 |
| | ≥25 μm | ≤600 particles/container | 8 | N.A. | 5 |

Exemplary Methods

Appearance

The appearance measurement including color, clarity and visible particulate were conducted using Particulate Viewer Lightbox (GTI Graphic Technology Inc., Model #: PPVS-2e) with established method which is compliant with USP <790> and European Pharmacopoeia 2.9.20.

Size-Exclusion Chromatography (SEC)

The SEC measurements were conducted using a Waters® HPLC system equipped with Waters® Alliance 2695 separations module, photodiode array (PDA) detector and Empower Software for analysis. TSkgel® G3000SWXL (Tosoh Bioscience, Part #08541, 30 cm length×7.8 mm ID) and a TSKgel® 7.8 mm Guard Column (Tosoh Bioscience, Part #08543) were used for the separation. The mobile phase was 0.1 M Sodium phosphate dibasic, 0.1 M sodium sulfate, pH6.8. The standards and samples were diluted in the mobile phase as 1.0 mg/mL before measurement or measured directly if the sample concentrations were no more than 1.0 mg/mL.

Imaged Capillary Isoelectric Focusing (icIEF)

The icIEF measurements were conducted on Maurice® Platform (ProteinSimple Inc, CA). In brief, samples were diluted with water to prepare 0.25 mg/mL solution. For samples less than 90 mg/mL, they were desalted using a 0.5 mL Zeba™ desalting column first. Before measurement, the final test sample were prepared by mixing 80 μL of the 0.25 mg/mL of standards or samples with 120 μL of the Master Mix, which were prepared from mixing 8 μL of 3-10 pharmalyte, 70 μL 1% methyl cellulose, 2 μL pI maker 4.05, 2 μL pI marker 9.50, 50 μL 8 M Urea. The separation of samples was conducted with 1.0 min at 1500 Volts followed by 7.0 min at 3000 Volts. The resulting data was first calibrated for the makers using the instrument software Compass with fluorescence exposure time of 10 seconds, and then the data was exported to Empower software for peak integration. The pI of the main peak, % area of the main peak, % area of total acidic species, and % area of total basic species were reported.

Non-Reduced Capillary Electrophoresis Analysis (NR CE-SDS)

The NR CE-SDS measurements were conducted on Maurice® Platform (ProteinSimple Inc, CA). In brief, samples were first diluted to 10 mg/mL with water. 20 μL of the sample solution was then mixed with 2 μL of internal standard (IS), 168 μL of 1× sample buffer (20 mM citrate-phosphate buffer, 1% SDS, pH 6.8), and 10 μL of 250 mM N-ethylmaleimide (NEM) in water. For samples with concentration lower than 10 mg/mL, the volume of 1× sample buffer was adjusted as needed to ensure a final concentration of 1 mg/mL while keeping IS and NEM final concentrations the same. The mixed solution was heated at 70±2° C. for 10±1 minute in a heated block or water bath, then cooled to room temperature. 100 μL of the prepared solution was loaded into 96-well plate for separation. The sample loading time was 30 seconds at 4600 Volts and the separation time was 40.0 min at 5750 Volts. The resulting data was first calibrated for the internal standard (IS) using the instrument software Compass with fluorescence exposure time of 10 seconds, and then the data was exported to Empower software for peak integration. Fragment peaks were impurity peaks with a relative migration time <IgG. Aggregate peaks were impurity peaks with a relative migration time >IgG. The percent of the main peak (IgG) area, the percent Total Fragment and Total Aggregate were reported.

Reduced Capillary Electrophoresis Analysis (NR CE-SDS)

The NR CE-SDS measurements were conducted on Maurice® Platform (ProteinSimple Inc, CA). In brief, samples were first diluted to 10 mg/mL with water. 20 μL of the sample solution was then mixed with 2 μL of internal standard (IS), 168 μL of 1× sample buffer (20 mM citrate-phosphate buffer, 1% SDS, pH 6.8), and 10 μL of Beta-mercaptoethanol (P-ME). For samples with concentration lower than 10 mg/mL, the volume of 1× sample buffer was adjusted as needed to ensure a final concentration of 1 mg/mL while keeping IS and P-ME final concentrations the same. The mixed solution was heated at 70±2° C. for 10±1 minute in a heated block or water bath, then cooled to room temperature. 100 μL of the prepared solution was loaded into 96-well plate for separation. The sample loading time was 20 seconds at 4600 Volts and the separation time was 40.0 min at 5750 Volts. The resulting data was first calibrated for the internal standard (IS) using the instrument software Compass with fluorescence exposure time of 10 seconds, and then the data was exported to Empower software for peak integration. Fragment peaks were impurity peaks with a relative migration time <IgG. Aggregate peaks were impurity peaks with a relative migration time >IgG. The percent of the main peak (IgG) area, the percent Total Fragment and Total Aggregate were reported.

Potency Analysis by Binding ELISA

The relative potency of Ab1 was measured by its ability to bind IL1R1 protein with Enzyme-linked immunosorbent assay (ELISA). A 96-well plate was precoated with 0.5 μg/mL IL1R1 protein solution followed by washing and blocking with bovine serum albumin solution. The Ab1 samples were diluted to 8000 ng/mL first and a series of dilutions triplicate three-fold serial dilutions was performed to generate 8 diluted sample solution. 100 μL of the diluted samples were added into the plate well, and then the plate was incubated on a plate shaker at 35° rpm for 60±5 min at room temperature. After incubation, the plate was washed, and 100 μL Mouse Anti-Human 1gG2 Fc-HRP solution was added to each well. The plate was covered, further incubated on a plate shaker at 35° rpm for 60±5 min at room temperature, and then washed. 100 μL of TMB substrate solution was added into each well and incubated at room temperature in dark (covered) for 10±1 minutes. 100 μL of stop solution (1 M/2N H2SO4) was added to each well to stop the reaction, and the plate was read at 450 nm and 570 nm on SpectraMax® M3 with SoftMax® Pro GxP software. The relative potency was calculated by EC50 of reference standard divided by the EC50 of the samples.

Sub-visible Particle (SVP) Characterization by HIAC

Sub-visible particle of drug product solution was measured using the high accuracy liquid particle counter (HIAC 9703+ Liquid Particle counter and PharmaSpec Software) and reported in accordance with USP <787>.

EQUIVALENTS AND SCOPE

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The invention claimed is:

1. A stable formulation comprising an anti-interleukin-1 receptor 1 (IL1R1) antibody, wherein the formulation comprises less than 130 mM arginine, a buffer and a pH of 4.4-6.5, wherein the anti-IL1R1 antibody comprises a HCDR1 of SEQ ID NO: 5 (FHWIA), a HCDR2 of SEQ ID NO: 6 (IIHPGASDTRYSPSFQG), a HCDR3 of SEQ ID NO: 7 (QRELDYFDY), a LCDR1 of SEQ ID NO: 8 (RASQSIGSSLH), a LCDR2 of SEQ ID NO: 9 (YASQSFS), and a LCDR3 of SEQ ID NO: 10 (HQSSSLPLT), and wherein the anti-IL1R1 antibody is present at a concentration of 50-200 mg/ml.

2. The stable formulation of claim 1, wherein the formulation comprises less than 67 mM arginine.

3. The stable formulation of claim 1, wherein the formulation is substantially free of arginine.

4. The stable formulation of claim 1, wherein the anti-IL1R1 antibody is present at a concentration of 100-165 mg/ml.

5. The stable formulation of claim 4, wherein the anti-IL1R1 antibody is present at a concentration of 150 mg/ml.

6. The stable formulation of claim 1, wherein the buffer is present at a concentration of 15 mM to 75 mM.

7. The stable formulation of claim 5, wherein the buffer comprises 25 mM sodium acetate.

8. The stable formulation of claim 1, wherein the pH is 4.6-5.7.

9. The stable formulation of claim 1, wherein the pH is 5.2.

10. The stable formulation of claim 1, wherein the formulation comprises sucrose at a concentration of 1-15% (w/v).

11. The stable formulation of claim 10, wherein the formulation comprises 7% (w/v) sucrose.

12. The stable formulation of claim 1, wherein the formulation comprises a surfactant.

13. The stable formulation of claim 12, wherein the formulation comprises the surfactant at a concentration of 0.005-2% (w/v).

14. The stable formulation of claim 13, wherein the formulation comprises the surfactant at a concentration of 0.01-1.0% (w/v).

15. The stable formulation of claim 13, wherein the formulation comprises the surfactant at a concentration of 0.02-0.5% (w/v).

16. The stable formulation of claim 13, wherein the surfactant is polysorbate-20 or polysorbate-80.

17. The stable formulation of claim 16, wherein the formulation comprises 0.001-0.05% (w/v) polysorbate-20.

18. The stable formulation of claim 1, wherein the formulation comprises proline at a concentration of 50-250 mM.

19. The stable formulation of claim 18, wherein the proline is present at a concentration of 225 mM.

20. The stable formulation of claim 18, wherein the proline is present at a concentration of 25.9 mg/mL.

21. The stable formulation of claim 1, wherein the anti-IL1R1 antibody comprises a variable heavy chain (VH) of SEQ ID NO: 3 and a variable light chain (VL) of SEQ ID NO: 4.

22. The stable formulation of claim 21, wherein the anti-IL1R1 antibody comprises an IgG2 Fc region.

23. The stable formulation of claim 1, wherein the anti-IL1R1 antibody comprises a heavy chain that is at least 95% identical to SEQ ID NO:1.

24. The stable formulation of claim 23, wherein the anti-IL1R1 antibody comprises a heavy chain of SEQ ID NO: 1 and a light chain of SEQ ID NO: 2.

*     *     *     *     *

SEQUENCE LISTING

Sequence total quantity: 12
SEQ ID NO: 1                 moltype = AA   length = 444
FEATURE                      Location/Qualifiers
source                       1..444
                             mol_type = protein
                             organism = synthetic construct
SEQUENCE: 1
EVQLMQSGAE VKKPGESLKI SCKGSGYSFS FHWIAWVRQM PGKGLEWMGI IHPGASDTRY   60
SPSFQGQVTI SADNSNSATY LQWSSLKASD TAMYFCARQR ELDYFDYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSNFGTQTYT CNVDHKPSNT KVDKTVERKC CVECPPCPAP PVAGPSVFLF   240
PPKPKDTLMI SRTPEVTCVV VDVSHEDPEV QFNWYVDGVE VHNAKTKPRE EQFNSTFRVV   300
SVLTVVHQDW LNGKEYKCKV SNKGLPAPIE KTISKTKGQP REPQVYTLPP SREEMTKNQV   360
SLTCLVKGFY PSDIAVEWES NGQPENNYKT TPPMLDSDGS FFLYSKLTVD KSRWQQGNVF   420
SCSVMHEALH NHYTQKSLSL SPGK                                         444

SEQ ID NO: 2                 moltype = AA   length = 214
FEATURE                      Location/Qualifiers
source                       1..214
                             mol_type = protein
                             organism = synthetic construct
SEQUENCE: 2
EIVLTQSPDF QSVTPKEKVT ITCRASQSIG SSLHWYQQKP DQSPKLLIKY ASQSFSGVPS   60
RFSGSGSGTD FTLTINSLEA EDAAAYYCHQ SSSLPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 3                 moltype = AA   length = 118
FEATURE                      Location/Qualifiers
source                       1..118
                             mol_type = protein
                             organism = synthetic construct
SEQUENCE: 3
EVQLMQSGAE VKKPGESLKI SCKGSGYSFS FHWIAWVRQM PGKGLEWMGI IHPGASDTRY   60
SPSFQGQVTI SADNSNSATY LQWSSLKASD TAMYFCARQR ELDYFDYWGQ GTLVTVSS     118

SEQ ID NO: 4                 moltype = AA   length = 107
FEATURE                      Location/Qualifiers
source                       1..107
                             mol_type = protein
                             organism = synthetic construct
SEQUENCE: 4
EIVLTQSPDF QSVTPKEKVT ITCRASQSIG SSLHWYQQKP DQSPKLLIKY ASQSFSGVPS   60
RFSGSGSGTD FTLTINSLEA EDAAAYYCHQ SSSLPLTFGG GTKVEIK               107

SEQ ID NO: 5                 moltype = AA   length = 5
FEATURE                      Location/Qualifiers
source                       1..5
                             mol_type = protein
                             organism = synthetic construct
SEQUENCE: 5
FHWIA                                                                5

SEQ ID NO: 6                 moltype = AA   length = 17
FEATURE                      Location/Qualifiers
source                       1..17
                             mol_type = protein
                             organism = synthetic construct
SEQUENCE: 6
IIHPGASDTR YSPSFQG                                                  17

SEQ ID NO: 7                 moltype = AA   length = 9
FEATURE                      Location/Qualifiers
source                       1..9
                             mol_type = protein
                             organism = synthetic construct
SEQUENCE: 7
QRELDYFDY                                                           9

SEQ ID NO: 8                 moltype = AA   length = 11
FEATURE                      Location/Qualifiers
source                       1..11
                             mol_type = protein
                             organism = synthetic construct
SEQUENCE: 8
RASQSIGSSL H                                                        11

SEQ ID NO: 9                 moltype = AA   length = 7

```
FEATURE              Location/Qualifiers
source               1..7
                     mol_type = protein
                     organism = synthetic construct
SEQUENCE: 9
YASQSFS                                                        7

SEQ ID NO: 10        moltype = AA  length = 9
FEATURE              Location/Qualifiers
source               1..9
                     mol_type = protein
                     organism = synthetic construct
SEQUENCE: 10
HQSSSLPLT                                                      9

SEQ ID NO: 11        moltype = AA  length = 326
FEATURE              Location/Qualifiers
source               1..326
                     mol_type = protein
                     organism = synthetic construct
SEQUENCE: 11
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 12        moltype = AA  length = 107
FEATURE              Location/Qualifiers
source               1..107
                     mol_type = protein
                     organism = synthetic construct
SEQUENCE: 12
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC              107
```